(12) United States Patent
Painter et al.

US010874683B2

(10) Patent No.: US 10,874,683 B2
(45) Date of Patent: Dec. 29, 2020

(54) N4-HYDROXYCYTIDINE AND DERIVATIVES AND ANTI-VIRAL USES RELATED THERETO

(71) Applicant: Emory University, Atlanta, GA (US)

(72) Inventors: George R. Painter, Atlanta, GA (US); David B. Guthrie, Avondale Estates, GA (US); Gregory R. Bluemling, Decatur, GA (US); Michael R. Natchus, Alpharetta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/083,177

(22) PCT Filed: Mar. 10, 2017

(86) PCT No.: PCT/US2017/021759
§ 371 (c)(1),
(2) Date: Sep. 7, 2018

(87) PCT Pub. No.: WO2017/156380
PCT Pub. Date: Sep. 14, 2017

(65) Prior Publication Data
US 2019/0083520 A1    Mar. 21, 2019

Related U.S. Application Data

(60) Provisional application No. 62/306,163, filed on Mar. 10, 2016.

(51) Int. Cl.
| | | |
|---|---|---|
| *A01N 43/04* | (2006.01) |
| *A61K 31/70* | (2006.01) |
| *A61K 31/7068* | (2006.01) |
| *C07H 19/10* | (2006.01) |
| *C07H 19/067* | (2006.01) |
| *A61P 31/14* | (2006.01) |
| *A61K 9/00* | (2006.01) |

(52) U.S. Cl.
CPC .......... *A61K 31/7068* (2013.01); *A61P 31/14* (2018.01); *C07H 19/067* (2013.01); *C07H 19/10* (2013.01); *A61K 9/008* (2013.01); *Y02A 50/391* (2018.01)

(58) Field of Classification Search
None
See application file for complete search history.

(56) References Cited

U.S. PATENT DOCUMENTS

| 6,086,376 A * | 7/2000 | Moussa .................. A61K 9/008 |
|---|---|---|
| | | 424/450 |
| 2003/0087873 A1 | 5/2003 | Stuyver et al. |
| 2014/0235566 A1 | 8/2014 | Amblard et al. |
| 2014/0273023 A1 | 9/2014 | Salamone et al. |
| 2014/0373831 A1 * | 12/2014 | Culbertson ............... B65B 7/16 |
| | | 128/200.21 |

FOREIGN PATENT DOCUMENTS

| WO | WO 93/01202 | 1/1993 |
|---|---|---|
| WO | WO 2009/143011 | 11/2009 |

OTHER PUBLICATIONS

Ivanov et al. Collect. Czech. Chem. Commun. (2006), vol. 71, pp. 1099-1106.*
Verreault, Daniel, et al. "Evaluation of inhaled cidofovir as postexposure prophylactic in an aerosol rabbitpox model." Antiviral research 93.1 (2012): 204-208.*
Remichkova et al. Antiviral Chemistry & Chemotherapy (2006), vol. 17, pp. 53-58.*
Saxena, S.K., Elahi, A., Gadugu, S. et al. Zika virus outbreak: an overview of the experimental therapeutics and treatment. VirusDis. 27, 111-115 (2016).*
International Search Report from PCT/US2017/021759, dated May 31, 2017.
PubChem Substance summary for CID 44342385 Deposit date Nov. 19, 2009 (Nov. 19, 2009), pp. 1-10.
PubChem Substance summary for CID 57398423 Deposit date Jul. 25, 2012 (Jul. 25, 2012), pp. 1-10.

* cited by examiner

*Primary Examiner* — Patrick T Lewis
(74) *Attorney, Agent, or Firm* — Meunier Carlin & Curfman LLC

(57) ABSTRACT

This disclosure relates to certain N4-hydroxycytidine derivatives, compositions, and methods related thereto. In certain embodiments, the disclosure relates to the treatment or prophylaxis of a Zika virus infection.

16 Claims, 10 Drawing Sheets

N4-HYDROXYCYTIDINE AND DERIVATIVES AND ANTI-VIRAL USES RELATED THERETO

CROSS REFERENCE TO RELATED APPLICATIONS

The application is a national stage application under 35 U.S.C. § 371 of International Application No. PCT/US2017/021759, filed Mar. 10, 2017, which claims priority to U.S. Provisional Application No. 62/306,163, filed Mar. 10, 2016. The complete disclosure of each of the above-identified applications is fully incorporated herein by reference.

STATEMENT REGARDING FEDERALLY SPONSORED RESEARCH OR DEVELOPMENT

This invention was made with government support under Grant No. HHSN272201500008C awarded by the National institutes of Health and Contract No. HDTRA1-15-C-0075 awarded by the Department of Defense. The government has certain rights in the invention.

FIELD

This disclosure relates to N4-hydroxycytidine nucleoside derivatives, as well as compositions and methods related thereto. In certain embodiments, the disclosure relates to the treatment or prophylaxis of viral infections, in particular, Zika virus infections.

BACKGROUND

The causative agents for Eastern, Western, and Venezuelan Equine Encephalitis (EEE, WEE and VEE, respectively) and Chikungunya fever (CHIK) are vector-borne viruses (family Togaviridae, genus *Alphavirus*) that can be transmitted to humans through mosquito bites. The equine encephalitis viruses are CDC Category B pathogens, and the CHIK virus is Category C. There is considerable concern about the use of virulent strains of VEE virus, delivered via aerosol, as a bioweapon against warfighters. Animal studies have demonstrated that infection with VEE virus by aerosol exposure rapidly leads to a massive infection of the brain, with high mortality and morbidity. See Roy et al., Pathogenesis of aerosolized Eastern equine encephalitis virus infection in guinea pigs. Virol J, 2009, 6:170.

Stuyver et al., report β-D-N(4)-hydroxycytidine (NHC) was found to have antipestivirus and antihepacivirus activities. Antimicrob Agents Chemother, 2003, 47(1):244-54. Constantini et al. report evaluations on the efficacy of 2'-C-MeC, 2'-F-2'-C-MeC, and NHC on Norwalk virus. See also Purohit et al. J Med Chem, 2012, 55(22):9988-9997. Ivanov et al., Collection of Czechoslovak Chemical Communications, 2006, 71(7):1099-1106. Fox et al., JACS, 1959, 81:178-87.

References cited herein are not an admission of prior art.

SUMMARY

Disclosed herein are certain N4-hydroxycytidine compounds and derivatives, pharmaceutical compositions comprising the compounds, and uses and methods related thereto. In certain exemplary embodiments, the N4-hydroxycytidine compounds are compounds of Formula I, Formula I or a pharmaceutically acceptable salt, derivative, or prodrug thereof, as defined herein.

In certain embodiments, the disclosure contemplates derivatives of compounds disclosed herein, such as those containing one or more, the same or different, substituents.

In certain embodiments, the disclosure contemplates pharmaceutical compositions comprising a pharmaceutically acceptable excipient and a compound disclosed herein. In certain embodiments, the pharmaceutical composition is in the form of a tablet, capsule, pill, or aqueous buffer, such as a saline or phosphate buffer.

In certain embodiments, the pharmaceutical composition comprises a compound disclosed herein and a propellant. In certain embodiments, the propellant is an aerosolizing propellant is compressed air, ethanol, nitrogen, carbon dioxide, nitrous oxide, hydrofluoroalkanes (HFAs), 1,1,1,2,-tetrafluoroethane, 1,1,1,2,3,3,3-heptafluoropropane or combinations thereof.

In certain embodiments, the disclosure contemplates a pressurized or unpressurized container comprising a compound or pharmaceutical composition as described herein. In certain embodiments, the container is a manual pump spray, inhaler, meter-dosed inhaler, dry powder inhaler, nebulizer, vibrating mesh nebulizer, jet nebulizer, or ultrasonic wave nebulizer.

In certain embodiments, the disclosure relates to methods of treating or preventing a viral infection comprising administering an effective amount of a compound or pharmaceutical composition disclosed herein to a subject in need thereof. In certain embodiments, the viral infection is a Zika virus infection.

In certain embodiments, the compound or pharmaceutical composition is administered orally, intravenously, or through the lungs, i.e., pulmonary administration.

In certain embodiments, the disclosure relates to the use of a compound as described herein in the production of a medicament for the treatment or prevention of a viral infection, such as a Zika virus infection.

In certain embodiments, the disclosure relates to method of making compounds disclosed herein by mixing starting materials and reagents disclosed herein under conditions such that the compounds are formed.

DETAILED DESCRIPTION

Figure 1:
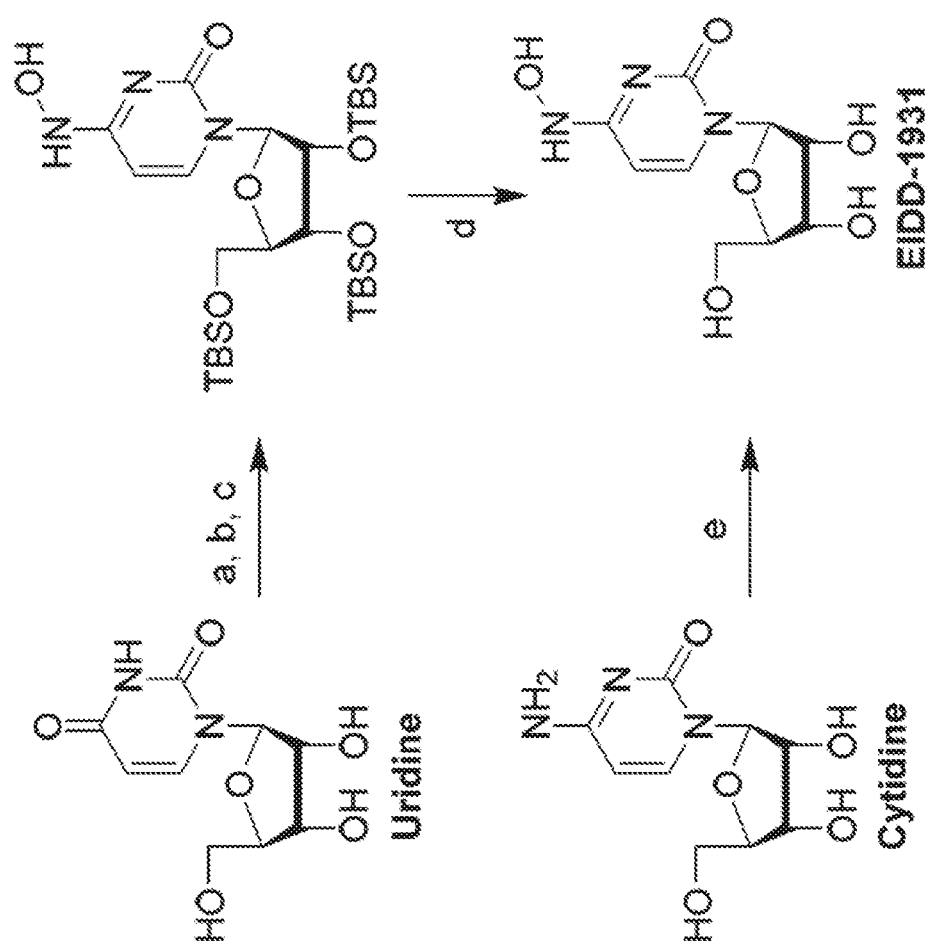
FIG. 1 illustrates the preparation of an exemplary β-D-N-hydroxycytidine compound. a. TBSCl, DMAP, DIPEA, DCM; b. (2,4,6-iPr)PhSO$_2$Cl, DIPEA, DMAP, DCM; c. NH$_2$OH—HCl, DIPEA, DCM; d. F-source; e. aq NH$_2$OH, AcOH, 50° C.
Figure 2:
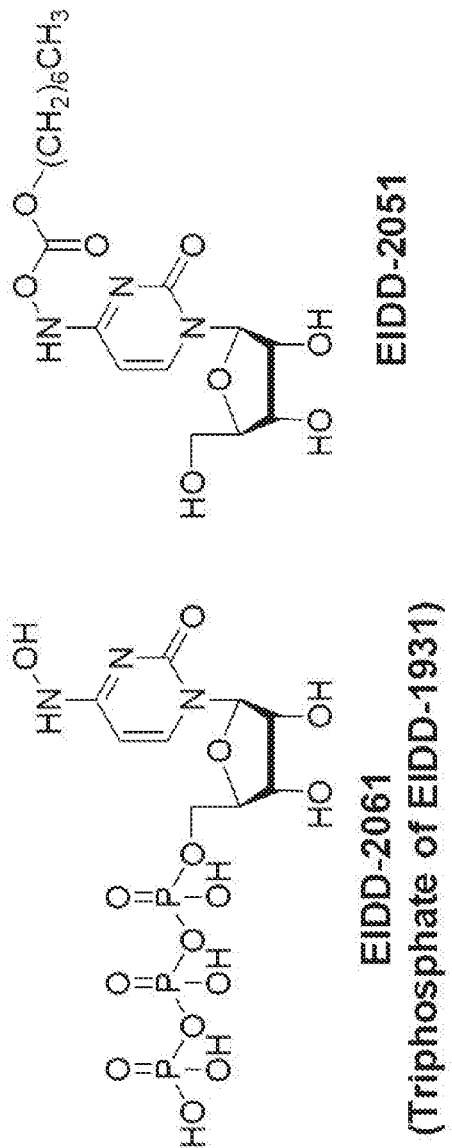
FIG. 2 illustrates certain exemplary compounds.
Figure 3:
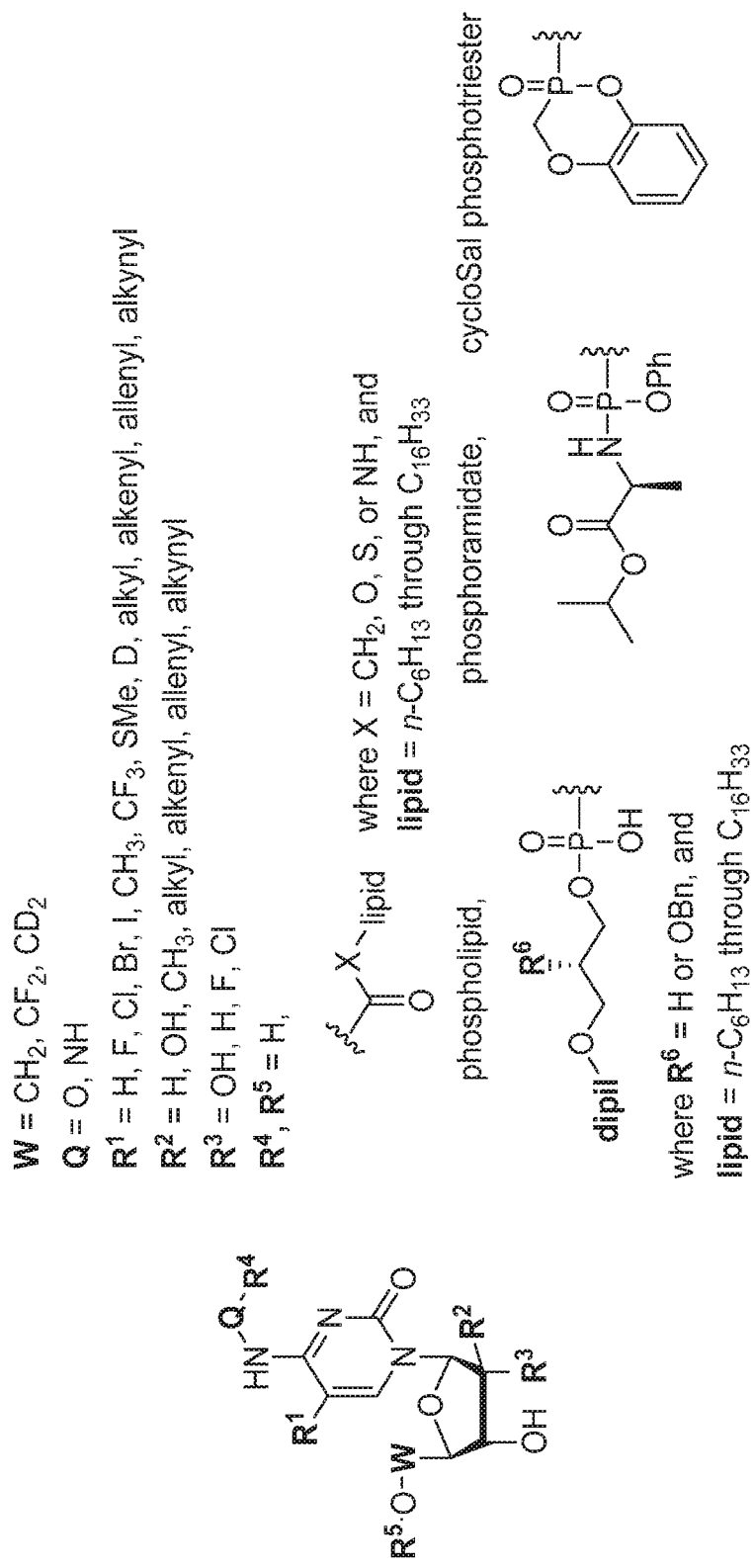
FIG. 3 illustrates certain exemplary compounds.
Figure 4:
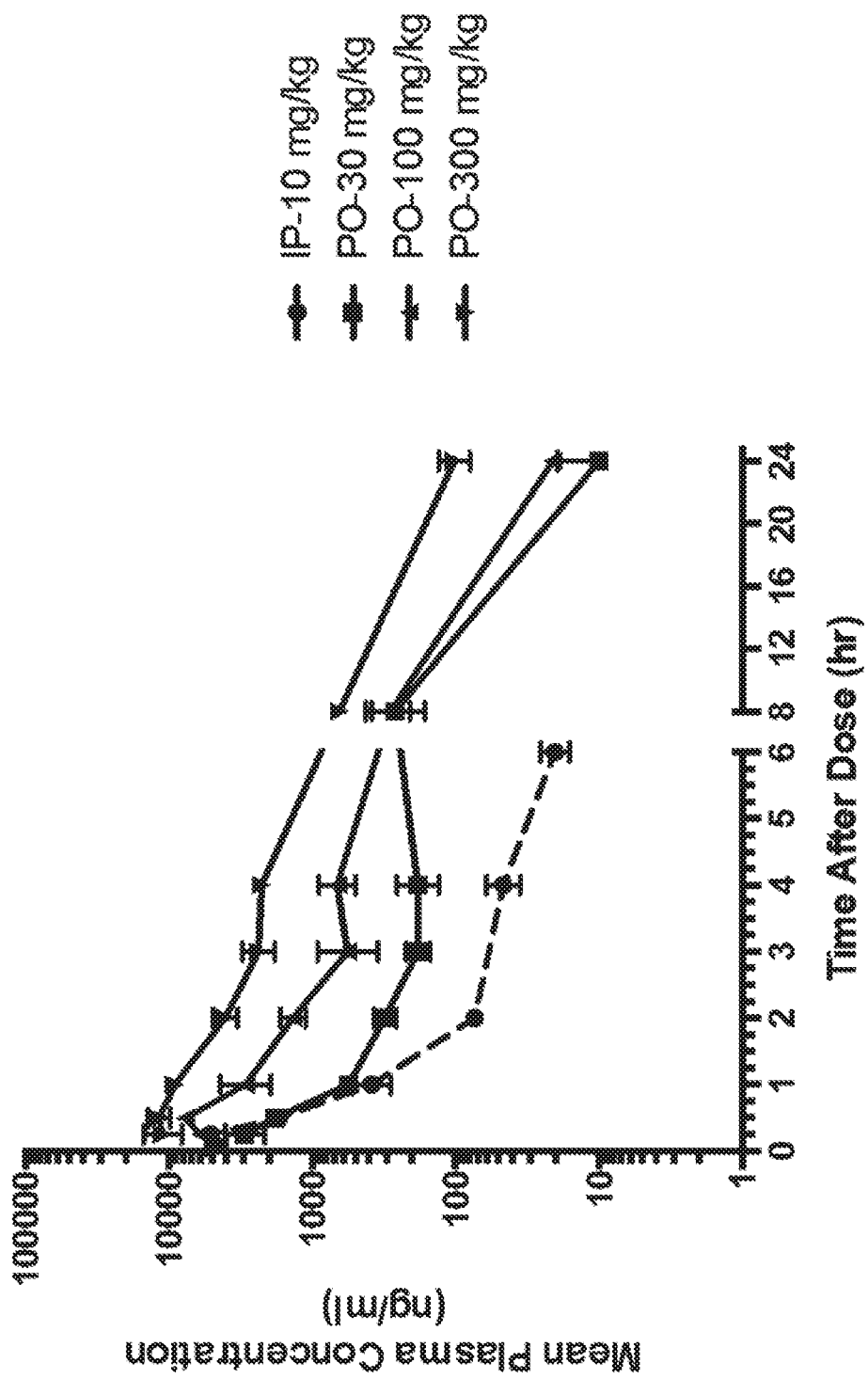
FIG. 4 shows mean plasma concentrations and pharmacokinetic parameters from mice treated with an exemplary compound.
Figure 5:
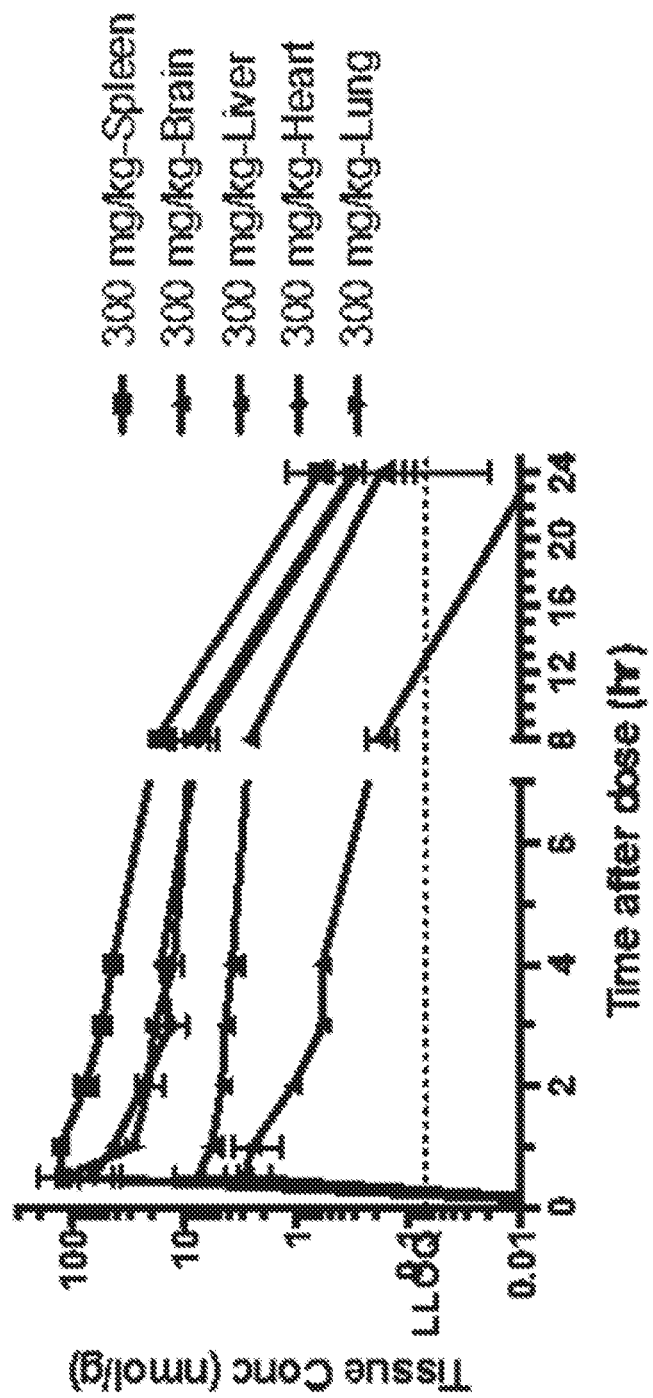
FIG. 5 shows nucleoside accumulation in mouse organs in mice treated with an exemplary compound.
Figure 6:
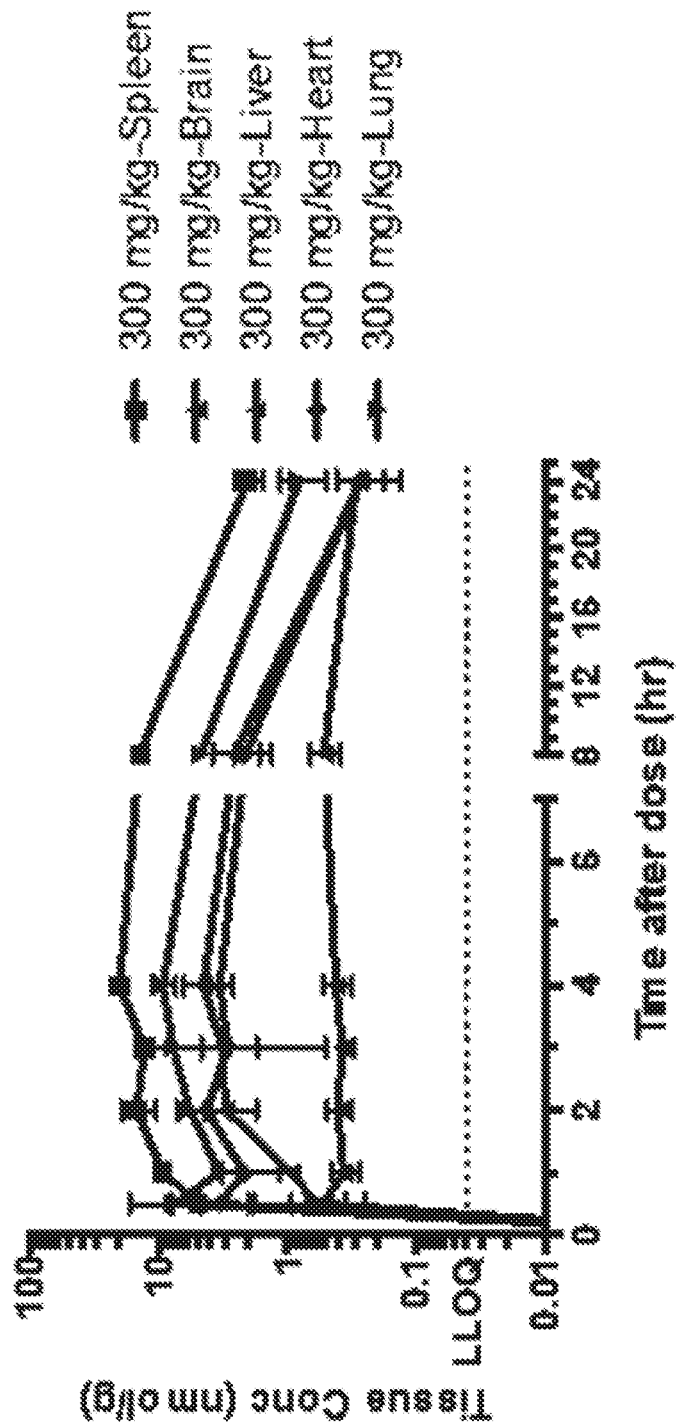
FIG. 6 shows triphosphate accumulation in mouse organs in mice treated with an exemplary compound.
Figure 7:
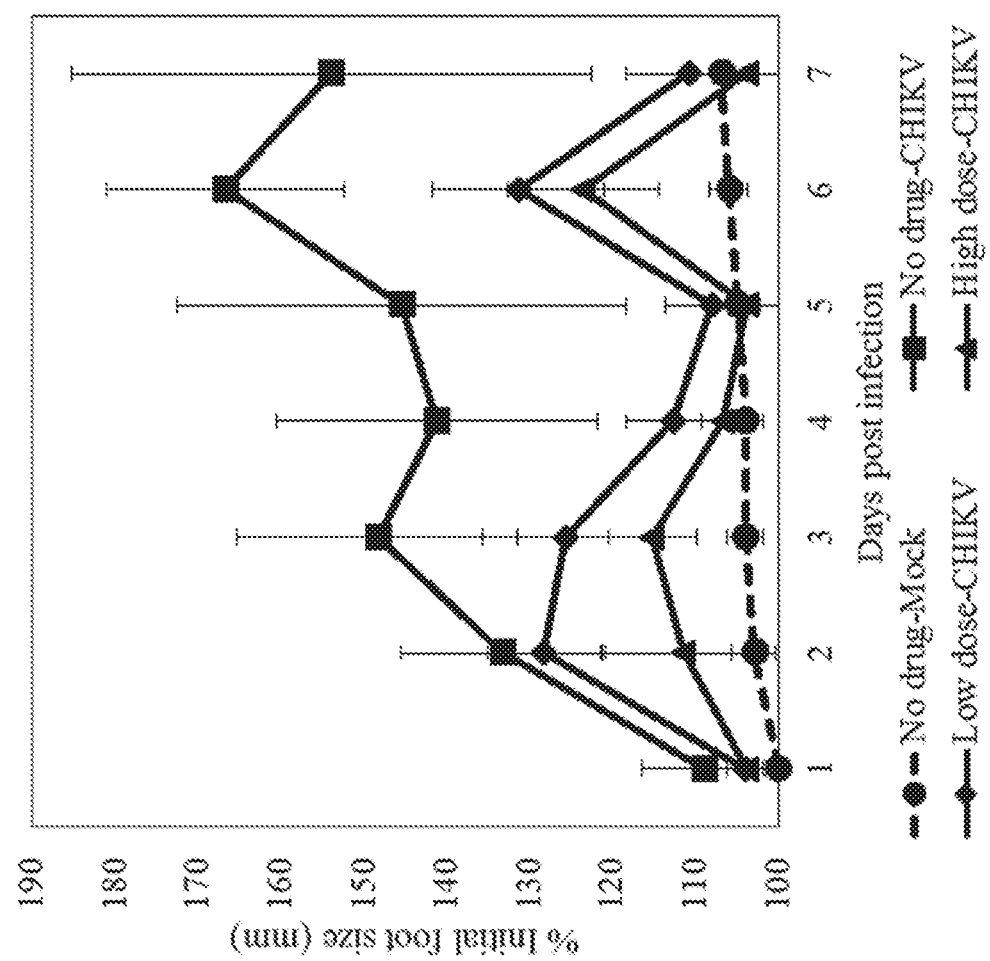
FIG. 7 shows reduction in footpad swelling in CHIKV-challenged mice treated with an exemplary compound.
Figure 8:
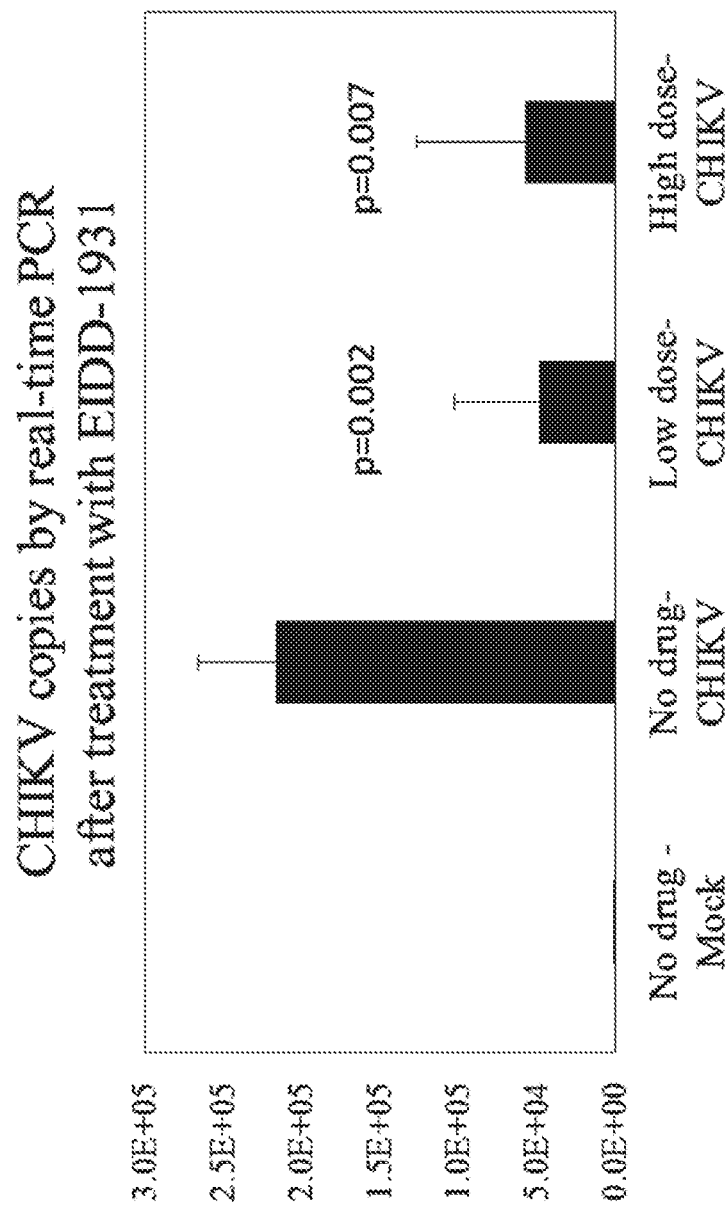
FIG. 8 shows reduction of CHIKV-RNA copies by PCR in CHIKV-challenged mice treated with an exemplary compound.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

"Subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, "alkyl" means a noncyclic straight chain or branched, unsaturated or saturated hydrocarbon such as those containing from 1 to 10 carbon atoms. A "higher alkyl" refers to unsaturated or saturated hydrocarbon having 6 or more carbon atoms. A "$C_6$-$C_{16}$" refers to an alkyl containing 6 to 16 carbon atoms. Likewise a "$C_6$-$C_{22}$" refers to an alkyl containing 6 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH$_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH$_3$).

"Alkanoyl" refers to an alkyl as defined above with the indicated number of carbon atoms attached through a carbonyl bride (i.e., —(C═O)alkyl).

"Alkylsulfonyl" refers to an alkyl as defined above with the indicated number of carbon atoms attached through a sulfonyl bridge (i.e., —S(═O)$_2$alkyl) such as mesyl and the like, and "Arylsulfonyl" refers to an aryl attached through a sulfonyl bridge (i.e., —S(═O)$_2$aryl).

"Alkylsulfamoyl" refers to an alkyl as defined above with the indicated number of carbon atoms attached through a sulfamoyl bridge (i.e., —NHS(═O)$_2$alkyl), and an "Arylsulfamoyl" refers to an alkyl attached through a sulfamoyl bridge (i.e., —NHS(═O)$_2$aryl).

"Alkylsulfinyl" refers to an alkyl as defined above with the indicated number of carbon atoms attached through a sulfinyl bridge (i.e. —S(═O)alkyl).

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

Compounds

In exemplary embodiments, the compound is a compound of Formula I,

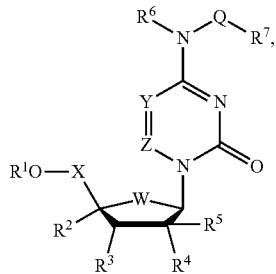

Formula I or a salt thereof, wherein
Q is O, —O(C═O)—, —O(C═O)Lipid, —O(C═O)V—, NH, or NR$^7$;
V is O, NH, NR$^7$, S, CH$_2$, or CHR$^7$;
W is CH$_2$, NH, S or O;
X is CH$_2$, CHMe, CMe$_2$, CHF, CF$_2$, or CD$_2$;
Y is N or CR";
Z is N or CR";

each R" is independently selected from H, D, F, Cl, Br, I, $CH_3$, $CD_3$, $CF_3$, alkyl, acyl, alkenyl, alkynyl, hydroxyl, formyl or $SCH_3$;
$R^1$ is hydrogen, monophosphate, diphosphate, triphosphate,
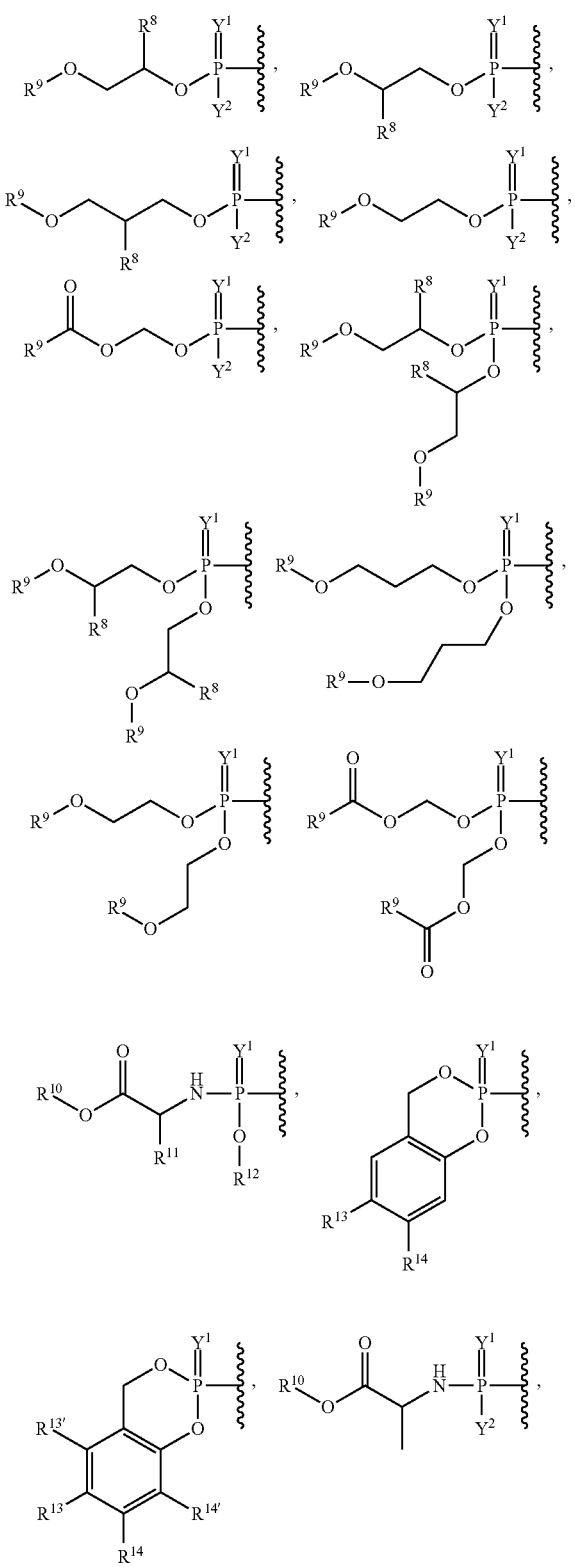
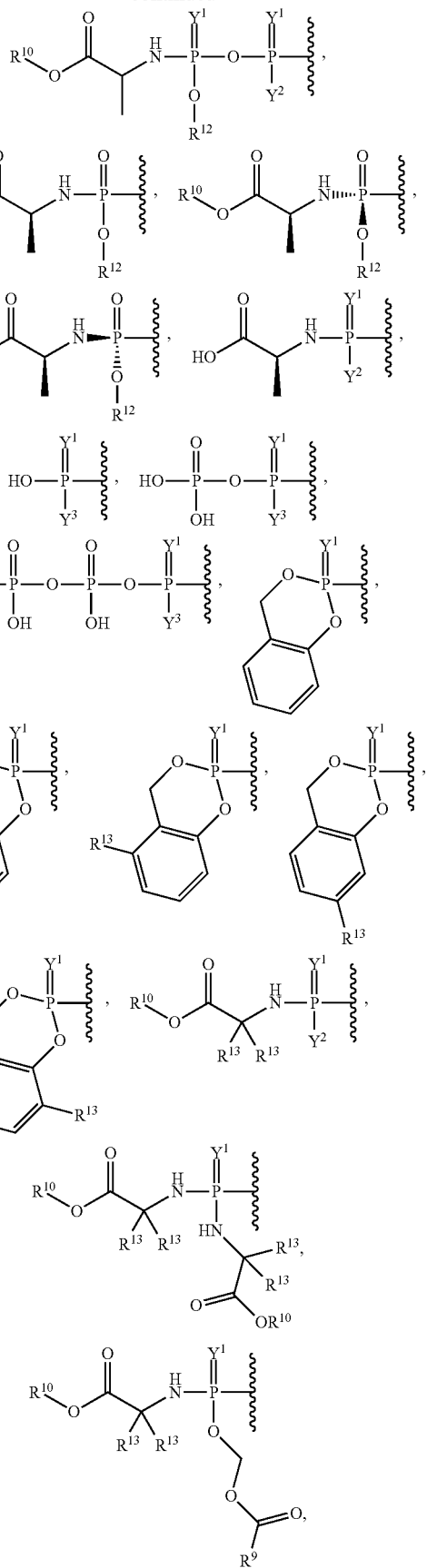

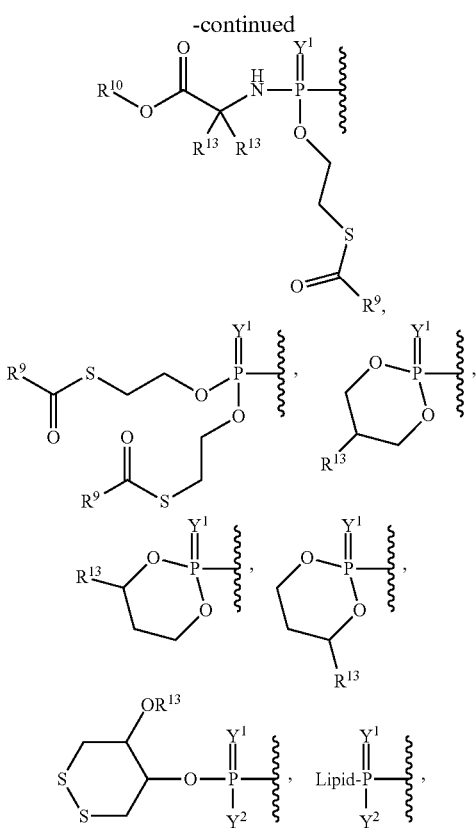

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{20}$;

each $R^7$ is independently selected from absent, hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6-C_{16})$alkyl, $(C_6-C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, $(C_6-C_{16})$alkyl, $(C_6-C_{22})$alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14'}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a C$_{6-22}$ alkyl, alkoxy, polyethylene glycol, or aryl substituted with an alkyl group, or a lipid as described herein.

In certain embodiments, the lipid is a fatty alcohol, fatty amine, or fatty thiol derived from essential and/or non-essential fatty acids.

In certain embodiments, the lipid is an unsaturated, polyunsaturated, omega unsaturated, or omega polyunsaturated fatty alcohol, fatty amine, or fatty thiol derived from essential and/or non-essential fatty acids.

In certain embodiments, the lipid is a fatty alcohol, fatty amine, or fatty thiol derived from essential and non-essential fatty acids that have one or more of its carbon units substituted with an oxygen, nitrogen, or sulfur.

In certain embodiments, the lipid is an unsaturated, polyunsaturated, omega unsaturated, or omega polyunsaturated fatty alcohol, fatty amine, or fatty thiol derived from essential and/or non-essential fatty acids that have one or more of its carbon units substituted with an oxygen, nitrogen, or sulfur.

In certain embodiments, the lipid is a fatty alcohol, fatty amine, or fatty thiol derived from essential and/or non-essential fatty acids that is optionally substituted.

In certain embodiments, the lipid is an unsaturated, polyunsaturated, omega unsaturated, or omega polyunsaturated fatty alcohol, fatty amine, or fatty thiol derived from essential and/or non-essential fatty acids that is optionally substituted.

In certain embodiments, the lipid is a fatty alcohol, fatty amine, or fatty thiol derived from essential and/or non-essential fatty acids that have one or more of its carbon units substituted with an oxygen, nitrogen, or sulfur that is optionally substituted.

In certain embodiments, the lipid is an unsaturated, polyunsaturated, omega unsaturated, or omega polyunsaturated fatty alcohol, fatty amine, or fatty thiol derived from essential and/or non-essential fatty acids that have one or more of its carbon units substituted with an oxygen, nitrogen, or sulfur that is also optionally substituted.

In certain embodiments, the lipid is hexadecyloxypropyl.

In certain embodiments, the lipid is 2-aminohexadecyloxypropyl.

In certain embodiments, the lipid is 2-aminoarachidyl.

In certain embodiments, the lipid is 2-benzyloxyhexadecyloxypropyl.

In certain embodiments, the lipid is lauryl, myristyl, palmityl, stearyl, arachidyl, behenyl, or lignoceryl.

In certain embodiments, the lipid is a sphingolipid of the formula:

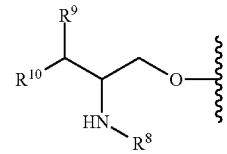

wherein, $R^8$ of the sphingolipid is hydrogen, alkyl, C(=O)R$^{12}$, C(=O)OR$^{12}$, or C(=O)NHR$^{12}$;

$R^9$ of the sphingolipid is hydrogen, fluoro, OR$^{12}$, OC(=O)R$^{12}$, OC(=O)OR$^{12}$, or OC(=O)NHR$^{12}$;

$R^{10}$ of the sphingolipid is a saturated or unsaturated alkyl chain of greater than 6 and less than 22 carbons optionally substituted with one or more halogen or hydroxy or a structure of the following formula:

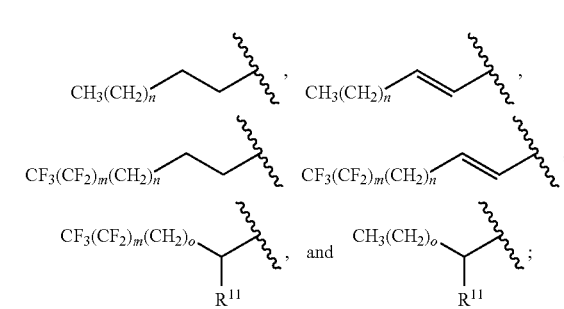

n is 8 to 14 or less than or equal to 8 to less than or equal to 14, o is 9 to 15 or less than or equal to 9 to less than or equal to 15, the total or m and n is 8 to 14 or less than or equal to 8 to less than or equal to 14, the total of m and o is 9 to 15 or less than or equal to 9 to less than or equal to 15; or

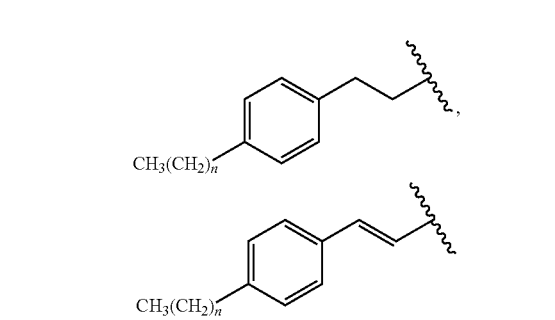

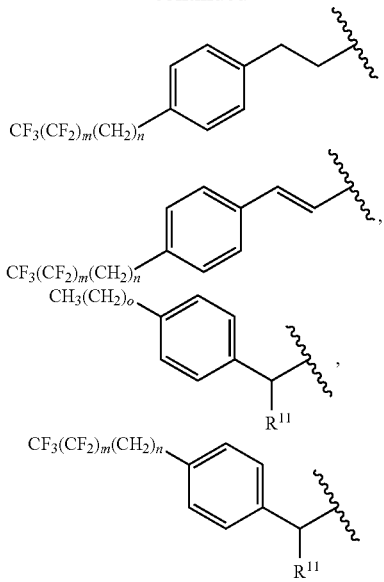

n is 4 to 10 or less than or equal to 4 to less than or equal to 10, o is 5 to 11 or less than or equal to 5 to less than or equal to 11, the total of m and n is 4 to 10 or less than or equal to 4 to less than or equal to 10, and the total of m and o is 5 to 11 or less than or equal to 5 to less than or equal to 11; or

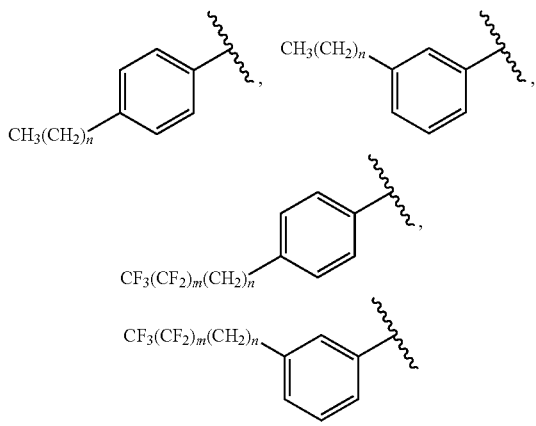

n is 6 to 12 or n is less than or equal to 6 to less than or equal to 12, the total of m and n is 6 to 12 or n is less than or equal to 6 to less than or equal to 12;

$R^{11}$ of the sphingolipid is $OR^{12}$, $OC(=O)R^{12}$, $OC(=O)OR^{12}$, or $OC(=O)NHR^{12}$;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated C12-C19 long chain alkyl.

In certain embodiments, the sphingolipid is a sphingolipid of the formula:

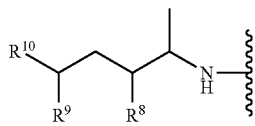

wherein, $R^8$ of the sphingolipid is hydrogen, hydroxy, fluoro, $OR^{12}$, $OC(=O)R^{12}$, $OC(=O)OR^{12}$, or $OC(=O)NHR^{12}$;

$R^9$ of the sphingolipid is hydrogen, hydroxy, fluoro, $OR^{12}$, $OC(=O)R^{12}$, $OC(=O)OR^{12}$, or $OC(=O)NHR^{12}$;

$R^{10}$ of the sphingolipid is a saturated or unsaturated alkyl chain of greater than 6 and less than 22 carbons optionally substituted with one or more halogens or a structure of the following formula:

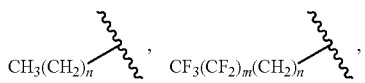

n is 8 to 14 or less than or equal to 8 to less than or equal to 14, the total or m and n is 8 to 14 or less than or equal to 8 to less than or equal to 14;

$R^{12}$ of the sphingolipid is hydrogen, a branched or strait chain $C_{1-12}$alkyl, $C_{13-22}$alkyl, cycloalkyl, or aryl selected from benzyl or phenyl, wherein the aryl is optionally substituted with one or more, the same or different $R^{13}$; and $R^{13}$ of the sphingolipid is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{12}$ of the sphingolipid is H, alkyl, methyl, ethyl, propyl, n-butyl, branched alkyl, isopropyl, 2-butyl, 1-ethylpropyl, 1-propylbutyl, cycloalkyl, cyclopropyl, cyclobutyl, cyclopentyl, cyclohexyl, benzyl, phenyl, monosubstituted phenyl, disubstituted phenyl, trisubstituted phenyl, or saturated or unsaturated $C_{12}$-$C_{19}$ long chain alkyl.

Suitable sphingolipids include, but are not limited to, sphingosine, ceramide, or sphingomyelin, or 2-aminoalkyl optionally substituted with one or more substituents.

Other suitable sphingolipids include, but are not limited to, 2-aminooctadecane-3,5-diol; (2S,3S,5S)-2-aminooctadecane-3,5-diol; (2S,3R,5S)-2-aminooctadecane-3,5-diol; 2-(methylamino)octadecane-3,5-diol; (2S,3R,5S)-2-(methylamino)octadecane-3,5-diol; 2-(dimethylamino)octadecane-3,5-diol; (2R,3S,5S)-2-(dimethylamino)octadecane-3,5-diol; 1-(pyrrolidin-2-yl)hexadecane-1,3-diol; (1S,3S)-1-((S)-pyrrolidin-2-yl)hexadecane-1,3-diol; 2-amino-11,11-difluorooctadecane-3,5-diol; (2S,3S,5S)-2-amino-11,11-difluorooctadecane-3,5-diol; 11,11-difluoro-2-(methylamino)octadecane-3,5-diol; (2S,3S,5S)-11,11-difluoro-2-(methylamino)octadecane-3,5-diol; N-((2S,3S,5S)-3,5-dihydroxyoctadecan-2-yl)acetamide; N-((2S,3S,5S)-3,5-dihydroxyoctadecan-2-yl)palmitamide; 1-(1-aminocyclopropyl)hexadecane-1,3-diol; (1S,3R)-1-(1-aminocyclopropyl)hexadecane-1,3-diol; (1S,3S)-1-(1-aminocyclopropyl)hexadecane-1,3-diol; 2-amino-2-methyloctadecane-3,5-diol; (3S,5S)-2-amino-2-methyloctadecane-3,5-diol; (3S,5R)-2-amino-2-methyloctadecane-3,5-diol; (3S,5S)-2-methyl-2-(methylamino)octadecane-3,5-diol; 2-amino-5-hydroxy-2-methyloctadecan-3-one; (Z)-2-amino-5-hydroxy-2-methyloctadecan-3-one oxime; (2S,3R,5R)-2-amino-6,6-difluorooctadecane-3,5-diol; (2S,3S,5R)-2-amino-6,6-difluorooctadecane-3,5-diol; (2S,3S,5S)-2-amino-6,6-difluorooctadecane-3,5-diol; (2S,3R,5S)-2-amino-6,6-difluorooctadecane-3,5-diol; and (2S,3S,5S)-2-amino-18,18,18-trifluorooctadecane-3,5-diol; which may be optionally substituted with one or more substituents.

In certain embodiments, Q is O.

In certain embodiments, each $R^7$ is independently selected from hydrogen, —(C=O)O($C_6$-$C_{16}$)alkyl or —(C=O)O ($C_6$-$C_{22}$)alkyl.

In certain embodiments, $R^1$ is

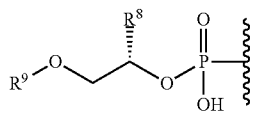

In certain embodiments, $R^8$ is hydrogen, hydroxy, or benzyloxy.

In certain embodiments, $R^9$ is higher alkyl, ($C_6$-$C_{16}$)alkyl or ($C_6$-$C_{22}$)alkyl.

In certain embodiments, $R^9$ is tert-butyl or isobutyl.

In certain embodiments, W is O;

In certain embodiments, Z is H.

In certain embodiments, $R^1$ is hydrogen, monophosphate, diphosphate, triphospate,

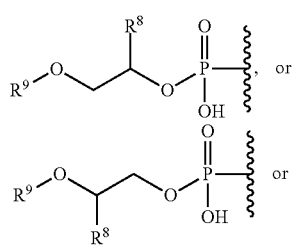

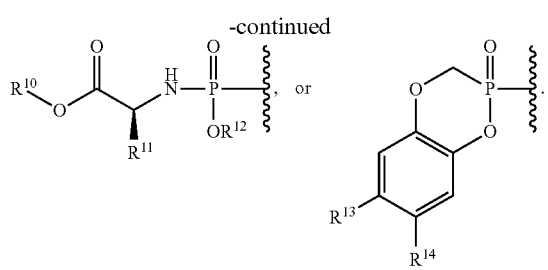

In certain embodiments, $R^8$ is hydrogen, hydroxy, or benzyloxy.

In certain embodiments, $R^9$ is higher alkyl, ($C_6$-$C_{16}$)alkyl or ($C_6$-$C_{22}$)alkyl.

In certain embodiments, $R^{10}$ is isopropyl.

In certain embodiments, $R^{11}$ is methyl.

In certain embodiments, $R^{12}$ is phenyl.

In certain embodiments, $R^{13}$ is hydrogen.

In certain embodiments, $R^{14}$ is hydrogen.

In certain embodiments, $R^2$ is hydrogen.

In certain embodiments, $R^3$ is hydroxy.

In certain embodiments, $R^4$ is hydrogen, hydroxy, alkyl, halogen, or fluoro.

In certain embodiments, $R^5$ is hydrogen, hydroxy, alkoxy, alkyl, methyl, ethynyl, or allenyl.

In certain embodiments, $R^6$ is hydrogen.

In certain embodiments, each $R^7$ is independently selected from hydrogen, —(C=O)Oalkyl, —(C=O)alkyl, —(C=O)NHalkyl, —(C=O)Salkyl, —(C=O)O($C_6$-$C_{16}$) alkyl, —(C=O)($C_6$-$C_{16}$) alkyl, —(C=O)NH($C_6$-$C_{16}$)alkyl, or —(C=O)S($C_6$-$C_{16}$)alkyl.

In certain embodiments, the compound is selected from:
1-((2R,3R,4S,5R)-3,4-dihydroxy-5-(hydroxymethyl)tetrahydrofuran-2-yl)-4-(hydroxyamino)pyrimidin-2(1H)-one,
1-((2R,3R,4S,5R)-3,4-dihydroxy-5-(hydroxymethyl)tetrahydrofuran-2-yl)-4-((nonanoyloxy)amino)pyrimidin-2(1H)-one, and
1-((2R,3R,4S,5R)-3,4-dihydroxy-5-(hydroxymethyl)tetrahydrofuran-2-yl)-4-((((heptyloxy)carbonyl)oxy)amino)pyrimidin-2(1H)-one.

In certain embodiments, the compound is a compound of Formula IA,

Formula IA

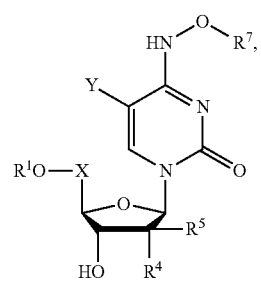

or a salt thereof,

X is $CH_2$, CHMe, $CMe_2$, CHF, $CF_2$, or $CD_2$;

Y is H, D, F, Cl, Br, I, $CH_3$, $CD_3$, $CF_3$, alkyl, acyl, alkenyl, alkynyl, hydroxyl, formyl or $SCH_3$;

$R^1$ is hydrogen, monophosphate, diphosphate, triphosphate,

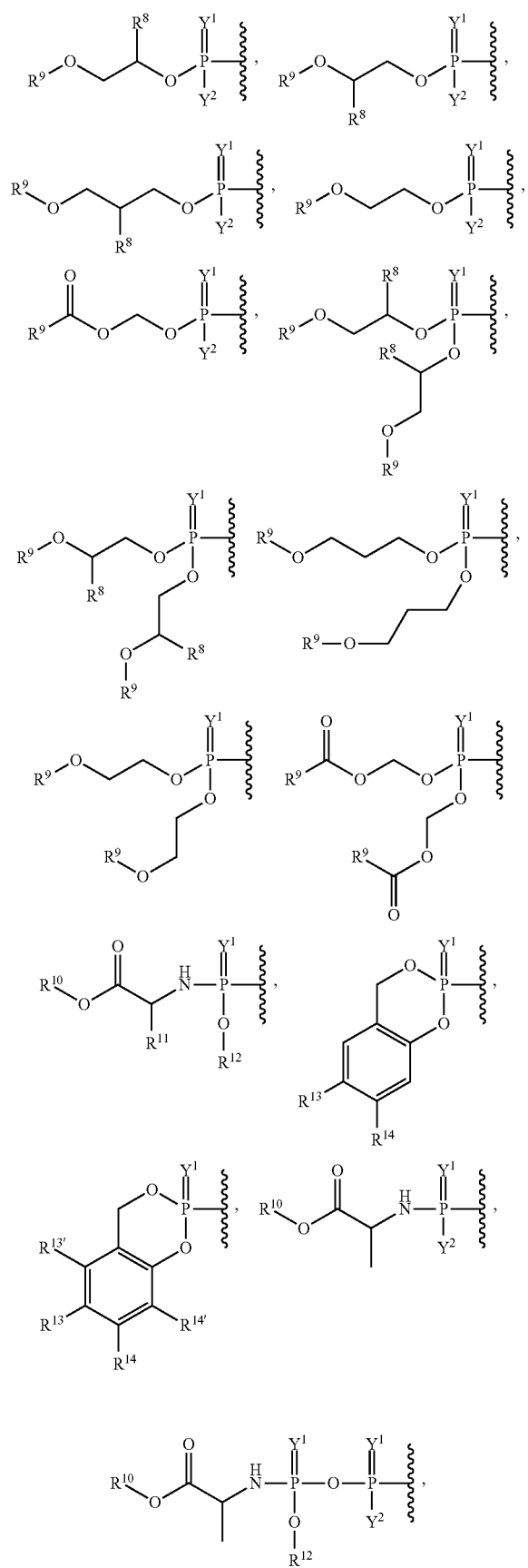
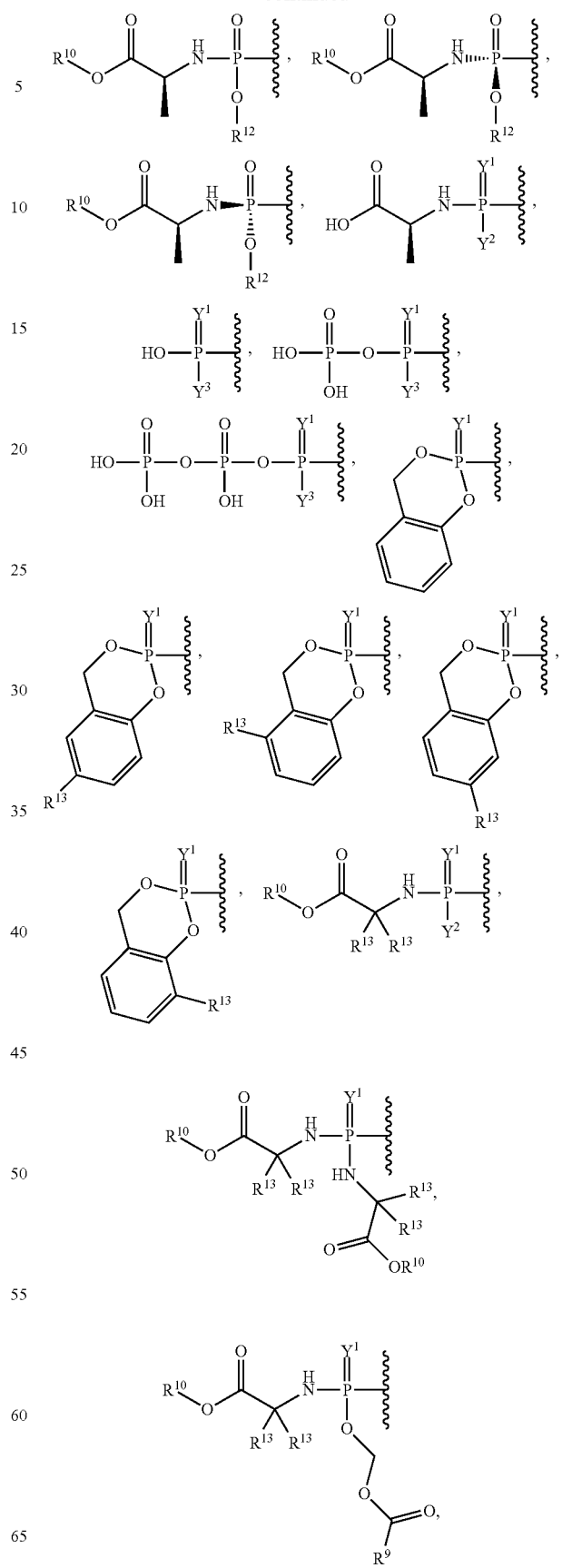

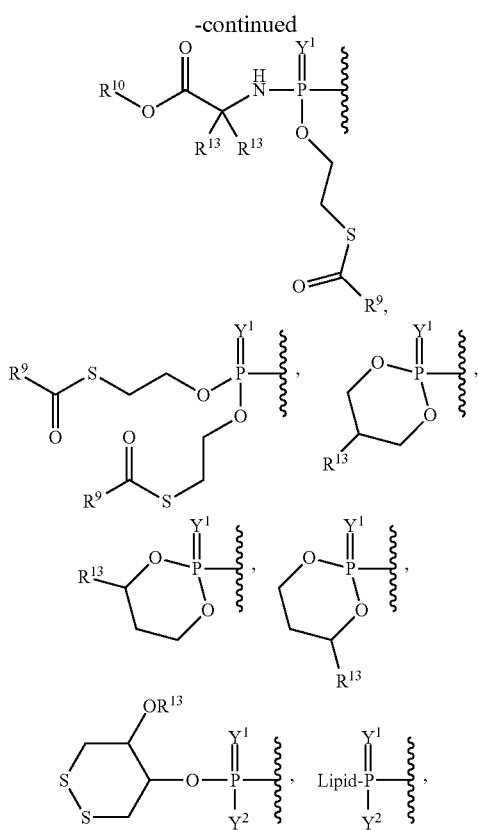

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

Each $R^7$ is independently selected from hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, (C$_6$-C$_{16}$)alkyl, (C$_6$-C$_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, (C$_6$-C$_{16}$)alkyl, (C$_6$-C$_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14'}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group, or a lipid as described herein. In certain embodiments, the compound is a compound of Formula IB,

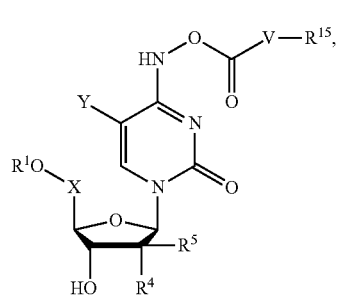

Formula IB or a salt thereof, wherein

V is absent, O, NH, $NR^{15}$, S, $CH_2$, or $CHR^{15}$;

X is $CH_2$, CHMe, $CMe_2$, CHF, $CF_2$, or $CD_2$;

Y is H, D, F, Cl, Br, I, $CH_3$, $CD_3$, $CF_3$, alkyl, acyl, alkenyl, alkynyl, hydroxyl, formyl or $SCH_3$;

$R^1$ is hydrogen, monophosphate, diphosphate, triphosphate,

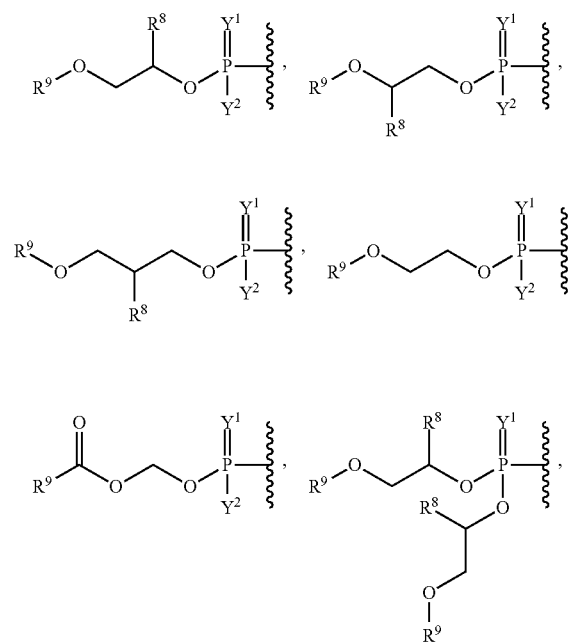

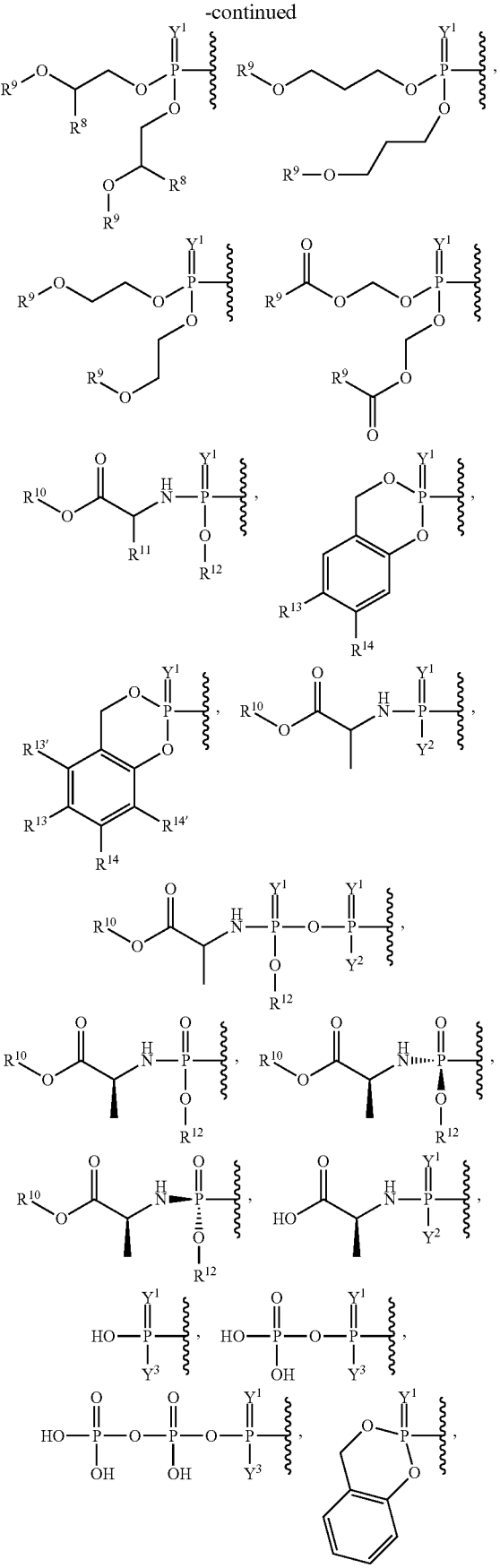

-continued

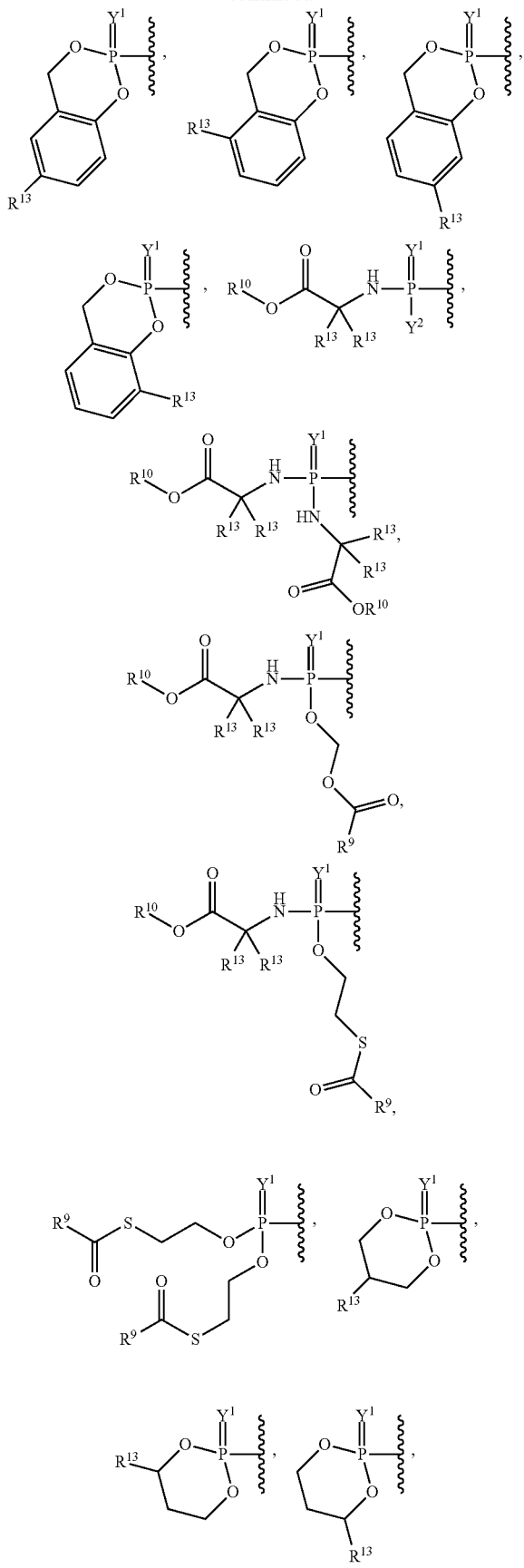
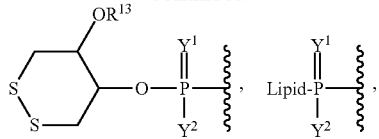

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, ($C_6$-$C_{16}$)alkyl, ($C_6$-$C_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkyl sulfonyl, aryl sulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkyl sulfonyl, aryl sulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

$R^{15}$ is hydrogen, Lipid, —(C=O)Oalkyl, —(C=O)alkyl, —(C=O)NHalkyl, —(C=O)N-dialkyl, —(C=O)Salkyl, hydroxy, alkoxy, alkyl, higher alkyl, (C₆-C₁₆)alkyl, (C₆-C₂₂) alkyl, halogen, nitro, cyano, amino, mercapto, formyl, carboxy, carbamoyl, alkoxy, alkylthio, alkylamino, (alkyl)₂amino, alkylsulfinyl, alkyl sulfonyl, aryl sulfonyl, carbocyclyl, aryl, or heterocyclyl, wherein $R^{15}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)₂amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a C₆₋₂₂ alkyl, alkoxy, polyethylene glycol, or aryl substituted with an alkyl group, or a lipid as described herein. In certain embodiments, the compound is a compound of Formula IC,

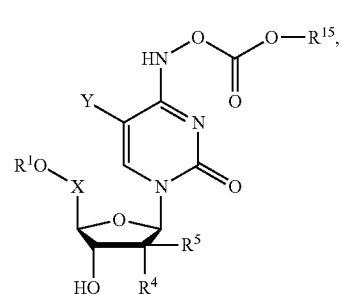

Formula IC or salts thereof, wherein

X is CH₂, CHMe, CMe₂, CHF, CF₂, or CD₂;

Y is H, D, F, Cl, Br, I, CH₃, CD₃, CF₃, alkyl, acyl, alkenyl, alkynyl, hydroxyl, formyl or SCH₃;

$R^1$ is hydrogen, monophosphate, diphosphate, triphosphate,

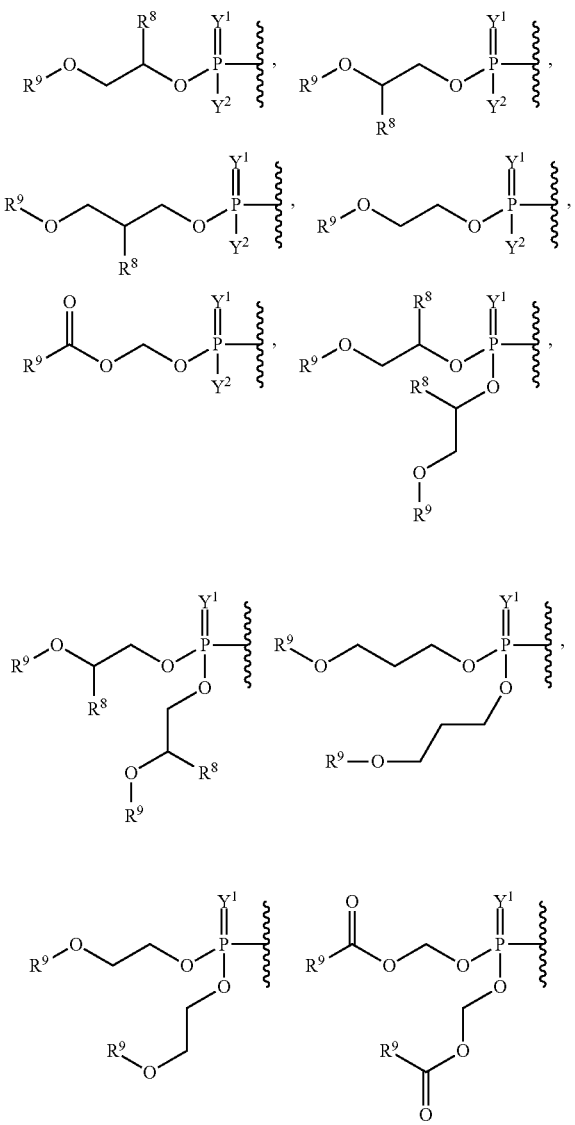

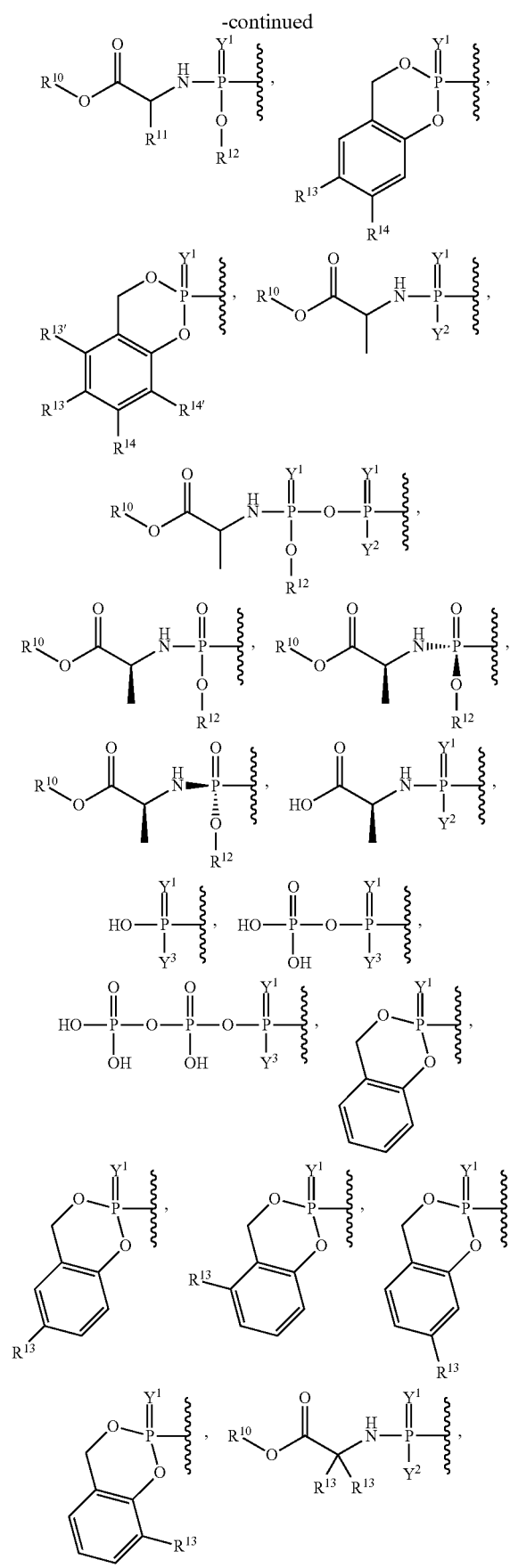
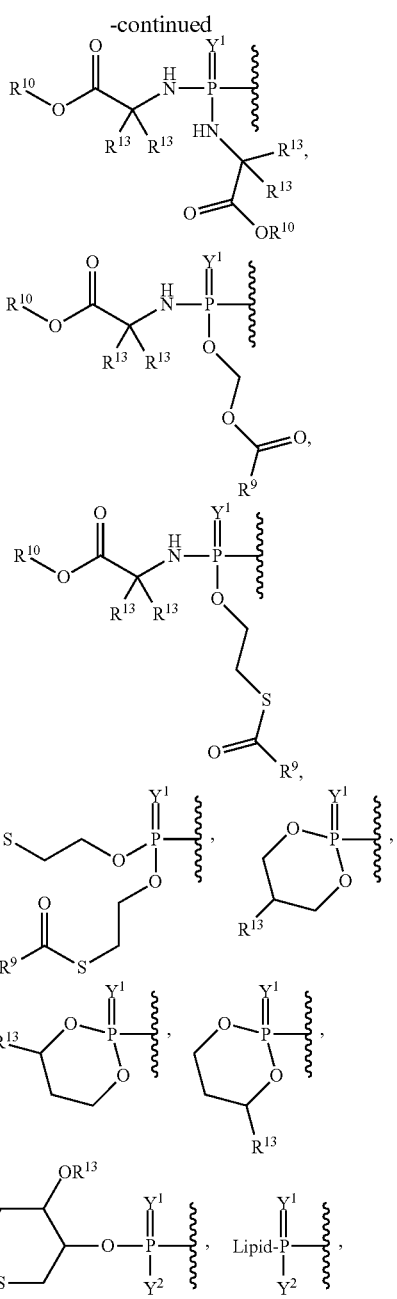

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, ($C_6$-$C_{16}$)alkyl, ($C_6$-$C_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

$R^{15}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, ($C_6$-$C_{16}$)alkyl, ($C_6$-$C_{22}$) alkyl, halogen, nitro, cyano, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{15}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group, or a lipid as described herein.

In certain embodiments, the compound is a compound of Formula ID,

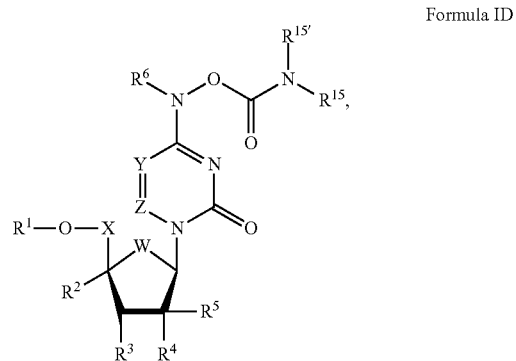

Formula ID or salt thereof, wherein

W is $CH_2$, NH, S or O;

X is $CH_2$, CHMe, $CMe_2$, CHF, $CF_2$, or $CD_2$;

Y is N or CR″;

Z is N or CR″;

each R″ is independently selected from is H, D, F, Cl, Br, I, $CH_3$, $CD_3$, $CF_3$, alkyl, acyl, alkenyl, alkynyl, hydroxyl, formyl or $SCH_3$;

$R^1$ is hydrogen, monophosphate, diphosphate, triphosphate,

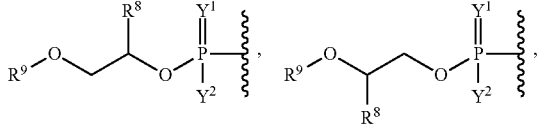

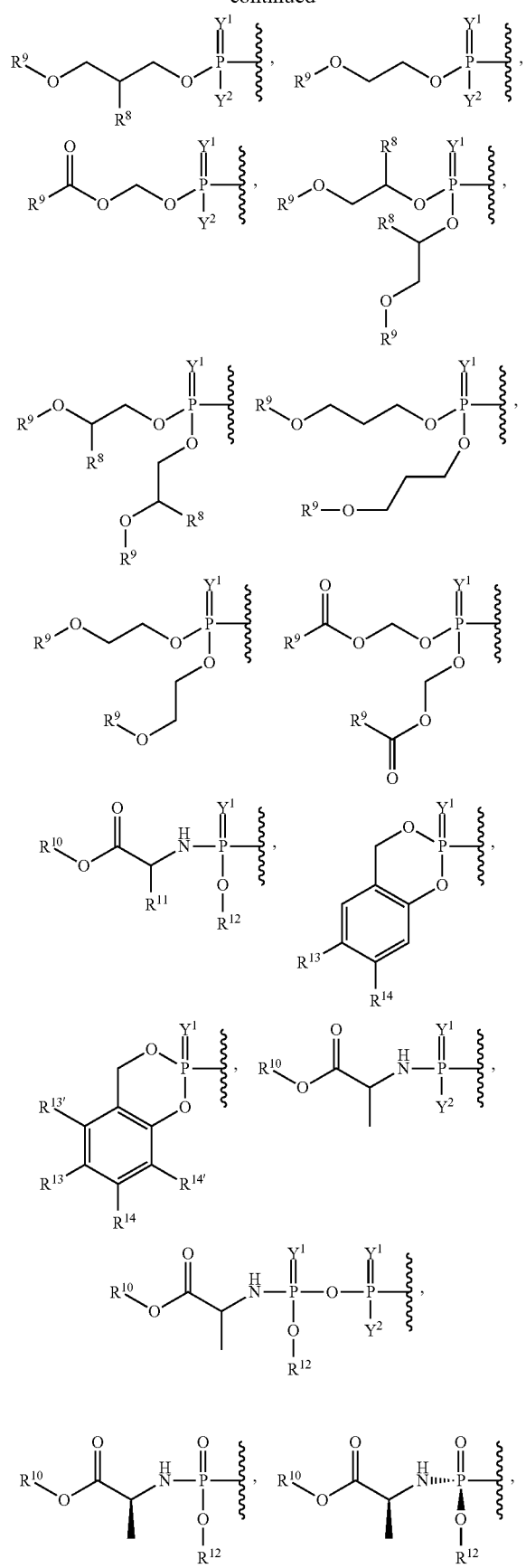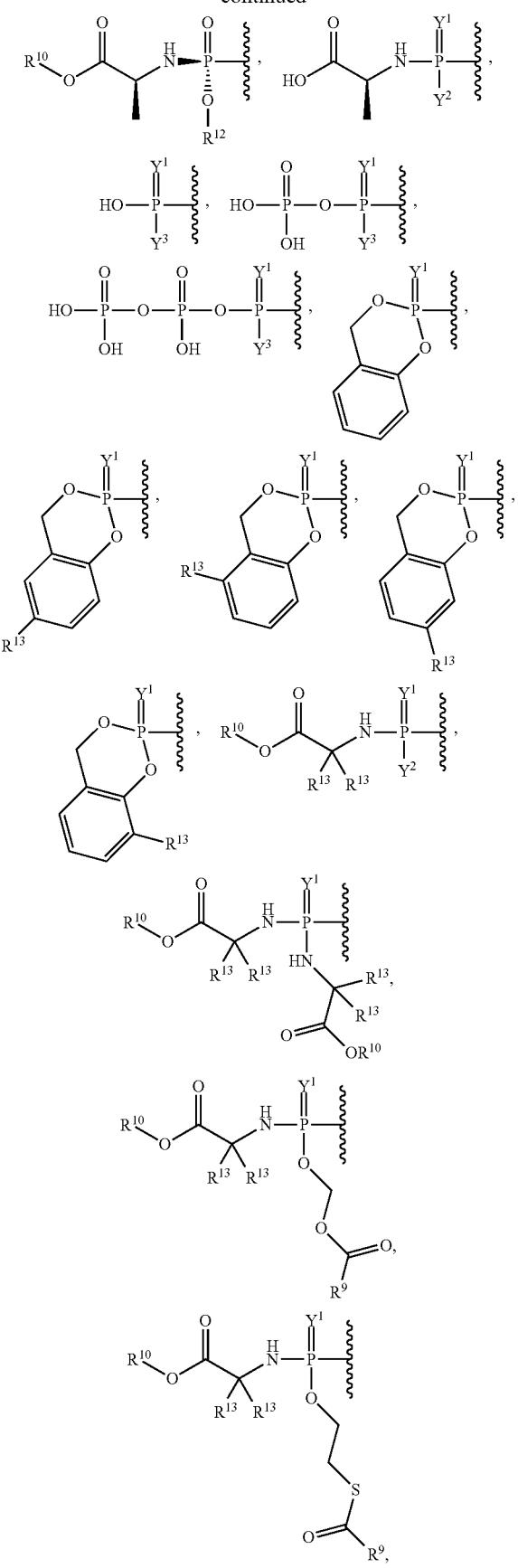

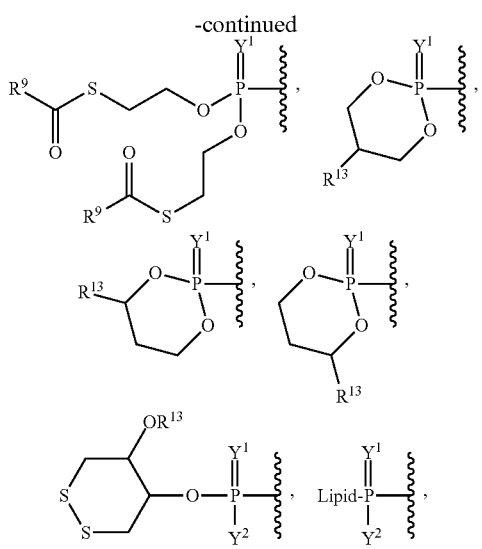

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein R$^1$ is optionally substituted with one or more, the same or different, R$^{20}$;

$Y^1$ is O or S;

$Y^2$ is OH, OR$^{12}$, OAlkyl, or BH$_3^-$M$^+$;

$Y^3$ is OH or BH$_3^-$M$^+$;

R$^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein R$^2$ is optionally substituted with one or more, the same or different, R$^{20}$;

R$^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{20}$;

R$^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{20}$;

R$^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^{20}$;

R$^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^6$ is optionally substituted with one or more, the same or different, R$^{20}$;

R$^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^8$ is optionally substituted with one or more, the same or different, R$^{20}$;

R$^9$ is hydrogen, methyl, ethyl, tert-butyl, alkyl, higher alkyl, (C$_6$-C$_{16}$)alkyl, (C$_6$-C$_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkyl sulfonyl, arylsulfonyl, carbocyclyl, aryl, or heterocyclyl, wherein R$^9$ is optionally substituted with one or more, the same or different, R$^{20}$;

R$^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^{10}$ is optionally substituted with one or more, the same or different, R$^{20}$;

R$^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{20}$;

R$^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein R$^{12}$ is optionally substituted with one or more, the same or different, R$^{20}$;

R$^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^{13}$ is optionally substituted with one or more, the same or different, R$^{20}$;

R$^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^{14}$ is optionally substituted with one or more, the same or different, R$^{20}$;

R$^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^{13'}$ is optionally substituted with one or more, the same or different, R$^{20}$;

R$^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein R$^{14'}$ is optionally substituted with one or more, the same or different, R$^{20}$;

R$^{15}$ is hydrogen, —(C═O)Oalkyl, —(C═O)alkyl, —(C═O)NHalkyl, —(C═O)N-dialkyl, —(C═O)Salkyl, hydroxy, alkoxy, alkyl, higher alkyl, (C$_6$-C$_{16}$)alkyl, (C$_6$-C$_{22}$) alkyl, halogen, nitro, cyano, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{15}$ is optionally substituted with one or more, the same or different, $R^{20}$;

$R^{15'}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6\text{-}C_{16})$alkyl, $(C_6\text{-}C_{22})$ alkyl, halogen, nitro, cyano, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each $R^7$ is optionally substituted with one or more, the same or different, $R^{20}$;

$R^{15}$ and $R^{15'}$ can form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6\text{-}22}$ alkyl, alkoxy, polyethylene glycol, or aryl substituted with an alkyl group, or a lipid as described herein.

In certain embodiments, the compound is a compound of Formula IE,

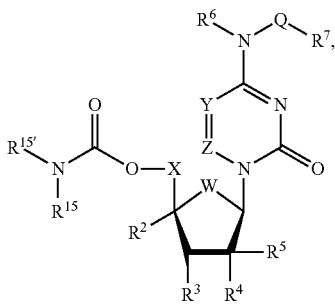

Formula IE or salt thereof, wherein

Q is O, —O(C=O)—, —O(C=O)Lipid, —O(C=O)V—, NH, or $NR^7$;

V is O, NH, $NR^7$, S, $CH_2$, or $CHR^7$;

W is $CH_2$, NH, S or O;

X is $CH_2$, CHMe, $CMe_2$, CHF, $CF_2$, or $CD_2$;

Y is N or CR";

Z is N or CR";

each R" is independently selected from is H, D, F, Cl, Br, I, $CH_3$, $CD_3$, $CF_3$, alkyl, acyl, alkenyl, alkynyl, hydroxyl, formyl or $SCH_3$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{20}$;

each $R^7$ is independently selected from absent, hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6\text{-}C_{16})$alkyl, $(C_6\text{-}C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^{15}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6\text{-}C_{16})$alkyl, $(C_6\text{-}C_{22})$ alkyl, halogen, nitro, cyano, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{15}$ is optionally substituted with one or more, the same or different, $R^{20}$;

$R^{15'}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6\text{-}C_{16})$alkyl, $(C_6\text{-}C_{22})$ alkyl, halogen, nitro, cyano, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein each $R^7$ is optionally substituted with one or more, the same or different, $R^{20}$;

$R^{15}$ and $R^{15'}$ can form a ring that is optionally substituted with one or more, the same or different, $R^{20}$;

If Q=—O(C=O)V— and V=$NR^7$ then the $R^7$s can together form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

Lipid as described herein.

In certain embodiments, the compound is a compound of Formula II,

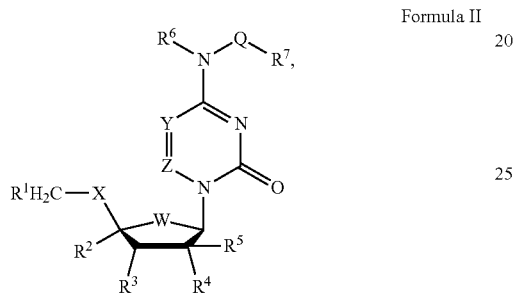

Formula II or salt thereof, wherein

Q is O, —O(C=O)—, —O(C=O)Lipid, —O(C=O)V—, NH, or $NR^7$;

V is O, NH, $NR^7$, S, $CH_2$, or $CHR^7$;

W is $CH_2$, NH, S or O;

X is $CH_2$ or O;

Y is N or CR″;

Z is N or CR″;

each R″ is independently selected from is H, D, F, Cl, Br, I, $CH_3$, $CD_3$, $CF_3$, alkyl, acyl, alkenyl, alkynyl, hydroxyl, formyl or $SCH_3$;

$R^1$ is monophosphate, diphosphate, triphosphate,

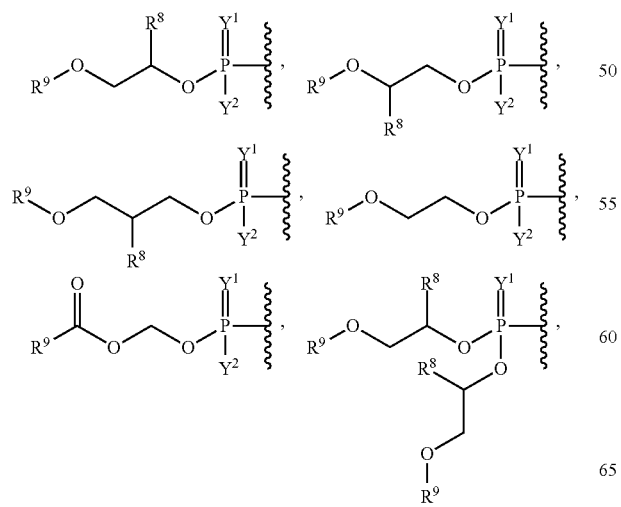

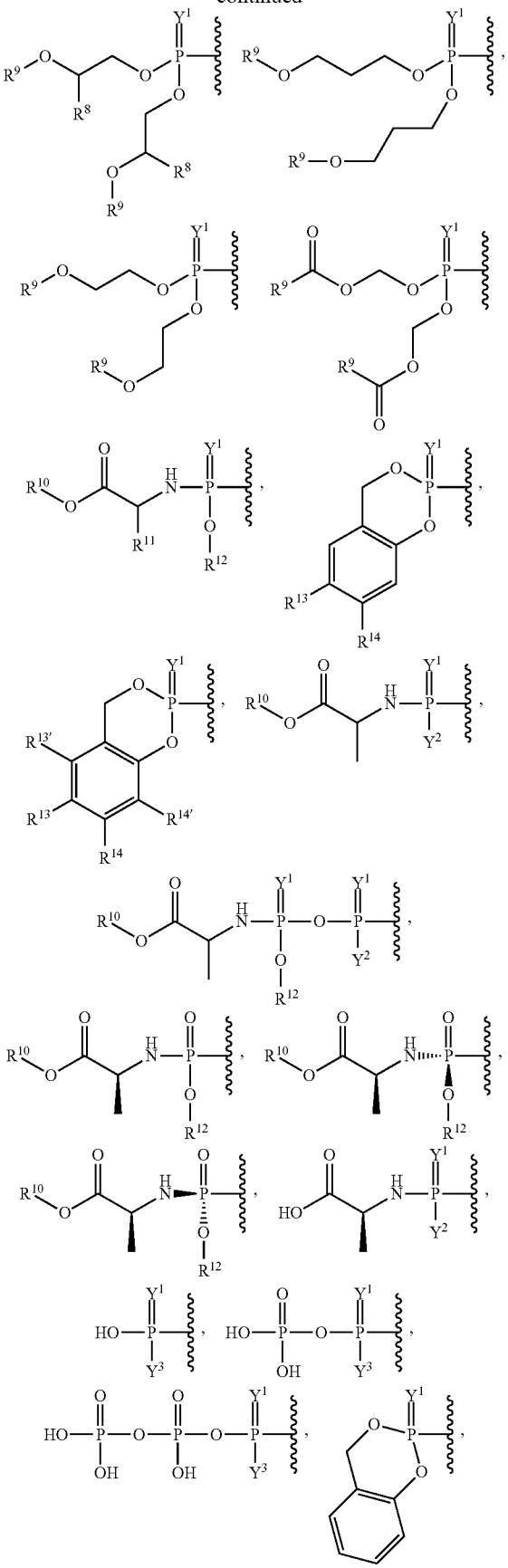

-continued

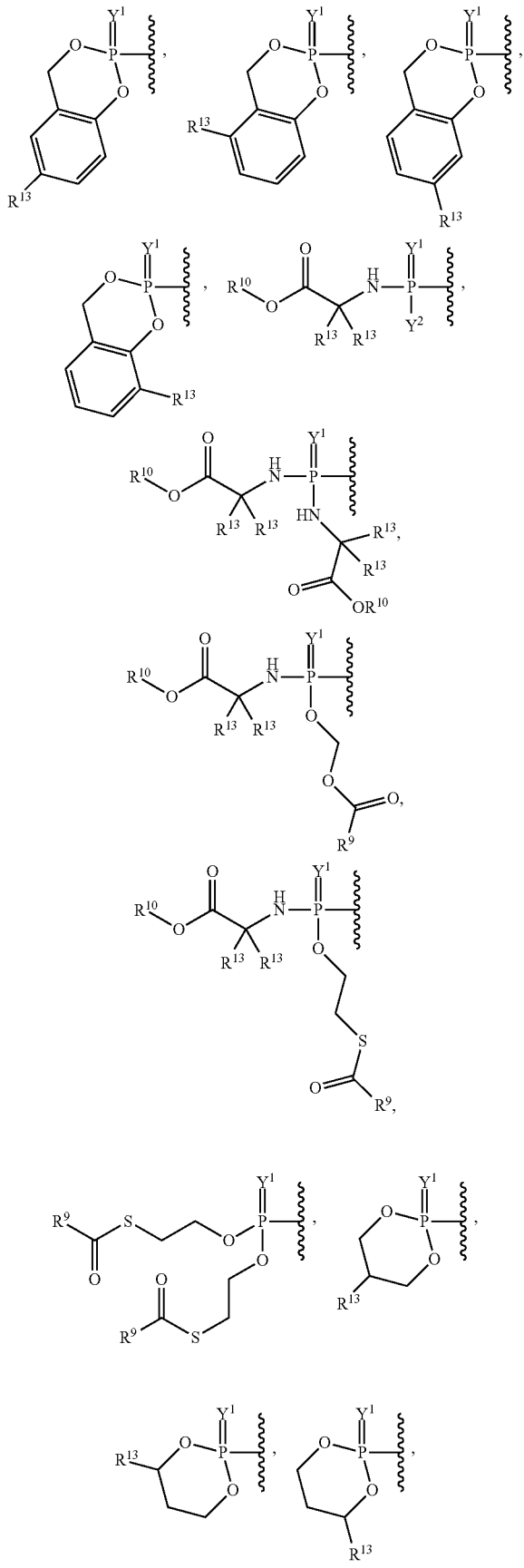

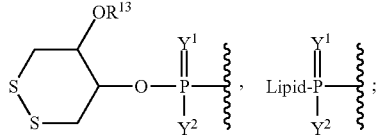

$Y^1$ is O or S;

$Y^2$ is OH, $OR^{12}$, OAlkyl, or $BH_3^-M^+$;

$Y^3$ is OH or $BH_3^-M^+$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{20}$;

each $R^7$ is independently selected from absent, hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, ($C_6$-$C_{16}$)alkyl, ($C_6$-$C_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, ($C_6$-$C_{16}$)alkyl, ($C_6$-$C_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{14'}$ is optionally substituted with one or more, the same or different, $R^{20}$;

If $Q=-O(C=O)V-$ and $V=NR^7$ then the $R^7$s can together form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{13}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group, or a lipid as described herein.

In certain embodiments, any citation of higher alkyl, $(C_6-C_{16})$alkyl may be substituted with a $(C_6-C_{22})$alkyl.

In certain embodiments, any citation of higher alkyl, $(C_6-C_{16})$alkyl or $(C_6-C_{22})$alkyl may be substituted with polyethylene glycol or $-CH_2(CH_2OCH_2)_nCH_3$, wherein n is 2, 3, 4, 5, 6, 7, 8, 9, 10, 11-20, or 30-100.

Methods of Use

In certain embodiments, the disclosure relates to methods of treating or preventing a viral infection comprising administering an effective amount of a compound or pharmaceutical composition disclosed herein to a subject in need thereof. In certain exemplary embodiments, a method of treating or preventing a Zika virus infection is provided, the method comprising administering an effective amount of a compound or pharmaceutical composition disclosed herein to a subject in need thereof.

In certain embodiments, the viral infection is, or is caused by, an alphavirus, flavivirus or coronaviruses orthomyxoviridae or paramyxoviridae, or RSV, influenza, Powassan virus or filoviridae or ebola.

In certain embodiments, the viral infection is, or is caused by, a virus selected from MERS coronavirus, Eastern equine encephalitis virus, Western equine encephalitis virus, Venezuelan equine encephalitis virus, Ross River virus, Barmah Forest virus, Powassan virus, Zika virus, and Chikungunya virus. In certain exemplary embodiments, the viral infection is, or is caused by, a Zika virus.

In certain embodiments, the compound is administered by inhalation through the lungs.

In some embodiments, the subject is at risk of, exhibiting symptoms of, or diagnosed with influenza A virus including subtype H1N1, H3N2, H7N9, or H5N1, influenza B virus, influenza C virus, rotavirus A, rotavirus B, rotavirus C, rotavirus D, rotavirus E, human coronavirus, SARS coronavirus, MERS coronavirus, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), Dengue virus, Zika virus, chikungunya, Eastern equine encephalitis virus (EEEV), Western equine encephalitis virus (WEEV), Venezuelan equine encephalitis virus (VEEV), Ross River virus, Barmah Forest virus, yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV), The Human T-lymphotropic virus Type I (HTLV-1), Friend spleen focus-forming virus (SFFV) or Xenotropic MuLV-Related Virus (XMRV). In some embodiments, the subject is at risk of, exhibiting symptoms of, or diagnosed with a Zika virus infection.

In certain embodiments, the subject is diagnosed with influenza A virus including subtypes H1N1, H3N2, H7N9, H5N1 (low path), and H5N1 (high path) influenza B virus, influenza C virus, rotavirus A, rotavirus B, rotavirus C, rotavirus D, rotavirus E, SARS coronavirus, MERS-CoV, human adenovirus types (HAdV-1 to 55), human papillomavirus (HPV) Types 16, 18, 31, 33, 35, 39, 45, 51, 52, 56, 58, and 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, parainfluenza viruses 1 and 3, rinderpest virus, chikungunya, eastern equine encephalitis virus (EEEV), Venezuelan equine encephalitis virus (VEEV), western equine encephalitis virus (WEEV), California encephalitis virus, Japanese encephalitis virus, Rift Valley fever virus (RVFV), hantavirus, Dengue virus serotypes 1, 2, 3 and 4, Zika virus, West Nile virus, Tacaribe virus, Junin, rabies virus, ebola virus, marburg virus, adenovirus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, or Kaposi's sarcoma-associated herpesvirus, hepatitis A, hepatitis B, hepatitis C, hepatitis D, hepatitis E or human immunodeficiency virus (HIV). In certain embodiments, the subject is diagnosed with a Zika virus infection.

In certain embodiments, the subject is diagnosed with gastroenteritis, acute respiratory disease, severe acute respiratory syndrome, post-viral fatigue syndrome, viral hemorrhagic fevers, acquired immunodeficiency syndrome or hepatitis.

Formulations

In exemplary embodiments, a pharmaceutical compositions comprises a pharmaceutically acceptable excipient, such as a pharmaceutically acceptable carrier, and an exemplary compound described herein.

In certain exemplary embodiments, the pharmaceutical composition comprises, or is in the form of, a pharmaceutically acceptable salt, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the exemplary compounds contain an acidic group as well as a basic group, the compounds may form internal salts, which may also be used in the compositions and methods described herein. When an exemplary compound contains a hydrogen-donating heteroatom (e.g. NH), salts are contemplated to cover isomers formed by transfer of said hydrogen atom to a basic group or atom within the molecule.

Pharmaceutically acceptable salts of the exemplary compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The exemplary compounds may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

The exemplary embodiments, the pharmaceutical composition comprises an effective amount of an exemplary compound and a pharmaceutically acceptable carrier. Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The exemplary pharmaceutical compositions can be in a unit dosage form, and may be suitably packaged, for example in a box, blister, vial, bottle, sachet, ampoule or in any other suitable single-dose or multi-dose holder or container (which may be properly labeled);

optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. In certain embodiments, the formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, P A: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the exemplary compound to pharmaceutically acceptable carrier, excipient and/or other substances may vary from about 0.5 to about 100 wt. % (weight percent). For oral use, the pharmaceutical composition will generally contain from about 5 to about 100% by weight of the active material. For other uses, the pharmaceutical composition will generally have from about 0.5 to about 50 wt. % of the active material.

The compositions described herein can be formulated for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl-celluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the trade name Eudragit®. In further preferred embodiments, the acrylic polymer comprises a mixture of two acrylic resin lacquers commercially available from Rohm Pharma under the trade names Eudragit® RL30D and Eudragit RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the trade name Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multilayer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., compound, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

In certain exemplary embodiments, a pharmcautical composition for treating or preventing a Zika virus infection comprises an effective amount of a compound selected from the group consisting of

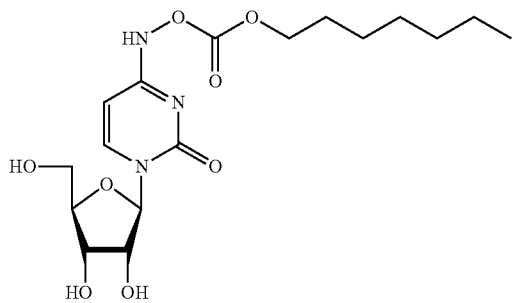

,

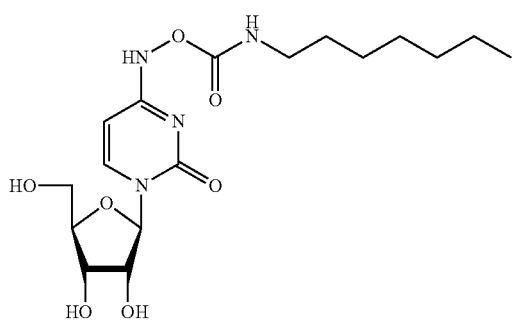

,

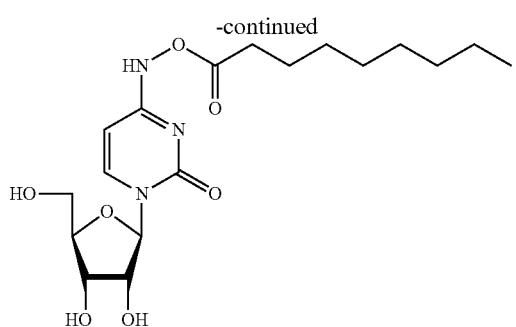

, and salts thereof.

In certain embodiments, a pharmaceutical composition for treating or preventing a Zika virus infection comprises an effective amount of a compound of the formula:

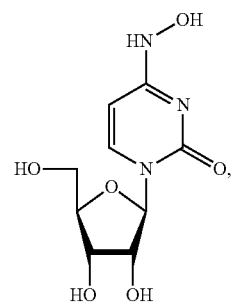

or its salt.

Combination Therapies

The compound described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastrointestinal drugs, muscle relaxants, nutritional agents, vitamins, parasympathomimetics, stimulants, anorectics, anti-narcoleptics, and antiviral agents. In a particular embodiment, the antiviral agent is a non-CNS targeting antiviral compound. "Adjunctive administration", as used herein, means the compound can be administered in the same dosage form or in separate dosage forms with one or more other active agents. The additional active agent(s) can be formulated for immediate release, controlled release, or combinations thereof.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methyl salicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

In certain embodiments, the exemplary compounds and pharmaceutical compositionscan be administered in combination with another antiviral agent(s) such as abacavir, acyclovir, acyclovir, adefovir, amantadine, amprenavir, ampligen, arbidol, atazanavir, atripla, boceprevir, cidofovir, combivir, daclatasvir, darunavir, dasabuvir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, ledipasvir, lopinavir, loviride, maraviroc, moroxydine, methisazone, nelfinavir, nevirapine, nexavir, ombitasvir, oseltamivir, paritaprevir, peginterferon alfa-2a, penciclovir, peramivir, pleconaril, podophyllotoxin, raltegravir, ribavirin, rimantadine, ritonavir, pyramidine, saquinavir, simeprevir, sofosbuvir, stavudine, telaprevir, telbivudine, tenofovir, tenofovir disoproxil, tipranavir, trifluridine, trizivir, tromantadine, truvada, valaciclovir, valganciclovir, vicriviroc, vidarabine, viramidine zalcitabine, zanamivir, or zidovudine and combinations thereof.

In certain embodiments, the antiviral agent is a non-CNS targeting antiviral compound. In certain embodiments, the exemplary compounds and pharmaceutical compositions can be administered in combination with one or more non-CNS targeting antiviral compounds. In exemplary embodiments, the non-CNS targeting antiviral compound is, for example, NITD008, BCX4430, and the like.

In certain exemplary embodiments, a pharmaceutical composition for treating or preventing a Zika virus infection comprises a non-CNS targeting antiviral compound and an effective amount of a compound selected from the group consisting of:

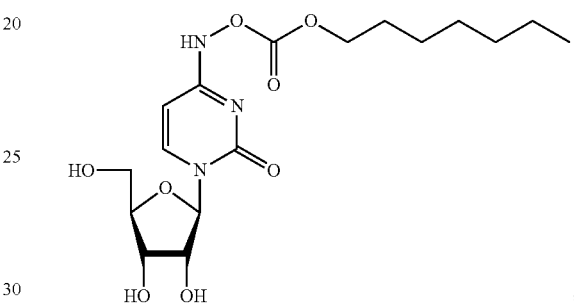

,

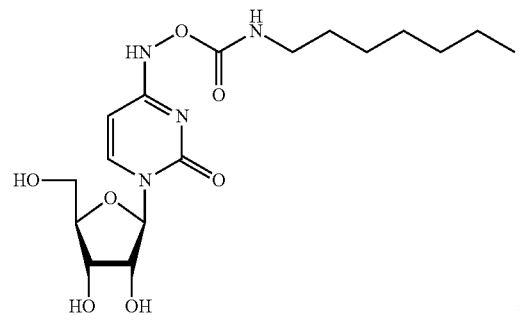

,

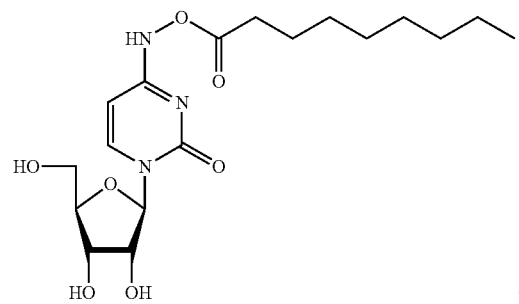

, and salts thereof.

In certain exemplary embodiments, a pharmaceutical composition for treating or preventing a Zika virus infection comprises a non-CNS targeting antiviral compound and an effective amount of a compound selected from the group consisting of:

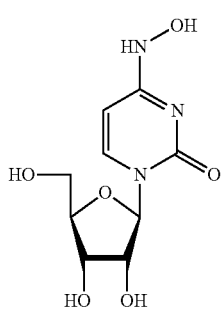

and salts thereof.

EXAMPLES

Example 1

The synthesis of N4-hydroxycytidine or 1-(3,4-dihydroxy-5-(hydroxymethyl) tetrahydrofuran-2-yl)-4-(hydroxyamino)pyrimidin-2-one (EIDD-01931)

Protection of uridine by persilylation is followed by activation of the 4-position of the nucleobase by a hindered arylsulfonyl group (See FIG. 1). Displacement of this group with hydroxylamine installs the N-4-hydroxy moiety. Global deprotection using one of any number of fluoride sources available gives the desired product.

The compound can be made in one step from cytidine by heating in a pH-adjusted solution of hydroxylamine. Despite being shorter, this route tends to give lower yields and requires purification by reverse phase flash column chromatography, limiting its use to producing smaller quantities.

Example 2

General Methods

All chemical reactions were performed in oven-dried glassware under a nitrogen atmosphere, except where noted. Chemicals and solvents were reagent-grade and purchased from commercial suppliers (typically Aldrich, Fisher, Acros, Carbosynth Limited, and Oakwood Chemical) and used as received, excepting where noted. In particular, EIDD-1910, EIDD-1993, and EIDD-2003 were purchased from Carbosynth Limited. Solvents used for reactions (tetrahydrofuran, methanol, acetonitrile, dichloromethane, toluene, pyridine, dimethylformamide) were ≥99.9% anhydrous in all cases. All reactions were followed by thin layer chromatography (TLC) to completion, unless stated otherwise. TLC analysis was performed on silica gel, using illumination with a UV lamp (254 nm) or staining with $KMnO_4$ and heating. Manual flash column chromatography was performed with 40-60 micron (60 Å particle size) RediSep $R_f$ silica gel, purchased from Teledyne Isco, as the stationary phase. Automated gradient flash column chromatography was performed on a Teledyne Isco CombiFlash Companion; normal phase separations were performed with pre-packed RediSep $R_f$ silica gel as the stationary phase, and reverse phase separations were performed with pre-packed RediSep $R_f C_{18}$ High Performance Gold stationary phase. Triphosphate purifications were performed using ion-exchange chromatography, with DEAE (diethylaminoethyl) Sephadex A-25 as the stationary phase, and aqueous TEAB (triethylammonium bicarbonate) as the mobile phase.

$^1$H NMR spectra were measured on a Varian 400 MHz instrument, and processed using MestReNova software, version 9.0.1. Chemical shifts were measured relative to the appropriate solvent peak: $CDCl_3$ (δ 7.27), DMSO-$d_6$ (δ 2.50), $CD_3OD$ (δ 3.31), $D_2O$ (δ 4.79).

The following abbreviations were used to describe coupling: s=singlet, d=doublet, t=triplet, q=quartet, p=pentet, m=multiplet, br=broad. $^{13}$C NMR spectra were measured on a Varian instrument at 100 MHz with chemical shifts relative to the appropriate solvent peak: $CDCl_3$ (δ 77.0), DMSO-$d_6$ (δ 39.5), $CD_3OD$ (δ 49.0). $^{19}$F spectra were measured on a Varian instrument at 376 MHz, and $^{31}$P spectra were measured on a Varian instrument at 162 MHz. Chemical shifts for $^{19}$F spectra, $^{31}$P spectra, and $^{13}$C spectra (in $D_2O$ only) were calibrated by MestReNova software using an absolute reference function to the corresponding $^1$H NMR spectrum in the same solvent.

Nominal (low resolution) liquid chromatography/mass spectrometry was performed using an Agilent 1200 series LC (UV absorption detector at 254 nm), using a Zorbax Eclipse XDB $C_{18}$ 4.6×50 mm, 3.5 micron column, eluting with a MeOH/water mixture (typically 95/5 isocratic) and an Agilent 6120 LCMS quadrupole instrument. High resolution mass spectrometry was performed by the Emory University Mass Spectrometry Center with a Thermo LTQ-FTMS using either APCI or ESI.

Example 3

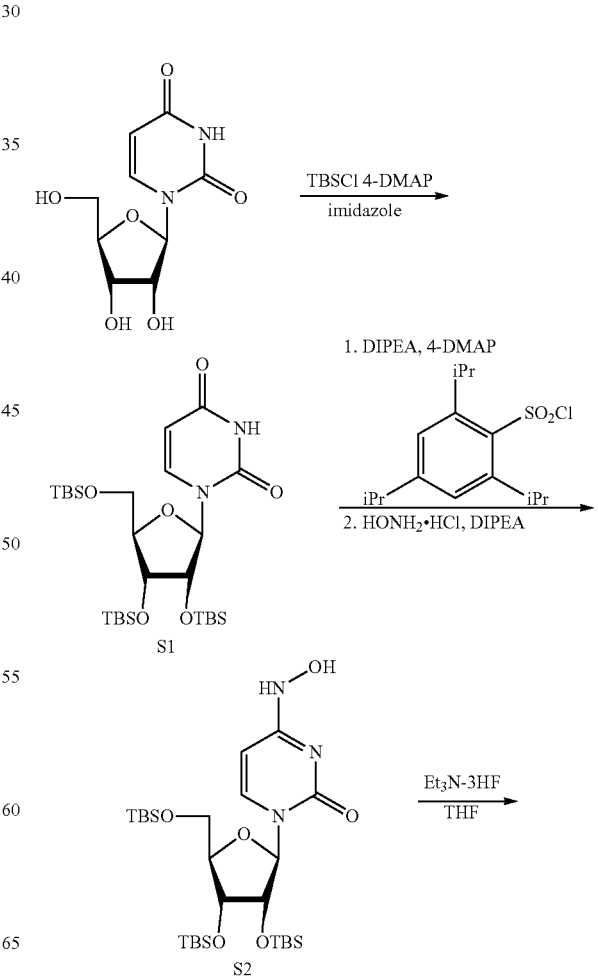

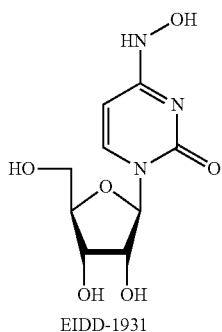

EIDD-1931

S1: A 2 L 3-neck flask equipped with an overhead stirrer and nitrogen inlet was charged with uridine (25 g, 102 mmol) and 1 L of dichloromethane. The resulting solution was cooled to 0° C. and 4-DMAP (1.251 g, 10.24 mmol) and imidazole (27.9 g, 409 mmol) were added sequentially. TBSCl (61.7 g, 409 mmol) was added over 10 minutes and the resulting mixture was warmed to ambient temperature and stirred for 18 hrs. Water (300 mL) was added to the reaction mixture and stirred at rt for 2 h, the layers were separated, and the aqueous layer was extracted with additional dichloromethane. The combined organic layers were washed with brine (1×300 mL), dried over sodium sulfate, filtered and concentrated under reduced pressure to yield 75 g of a clear colorless oil. Purification by flash chromatography (5 to 20% gradient of EtOAc in hexanes) to yield S1 (45 g, 75%) as a clear, colorless oil, which solidified when dried in vacuo: $^1$H NMR (400 MHz, CDCl$_3$) δ 8.09 (s, 1H), 8.02 (d, J=8.2 Hz, 1H), 5.87 (d, J=3.6 Hz, 1H), 5.67 (dd, J=8.1, 2.2 Hz, 1H), 4.07 (q, J=3.8, 3.3 Hz, 1H), 3.98 (dd, J=11.7, 1.7 Hz, 1H), 3.75 (dd, J=11.7, 1.1 Hz, 1H), 0.94 (s, 9H), 0.90 (s, 9H), 0.88 (s, 9H), 0.13 (s, 3H), 0.12 (s, 3H), 0.08 (s, 3H), 0.07 (s, 3H), 0.07 (s, 3H), 0.06 (s, 3H).

S2: A 1 L round bottom flask was charged with S1 (28 g, 47.7 mmol) and dichloromethane (700 mL). The solution was cooled to 0° C. using an ice bath; 4-DMAP (0.583 g, 4.77 mmol) and N,N-diisopropylethylamine (41.7 ml, 239 mmol) were added sequentially. 2,4,6-Triisopropylbenzene-1-sulfonyl chloride (28.9 g, 95 mmol) was slowly added to the flask, and after addition was complete, the flask was warmed to ambient temperature and stirred for 18 hrs. The dark orange solution was cooled to 0° C. with an ice bath and N,N-diisopropylethylamine (24.66 g, 191 mmol) was added via syringe, followed by solid hydroxylamine hydrochloride (13.26 g, 191 mmol) all at once. The mixture was warmed to room temperature and stirred for 3 hrs. The reaction was quenched with water (200 mL) and the resulting layers were separated. The aqueous layer was extracted with dichloromethane (200 mL), and the combined organics were washed with brine, dried over sodium sulfate, and concentrated under reduced pressure to yield a dark orange oil. Purification by flash chromatography (15 to 50% gradient of EtOAc in hexanes) to yield S2 (19.8 g, 69% over 2 steps) as an oil which solidified to a semi solid upon drying in vacuo: $^1$H NMR (400 MHz, CDCl$_3$) δ 8.15 (s, 1H), 6.31 (s, 1H), 5.91 (d, J=4.6 Hz, 1H), 5.56 (dd, J=8.2, 2.0 Hz, 1H), 4.07 (m, 2H), 4.02 (m, 1H), 3.91 (dd, J=11.6, 2.4 Hz, 1H), 3.73 (dd, J=11.6, 2.4 Hz, 1H), 0.95 (s, 9H), 0.92 (s, 9H), 0.89 (s, 9H), 0.12 (s, 6H), 0.098 (s, 3H), 0.083 (s, 3H), 0.063 (s, 3H), 0.057 (s, 3H); LRMS m/z 602.3 [M+H]$^+$.

EIDD-1931: A 50 mL round bottom flask was charged with S2 (23.3 g, 38.7 mmol) and THF (50 mL). Triethylamine trihydrofluoride (6.30 mL, 38.7 mmol) was added all at once, and the mixture was stirred at ambient temperature for 18 hours. The mixture was concentrated under reduced pressure, and the residue was dissolved in a minimal amount of MeOH, and this solution was slowly added to a Erlenmeyer flask containing rapidly stirred dichloromethane (500 mL) to precipitate the product; the mixture was stirred at rt for 15 minutes. The triturated solid was collected by vacuum filtration and washed with dichloromethane, then ether. The solid was dried in vacuo to yield the title compound (7.10 g, 71%) as a white solid: $^1$H NMR (400 MHz, CD$_3$OD) δ 7.16 (d, J=8.2 Hz, 1H), 5.86 (d, J=5.6 Hz, 1H), 5.59 (d, J=8.2 Hz, 1H), 4.19-4.04 (m, 2H), 3.93 (q, J=3.3 Hz, 1H), 3.77 (dd, J=12.2, 2.9 Hz, 1H), 3.68 (dd, J=12.1, 2.9 Hz, 1H); $^1$H NMR (400 MHz, DMSO-d$_6$) δ 9.95 (s, 1H), 9.46 (s, 1H), 7.02 (d, J=8.2 Hz, 1H), 5.71 (d, J=6.3 Hz, 1H), 5.54 (d, J=7.7 Hz, 1H), 5.23 (d, J=6.0 Hz, 1H), 5.02 (d, J=4.6 Hz, 1H), 4.98 (t, J=5.1 Hz, 1H), 3.95 (q, J=5.9 Hz, 1H), 3.89 (td, J=4.9 Hz, 3.0 Hz, 1H), 3.75 (q, J=3.4 Hz, 1H), 3.50 (qdd, J=11.9 Hz, 5.2 Hz, 3.5 Hz, 2H); $^{13}$C NMR (101 MHz, DMSO-d$_6$) δ 150.0, 143.9, 130.5, 98.89, 87.1, 85.0, 72.8, 70.8, 61.8. LRMS m/z 260.1 [M+H]$^+$.

Example 4

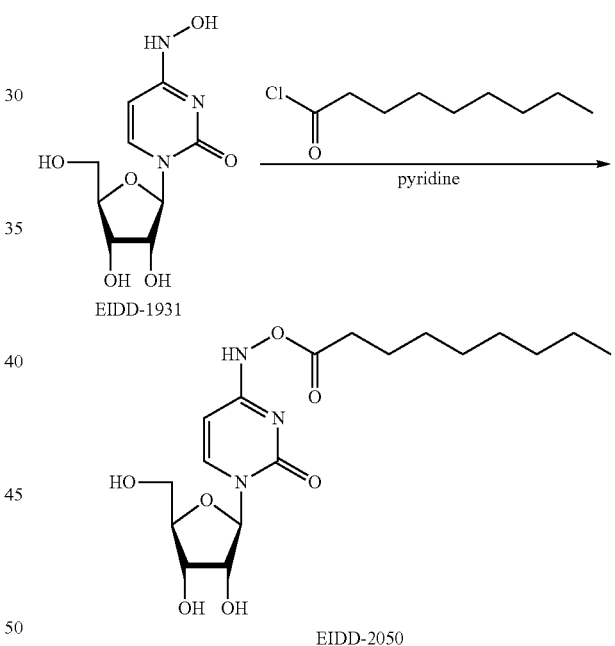

EIDD-2050: A solution of EIDD-1931 (124 mg, 0.478 mmol) in anhydrous pyridine (5 mL) was cooled to −20° C. and treated dropwise with nonanoyl chloride (95 μL, 0.528 mmol) over a 5 min period. The mixture was stirred at 0° C. for 15 h and then quenched with methanol (2 mL). After 20 min at rt the mixture was concentrated to dryness, and then purified by flash chromatography (1 to 5% gradient of MeOH in DCM). The resulting purified solid was co-evaporated with methylene chloride (3×10 mL) and then dried under high vacuum for 40 h to give the title compound (82 mg, 43%) as a white solid: $^1$H NMR (400 MHz, CD$_3$OD) δ 7.50 (d, J=8.3 Hz, 1H), 5.88 (d, J=5.1 Hz, 1H), 5.70 (d, J=8.2 Hz, 1H), 4.19-4.08 (m, 1H), 3.97 (q, J=3.1 Hz, 1H), 3.80 (dd, J=12.2, 2.9 Hz, 1H), 3.70 (dd, J=12.2, 3.3 Hz, 1H), 2.49 (t, J=7.4 Hz, 2H), 1.67 (p, J=7.4 Hz, 2H), 1.37-1.24 (m, 9H), 0.93-0.84 (m, 3H); $^{13}$C NMR (101 MHz, CD$_3$OD) δ 171.4, 149.7, 149.4, 134.6, 9597, 88.5, 84.9, 73.7, 70.2, 61.1, 31.8, 31.6, 28.9, 28.9, 28.8, 24.6, 22.3, 13.0; LRMS m/z 400.2 [M+H]$^+$.

Example 5

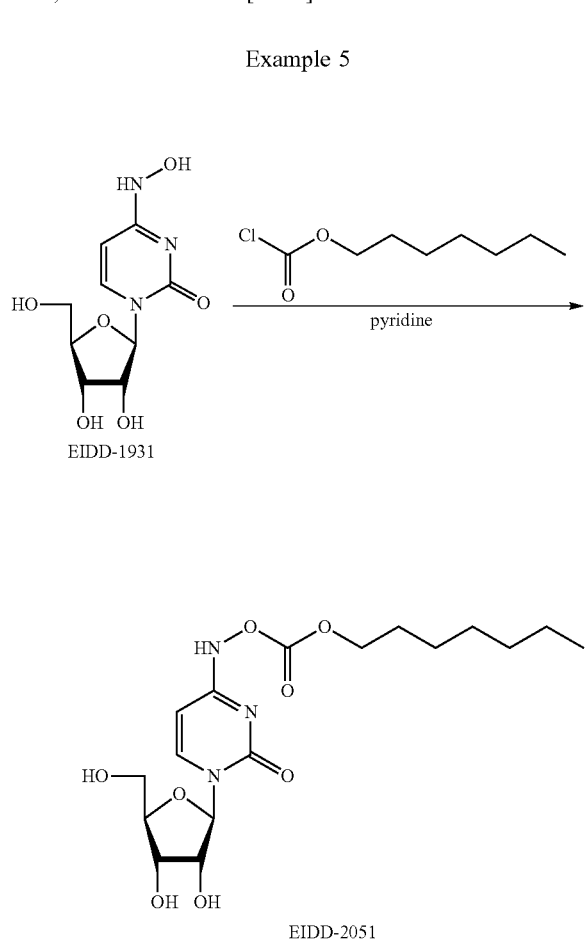

EIDD-2051: To a stirred solution of EIDD-1931 (0.194 g, 0.75 mmol) in pyridine (4.8 mL) at 0° C. under nitrogen, was added heptyl chloroformate (0.15 mL, 0.825 mmol) dropwise via syringe. The mixture was stirred at 0° C. for 4 h and then concentrated by rotary evaporation. The mixture was taken up in DCM with a drop of MeOH, and automated flash chromatography (40 g column, 0 to 15% gradient of MeOH in DCM) gave the title compound (0.126 g, 42%) as a powdery white solid. NMR analysis shows a 9:1 mixture of rotamers (most signals near the nucleobase are doubled, or are single but broadened): $^1$H NMR (400 MHz, CD$_3$OD, major rotamer only) δ 7.50 (d, J=8.3 Hz, 1H), 5.86 (d, J=5.0 Hz, 1H), 5.69 (d, J=8.2 Hz, 1H), 4.23 (t, J=6.6 Hz, 2H), 4.13 (q, J=5.1 Hz, 1H), 4.10 (q, J=4.0 Hz, 1H), 3.96 (q, J=3.4 Hz, 1H), 3.79 (dd, J=12.2, 2.8 Hz, 1H), 3.69 (dd, J=12.2 Hz, 3.2 Hz, 1H), 1.77-1.65 (m, 2H), 1.45-1.25 (m, 8H), 0.90 (t, J=6.9 Hz, 3H); $^{13}$C NMR (100 MHz, CD$_3$OD, major rotamer only) δ 153.3, 149.0, 148.7, 133.9, 94.9, 88.0, 84.2, 73.1, 69.5, 68.0, 60.5, 30.9, 28.0, 27.7, 24.7, 21.6, 12.4; HRMS calcd for C$_{17}$H$_{28}$N$_3$O$_8$ [M+H]$^+$: 402.18709, found: 402.18774.

Example 6

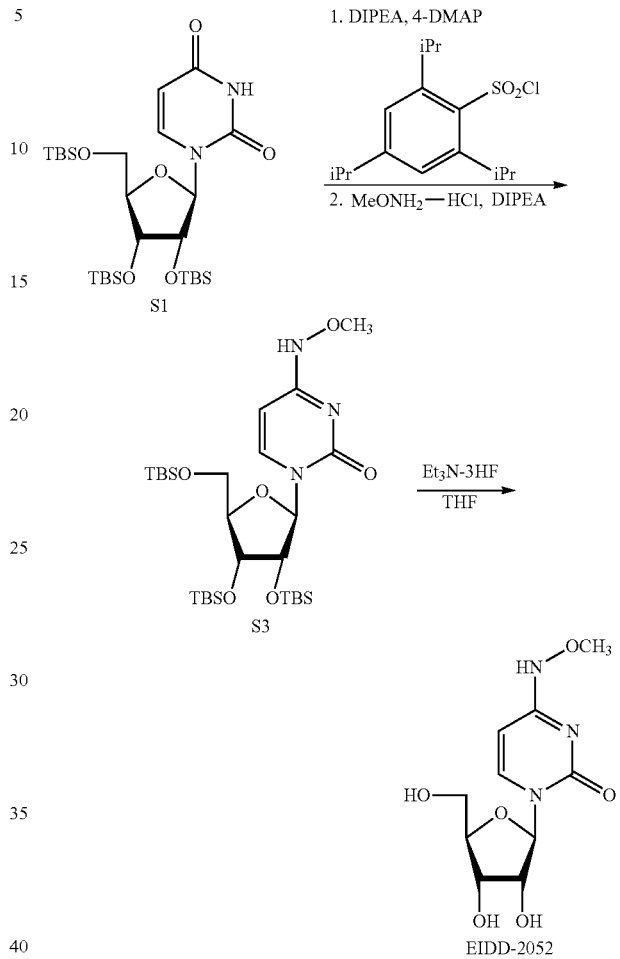

S3: To a stirred solution of S1 (2.20 g, 3.75 mmol) in DCM (37 mL) at 0° C. under nitrogen, was added sequentially 4-DMAP (0.460 g, 3.75 mmol), triethylamine (0.78 mL, 5.62 mmol), and 2,4,6-triisopropylbenzene-1-sulfonyl chloride (1.70 g, 5.62 mmol). The mixture was warmed to room temperature and stirred 16 h. The mixture was recooled to 0° C., and triethylamine (2.60 mL, 18.75 mmol) was added via syringe, followed by O-methylhydroxyamine hydrochloride (1.56 g, 18.75 mmol) all at once. The mixture was warmed to rt and stirred 3 h, then quenched by addition of water. The organic layer was removed, and the organic layer was washed with brine. The combined aqueous layers were extracted with DCM (2×25 mL), and the combined organic layers were dried over Na$_2$SO$_4$, filtered, and concentrated by rotary evaporation. The crude was purified by flash chromatography (10 to 20% gradient of EtOAc in hexanes) to give S3 (1.72 g, 74%) as a white foam. All NMR peaks were broad, likely due to N—OMe rotamers. The spectrum was not deconvoluted. LRMS m/z 617.3 [M+H]$^+$.

EIDD-2052: To a stirred solution of S3 (0.300 g, 0.487 mmol) in MeOH (5 mL) at 0° C. under nitrogen, was added a 1.25 M HCl solution in MeOH (2.3 mL, 2.92 mmol) dropwise via syringe. The mixture stirred at rt for 24 h. Triethylamine (0.70 mL, 5.05 mmol) was added, and the mixture was stirred for 2 h. The mixture was concentrated by rotary evaporation, and flash chromatography (5 to 20% gradient of iPrOH in EtOAc) gave the title compound (85 mg, 64%) as an off-white solid: $^1$H NMR (400 MHz, D$_2$O) δ 7.19 (d, J=8.2 Hz, 1H), 5.82 (d, J=5.4 Hz, 1H), 5.55 (d, J=8.2 Hz, 1H), 4.15-4.07 (m, 2H), 3.92 (q, J=3.5 Hz, 1H), 3.76 (dd, J=12.2 Hz, 2.9 Hz, 1H), 3.76 (s, 3H), 3.67 (dd, J=12.1 Hz, 3.4 Hz, 1H); $^{13}$C NMR (100 MHz, CD$_3$OD) δ 151.4, 146.2, 133.0, 98.6, 89.8, 86.1, 74.7, 71.7, 62.7, 61.9, 25.2; LRMS m/z 274.1 [M+H]$^+$.

Example 7

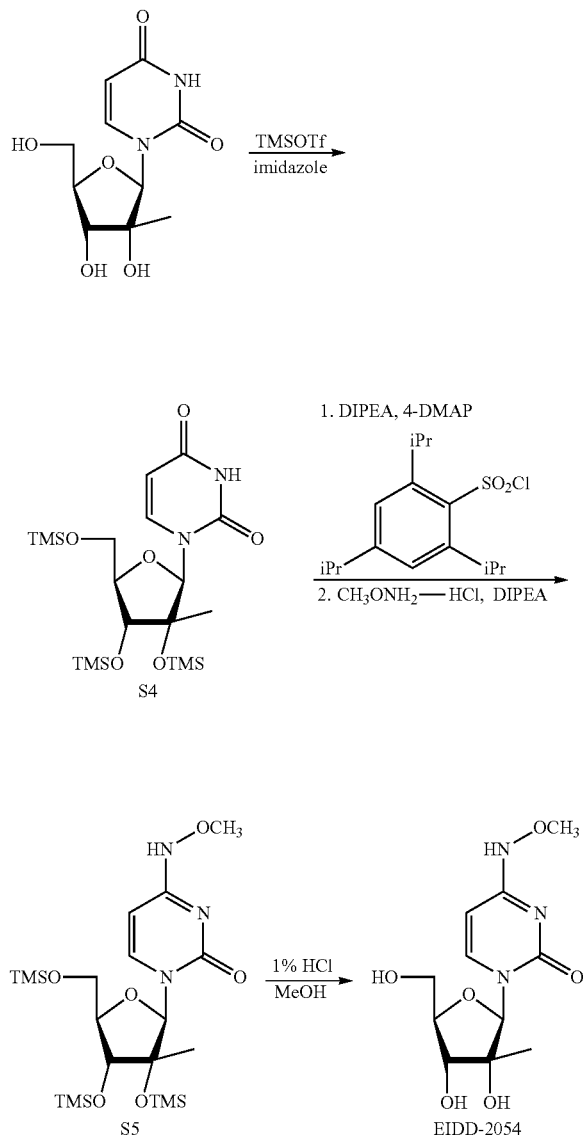

S4: A round bottom flask was charged with 2'-methyluridine (0.850 g, 3.29 mmol), imidazole (0.896 g, 13.17 mmol), and DCM (6.5 mL), and the mixture was cooled to 0° C. under nitrogen with stirring. Trimethylsilyl triflate (2.24 mL, 12.34 mmol) was added dropwise via syringe over 15 min. The mixture was warmed to rt and stirred overnight. After 16 h stirring, the mixture was diluted with DCM (200 mL) and poured into ice-cold water (100 mL). The organic layer was removed, and the aqueous layer was extracted with DCM (1×100 mL). The combined organic layers were washed with ice-cold brine (1×100 mL), dried over Na$_2$SO$_4$, filtered, and concentrated by rotary evaporation to give 1.8 g crude. The material was taken up in hexanes, and automated flash chromatography (40 g column, gradient of 5 to 20% EtOAc in hexanes) gave S4 (1.50 g, 96%) as a white flaky solid: $^1$H NMR (400 MHz, CDCl$_3$) δ 8.27 (d, J=8.2 Hz, 1H), 7.92 (s, 1H), 5.92 (s, 1H), 5.64 (dd, J=8.2 Hz, 2.3 Hz, 1H), 4.05-3.95 (m, 2H), 3.83 (d, J=9.1 Hz, 1H), 3.73 (d, J=11.2 Hz, 1H), 1.21 (s, 3H), 0.20 (s, 9H), 0.18 (s, 9H), 0.17 (s, 9H); LRMS m/z 475.2 [M+H]$^+$.

S5: To a stirred solution of S4 (1.50 g, 3.16 mmol) and 4-DMAP (0.039 g, 0.316 mmol) in DCM (20 mL) at 0° C. under nitrogen, was added N,N-diisopropylethylamine (2.75 mL, 15.80 mmol) via syringe, followed by solid 2,4,6-triisopropylbenzene-1-sulfonyl chloride (1.91 g, 6.32 mmol) all at once. The stirred mixture was allowed to warm to rt. After 16 h stirring at rt, the mixture was cooled to 0° C. and washed with ice-cold sat. aq. NaHCO$_3$ (3×25 mL), dried over Na$_2$SO$_4$, filtered, and concentrated by rotary evaporation to give 4.2 g crude as a brown oil. The crude was taken up in hexanes, and automated flash chromatography (80 g column, 1 to 10% gradient of EtOAc in hexanes) gave the desired product of sulfonyl activation (~1.57 g, ~2.12 mmol), mostly pure by LCMS (putative identity confirmed by $^1$H NMR). The entirety of this mixture was immediately taken on to the next step without further purification or analysis.

To a stirred solution of the freshly prepared material described above (~1.57 g, ~2.12 mmol) in MeCN (21 mL) at 0° C. under nitrogen, was added triethylamine (0.89 mL, 6.35 mmol) via syringe followed by O-methylhydroxylamine hydrochloride (0.531 g, 6.35 mmol) as a solid all at once. The mixture was warmed to rt and stirred overnight. After 16 h stirring, the mixture was poured into sat. aq. NaHCO$_3$ (50 mL) and extracted with DCM (3×50 mL). The combined organic layers were dried over Na$_2$SO$_4$, filtered, and concentrated by rotary evaporation. Automated flash chromatography on a CombiFlash (80 g column, 5 to 15% gradient of EtOAc in hexanes) gave S5 (0.571 g, 36% over 2 steps) as a clear viscous oil, present as a 9:1 ratio of tautomers by NMR: $^1$H NMR (400 MHz, CDCl$_3$, major tautomer only) δ 8.01 (br s, 1H), 7.59 (d, J=8.3 Hz, 1H), 5.88 (s, 1H), 5.54 (d, J=8.1 Hz, 1H), 4.03-3.93 (m, 2H), 3.84 (s, 3H), 3.82 (d, J=9.0 Hz, 1H), 3.71 (d, J=12.0 Hz, 1H), 1.20 (s, 3H), 0.23-0.15 (m, 27H); LRMS m/z 504.2 [M+H]$^+$.

EIDD-2054: A round bottom flask was charged with S5 (0.510 g, 1.01 mmol) and a stir bar under nitrogen at rt. A solution of conc. HCl, 1% v/v in MeOH (10 mL, 1.20 mmol HCl) was added via syringe and the mixture was stirred at rt for 30 min. Solid Na$_2$CO$_3$ (1 g) was added all at once, and the mixture was stirred at rt 30 min. Celite was added, and the mixture was concentrated by rotary evaporation to give the crude immobilized on the solid. Automated flash chromatography (12 g column, 0 to 10% gradient of MeOH in DCM) gave the title compound (0.265 g, 91%) as a white powdery solid: $^1$H NMR (400 MHz, CD$_3$OD) δ 7.36 (d, J=8.3 Hz, 1H), 5.89 (s, 1H), 5.54 (d, J=8.2 Hz, 1H), 3.95 (dd, J=12.5 Hz, 2.2 Hz, 1H), 3.86 (dt, J=9.2 Hz, 2.4 Hz, 1H), 3.82-3.72 (m, 2H), 3.78 (s, 3H), 1.17 (s, 3H); $^{13}$C NMR (100 MHz, CD$_3$OD) δ 151.3, 146.2, 132.8, 98.2, 92.6, 83.4, 79.8, 73.8, 61.9, 60.7, 20.3; LRMS m/z 288.1 [M+H]$^+$.

Example 8

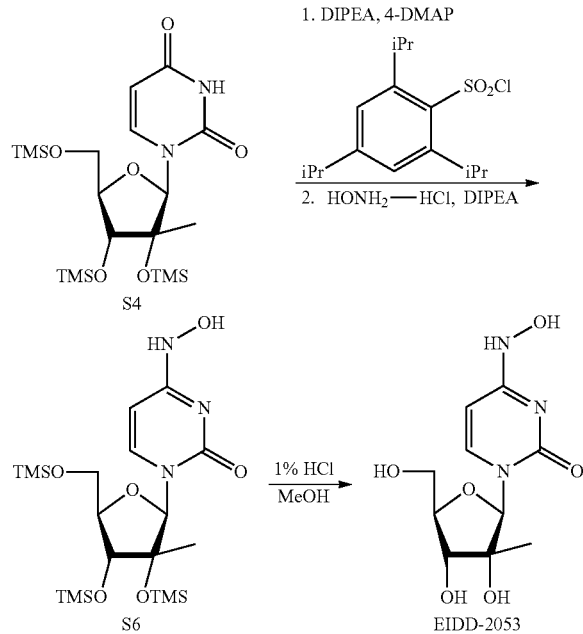

S6: To a stirred solution of S4 (1.67 g, 3.52 mmol) and 4-DMAP (0.043 g, 0.352 mmol) in DCM (25 mL) at 0° C. under nitrogen, was added N,N-diisopropylethylamine (3.06 mL, 17.59 mmol) via syringe, followed by solid 2,4,6-triisopropylbenzene-1-sulfonyl chloride (1.92 g, 6.33 mmol) all at once. The stirred mixture was allowed to warm to rt. After 16 h stirring at rt, the mixture was cooled to 0° C. and washed with ice-cold sat. aq. NaHCO$_3$ (3×25 mL), dried over Na$_2$SO$_4$, filtered, and concentrated by rotary evaporation to give 4.1 g crude as a brown oil. The crude was taken up in hexanes, and automated flash chromatography (80 g column, 1 to 10% gradient of EtOAc in hexanes) gave the desired product of sulfonyl activation (~1.81 g, ~2.44 mmol), mostly pure by LCMS (putative identity confirmed by $^1$H NMR). The entirety of this mixture was immediately taken on to the next step without further purification.

To a stirred solution of the freshly prepared material described above (~1.81 g, ~2.44 mmol) in MeCN (25 mL) at 0° C. under nitrogen, was added triethylamine (1.02 mL, 7.33 mmol) via syringe followed by hydroxylamine hydrochloride (0.509 g, 7.33 mmol) as a solid all at once. The mixture was warmed to rt and stirred 2 h. The mixture was poured into sat. aq. NaHCO$_3$ (50 mL) and extracted with DCM (3×50 mL). The combined organic layers were dried over Na$_2$SO$_4$, filtered, and concentrated by rotary evaporation. Automated flash chromatography (40 g column, gradient of 5 to 35% EtOAc in hexanes) gave S6 (0.931 g, 54% over 2 steps) as a white flaky solid, present as a 7:1 ratio of tautomers by NMR: $^1$H NMR (400 MHz, DMSO-d$_6$, major tautomer only) δ 9.99 (s, 1H), 9.57 (d, J=2.1 Hz, 1H), 7.25 (d, J=8.3 Hz, 1H), 5.72 (s, 1H), 5.45 (dd, J=8.2 Hz, 2.1 Hz, 1H), 3.92 (d, J=12.0 Hz, 1H), 3.85-3.75 (m, 2H), 3.66 (d, J=12.0 Hz, 1H), 1.13 (s, 3H), 0.15 (s, 9H), 0.14 (s, 9H), 0.12 (s, 9H); LRMS m/z 490.0 [M+H]$^+$.

EIDD-2053: A round bottom flask was charged with S6 (0.200 g, 0.408 mmol) and a stir bar under nitrogen at rt. A solution of conc. HCl, 1% v/v in MeOH (6 mL, 0.72 mmol HCl) was added via syringe and the mixture was stirred at rt for 30 min. Solid Na$_2$CO$_3$ (0.75 g) was added all at once, and the mixture was stirred at rt 30 min. Celite was added, and the mixture was concentrated by rotary evaporation to give the crude immobilized on the solid. Automated flash chromatography (4 g column, gradient of 5 to 25% MeOH in DCM) gave the title compound (0.110 g, 99%) as a white powdery solid: $^1$H NMR (400 MHz, CD$_3$OD) δ 7.30 (d, J=8.3 Hz, 1H), 5.90 (s, 1H), 5.56 (d, J=8.2 Hz, 1H), 3.95 (dd, J=12.5 Hz, 2.1 Hz, 1H), 3.86 (dt, J=9.2 Hz, 2.7 Hz, 1H), 3.80 (d, J=9.2 Hz, 1H), 3.75 (dd, J=12.5 Hz, 3.0 Hz, 1H), 1.18 (s, 3H); $^{13}$C NMR (100 MHz, D$_2$O) δ 151.6, 147.3, 131.8, 98.9, 91.7, 81.9, 79.5, 73.3, 60.4, 49.5, 19.6; LRMS m/z 274.1 [M+H]$^+$.

Example 9

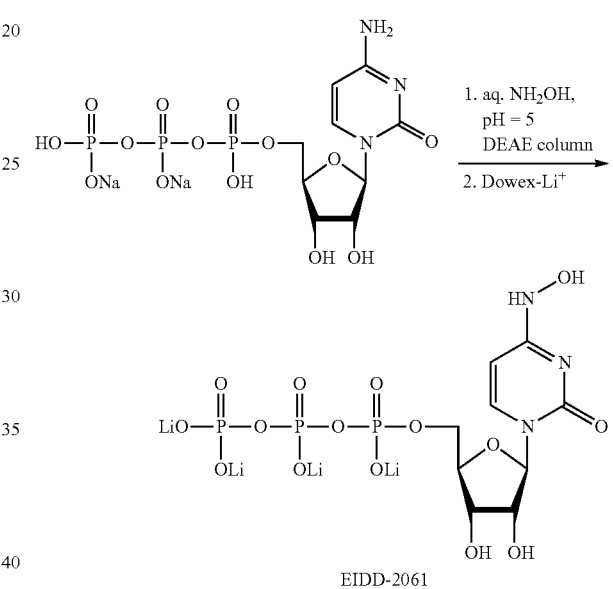

EIDD-2061: A sealable pressure tube was charged with a stir bar, cytidine triphosphate disodium salt (0.137 g, 0.260 mmol), and a 2 N aqueous hydroxylamine solution adjusted to pH=5 (2.0 mL, 4.0 mmol). After mixing the reagents, the pH of the solution was measured (pH=3) and additional drops of 10% w/w aq. NaOH solution were added to readjust the solution to pH=5. The tube was sealed and heated with stirring at 55° C. for 5 h. The mixture was cooled to rt, the sealed tube was opened, and a solution of 100 mM triethylammonium bicarbonate (TEAB) (2 mL) was added. The contents of the tube were transferred to a round bottom flask, and concentrated by rotary evaporation. The crude material was taken up in 100 mM TEAB, and chromatography on DEAE followed by lyophilization of the product gave a triethylammonium salt of the desired product.

An ion-exchange column (17 mL CV) of freshly prepared Dowex (Li$^+$ form) was rinsed with 5 CV water. The prepared triethylammonium salt was taken up in water and eluted through the ion-exchange column. Fractions containing product were combined and lyophilized to give the title compound (0.030 g, 22%) as a fluffy tan solid: $^1$H NMR (400 MHz, D$_2$O) δ 7.19 (d, J=8.3 Hz, 1H), 5.95 (d, J=6.3 Hz, 1H), 5.82 (d, J=8.3 Hz, 1H), 4.42-4.34 (m, 2H), 4.24-4.10 (m, 3H); $^{31}$P NMR (162 MHz, D$_2$O) δ −8.5 (br s), −11.2 (d, J=19.6 Hz), −22.0 (t, J=19.3 Hz); LRMS m/z 498.0 [M−H]$^-$.

Example 10

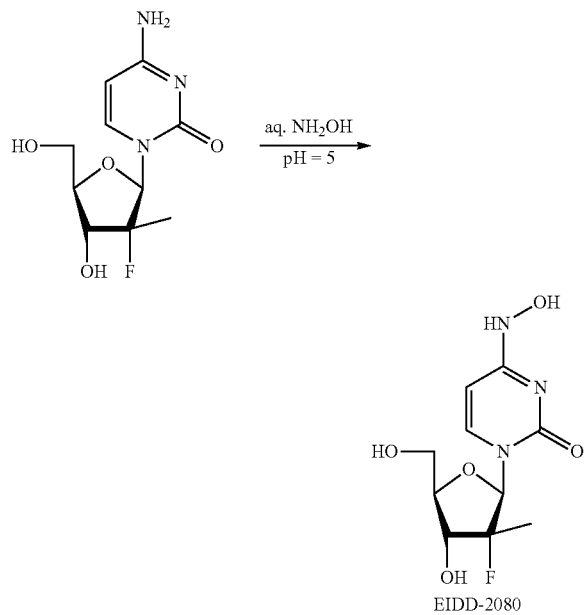

EIDD-2080: A round bottom flask was charged with 2'-deoxy-2'-fluoro-2'-methylcytidine (120 mg, 0.463 mmol) and a 2 N aqueous hydroxylamine solution adjusted to pH=5 (1.1 mL, 2.2 mmol), and the mixture was heated to 50° C. After 16 h, the mixture was concentrated to dryness and then purified by flash chromatography (19 mm×170 mm column volume, 10% MeOH in DCM). The resulting gum was co-evaporated with DCM (3×4 mL) to give a white solid that was further dried under high vacuum at 40° C. for 24 h to yield the title compound (94 mg, 74%) as a white powder: $^1$H NMR (400 MHz, CD$_3$OD) δ 7.23 (d, J=8.3 Hz, 1H), 6.07 (d, J=19.8 Hz, 1H), 5.60 (d, J=8.3 Hz, 1H), 4.04-3.95 (m, 1H), 3.91 (d, J=8.3 Hz, 2H), 3.77 (dd, J=12.5, 2.3 Hz, 1H), 1.36 (d, J=22.2 Hz, 3H); $^{13}$C NMR (101 MHz, CD$_3$OD) δ 150.0, 144.6, 129.9, 101.4, 99.6, 98.0, 88.7 (d, J=46.5 Hz), 81.5, 71.5 (d, J=18.1 Hz), 58.9, 15.5 (d, J=25.8 Hz); HRMS calcd. for C$_{10}$H$_{15}$FN$_3$O$_5$ [M+H]$^+$: 276.09903, found: 276.09910.

Example 11

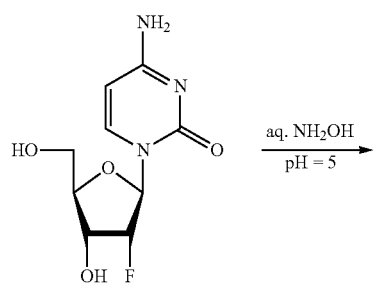

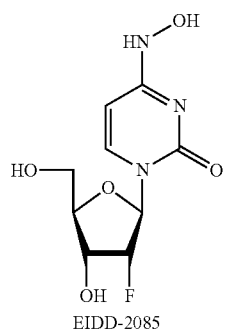

EIDD-2085

EIDD-2085: A ~2 N solution of hydroxylamine hydrochloride (3.33 g, 48.0 mmol) in water (24 mL) was prepared, and adjusted to pH=5 with a small amount of aq. NaOH (10% w/w). A sealable pressure tube was charged with this solution and 2'-fluoro-2'deoxycytidine (0.736 g, 3.00 mmol), the flask was sealed, and heated with stirring at 55° C. for 16 h. The mixture was cooled to room temperature, transferred to a round bottom flask, and concentrated by rotary evaporation. The crude material was suspended in MeOH and immobilized on Celite. Automated flash chromatography (40 g column, 5 to 25% gradient of MeOH in DCM) gave the title compound (0.365 g, 47%) as an off-white solid. NMR analysis showed the compound to be ~90% pure by weight, with the remainder being occluded DCM and MeOH. A sample (103 mg) was dissolved in water, frozen in a dry ice bath, and lyophilized to give 91 mg of the title compound, solvent-free. This purified material was used for all biological testing: $^1$H NMR (400 MHz, D$_2$O) δ 7.00 (d, J=8.3 Hz, 1H), 5.91 (dd, J=21.0 Hz, 2.0 Hz, 1H), 5.71 (d, J=8.2 Hz, 1H), 5.19 (ddd, J=53.1 Hz, 5.0 Hz, 2.0 Hz, 1H), 4.36 (ddd, J=20.0 Hz, 8.2 Hz, 5.0 Hz, 1H), 4.08-4.02 (br m, 1H), 3.95 (dd, J=12.9 Hz, 2.5 Hz, 1H), 3.78 (dd, J=12.9 Hz, 4.6 Hz, 1H); $^{13}$C NMR (100 MHz, D$_2$O) δ 150.8, 146.7, 132.5, 98.4, 93.1 (d, J=183.1 Hz), 89.0 (d, J=35.9 Hz), 82.1, 68.3 (d, J=16.5 Hz), 60.2 Hz; $^{19}$F NMR (376 MHz, D$_2$O) δ −200.51 (dt, J=53.1 Hz, 20.4 Hz); HRMS calcd. for C$_9$H$_{13}$FN$_3$O$_5$ [M+H]$^+$: 262.08338, found: 262.08332.

Example 12

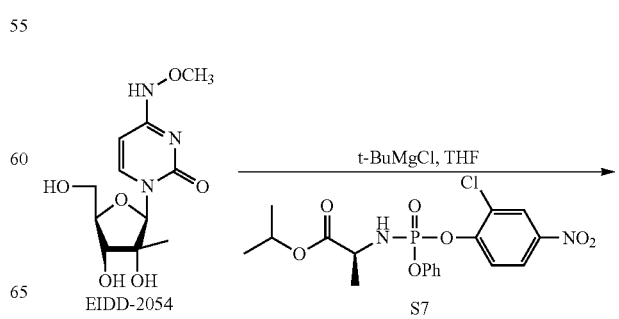

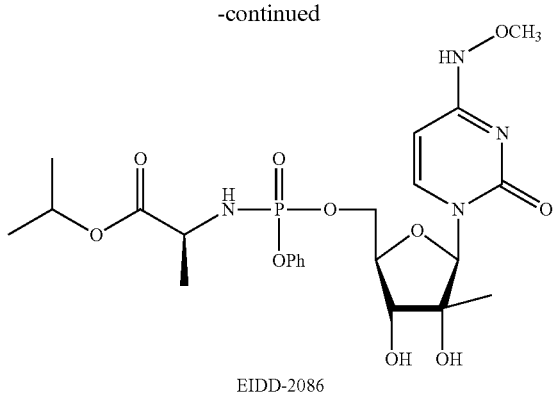

EIDD-2086

EIDD-2086: A solution of EIDD-2054 (45 mg, 0.16 mmol) in anhydrous THF (1 mL) at 0° C. was treated with a 1 M THF solution of tert-butylmagnesium chloride (0.31 mL, 0.31 mmol). After 1 h at 0° C., the mixture was treated dropwise with a solution of S7 (139 mg, 0.31 mmol) in anhydrous THF (1 mL) over a 5 min period. The mixture was allowed to warm to rt and was stirred overnight. The mixture was quenched with sat. aq. NH₄Cl (5 mL) and then extracted with ethyl acetate (50 mL). The organic phase was washed with sat. aq. NaHCO₃ (2×15 mL), dried over Na₂SO₄, filtered and concentrated to dryness. The resulting crude yellow oil was purified by flash chromatography (column volume 19 mm×170 mm, 5 to 10% gradient of MeOH in DCM) to give a 1:1 diastereomeric mixture of the title compound (49 mg, 56%) as an off-white solid: ¹H NMR (400 MHz, CDCl₃, diastereomeric mixture) δ 8.25 (s, 1H), 7.32 (t, J=7.7 Hz, 2H), 7.18 (dd, J=16.8, 8.0 Hz, 3H), 6.81 (d, J=8.2 Hz, 1H), 6.66 (d, J=8.2 Hz, 1H), 5.87 (d, J=14.0 Hz, 1H), 5.55 (d, J=8.2 Hz, 1H), 5.48 (d, J=8.2 Hz, 1H), 5.00 (h, J=6.3 Hz, 1H), 4.49-4.39 (m, 2H), 4.34 (ddd, J=11.8, 8.3, 3.4 Hz, 1H), 4.07-3.86 (m, 2H), 3.82 (s, 3H), 3.74 (dd, J=38.5, 8.4 Hz, 1H), 1.36 (d, J=2.2 Hz, 3H), 1.35 (d, J=2.2 Hz, 3H), 1.25-1.20 (m, 6H), 1.17 (s, 3H), 1.11 (s, 3H); ³¹P NMR (162 MHz, CDCl₃, diastereomeric mixture) δ 3.55, 3.19; ¹³C NMR (101 MHz, CDCl₃, diastereomeric mixture) δ 173.02, 172.95, 172.91, 172.84, 150.49, 150.42, 149.28, 149.18, 144.31, 144.22, 130.74, 130.46, 129.87, 129.83, 125.28, 125.16, 119.93, 119.88, 97.94, 91.57, 91.18, 77.33, 73.52, 73.03, 69.55, 69.51, 65.05, 64.99, 64.51, 61.80, 50.41, 50.32, 29.68, 21.70, 21.67, 21.61, 21.58, 20.93, 20.88, 20.82, 20.46; HRMS calcd. for C₂₃H₃₃N₄O₁₀PNa [M+Na]⁺: 579.18265; found: 579.18184.

Example 13

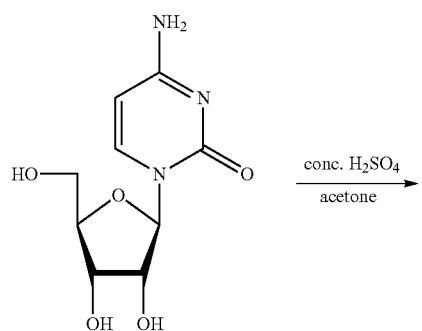

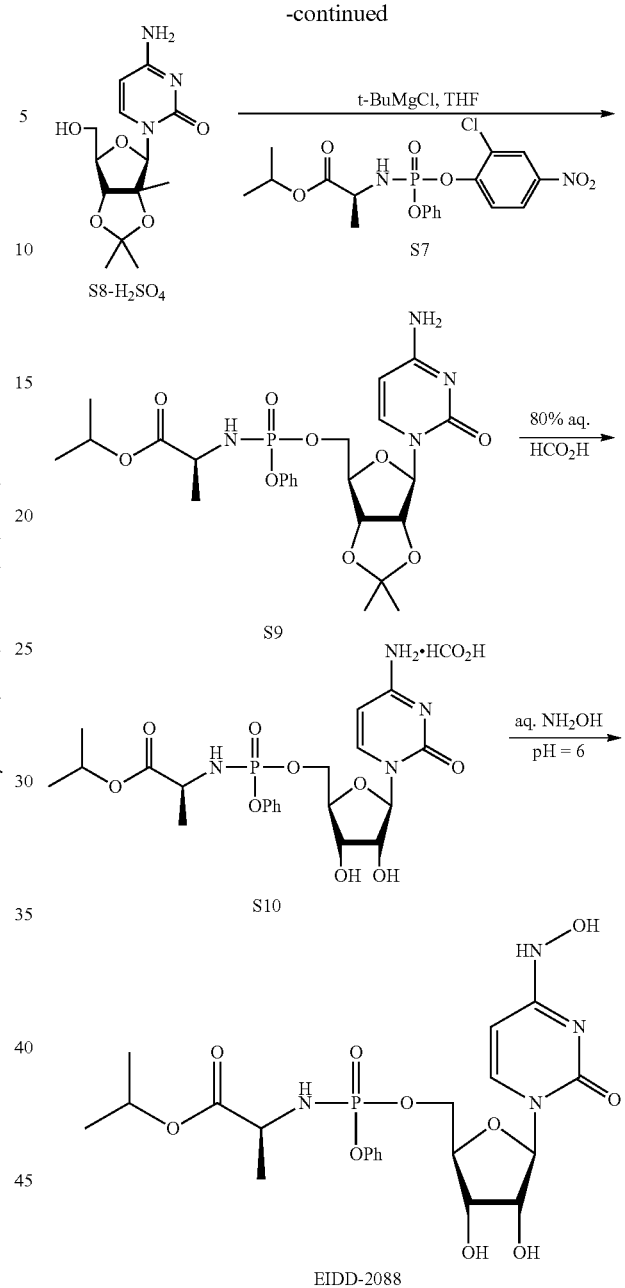

S8: To a stirred suspension of cytidine (0.972 g, 4.00 mmol) in dry acetone (50.0 mL) was dropwise added a catalytic amount of H₂SO₄ (0.13 ml, 2.439 mmol). The resulting reaction was stirred at rt overnight. After filtration, the obtained white solid was redissolved in MeOH with a little heating, then reevaporated to give a white solid as a sulfate salt form of the desired product (>95% yield), which was used without further purification: ¹H NMR (400 MHz, CD₃OD) δ 8.23 (d, J=7.9 Hz, 1H), 6.09 (d, J=7.9 Hz, 1H), 5.86 (d, J=2.4 Hz, 1H), 4.90 (dd, J₁=6.2 Hz, J₂=2.3 Hz, 1H), 4.82 (dd, J₁=6.1 Hz, J₂=2.7 Hz, 1H), 4.35 (q, J=3.4 Hz, 1H), 3.80 (dd, J₁=12.1 Hz, J₂=3.2 Hz, 1H), 3.71 (dd, J₁=12.1 Hz, J₂=4.1 Hz, 1H), 1.54 (s, 3H), 1.35 (s, 3H); ¹³C NMR (100 MHz, CD₃OD) δ 161.33, 148.49, 147.34, 114.86, 95.58, 94.22, 89.56, 86.59, 82.34, 62.85, 27.42, 25.41; HRMS calcd. for C₁₂H₁₈O₅N₃ [M+H]⁺: 284.12410, found: 284.12424.

S9: To a suspension of S8 (0.566 g, 2.00 mmol) in THF (20.0 ml) was dropwise added a 1 M solution of t-butylmagnesium chloride in THF (3.00 mL, 3.00 mmol) via syringe at 0° C. under argon, and the resulting mixture was stirred at the same temperature for 1 hr. A solution of S7 (1.33 g, 3.00 mmol) in THF (20 mL) was added at 0° C., upon which the mixture was allowed to warm to rt and stirred for another 27 hrs. The reaction was carefully quenched by the addition of sat. aq. NH$_4$Cl at 0° C. The obtained mixture was filtered through a Celite pad, and the pad was washed with MeOH. The filtrate was concentrated by rotary evaporation to give a brown solid, which was purified by flash chromatography (5% MeOH in DCM) to give a semipure product. The mixture was further purified by automated flash chromagraphy (40 g column, 0 to 25% gradient of MeOH in DCM) to give S9 (0.744 g, 67% over 2 steps) as a white solid present as a mixture of two diastereomers in a ratio of 1:2 based on the integration of $^{31}$P-NMR: $^1$H NMR (400 MHz, CD$_3$OD, diastereomeric mixture) δ 7.61 (m, 1H), 7.34 (t, J=7.9 Hz, 2H), 7.27-7.09 (m, 3H), 5.93-5.69 (m, 2H), 4.95 (p, J=6.3 Hz, 1H), 4.90 (dd, J=6.4 Hz, 2.2 Hz, 1H), 4.84-4.71 (m, 1H), 4.46-4.20 (m, 3H), 3.88 (p, J=7.8 Hz, 1H), 2.15 (s, 1H), 1.53 (s, 3H), 1.32 (m, 6H), 1.21 (m, 6H); $^{13}$C NMR (100 MHz, CD$_3$OD, both diastereomers) δ 210.06, 174.62, 174.57, 174.41, 174.35, 167.89, 157.81, 152.18, 152.11, 144.64, 144.38, 130.82, 130.78, 130.77, 126.24, 126.22, 126.17, 126.16, 121.48, 121.45, 121.43, 121.40, 115.18, 115.08, 96.18, 95.96, 87.13, 87.05, 86.96, 86.88, 86.23, 82.48, 82.47, 70.14, 68.02, 51.81, 51.67, 49.64, 49.43, 49.21, 49.00, 48.79, 48.57, 48.36, 30.68, 27.46, 27.43, 25.51, 25.46, 22.00, 21.98, 21.90, 20.56, 20.49, 20.30; $^{31}$P NMR (162 MHz, CD$_3$OD) δ 3.68, 3.45; HRMS calcd. for C$_{24}$H$_{33}$O$_9$N$_4$NaP [M+Na]$^+$: 575.18774, found: 575.18824.

S10: A solution of S9 (0.289 g, 0.502 mmol) in 80% aq. HCOOH (12.40 mL) was stirred at rt for 3.5 hrs. The reaction was concentrated by rotary evaporation, and coevaporated with MeOH (3×10 mL). The crude product S9 (0.257 g, quant.) was obtained as a brown glassy solid that was used in the next step without further purification: $^1$H NMR (400 MHz, CD$_3$OD, diastereomeric mixture) δ 8.16 (s, 1H), 7.79 (d, J=7.5 Hz, 1H), 7.73 (d, J=7.5 Hz, 1H), 7.50-7.08 (m, 5H), 6.03-5.68 (m, 2H), 4.96 (septet, J=8 Hz, 1H), 4.55-4.24 (m, 2H), 4.23-4.08 (m, 2H), 4.08-3.99 (m, 1H), 3.97-3.82 (m, 1H), 1.43-1.26 (m, 4H), 1.26-1.10 (m, 6H); $^{13}$C NMR (100 MHz, CD$_3$OD, both diastereomers) δ 174.65, 174.61, 174.38, 174.33, 166.90, 157.46, 152.15, 152.08, 142.73, 130.89, 130.88, 130.85, 130.85, 126.28, 126.26, 121.42, 121.40, 121.37, 121.36, 96.19, 92.05, 91.97, 83.49, 83.42, 75.90, 75.84, 70.70, 70.64, 70.18, 67.14, 67.08, 51.88, 51.87, 51.71, 51.70, 49.64, 49.43, 49.21, 49.00, 48.79, 48.57, 48.36, 21.98, 21.91, 21.89, 21.80, 20.61, 20.55, 20.30; $^{31}$P NMR (162 MHz, CD$_3$OD) δ 3.91, 3.76; HRMS calcd. for C$_{21}$H$_{30}$O$_9$N$_4$P [M+H]$^+$: 513.17449, found: 513.17413.

EIDD-2088: To a solution of S10 (0.257 g, 0.502 mmol) in THF (5 mL) was added a 2 N hydroxylamine at pH 6 (6.27 ml, 12.54 mmol), and the resulted mixture was stirred at 37° C. for 1.5 days. The reaction mixture was concentrated by rotary evaporation. The obtained yellow solid was redissolved in MeOH and immobilized onto silica gel, which was loaded onto a silica plug. Elution with 10% MeOH in CH$_2$Cl$_2$ through the silica plug, gave a light brown liquid after rotary evaporation of fractions containing product. Automated flash chromatography (12 g column, 2.5 to 15% gradient of MeOH in DCM) provided the title compound (0.155 mg, 59%) as an off-white foam: $^1$H NMR (400 MHz, CD$_3$OD, diastereomeric mixture) δ 7.89 (d, J=8.0 Hz, 0.3H), 7.80 (d, J=8.1 Hz, 0.65H), 7.48-7.31 (m, 2H), 7.31-7.13 (m, 3H), 6.02-5.79 (m, 2H), 4.97 (hept, J=8 Hz, 1H), 4.55-4.08 (m, 6H), 3.90 (m, 1H), 1.44-1.26 (m, 4H), 1.22 (m, 6H); $^{13}$C NMR (100 MHz, CD$_3$OD, both diastereomers) δ 174.72, 174.68, 174.36, 174.30, 155.25, 152.10, 152.03, 148.74, 148.68, 142.86, 130.92, 130.87, 126.33, 126.32, 121.43, 121.39, 91.71, 91.63, 91.58, 84.08, 84.02, 83.95, 75.48, 75.41, 70.71, 70.67, 70.20, 67.03, 51.90, 51.73, 51.71, 49.64, 49.43, 49.21, 49.00, 48.79, 48.57, 48.36, 21.98, 21.92, 21.89, 21.79, 20.59, 20.53, 20.31; $^{31}$P NMR (162 MHz, CD$_3$OD) δ 3.98, 3.81; HRMS calcd. for C$_{21}$H$_{30}$O$_{10}$N$_4$P [M+H]$^+$: 529.16941, found: 529.16900.

Example 14

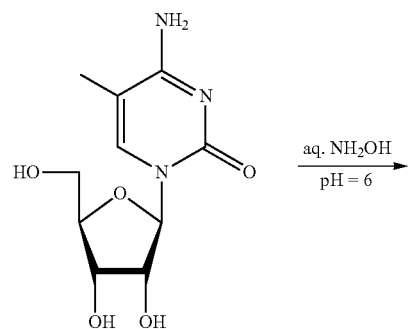

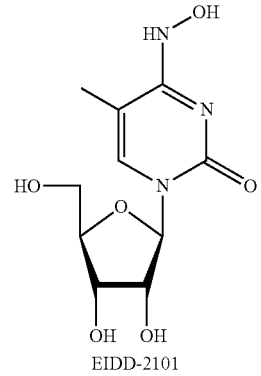

EIDD-2101

EIDD-2101: A solution of 5-methylcytidine (0.257 g, 1.00 mmol) in a 2N aq. hydroxylamine solution with pH 6 (8 mL, 16.0 mmol) was heated to 55° C. in a sealed tube with stirring for 5 hrs. The solution was cooled to rt, transferred to a round bottom flask, concentrated by rotary evaporation, and coevaporated with MeOH (2×20 mL). The crude residue was taken up in MeOH and immobilized on silica gel. Flash chromatography (2 to 10% gradient of MeOH in DCM) provided the title compound (140 mg, 51%) as a light purple solid: $^1$H NMR (400 MHz, CD$_3$OD) δ 6.99 (s, 1H), 5.86 (d, J=5.7 Hz, 1H), 4.23-4.06 (m, 2H), 3.93 (q, J=3.2 Hz, 1H), 3.78 (dd, J=12.1 Hz, 2.8 Hz, 1H), 3.70 (dd, J=12.1 Hz, 3.4 Hz, 1H), 1.79 (s, 3H); $^{13}$C NMR (100 MHz, CD$_3$OD) δ 152.0, 146.6, 128.4, 108.4, 89.4, 86.1, 74.4, 71.8, 62.8, 12.9; HRMS calcd. for C$_{10}$H$_{16}$O$_6$N$_3$ [M+H]$^+$: 274.10336, found: 274.10350.

Example 15

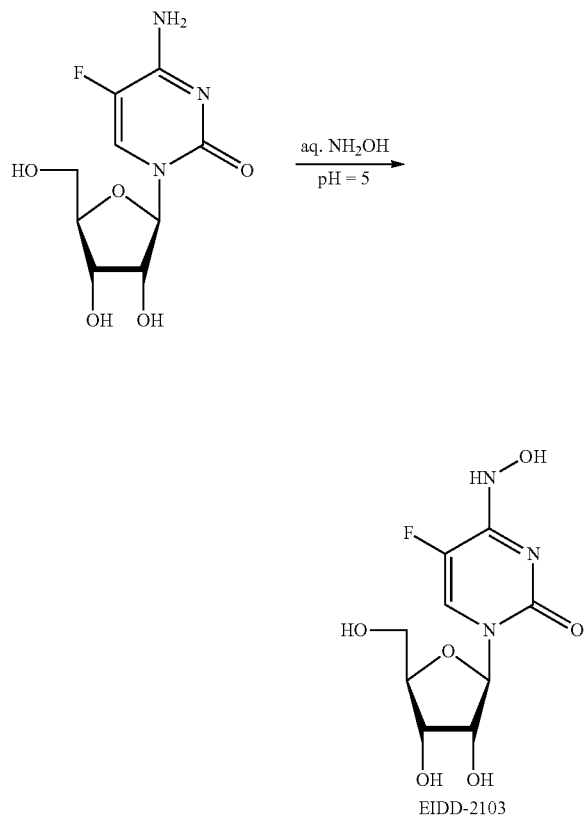

EIDD-2103: A ~2 N solution of hydroxylamine hydrochloride (1.11 g, 16.0 mmol) in water (8 mL) was prepared, and adjusted to pH=5 with a small amount of aq. NaOH (10% w/w). A sealable pressure tube was charged with this solution and 5-fluorocytidine (0.261 g, 1.00 mmol), the flask was sealed, and heated with stirring at 55° C. for 16 h. The mixture was cooled to room temperature, transferred to a round bottom flask, and concentrated by rotary evaporation. The crude material was suspended in MeOH and immobilized on Celite. Automated flash chromatography (40 g column, 0 to 20% gradient of MeOH in DCM) gave 600 mg of a semipure pink solid. This solid was dissolved in 2 mL water, and automated reverse phase chromatography (43 g column, 5 to 100% gradient of MeOH in water) gave the desired product free from organic and inorganic impurities. The solid was dissolved in water, frozen in a dry ice/acetone bath, and lyophilized to provide the title compound (0.066 g, 0.238 mmol, 24% yield) as a white flocculent solid. $^1$H NMR (400 MHz, D$_2$O) δ 7.31 (d, J=7.6 Hz, 1H), 5.87 (dd, J=5.5 Hz, 1.8 Hz, 1H), 4.26 (t, J=5.5 Hz, 1H), 4.19 (t, J=4.8 Hz, 1H), 4.07 (q, J=3.8 Hz, 1H), 3.85 (dd, J=12.8 Hz, 3.1 Hz, 1H), 3.77 (dd, J=12.7 Hz, 4.2 Hz, 1H); $^{13}$C NMR (100 MHz, D$_2$O) δ 150.0, 139.7, 137.4, 115.6 (d, J=36.1 Hz), 88.0, 84.2, 72.8, 69.8, 61.0; $^{19}$F NMR (376 MHz, D$_2$O) δ −164.70 (d, J=7.6 Hz); HRMS calcd. for C$_9$H$_{13}$FN$_3$O$_6$ [M+H]$^+$: 278.07829, found: 278.07848.

Example 16

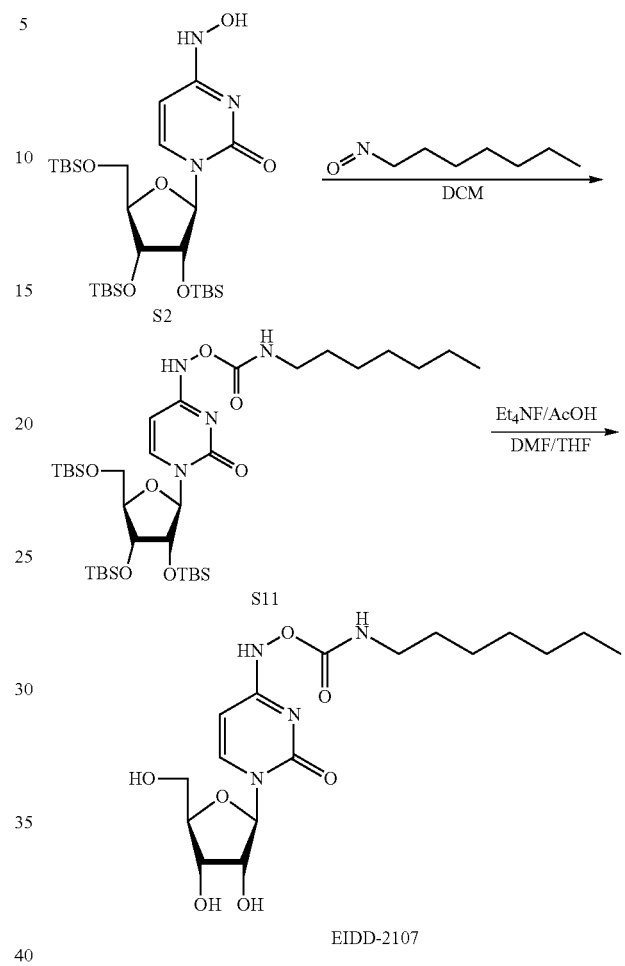

S11: To a stirred solution of S2 (0.903 g, 1.50 mmol) in DCM (15 mL) under nitrogen at rt, was added heptyl isocyanate (0.266 mL, 1.65 mmol) dropwise via syringe over 2 minutes. The reaction was stirred at rt for 6 h, then concentrated by rotary evaporation to give crude residue. Automated flash chromatography (40 g column, 5 to 25% gradient of EtOAc in hexanes) gave S11 (0.930 g, 83%) as a flaky light pink solid: $^1$H NMR (400 MHz, CDCl$_3$) δ 8.26 (br s, 1H), 7.50 (d, J=8.3 Hz, 1H), 6.29 (t, J=5.8 Hz, 1H), 5.90 (d, J=4.4 Hz, 1H), 5.57 (dd, J=8.2 Hz, 2.3 Hz, 1H), 4.10-4.00 (m, 3H), 3.93 (dd, J=11.6 Hz, 2.3 Hz, 1H), 3.74 (d, J=11.6 Hz, 1H), 3.28 (q, J=6.7 Hz, 1H), 1.62-1.52 (m, 2H), 1.40-1.25 (m, 8H), 0.96 (s, 9H), 0.91 (s, 9H), 0.91-0.86 (m, 3H), 0.89 (s, 9H), 0.13 (s, 6H), 0.10 (s, 3H), 0.08 (s, 3H), 0.05 (s, 6H).

EIDD-2107: To a stirred solution of S11 (0.910 g, 1.22 mmol) in a mixture of THF (18 mL) and DMF (6 mL) at 0° C. under nitrogen, was added acetic acid (0.350 mL, 6.12 mmol) followed by solid tetraethylammonium fluoride (0.877 g, 5.88 mmol) all at once. The mixture was warmed to rt and stirred for 20 h. The mixture was then concentrated by rotary evaporation to give crude as an oil. The oil was taken up in DCM, and automated flash chromatography (40 g column, 1 to 10% gradient of MeOH in DCM) gave 300 mg of a flaky white solid, consisting of desired product and tetraethylammonium acetate. The mixture was taken up in MeOH and immobilized on Celite. A second automated flash chromatography (12 g column, 1 to 10% gradient of MeOH in DCM) gave the title compound (0.228 g, 47% yield) as a white powdery solid. NMR analysis showed a 5:1 ratio of signals, most likely rotamers about one of the bonds of the carbamate (most signals associated with the nucleobase are doubled or single but broadened) $^1$H NMR (400 MHz, DMSO-$d_6$, major rotamer only) δ 10.30 (s, 1H), 7.38 (d, J=8.2 Hz, 1H), 6.85 (t, J=5.8 Hz, 1H), 5.75 (d, J=5.8 Hz, 1H), 5.69 (dd, J=8.4 Hz, 2.2 Hz, 1H), 5.32 (d, J=5.9 Hz, 1H), 5.10-5.00 (m, 2H), 3.99 (q, J=5.6 Hz, 1H), 3.94 (q, J=4.7 Hz, 1H), 3.83-3.76 (m, 1H), 3.63-3.46 (m, 2H), 3.04 (q, J=6.5 Hz, 1H), 1.46-1.36 (m, 2H), 1.32-1.19 (m, 8H), 0.86 (t, J=7.0 Hz, 3H); $^{13}$C NMR (100 MHz, CD$_3$OD, major rotamer peaks only) δ 157.5, 150.8, 149.3, 135.3, 97.5, 89.9, 86.1, 75.0, 71.5, 64.7, 62.5, 41.9, 32.9, 30.8, 30.1, 27.7, 23.6, 14.4; HRMS calcd. for C$_{17}$H$_{29}$N$_4$O$_7$ [M+H]$^+$: 401.20308, found: 401.20319.

Example 17

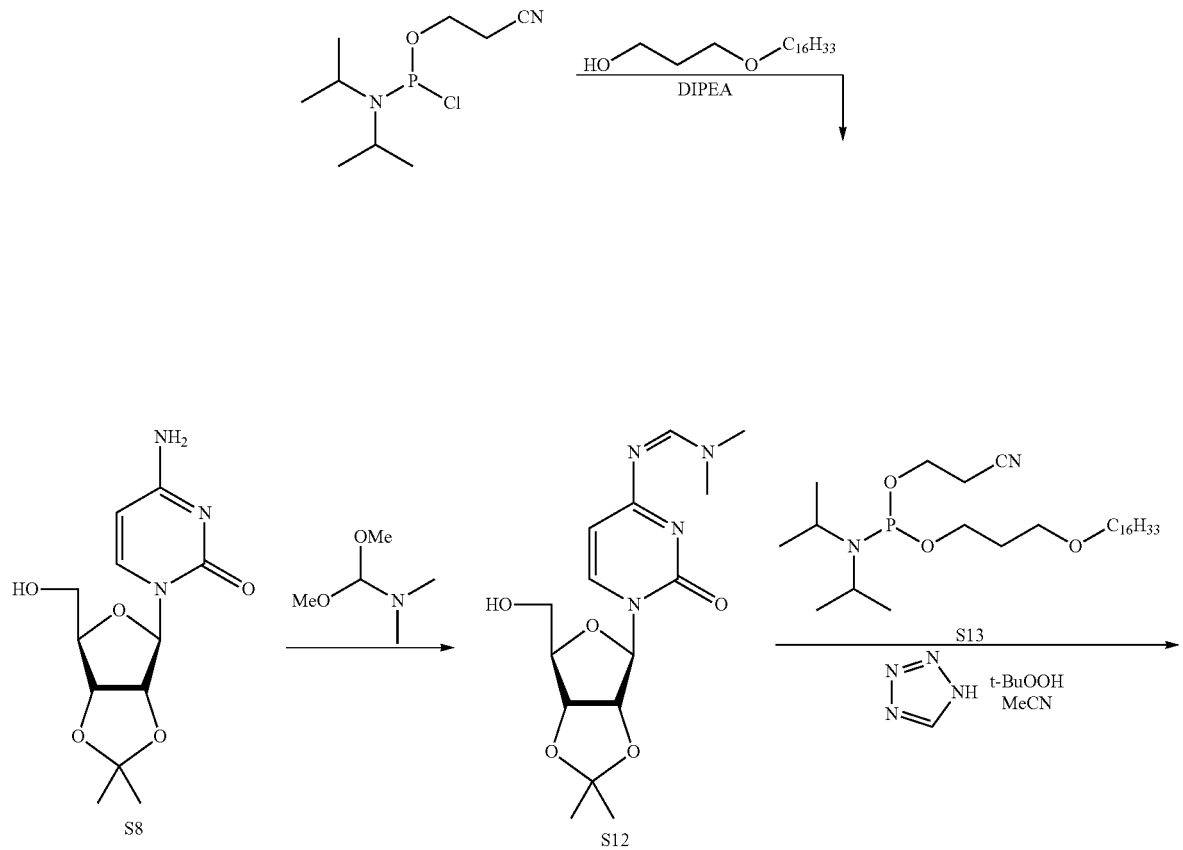

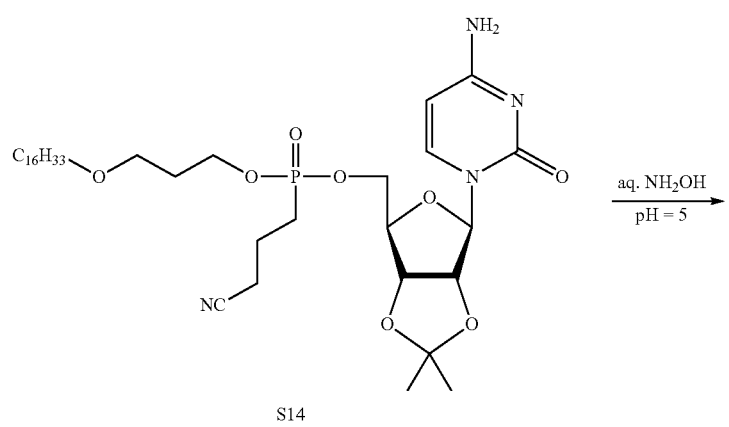

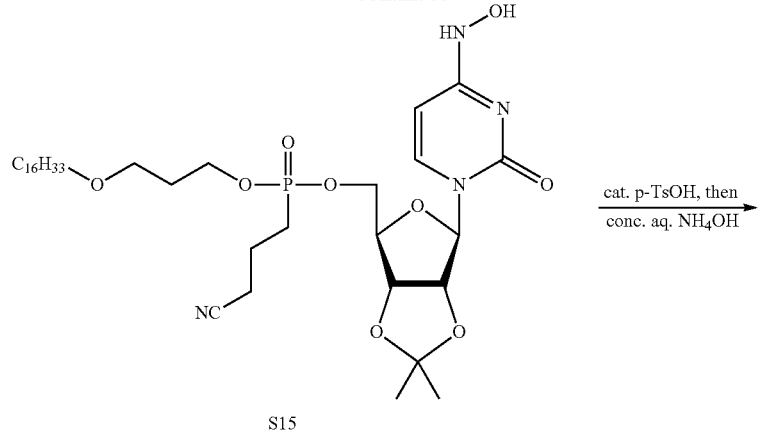

S15

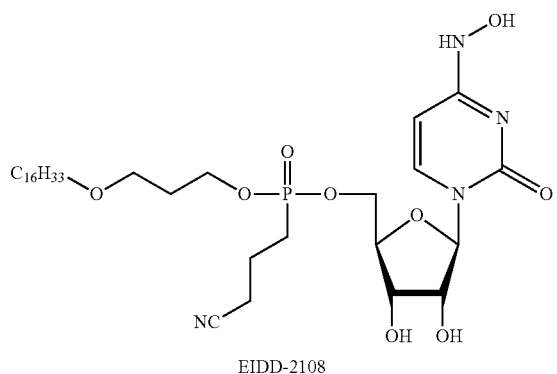

EIDD-2108

S12: A solution of S8 in anhydrous DMF (56 mL) was treated with 1,1-dimethoxy-N,N-dimethylmethanamine (9.4 mL, 70.6 mmol). After 18 h at rt, the reaction mixture was concentrated to dryness and the crude white solid triturated with ether (3×100 mL). The solid was collected by filtration and dried under high vacuum for 12 h to yield S12 (4.52 g, 95%) as a white solid: $^1$H NMR (400 MHz, CD$_3$OD) δ 8.67 (s, 1H), 7.99 (d, J=7.3 Hz, 1H), 6.14 (d, J=7.2 Hz, 1H), 5.87 (d, J=2.4 Hz, 1H), 4.92 (dd, J=6.3, 2.4 Hz, 1H), 4.84 (dd, J=6.3, 3.5 Hz, 1H), 4.25 (q, J=4.7, 1H), 3.81 (dd, J=11.9, 3.6 Hz, 1H), 3.73 (dd, J=11.9, 4.6 Hz, 1H), 3.22 (s, 3H), 3.14 (s, 3H), 1.55 (s, 3H), 1.34 (s, 3H).

S13: A suspension of 3-hexadecyloxypropan-1-ol (1.58 g, 5.26 mmol) and DIPEA (0.92 mL, 5.26 mmol) in anhydrous acetonitrile (25 mL) was treated dropwise over a 10 min period with 3-((chloro(diisopropylamino)phosphino)oxy)-propanenitrile (1.2 mL, 5.26 mmol). After 18 h at rt, the mixture was quenched with sat. aq. NaHCO$_3$ (15 mL) and extracted with ethyl acetate (2×100 mL). The combined organic phases were concentrated by rotary evaporation, and flash chromatography (column volume 25 mm×140 mm, 10 to 20% gradient of EtOAc in hexanes) provided S13 (1.40 g, 53%) as a white solid: $^1$H NMR (400 MHz, CDCl$_3$) δ 3.89-3.54 (m, 6H), 3.49 (t, J=6.3 Hz, 2H), 3.39 (t, J=6.7 Hz, 2H), 2.64 (t, J=6.6 Hz, 2H), 1.87 (p, J=6.3 Hz, 2H), 1.57 (p, J=6.3 Hz, 2H), 1.25 (s, 26H), 1.18 (dd, J=6.8, 3.5 Hz, 12H), 0.87 (t, J=6.6 Hz, 3H); $^{31}$P NMR (162 MHz, CDCl$_3$) δ 147.40.

S14: A solution of S12 (800 mg, 2.36 mmol) and S13 (2.15 g, 4.29 mmol) in anhydrous THF (20 mL) was treated dropwise with a solution of tetrazole (19 mL of a 0.45 M solution in acetonitrile, 8.59 mmol). After 19 h at rt, the mixture was treated dropwise with a nonane solution of tert-butyl hydroperoxide (1.9 mL of a 5.5 M solution, 10.73 mmol) and stirring continued for an additional 1 h. Excess tert-butyl hydroperoxide was quenched with saturated sodium thiosulfate solution (50 mL), the mixture was stirred for 45 min and then extracted with ethyl acetate (2×100 mL). Combined organic phases were concentrated by rotary evaporation, and flash chromatography (25 mm×180 mm column volume, 0 to 5% gradient of MeOH in DCM) gave S14 (1.2 g, 80%) as a foam, a mixture of diastereomers: $^1$H NMR (400 MHz, CDCl$_3$, diastereomeric mixture) δ 7.38 (d, J=7.6 Hz, 1H, diastereomer a), 7.37 (d, J=7.6, 1H, diastereomer b), 5.78 (d, J=7.3 Hz, 1H), 5.54 (d, J=5.6, 1H, diastereomer a), 5.53 (d, J=5.6, 1H, diastereomer b), 5.14 (ddd, J=6.5, 3.1, 1.4 Hz, 1H), 4.93 (dt, J=7.0, 3.6 Hz, 1H), 4.34 (td, J=7.4, 6.8, 4.8 Hz, 3H), 4.28-4.08 (m, 4H), 3.48 (t, J=6.1, 2H), 3.38 (t, J=6.8, 2H), 2.78 (t, J=6.5 Hz, 2H, diastereomer a), 2.75 (t, J=6.5 Hz, 2H diastereomer b), 1.93 (m, 2H), 1.55 (s, 5H), 1.34 (s, 3H), 1.25 (s, 26H), 0.87 (t, J=6.8, 3H); $^{13}$C NMR (101 MHz, CDCl$_3$, diastereomeric mixture) δ 166.26, 155.40, 144.20, 144.16, 116.62, 116.59, 113.93, 97.45, 97.38, 95.74, 95.69, 86.73, 86.64, 86.54, 84.90, 84.80, 81.87, 81.66, 71.23, 67.84, 67.79, 67.69, 67.64, 66.25, 66.22, 66.03, 65.97, 62.08, 62.03, 31.90, 30.51, 30.50, 30.44, 30.43, 29.68, 29.67, 29.64, 29.61, 29.52, 29.34, 27.06, 27.04, 26.13, 25.23, 25.21, 22.67, 19.57, 19.50, 14.12; $^{31}$P NMR (162 MHz, CDCl$_3$, diastereomeric mixture) δ −1.75, −1.83; LRMS m/z 699.4 [M+H]$^+$.

S15: A solution of S14 (310 mg, 0.44 mmol) in THF (4 mL) was treated with an 2M aqueous solution of hydroxylamine at pH 5 (1.1 mL, 2.2 mmol) with stirring at 50° C. After 19 h, TLC (10% methanol in methylene chloride) indicated approximately 50% conversion to a more nonpolar component. Additional hydroxylamine and extended reaction time did not increase conversion beyond 50%. After cooling to rt, the mixture was partitioned between ethyl acetate (100 mL) and brine (10 mL). The organic phase was concentrated, and flash chromatography of the crude (column volume 19 mm×170 mm, 1 to 5% gradient of MeOH in DCM) yielded S15 (70 mg, 22%) as a foam, in a 1:1 mixture of diastereomers: $^1$H NMR (400 MHz, CDCl$_3$) δ 8.94 (s, 1H), 6.60 (d, J=8.1, 1H, diastereomer a), 6.58 (d, J=8.1, 1H, diastereomer b), 5.67 (d, J=8.1, 1H, diastereomer a), 5.65 (d, J=8.1, 1H, diastereomer b), 5.59 (d, J=2.1 Hz, 1H, diastereomer a), 5.55 (d, J=2.1 Hz, 1H, diastereomer b), 4.98 (m, 1H), 4.84 (m, 1H), 4.35-4.10 (m, 6H), 3.48 (t, J=6.1 Hz, 2H), 3.38 (t, J=6.7, 2H), 2.76 (m, 2H), 1.94 (m, 2H), 1.59-1.49 (m, 5H), 1.34 (s, 3H), 1.24 (s, 26H), 0.87 (t, J=6.7 Hz, 3H); $^{31}$P NMR (162 MHz, CDCl$_3$, diastereomeric mixture) δ −1.57, −1.64. LRMS m/z 715.3 [M+H]$^+$.

EIDD-2108: A solution of S15 (62 mg, 0.087 mmol) in methanol (4 mL) was treated with a catalytic amount of para-toluenesulfonic acid (3.3 mg, 0.017 mmol). After 16 h stirring at rt, the mixture was treated with saturated aqueous ammonium hydroxide solution (1.5 mL) and allowed to stir for an additional 4 h at rt. The mixture was concentrated by rotary evaporation, and the resulting residue was triturated with 5% acetonitrile in methanol (2×15 mL). The resulting white solid was purified by flash chromatography (11 mm×45 mm column volume, 25% MeOH in DCM, 2.5% v/v sat. aq. NH$_4$OH) to give the title compound (25 mg, 46%) as a white solid: $^1$H NMR (400 MHz, CD$_3$OD) δ 7.21 (d, J=8.2 Hz, 1H), 5.95 (d, J=5.5 Hz, 1H), 5.67 (d, J=8.2 Hz, 1H), 4.22-4.16 (m, 2H), 4.07-3.98 (m, 3H), 3.94 (q, J=6.3 Hz, 2H), 3.52 (t, J=6.3 Hz, 2H), 3.41 (t, J=6.6 Hz, 2H), 1.87 (p, J=6.3 Hz, 2H), 1.53 (q, J=6.9 Hz, 2H), 1.28 (s, 28H), 0.92-0.85 (m, 3H); $^{13}$C NMR (101 MHz, CD$_3$OD) δ 150.45, 144.99, 130.77, 98.13, 87.51, 83.39, 83.30, 72.98, 70.72, 70.55, 66.89, 64.80, 62.51, 62.46, 31.66, 30.71, 30.63, 29.38, 29.35, 29.24, 29.07, 25.87, 22.33, 13.07; $^{31}$P NMR (162 MHz, CD$_3$OD) δ 0.34; HRMS calcd. for C$_{28}$H$_{51}$N$_3$O$_{10}$P [M−H]$^-$: 620.33175; found, 620.33205.

Example 18

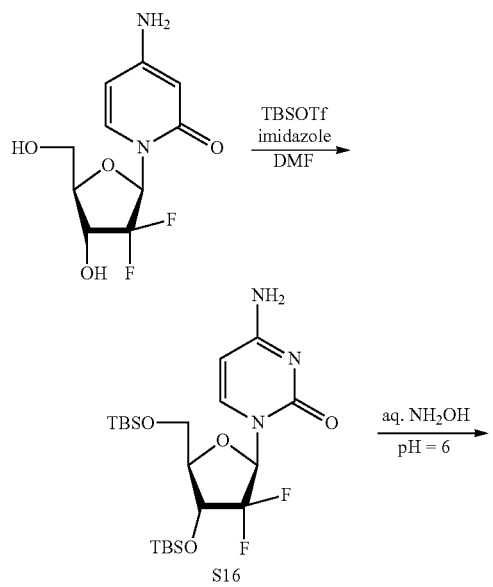

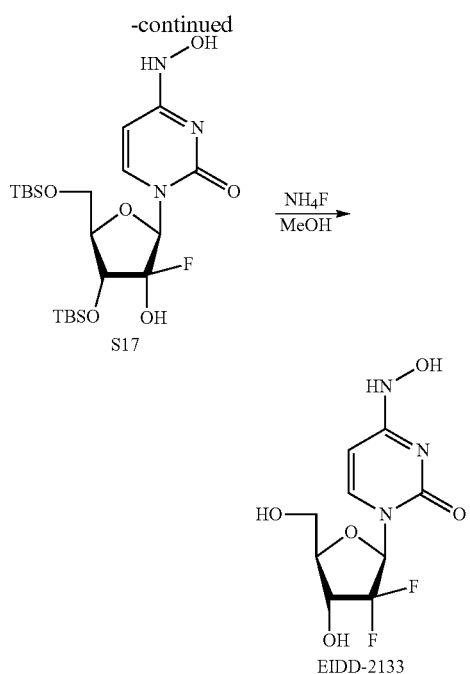

S16: To a solution of 2'-deoxy-2',2'-difluorocytidine (0.526 g, 2.00 mmol) and imidazole (0.408 g, 6.00 mmol) in DMF (10 ml) was added TBS triflate (1.147 ml, 5.00 mmol) at 0° C. under argon. The resulting mixture was stirred at 0° C. for 2 hrs, then it was slowly warmed to rt and stirred overnight. After being partitioned between Et$_2$O and water, the organic layer was separated and washed with H$_2$O and brine, dried over Na$_2$SO$_4$, filtered, and concentrated by rotary evaporation. Automated flash chromatography (24 g column, 0 to 12.5% gradient of MeOH in DCM) yielded S16 (0.71 g, 72%) as a clear colorless oil: $^1$H NMR (400 MHz, CDCl$_3$) δ 8.23 (s, 1H), 7.71 (d, J=7.6 Hz, 1H), 6.72 (s, 1H), 6.25 (dd, J=10.4 Hz, 4.2 Hz, 1H), 5.97 (d, J=7.6 Hz, 1H), 4.30 (m, 1H), 3.98 (m, 1H), 3.89 (m, 1H), 3.79 (dd, J=11.8 Hz, 2.1 Hz, 1H), 0.93 (s, 9H), 0.90 (s, 9H), 0.11 (t, J=4.1 Hz, 12H); $^{13}$C NMR (100 MHz, CDCl$_3$) δ 164.6, 154.6, 140.8, 121.9 (t, J=259 Hz), 95.7, 84.1 (dd, J=40 Hz, 24 Hz), 81.3 (d, J=9 Hz), 77.2, 69.7 (dd, J=28 Hz, 18 Hz), 60.1, 53.4, 25.8, 25.5, 18.3, 18.0, −4.8, −5.3, −5.49, −5.52; $^{19}$F NMR (376 MHz, CDCl$_3$) δ −115.95 (dd, J=238.4 Hz, 12.1 Hz), −117.55 (dt, J=239.1 Hz, 10.7 Hz); HRMS calcd. for C$_{21}$H$_{40}$O$_4$N$_3$F$_2$Si$_2$ [M+H]$^+$: 492.25199, found: 492.25172.

S17: To a solution of S16 (0.250 g, 0.508 mmol) in THF (5.1 mL) was added an aqueous 2N solution of hydroxylamine at pH 6 (6.4 mL, 12.71 mmol), and the resulting mixture was stirred at 55° C. for 1.5 days. After being partitioned between EtOAc and H$_2$O, the aqueous layer was separated and extracted with EtOAc (2×15 mL). The combined organic layers were washed with water and brine, dried over Na$_2$SO$_4$, filtered, and concentrated by rotary evaporation. Automated flash chromatography (24 g column, 0 to 7.5% gradient of MeOH in DCM) provided S17 (0.124 g, 48%) as a white solid: $^1$H NMR (400 MHz, CDCl$_3$) δ 8.69 (s, 1H), 8.34 (s, 1H), 6.94 (d, J=8.2 Hz, 1H), 6.13 (dd, J=11.0 Hz, 4.8 Hz, 1H), 5.62 (d, J=8.3 Hz, 1H), 4.30 (dq, J=12 Hz, 4 Hz, 1H), 3.95 (d, J=12 Hz, 1H), 3.83 (d, J=4 Hz, 1H), 3.77 (dd, J=12 Hz, 4 Hz, 1H), 0.92 (s, 9H), 0.90 (s, 9H), 0.18-0.03 (m, 12H); $^{13}$C NMR (100 MHz, CDCl$_3$) δ 149.1, 144.8, 130.2, 122.1 (t, J=259 Hz), 98.4, 83.4 (dd, J=40 Hz, 24 Hz), 80.8 (d, J=9 Hz), 69.8 (dd, J=27 Hz, 18 Hz), 77.2, 60.0, 25.8, 25.5, 18.3, 18.0, 4.8, −5.3, −5.5, −5.6; $^{19}$F NMR (376 MHz, CDCl$_3$) δ −115.67 (dd, J=239.5 Hz, 12.4 Hz), −117.02 (dt, J=239.4 Hz, 10.8 Hz); HRMS calcd. for C$_{21}$H$_{40}$O$_5$N$_3$F$_2$Si$_2$ [M+H]$^+$: 508.24691, found: 508.24697.

EIDD-2133: A mixture of S17 (0.220 g, 0.433 mmol) and NH$_4$F (0.128 g, 3.47 mmol) in MeOH (22 mL) was stirred under reflux overnight. The mixture was cooled to rt and concentrated by rotary evaporation. Flash chromatography (5 to 10% gradient of MeOH in DCM) gave semipure product. After another two rounds of flash chromatography purification (the desired coeluted with an unknown impurity, only the fractions that could NOT be instantaneously stained by KMnO$_4$ on TLC were collected), the title compound (18 mg, 15% yield) was obtained as a white solid: $^1$H NMR (400 MHz, CD$_3$OD) δ 7.05 (d, J=8.3 Hz, 1H), 6.06 (m, 1H), 5.59 (d, J=8.3 Hz, 1H), 4.21 (m, 1H), 3.90 (d, J=12.6 Hz, 1H), 3.81 (td, J=12 Hz, 4 Hz, 1H), 3.74 (dd, J=12 Hz, 4 Hz, 1H); $^{13}$C NMR (100 MHz, CD$_3$OD) δ 151.1, 145.7, 131.5, 124.1 (t, J=256 Hz), 99.3, 84.8 (dd, J=39 Hz, 26 Hz), 82.0 (d, J=9 Hz), 70.7 (dd, J=26 Hz, 21 Hz), 60.6. $^{19}$F NMR (376 MHz, CD$_3$OD) δ 118.62 (ddd, J=240.2 Hz, 13.4 Hz, 6.1 Hz), −119.67 (broad d, J=240.7 Hz); HRMS calcd. for C$_9$H$_{12}$O$_5$N$_3$F$_2$ [M+H]$^+$: 280.07395, found: 280.07347.

Example 19

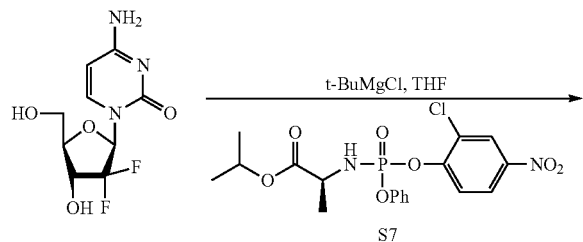

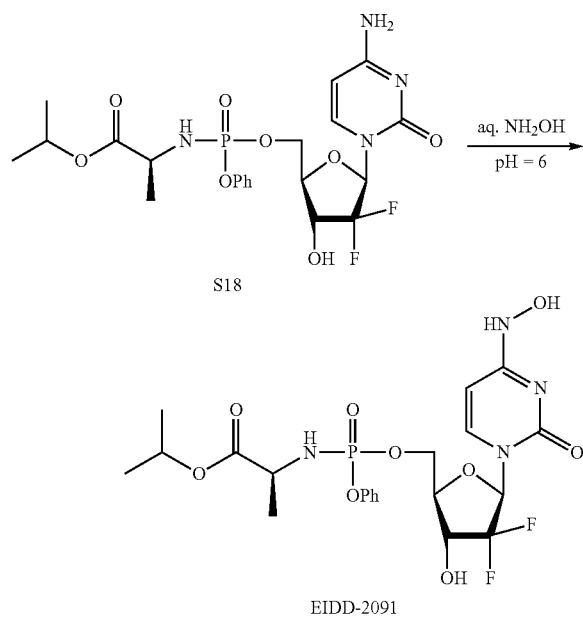

S18: To a suspension of 2'-Deoxy-2',2'-difluorocytidine (0.526 g, 1.998 mmol) in THF (13.32 ml) at 0° C. under nitrogen, was dropwise added via syringe a 1M THF solution of t-butylmagnesium chloride (4.00 mL, 4.00 mmol), and the resulting mixture was stirred at the same temperature for 30 min. A solution of S7 (1.770 g, 4.00 mmol) in THF (13.32 mL) at 0° C. was added dropwise via syringe, the mixture was allowed to warm to rt and was stirred for another 24 hrs. The reaction was cooled to 0° C. and carefully quenched with sat. aq. NH$_4$Cl. The mixture was concentrated by rotary evaporation, and the obtained solid was redissolved in MeOH and filtered through a plug of Celite, rinsing the plug with MeOH. The filtrate was concentrated by rotary evaporation, and automated flash chromatography (40 g column, 0 to 15% gradient of MeOH in DCM) gave S18 (0.620 g, 58%) as a brown foam, as a diastereomeric mixture. $^1$H NMR (400 MHz, CD$_3$OD, diastereomeric mixture) δ 7.60 (dd, J=26.1 Hz, 7.4 Hz, 1H), 7.43-7.30 (m, 2H), 7.31-7.12 (m, 3H), 6.26 (q, J=7.7 Hz, 1H), 5.92 (dd, J=21.2 Hz, 7.2 Hz, 1H), 4.97 (m, 1H), 4.60-4.30 (m, 2H), 4.29-4.15 (m, 1H), 4.10 (m, 1H), 3.88 (m, 1H), 1.33 (t, J=8.0 Hz, 3H), 1.22 (m, 6H); $^{13}$C NMR (100 MHz, CD$_3$OD, diastereomeric mixture) δ 174.61, 174.57, 174.35, 174.30, 167.18, 154.42, 152.15, 152.08, 142.62, 142.52, 139.86, 130.84, 130.20, 126.30, 124.17, 121.49, 121.44, 80.45, 70.18, 69.95, 66.90, 65.69, 51.88, 51.72, 21.97, 21.94, 21.91, 21.89, 21.85, 21.25, 21.19, 20.52, 20.45, 20.34, 20.26, 15.44; $^{19}$F NMR (376 MHz, CD$_3$OD) δ −118.20 (dd, J=238.6 Hz, 73.5 Hz), −120.20 (d, J=237.0 Hz); $^{31}$P NMR (162 MHz, CD$_3$OD) δ 3.81, 3.74; HRMS calcd. for C$_{21}$H$_{28}$O$_8$N$_4$F$_2$P [M+H]$^+$: 533.16073, found: 533.16038.

EIDD-2091: To a suspension of S18 (0.266 g, 0.500 mmol) in THF (5 mL) was added a 2 N aq. Hydroxylamine solution at pH 6 (6.3 ml, 12.49 mmol), and the resulting mixture was stirred at 37° C. for 1.5 days. The reaction (incomplete by TLC) was partitioned between EtOAc and H$_2$O. The aqueous layer was extracted with EtOAc (2×15 mL). The combined organic layers were washed with H$_2$O and brine, dried over Na$_2$SO$_4$, filtered, and concentrated by rotary evaporation. Automated flash chromatography (24 g column, 0 to 10% gradient of MeOH in DCM) provided the title compound (34 mg, 12%) as a white solid, in a mixture of diastereomers. $^1$H NMR (400 MHz, CD$_3$OD, diastereomeric mixture) δ 7.36 (t, J=7.7 Hz, 2H), 7.28-7.12 (m, 3H), 6.78 (t, J=9.0 Hz, 1H), 6.09 (q, J=8 Hz, 1H), 5.55 (dd, J=19.8 Hz, 8.3 Hz, 1H), 4.97 (sept, J=6.3 Hz, 1H), 4.63-4.27 (m, 3H), 4.20 (m, 1H), 4.10-3.96 (m, 1H), 3.95-3.76 (m, 1H), 1.33 (t, J=7.8 Hz, 3H), 1.22 (m, 6H); $^{13}$C NMR (100 MHz, CD$_3$OD, diastereomeric mixture) δ 174.58, 174.54, 174.36, 174.31, 152.14, 152.07, 150.98, 145.48, 131.51, 131.34, 130.83, 126.26, 121.39, 121.37, 121.34, 121.32, 99.77, 85.24, 84.60, 80.02, 79.93, 79.88, 79.78, 71.52, 71.30, 71.05, 70.83, 70.18, 65.78, 65.72, 65.49, 65.44, 51.79, 51.66, 49.64, 49.43, 49.21, 49.00, 48.79, 48.57, 48.36, 21.97, 21.89, 20.54, 20.48, 20.39, 20.31; $^{19}$F NMR (376 MHz, CD$_3$OD) δ −118.04 (dd, J=240.8, 22.2 Hz), −119.47 (d, J=242.6 Hz); $^{31}$P NMR (162 MHz, CD$_3$OD) δ 3.76, 3.69; HRMS calcd. for $C_{21}H_{27}O_8N_4F_2NaP$ [M+Na]$^+$: 571.13759, found: 571.13708.

Example 20 gradient of EtOAc in hexanes) provided S19 (11.24 g, 63.8% yield) as a pale yellow liquid: $^1$H NMR (400 MHz, CDCl$_3$) δ 5.67 (s, 3H), 5.64 (s, 3H), 1.23 (s, 27H); $^{13}$C NMR (100 MHz, CDCl$_3$) δ 176.6, 82.7 (d, J=5 Hz), 38.7, 26.8; $^{31}$P NMR (162 MHz, CDCl$_3$) δ −5.24; HRMS calcd. for $C_{18}H_{33}O_{10}NaP$ [M+Na]$^+$: 463.17035, found: 463.17022.

S20: A solution of S19 in piperidine (51.0 mL, 25.5 mmol) was stirred at rt for 7 hrs. The reaction was concen-

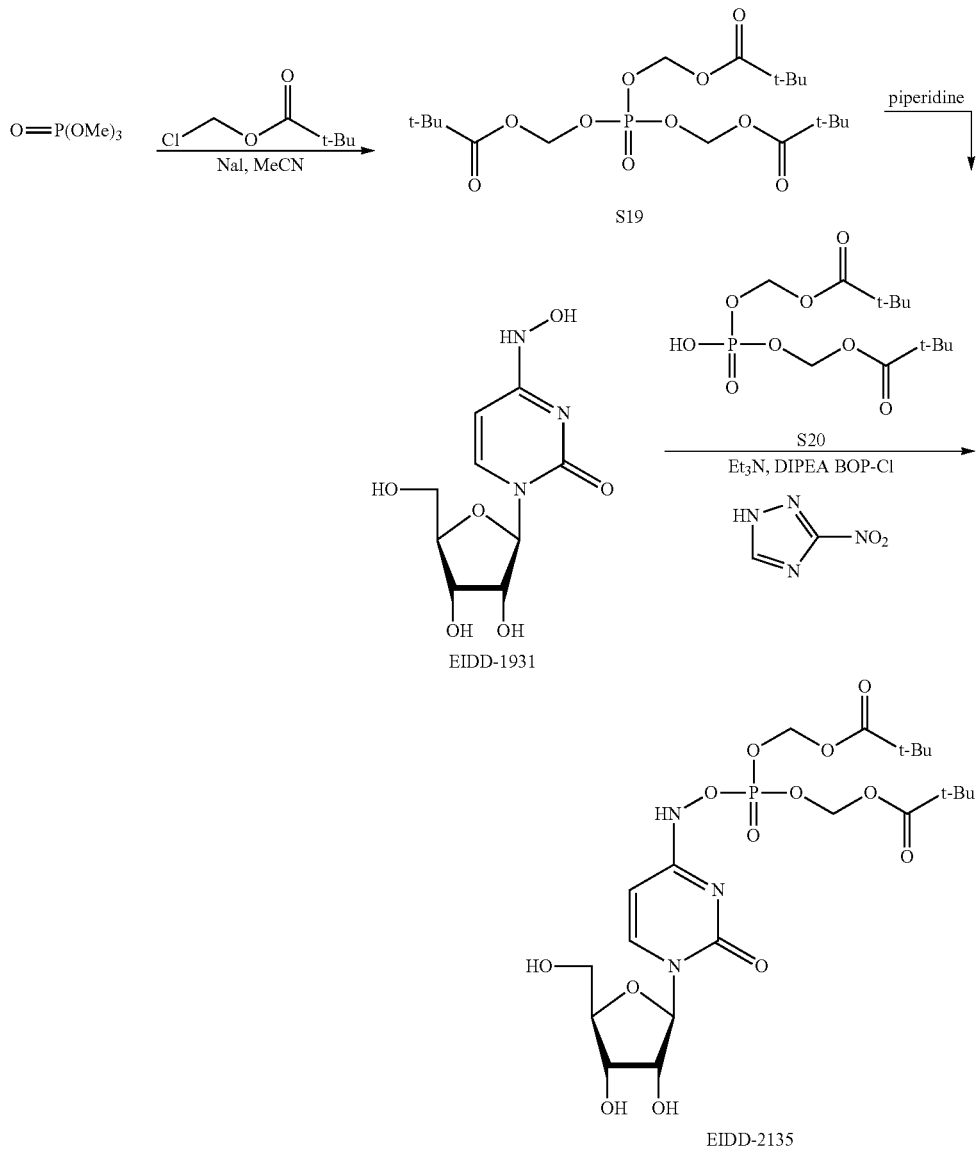

trated by rotary evaporation and then was redissolved in CH$_2$Cl$_2$. The organic solution was washed with ~0.5N ice cold HCl (4×200 mL) and brine, and dried over Na$_2$SO$_4$. After filtrating and concentration by rotary evaporation, the yellow residue was lyophilized to give S19 (8.1 g, 97%) as a light yellow wax: $^1$H NMR (400 MHz, CDCl$_3$) δ 12.20 (s, 1H), 5.61 (s, 2H), 5.57 (s, 2H), 1.21 (s, 18H); $^{13}$C NMR (100 MHz, CDCl$_3$) δ 177.2, 82.7, 38.7, 26.8; $^{31}$P NMR (162 MHz, CDCl$_3$) δ −3.58; Positive mode HRMS calcd. for $C_{12}H_{24}O_8P$ [M+H]$^+$: 327.12033, found: 327.12053; Negative mode HRMS calcd. for $C_{12}H_{22}O_8P$ [M−H]$^−$: 325.10578, found: 325.10568.

S19: To a solution of trimethyl phosphate (4.68 mL, 40.0 mmol) in MeCN (40.0 mL) was sequentially added chloromethyl pivalate (23 mL, 160 mmol) and NaI (17.98 g, 120 mmol). The resulting yellow mixture was stirred under reflux overnight in the presence of 4 Å molecular sieves. Product could be visualized on TLC plate by phosphomolybdic acid. After cooling to r.t., the reaction was filtered through a plug of celite and condensed on rotavap. The obtained yellow residue was redissolved in Et$_2$O, washed with H$_2$O, brine, and finally dried over Na$_2$SO$_4$. The organics were combined and condensed on rotavap to give a brownish-red residue. Flash chromatography (10 to 20%

EIDD-2135: A solution of triethylammonium bis(POM) phosphate was prepared by adding triethylamine (0.362 mL, 2.60 mmol) to a solution of S20 (0.782 g, 2.398 mmol) in THF (8 mL). To a solution of EIDD-1931 (0.518 g, 1.998 mmol) in THF (32 mL) under nitrogen was added the prepared solution of triethylammonium bis(POM)phosphate at rt, then it was cooled to 0° C. DIPEA (1.392 mL, 7.99 mmol), BOP—Cl (1.017 g, 4.00 mmol) and 3-nitro-1H-1,2,4-triazole (0.456 g, 4.00 mmol) were sequentially added to the reaction, and the resulting mixture was stirred at 0° C. for 6 hrs followed by warming to rt and stirring overnight. The reaction mixture was partitioned between EtOAc and saturated aq. $NaHCO_3$. The aqueous layer was extracted with EtOAc, and the combined organic layers were washed with brine, dried over $Na_2SO_4$, filtered, and concentrated by rotary evaporation. Automated flash chromatography (40 g column, 0 to 10% gradient of MeOH in DCM) gave the title compound (30. mg, 2.6%) as a white foam: $^1H$ NMR (400 MHz, CDCl3) δ 10.25 (s, 1H), 7.43 (d, J=8.2 Hz, 1H), 6.83 (d, J=8.1 Hz, 1H), 5.99-5.42 (m, 6H), 4.58-4.00 (m, 5H), 3.89 (m, 2H), 1.21 (s, 18H); $^{31}P$ NMR (162 MHz, $CDCl_3$) δ −4.77, −5.16; HRMS calcd. for $C_{21}H_{34}O_{13}N_3NaP$ [M+Na]$^+$: 590.17215, found: 590.17171.

Example 21

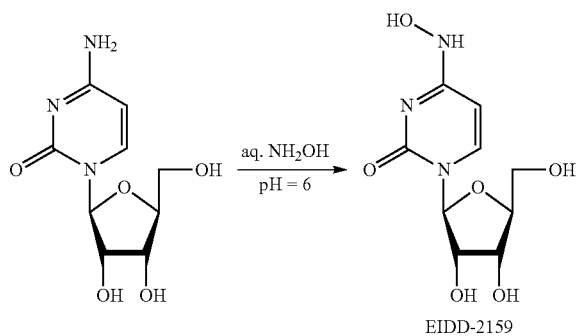

EIDD-2159: A 2 N hydroxylamine (30.0 mL, 60.0 mmol) aqueous solution was made by adjusting a 50% w/w aq. $NH_2OH$ solution with glacial AcOH and then diluting with water to achieve the desired concentration. A sealable pressure vessel was charged with the above solution, L-cytidine (0.486 g, 2.0 mmol), and a stir bar. The vessel was sealed and the mixture was heated at 50° C. for 40 h. The mixture was cooled to rt and concentrated by rotary evaporation. The crude reside was dissolved in water, and automated reverse phase flash chromatography (100 g column, gradient of 100% water to 100% MeCN) gave 300 mg of semipure material as a yellow flaky solid. The compound was taken up in MeOH and immobilized on Celite. Automated flash chromatography (12 g column, gradient of 10 to 25% MeOH in DCM) gave ~150 mg of a white flaky solid containing some occluded solvent. The residue was dissolved in water, frozen in a dry ice/acetone bath, and lyophilized to give the title compound (0.128 g, 0.494 mmol, 25% yield) as an off-white flocculent solid. Spectral analysis showed 90-95% purity; the impurity was unknown and inseparable by chromatography. $^1H$ NMR (400 MHz, $D_2O$) δ 7.04 (d, J=8.3 Hz, 1H), 5.83 (d, J=5.7 Hz, 1H), 5.72 (d, J=8.2 Hz, 1H), 4.27 (t, J=5.5 Hz, 1H), 4.16 (t, J=4.7 Hz, 1H), 4.03 (q, J=3.9 Hz, 1H), 3.80 (dd, J=12.9 Hz, 3.0 Hz, 1H), 3.72 (dd, J=12.9 Hz, 4.2 Hz, 1H); $^{13}C$ NMR (100 MHz, $D_2O$) δ 151.1, 146.5, 131.2, 98.6, 87.8, 83.9, 72.4, 69.7, 60.9; HRMS calcd. for $C_9H_{14}N_3O_6$ [M+H]$^+$: 260.08771, found: 260.08734.

Example 22

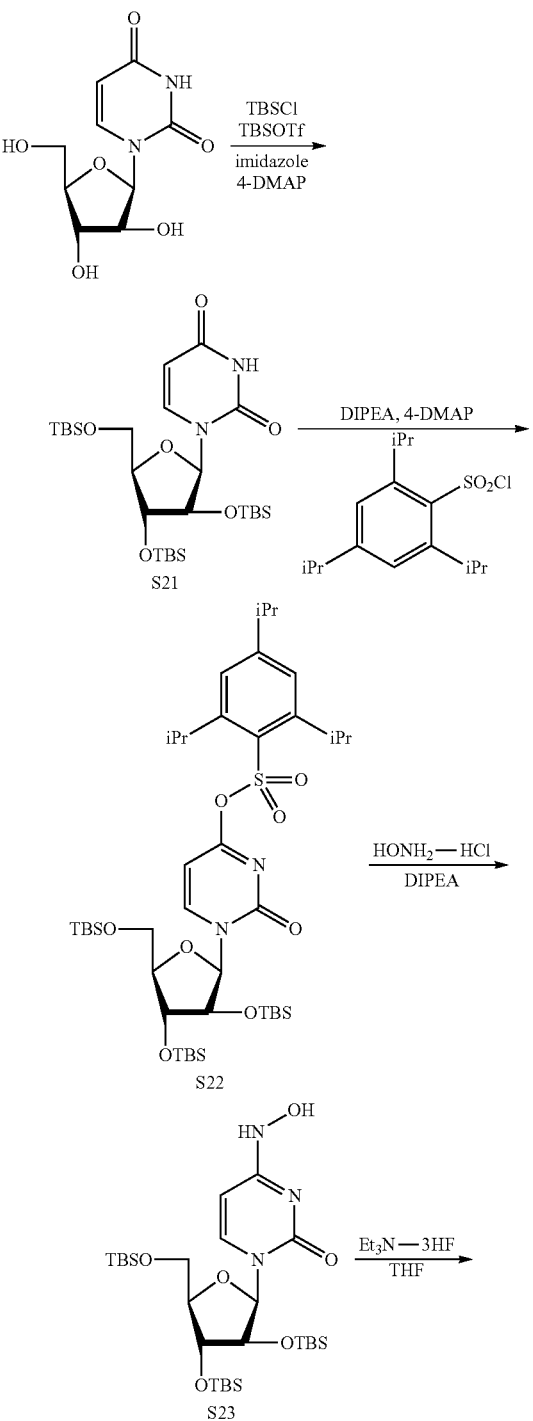

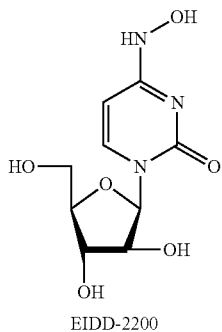

EIDD-2200

S21: A round bottom flask was charged with 1-β-D-arabinofuranosyluracil (4.88 g, 20.0 mmol) and dichloromethane (40 mL). The resulting mixture was cooled to 0° C. and 4-DMAP (0.244 g, 2.00 mmol) and imidazole (5.45 g, 80.0 mmol) were added all at once. TBSCl (12.06 g, 80.0 mmol) was added all at once as a solid, the mixture was warmed to ambient temperature, and stirred for 16 hours. Water (100 mL) was added to the reaction mixture, the layers were separated, and the aqueous layer was extracted with dichloromethane (2×100 mL). The combined organic layers were washed with brine (1×100 mL), dried over $Na_2SO_4$, filtered, and concentrated by rotary evaporation to give ~12 g crude. $^1$H NMR and LCMS analysis showed a 3:1 ratio of bis-silylated to persilylated products. The crude was redissolved in dichloromethane (40 mL), and imidazole (2.04 g, 30.0 mmol) and 4-DMAP (0.122 g, 1.00 mmol) were added all at once. TBS triflate (6.89 mL, 30.0 mmol) was added dropwise via syringe, and the mixture was stirred for 16 hours at ambient temperature. Water (100 mL) was added to the reaction mixture, the layers were separated, and the aqueous layer was extracted with dichloromethane (2×100 mL). The combined organic layers were washed with brine (1×100 mL), dried over $Na_2SO_4$, filtered, and concentrated by rotary evaporation to give ~25 g crude. Automated flash chromatography (330 g column, 5 to 60% gradient of EtOAc in hexanes) gave S21 (2.90 g, 25%) as a clear colorless oil: $^1$H NMR (400 MHz, CDCl$_3$) δ 7.93 (s, 1H), 7.51 (d, J=8.2 Hz, 1H), 6.15 (d, J=3.2 Hz, 1H), 5.67 (dd, J=8.2 Hz, 2.8 Hz, 1H), 4.18 (s, 1H), 4.12 (d, J=3.2 Hz, 1.3 Hz, 1H), 3.97 (dd, J=8.6 Hz, 5.8 Hz, 1H), 3.82 (dd, J=9.8 Hz, 5.7 Hz, 1H), 3.74 (dd, J=9.7 Hz, 8.6 Hz, 1H), 0.92 (s, 9H), 0.91 (s, 9H), 0.84 (s, 9H), 0.13 (s, 3H), 0.12 (s, 3H), 0.09 (s, 3H), 0.08 (s, 3H), 0.07 (s, 3H), −0.06 (s, 3H); LRMS m/z 587.3 [M+H]$^+$, 609.3 [M+Na]$^+$.

S22: To a stirred solution of S21 (2.90 g, 4.94 mmol) and 4-DMAP (0.060 g, 0.49 mmol) in dichloromethane (50 mL) at 0° C. under nitrogen, was added N,N-diisopropylethylamine (4.30 mL, 24.70 mmol) via syringe, followed by solid 2,4,6-triisopropylbenzene-1-sulfonyl chloride (2.99 g, 9.88 mmol) in one portion. The mixture was warmed to ambient temperature and stirred for 4 h, then recooled to 0° C. The mixture was washed with ice-cold sat. aq. NaHCO$_3$ (3×50 mL), dried over Na$_2$SO$_4$, filtered, and concentrated by rotary evaporation. The crude oil was taken up in dichloromethane, and automated flash chromatography (80 g column, 1 to 10% gradient of EtOAc in hexanes) gave S22 (3.30 g, 78%) as a clear colorless oil: $^1$H NMR (400 MHz, CDCl$_3$) δ 7.92 (d, J=7.3 Hz, 1H), 7.20 (s, 2H), 6.10 (d, J=3.0 Hz, 1H), 6.05 (d, J=7.3 Hz, 1H), 4.33-4.23 (m, 3H), 4.14 (s, 1H), 4.01 (dd, J=8.8 Hz, 6.2 Hz, 1H), 3.80 (dd, J=9.6 Hz, 6.2 Hz, 1H), 3.70 (t, J=9.3 Hz, 1H), 2.90 (p, J=7.0 Hz, 1H), 1.32-1.22 (m, 21H), 0.91 (s, 9H), 0.89 (s, 9H), 0.72 (s, 9H), 0.10 (s, 6H), 0.08 (s, 3H), 0.07 (s, 3H), −0.03 (s, 3H), −0.34 (s, 3H).

S23: To a stirred solution of S22 (3.30 g, 3.87 mmol) in acetonitrile (40 mL) under nitrogen at 0° C., was added triethylamine (1.08 mL, 7.73 mmol) via syringe, followed by solid hydroxylamine hydrochloride (0.537 g, 7.73 mmol) in one portion. The mixture was warmed to ambient temperature and stirred 16 h. The mixture was recooled to 0° C., and sat. aq. NaHCO$_3$ (80 mL) was added. The mixture was extracted with dichloromethane (3×80 mL), and the combined organic layers were dried over Na$_2$SO$_4$, filtered, and concentrated by rotary evaporation. The crude was subjected to automated flash chromatography (80 g column, 5 to 20% gradient of EtOAc in dichloromethane) to give semipure material. A second automated flash chromatography (80 g column, 5 to 50% gradient of EtOAc in hexanes) gave S23 (1.17 g, 50%) as a white flaky solid: $^1$H NMR (400 MHz, CDCl$_3$) δ 8.20 (br s, 1H), 6.90 (d, J=8.4 Hz, 1H), 6.42 (s, 1H), 6.12 (d, J=3.4 Hz, 1H), 5.51 (dd, J=8.3 Hz, 1.8 Hz, 1H), 4.15 (br m, 1H), 4.07 (dd, J=3.4 Hz, 1.4 Hz, 1H), 3.91 (dd, J=8.2 Hz, 6.4 Hz, 1H), 3.80 (dd, J=9.8 Hz, 5.6 Hz, 1H), 3.74 (dd, J=9.8 Hz, 8.6 Hz, 1H), 0.91 (s, 9H), 0.90 (s, 9H), 0.86 (s, 9H), 0.12 (s, 3H), 0.11 (s, 3H), 0.08 (s, 3H), 0.07 (s, 6H), −0.02 (s, 3H); LRMS m/z 602.3 [M+H]$^+$.

EIDD-02200: To a stirred solution of S23 (0.602 g, 1.00 mmol) in THF (8 mL) at room temperature under nitrogen, was added triethylamine trihydrofluoride (0.163 mL, 1.00 mmol) dropwise via syringe. The mixture was stirred at ambient temperature for 4 days. Celite was added to the reaction mixture, and rotary evaporation immobilized the crude onto Celite. Automated flash chromatography (24 g column, 5 to 25% gradient of MeOH in dichloromethane) gave 600 mg of semipure product. The mixture was taken up in water, and automated reverse phase flash chromatography (43 g column, 0 to 15% gradient of acetonitrile in water) gave the desired product free from impurities. The solid was dissolved in water, frozen in a dry ice/acetone bath, and lyophilized to provide the title compound (0.164 g, 63% yield) as a white flocculent solid: $^1$H NMR (400 MHz, CD$_3$OD) δ 7.13 (d, J=8.3 Hz, 1H), 6.07 (d, J=4.4 Hz, 1H), 5.51 (d, J=8.3 Hz, 1H), 4.10 (dd, J=4.5 Hz, 1.3 Hz, 1H), 4.03 (t, J=3.4 Hz, 1H), 3.87-3.72 (m, 3H); $^1$H NMR (400 MHz, D$_2$O) δ 7.08 (d, J=8.3 Hz, 1H), 6.09 (d, J=5.6 Hz, 1H), 5.67 (d, J=8.3 Hz, 1H), 4.33 (t, J=5.4 Hz, 1H), 4.06 (t, J=5.6 Hz, 1H), 3.89-3.86 (m, 2H), 3.76 (dd, J=13.1 Hz, 6.1 Hz, 1H); $^{13}$C NMR (100 MHz, D$_2$O) δ 150.9, 146.8, 132.8, 97.0, 84.1, 82.1, 75.8, 74.8, 60.4; LRMS m/z 260.1 [M+H]$^+$.

Example 23

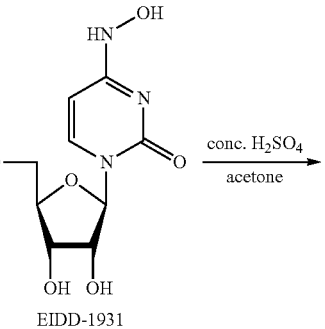

EIDD-1931

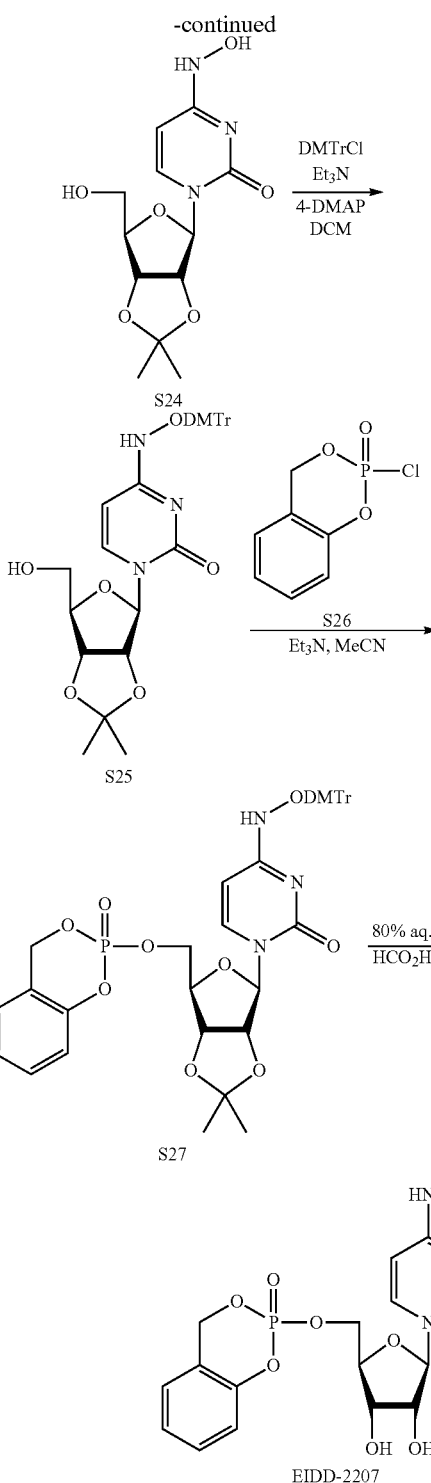

(d, J=3.2 Hz, 1H), 5.58 (d, J=8.2 Hz, 1H), 4.86 (dd, J=6.5 Hz, 3.2 Hz, 1H), 4.79 (dd, J=6.4 Hz, 3.6 Hz, 1H), 4.10 (q, J=4.0 Hz, 1H), 3.75 (dd, J=11.9 Hz, 3.7 Hz, 1H), 3.70 (dd, J=12.0 Hz, 4.5 Hz, 1H), 1.54 (s, 3H), 1.35 (s, 3H).

S25: To a stirred suspension of S24 (0.831 g, 2.78 mmol) in dichloromethane (14 mL) at room temperature under nitrogen, was added triethylamine (0.58 mL, 4.16 mmol) and 4-DMAP (3.4 mg, 0.028 mmol), and the mixture was stirred at room temperature for 15 min. A solution of 4,4'-dimethoxytrityl chloride (0.988 g, 2.92 mmol) in dichloromethane (14 mL) was added dropwise, and the mixture was stirred overnight at room temperature. The reaction mixture was washed with brine (1×30 mL), dried over $Na_2SO_4$, filtered, and concentrated by rotary evaporation. Flash chromatography (9:1 hexanes:EtOAc, 2.5% v/v $Et_3N$) gave S25 (1.39 g, 83%) as a yellow foam: $^1$H NMR (400 MHz, $CD_3OD$) δ 7.35-7.20 (m, 10H), 7.01 (d, J=8.3 Hz, 1H), 6.85-6.80 (m, 4H), 5.80 (d, J=3.0 Hz, 1H), 5.52 (d, J=8.2 Hz, 1H), 4.84 (dd, J=6.4 Hz, 3.0 Hz, 1H), 4.77 (dd, J=6.4 Hz, 3.6 Hz, 1H), 4.10 (q, J=4.0 Hz, 1H), 3.73 (dd, J=11.9 Hz, 3.6 Hz, 1H), 3.68 (dd, J=12.0 Hz, 4.6 Hz, 1H), 1.53 (s, 3H), 1.34 (s, 3H).

S27: To a stirred solution of S26 (0.523 g, 2.56 mmol) and N,N-diisopropylethylamine (0.46 mL, 2.64 mmol) in acetonitrile (5 mL) at 0° C. under nitrogen, was added S25 (0.300 g, 0.499 mmol). The resulting mixture was warmed to room temperature and stirred 22 h, then diluted with EtOAc (50 mL), washed with brine (2×50 mL), dried over $Na_2SO_4$, and concentrated by rotary evaporation. The crude residue was taken directly to the next step without further purification.

EIDD-2207: The entirety of the crude S27 prepared in the previous step was mixed with 80% w/w aq. formic acid (10 mL), and the mixture was stirred at room temperature for 20 hours. The mixture was concentrated by rotary evaporation, and automated flash chromatography (40 g column, 0 to 15% gradient of methanol in dichloromethane) gave the title compound (0.104 g, 48% over 2 steps) as a yellow foam, in a ~1:1 diastereomeric mixture at phosphorus: $^1$H NMR (400 MHz, $CD_3OD$, diastereomeric mixture) δ 7.41-7.35 (m, 1H), 7.26-7.18 (m, 2H), 7.12 (d, J=8.3 Hz, 1H), 6.75 (d, J=8.3 Hz, 0.5×1H), 6.69 (d, J=8.3 Hz, 0.5×1H), 5.79 (d, J=4.8 Hz, 0.5×1H), 5.75 (d, J=4.8 Hz, 0.5×1H), 5.54-5.42 (m, 2H), 5.46 (d, J=8.2 Hz, 0.5×1H), 5.32 (d, J=8.2 Hz, 0.5×1H), 4.56-4.25 (m, 2H), 4.13-4.02 (m, 3H); $^{31}$P NMR (162 MHz, $CD_3OD$, diastereomeric mixture) δ −9.13, −9.33; HRMS calcd. for $C_{16}H_{18}N_3O_9PNa$ [M+Na]$^+$: 450.06729; found: 450.06777.

Example 24

S24: To a stirred suspension of EIDD-1931 (1.25 g, 4.82 mmol) in dry acetone (60 mL) under nitrogen at room temperature was added conc. $H_2SO_4$ (0.05 mL, 0.964 mmol), and the mixture was stirred at room temperature overnight. The acid was neutralized by addition of triethylamine (0.27 mL, 1.93 mmol), and the mixture was concentrated by rotary evaporation. Automated flash chromatography (80 g column, 0 to 10% gradient of methanol in dichloromethane) gave S24 (0.831 g, 58%) as a white solid: $^1$H NMR (400 MHz, $CD_3OD$) δ 7.03 (d, J=8.2 Hz, 1H), 5.81

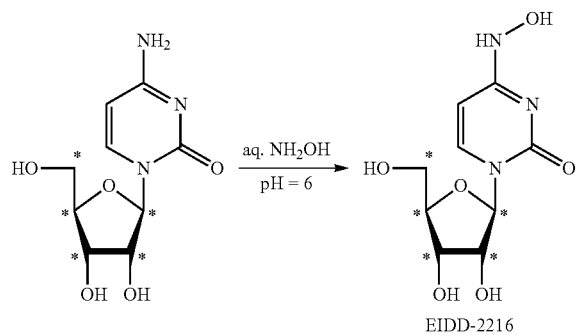

EIDD-2216: A ~5 N solution of hydroxylamine hydrochloride (4.71 g, 67.8 mmol) in water (13.5 mL) was prepared, and adjusted to pH=6 with a small amount of aq. NaOH (10% w/w). A sealable pressure tube was charged with this solution and [1',2',3',4',5'-$^{13}C_5$]cytidine (0.661 g, 2.26 mmol), the flask was sealed, and heated with stirring at 37° C. for 16 h. The mixture was cooled to room temperature, transferred to a round bottom flask, and concentrated by rotary evaporation. The crude material was taken up in water, and automated reverse phase flash chromatography (240 g C18 column, 0 to 100% gradient of acetonitrile in water) removed bulk impurities to give 1.4 g of a wet solid. This solid was dissolved in water, and a second automated reverse phase chromatography (240 g C18 column, 0 to 100% gradient of acetonitrile in water) removed more impurities to give 400 mg semipure material. The material was dissolved in MeOH and immobilized on Celite. Automated flash chromatography (24 g column, 5 to 25% gradient of MeOH in dichloromethane) gave ~200 mg of nearly pure product. The solid was dissolved in water, and a final automated reverse phase chromatography (48 g C18 column, 0 to 100% gradient of acetonitrile in water) gave the desired product free from organic and inorganic impurities. The solid was dissolved in water, frozen in a dry ice/acetone bath, and lyophilized to provide the title compound (0.119 g, 20%) as a pale purple flocculent solid, ~95% pure by NMR/LCMS analysis: $^1$H NMR (400 MHz, D$_2$O) δ 7.03 (dd, J=8.2 Hz, 2.2 Hz, 1H), 5.82 (ddd, J=167.5 Hz, 5.3 Hz, 2.9 Hz, 1H), 5.70 (d, J=8.2 Hz, 1H), 4.47-4.30 (br m, 1H), 4.23-4.03 (br m, 1H), 4.00-3.80 (br m, 2H), 3.65-3.50 (br m, 1H); $^{13}$C NMR (100 MHz, D$_2$O) δ 151.3, 146.6, 131.3, 98.7, 87.9 (dd, J=43.1 Hz, 4.0 Hz), 84.0 (dd, J=41.5 Hz, 38.0 Hz), 72.5 (dd, J=43.3 Hz, 37.8 Hz), 69.8 (td, J=37.9 Hz, 3.9 Hz), 61.1 (d, J=41.5 Hz); LRMS m/z 265.1 [M+H]$^+$.

Example 25

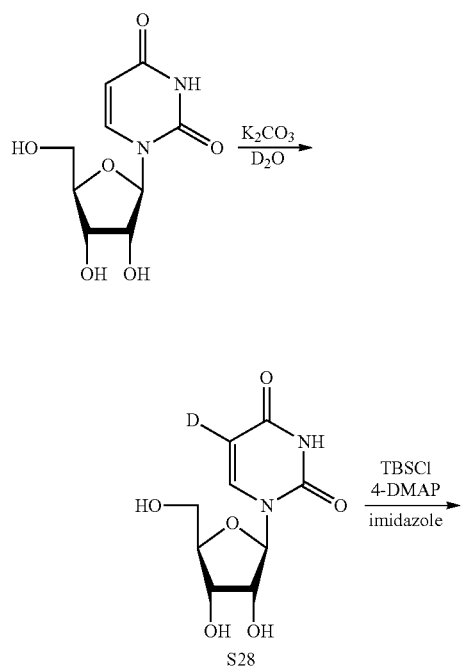

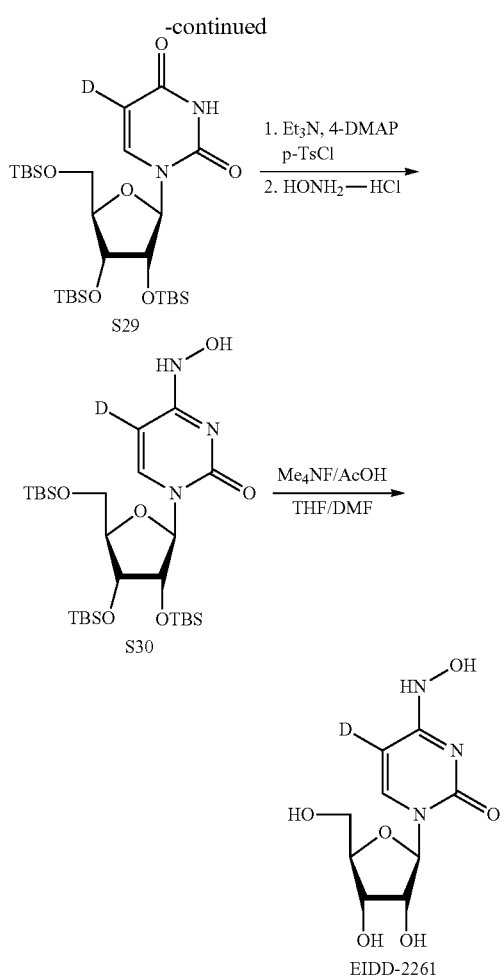

S28: A sealable pressure tube was charged with uridine (1.00 g, 4.09 mmol), K$_2$CO$_3$ (0.679 g, 4.91 mmol), and deuterium oxide (8.2 mL). The mixture was purged with nitrogen for 15 minutes, the tubed was sealed, and the contents were heated with stirring at 95° C. for 16 h. The mixture was cooled to rt, the tube was unsealed, and the mixture was transferred to a round-bottom flask and concentrated by rotary evaporation. The resulting crude was coevaporated with MeOH (×3) to remove water. NMR analysis showed >95% deuterium incorporation at the 5-position on the nucleobase. The light brown solid S28 (1.00 g, 100%) was used in the next step without further purification: $^1$H NMR (400 MHz, CD$_3$OD) δ 7.76 (s, 1H), 5.88 (d, J=4.2 Hz, 1H), 4.17-4.12 (m, 2H), 4.00-3.96 (m, 1H), 3.84 (dd, J=12.3 Hz, 2.8 Hz, 1H), 3.72 (dd, J=12.3 Hz, 3.5 Hz, 1H); $^{13}$C NMR (100 MHz, CD$_3$OD) δ 185.6, 177.4, 160.4, 141.1, 91.8, 85.8, 75.9, 71.2, 62.4.

S29: A round bottom flask was charged with S28 (1.00 g, 4.09 mmol) and dichloromethane (8 mL) under nitrogen. The resulting mixture was cooled to 0° C. and 4-DMAP (0.050 g, 0.408 mmol) and imidazole (1.11 g, 16.3 mmol) were added all at once. TBSCl (2.15 g, 14.3 mmol) was added all at once as a solid, the mixture was warmed to ambient temperature, and stirred for 16 hours. Water (25 mL) was added to the reaction mixture, the layers were separated, and the aqueous layer was extracted with dichloromethane (2×25 mL). The combined organic layers were washed with brine (1×25 mL), dried over Na$_2$SO$_4$, filtered, and concentrated by rotary evaporation. Automated flash chromatography (40 g column, 0 to 35% gradient of EtOAc in hexanes) gave S29 (2.52 g, 84%) as an off-white foam: ¹H NMR (400 MHz, CDCl₃) δ 8.08 (br s, 1H), 8.03 (s, 1H), 5.89 (d, J=3.6 Hz, 1H), 4.12-4.06 (m, 3H), 3.99 (dd, J=11.5 Hz, 1.8 Hz, 1H), 3.76 (d, J=12.0 Hz, 1H), 0.96 (s, 9H), 0.92 (s, 9H), 0.90 (s, 9H), 0.14 (s, 3H), 0.13 (s, 3H), 0.10 (s, 3H), 0.09 (s, 3H), 0.08 (s, 3H), 0.07 (s, 3H); ¹³C NMR (100 MHz, CDCl₃) δ 163.7, 150.3, 140.3, 89.0, 84.3, 76.1, 70.5, 61.6, 26.0 (3C), 25.8 (3C), 25.7 (3C), 18.4, 18.3, 17.9, −4.2, −4.6, −4.8, −4.9, −5.4, −5.6; HRMS calcd. for C₂₇H₅₄DN₂NaO₆Si [M+Na]⁺: 610.32446, found: 610.32482.

S30: To a stirred solution of S29 (0.840 g, 1.43 mmol) in acetonitrile (14.3 mL) at 0° C. under nitrogen, were added sequentially p-toluenesulfonyl chloride (0.545 g, 2.86 mmol), 4-DMAP (0.175 g, 1.43 mmol), and triethylamine (0.80 mL, 5.71 mmol). The mixture was stirred at 0° C. for 2.5 h, at which time hydroxylamine hydrochloride (0.993 g, 14.3 mmol) was added all at once as a solid. The mixture was heated at 50° C. for 3 days, then cooled to rt. The reaction mixture was diluted with EtOAc (100 mL), then washed with water (2×100 mL) and brine (1×100 mL), dried over Na₂SO₄, filtered, and concentrated by rotary evaporation. Automated flash chromatography (40 g column, 5 to 35% gradient of EtOAc in hexanes) produced a mixture of starting material and desired product. A second automated flash chromatography (24 g column, 10 to 40% gradient of EtOAc in hexanes), gave S30 (0.332 g, 39%) as an off-white foam: ¹H NMR (400 MHz, CDCl₃) δ 8.37 (br s, 1H), 5.92 (d, J=4.6 Hz, 1H), 4.10-4.05 (m, 2H), 4.04-4.00 (m, 1H), 3.91 (dd, J=11.6 Hz, 2.4 Hz, 1H), 3.73 (dd, J=11.6 Hz, 1.8 Hz, 1H), 0.95 (s, 9H), 0.92 (s, 9H), 0.89 (s, 9H), 0.12 (s, 6H), 0.10 (s, 3H), 0.08 (s, 3H), 0.06 (s, 3H), 0.05 (s, 3H).

EIDD-2261: A round bottom flask was charged with S30 (0.332 g, 0.551 mmol), tetramethylammonium fluoride (0.196 g, 2.64 mmol), THF (8.25 mL), and DMF (2.75 mL) under nitrogen at 0° C. Acetic acid (0.157 mL, 2.75 mmol) was added all at once via syringe. The mixture was warmed to 45° C. and heated with stirring for 4 days, then concentrated by rotary evaporation. Automated flash chromatography (40 g column, 0 to 20% gradient of MeOH in DCM) gave the title compound (0.106 g, 74%) as a white solid. Final NMR analysis showed >95% deuterium incorporation at the 5-position of the nucleobase: ¹H NMR (400 MHz, D₂O) δ 7.16 (s, 1H), 5.85 (d, J=5.6 Hz, 1H), 4.14 (t, J=5.5 Hz, 1H), 4.10 (dd, J=5.6 Hz, 3.8 Hz, 1H), 3.93 (q, J=3.4 Hz, 1H), 3.77 (dd, J=12.2 Hz, 2.9 Hz, 1H), 3.68 (dd, J=12.2 Hz, 3.4 Hz, 1H); ¹³C NMR (100 MHz, CD₃OD) δ 151.8, 146.3, 132.1, 89.7, 86.1, 74.6, 71.8, 62.8; HRMS calcd. for C₉H₁₃DN₃O₆ [M+H]⁺: 261.09399, found: 261.09371.

Example 26

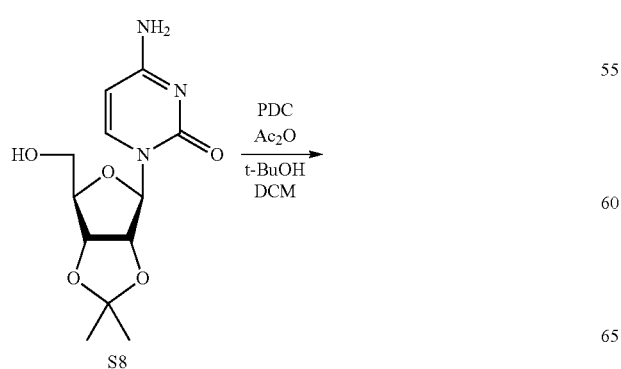

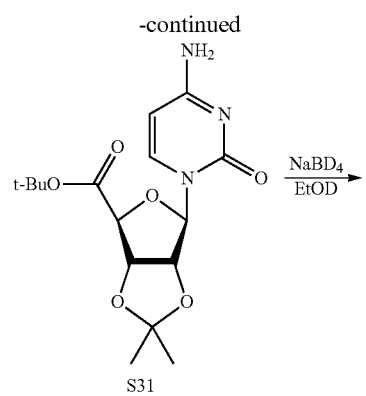

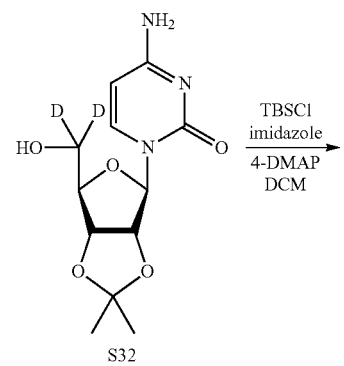

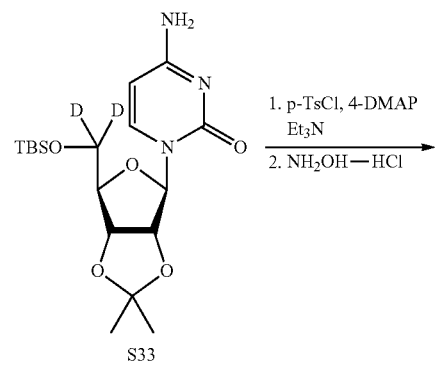

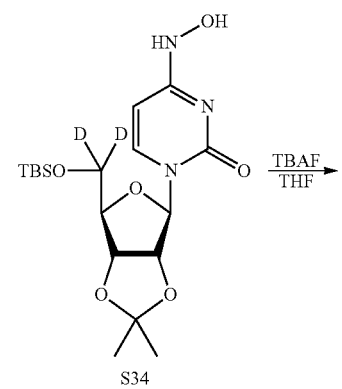

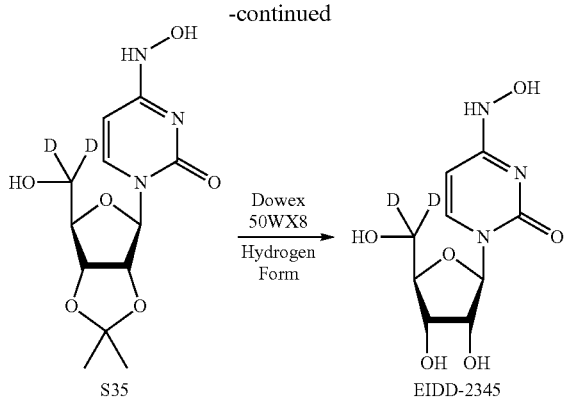

S31: A round bottom flask was charged with S8 (3.13 g, 11.0 mmol) and dichloromethane (75 mL) under nitrogen at room temperature. To this stirred mixture was added sequentially pyridinium dichromate (8.28 g, 22.0 mmol), acetic anhydride (10.4 mL, 110 mmol) and t-butanol (21.1 mL, 220 mmol) at room temperature. The mixture was stirred for 22 hours at room temperature, then washed with water (1×75 mL). The aqueous layer was extracted with dichloromethane (2×75 mL) and the combined organic layers were washed with brine (1×100 mL), dried over $Na_2SO_4$, filtered, and concentrated by rotary evaporation. The obtained residue was taken up in EtOAc and filtered through a Celite plug, followed by washing with EtOAc. The filtrate was concentrated by rotary evaporation, and automated flash chromatography (120 g column, 40 to 80% gradient of EtOAc in hexanes) gave S31 (3.10 g, 72%) as an off-white foam: $^1$H NMR (400 MHz, CDCl$_3$) δ 8.36 (br s, 1H), 7.42 (d, J=8.0 Hz, 1H), 5.76 (dd, J=8.0 Hz, 2.3 Hz, 1H), 5.59 (s, 1H), 5.27 (dd, J=6.0 Hz, 1.8 Hz, 1H), 5.19 (d, J=6.0 Hz, 1H), 4.62 (d, J=1.8 Hz, 1H), 1.56 (s, 3H), 1.48 (s, 9H), 1.39 (s, 3H).

S32: To a stirred solution of S31 (2.61 g, 7.37 mmol) in EtOD (75 mL) at room temperature under nitrogen, was added NaBD$_4$ (1.234 g, 29.5 mmol) in one portion. The mixture was stirred at room temperature for 1 hour, heated to 55° C. for 6 hours, then overnight at room temperature. The mixture was cooled to 0° C. and excess reagent was quenched with AcOD. The mixture was concentrated by rotary evaporation to give crude S32 (2.57 g) which was taken directly on to the next step without further purification.

S33: To a stirred suspension of crude S32 (2.00 g impure material, ~5.74 mmol) in dichloromethane (70 mL) at 0° C., was added solid imidazole (1.90 g, 27.9 mmol) and 4-DMAP (0.171 g, 1.40 mmol). Solid t-butyldimethylsilyl chloride (2.11 g, 14.0 mmol) was added, and the mixture was warmed to room temperature and stirred for 4 days. The mixture was washed sequentially with water and brine (1×70 mL each), dried over $Na_2SO_4$, filtered, and concentrated by rotary evaporation. Automated flash chromatography (120 g column, 0 to 35% gradient of EtOAc in hexanes) gave S33 (1.42 g, 66% over 2 steps) as a white solid: $^1$H NMR (400 MHz, CDCl$_3$) δ 8.30 (br s, 1H), 7.72 (m, 1H), 5.99 (d, J=2.8 Hz, 1H), 5.69 (dd, J=8.2 Hz, 2.3 Hz, 1H), 4.77 (dd, J=6.1 Hz, 2.9 Hz, 1H), 4.69 (dd, J=6.2 Hz, 2.8 Hz, 1H), 4.33 (d, J=3.0 Hz, 1H), 1.60 (s, 3H), 1.37 (s, 3H), 0.91 (s, 9H), 0.11 (s, 3), 0.10 (s, 3H); $^{13}$C NMR (100 MHz, CDCl$_3$) δ 162.7, 149.9, 140.5, 114.1, 102.1, 91.9, 86.5, 85.4, 80.3, 27.4, 25.9 (3C), 25.4, 18.4, −5.4, −5.5; HRMS calcd. for $C_{18}H_{29}D_2N_2O_6Si$ [M+H]$^+$: 401.20714, found: 401.20663.

S34: To a stirred solution of S33 (1.42 g, 3.55 mmol) in acetonitrile (35 mL) at 0° C. under nitrogen, was added sequentially p-toluenesulfonyl chloride (1.35 g, 7.09 mmol), 4-DMAP (0.433 g, 3.55 mmol), and triethylamine (9.88 mL, 70.9 mmol). The resulting mixture was stirred at 0° C. for 2.5 hours. Hydroxylamine hydrochloride (2.46 g, 35.5 mmol) was added, and the mixture was heated with stirring at 50° C. for 2 days. The mixture was recooled to rt and diluted with EtOAc (100 mL), then washed with water (2×50 mL) and brine (1×50 mL), dried over $Na_2SO_4$, filtered, and concentrated by rotary evaporation. Automated flash chromatography (120 g column, 1 to 3.5% gradient of methanol in dichloromethane) gave S34 (0.416 g, 28%) as an off-white solid: $^1$H NMR (400 MHz, CDCl$_3$) δ 8.36 (br s, 1H), 7.00 (m, 1H), 5.97 (d, J=3.1 Hz, 1H), 5.58 (d, J=8.2 Hz, 1H), 4.77 (dd, J=6.2 Hz, 3.2 Hz, 1H), 4.68 (dd, J=6.3 Hz, 3.2 Hz, 1H), 4.22 (d, J=3.2 Hz, 1H), 1.59 (s, 3H), 1.36 (s, 3H), 0.92 (s, 9H), 0.11 (s, 3H), 0.10 (s, 3H); $^{13}$C NMR (100 MHz, CDCl$_3$) δ 149.0, 145.4, 131.4, 114.1, 98.3, 90.8, 85.5, 84.5, 80.2, 27.4, 25.9 (3C), 25.5, 18.4, −5.4, −5.5; HRMS calcd. for $C_{18}H_{29}D_2N_3O_6Si$ [M+H]$^+$: 416.21804, found: 416.21827.

S35: To a stirred solution of S34 (0.416 g, 1.00 mmol) in THF (5 mL) at 0° C. under nitrogen, was added a 1.0 M THF solution of TBAF (1.50 mL, 1.5 mmol), and the resulting mixture was kept at 0° C. for 24 hours. The reaction mixture was concentrated by rotary evaporation, and automated flash chromatography (40 g column, 0 to 8% gradient of methanol in dichloromethane) gave S35 (0.257 g, 85%) as a white solid: $^1$H NMR (400 MHz, CD$_3$OD) δ 7.02 (m, 1H), 5.81 (d, J=3.2 Hz, 1H), 5.58 (d, J=8.2 Hz, 1H), 4.86 (dd, J=6.4 Hz, 3.2 Hz, 1H), 4.79 (dd, J=6.5 Hz, 3.6 Hz, 1H), 4.09 (d, J=3.7 Hz, 1H), 1.54 (s, 3H), 1.34 (s, 3H); $^{13}$C NMR (100 MHz, CD$_3$OD) δ 151.3, 146.2, 133.4, 115.2, 99.4, 92.9, 87.2, 84.9, 82.1, 27.6, 25.6; HRMS calcd. for $C_{12}H_{16}D_2N_3O_6$ [M+H]$^+$: 302.13157, found: 302.13130.

EIDD-2345: To a stirred solution of S35 (0.140 g, 0.465 mmol) in methanol (8.4 mL) and water (0.93 mL) at room temperature, was added Dowex 50WX8 hydrogen form (0.30 g), and the mixture was stirred at room temperature for 24 hours. The reaction mixture was filtered, and the filtrate was concentrated by rotary evaporation. Automated flash chromatography (40 g column, 5 to 20% gradient of methanol in dichloromethane) gave the title compound (0.050 g, 41%) as an off-white solid: $^1$H NMR (400 MHz, CD$_3$OD) δ 7.17 (m, 1H), 5.86 (d, J=5.6 Hz, 1H), 5.60 (d, J=8.2 Hz, 1H), 4.15 (t, J=5.5 Hz, 1H), 4.11 (dd, J=5.6 Hz, 3.5 Hz, 1H), 3.94 (d, J=3.8 Hz, 1H); $^{13}$C NMR (100 MHz, CD$_3$OD) δ 151.8, 146.3, 132.2, 99.3, 89.7, 86.0, 74.6, 71.7, HRMS calcd. for $C_9H_{10}D_2N_3O_6$ [M+H]$^+$: 260.08571, found: 260.08578.

Example 27

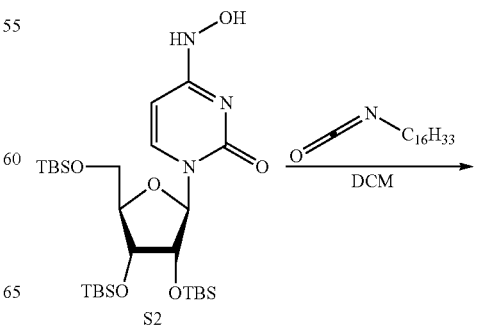

95
-continued

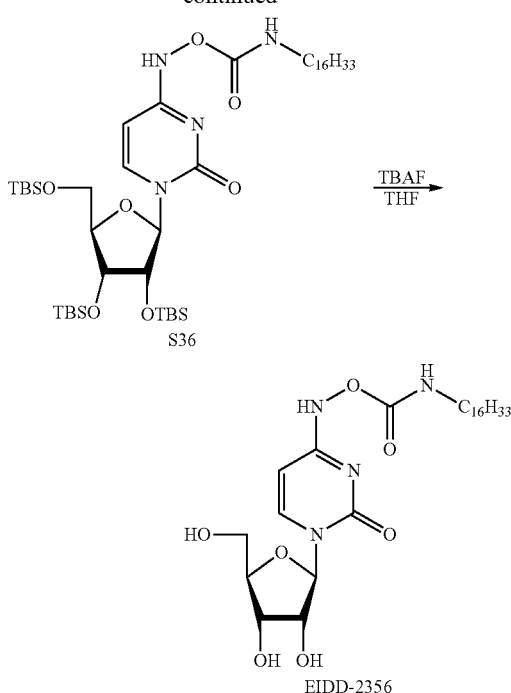

S36

EIDD-2356

S36: To a stirred solution of S2 (0.090 g, 0.150 mmol) in DCM (1.5 mL) under nitrogen at rt, was added hexadecyl isocyanate (0.051 mL, 0.165 mmol) dropwise via syringe over 2 minutes. The reaction was stirred at rt for 4 h, then concentrated by rotary evaporation to give crude residue. Automated flash chromatography (12 g column, 0 to 20% gradient of EtOAc in hexanes) gave S36 (0.120 g, 92%) as an off-white foam: $^1$H NMR (400 MHz, CDCl$_3$) δ 8.27 (br s, 1H), 7.51 (d, J=8.4 Hz, 1H), 6.29 (t, J=5.8 Hz, 1H), 5.90 (d, J=4.5 Hz, 1H), 5.57 (dd, J=8.2 Hz, 2.2 Hz, 1H), 4.09-4.02 (m, 3H), 3.93 (dd, J=11.7 Hz, 2.2 Hz, 1H), 3.73 (dd, J=11.6 Hz, 1.6 Hz, 1H), 3.27 (q, J=6.6 Hz, 2H), 1.56 (m, 2H), 1.26 (br s, 28H), 0.95 (s, 9H), 0.91 (s, 9H), 0.89 (s, 9H), 0.89 (m, 3H), 0.13 (s, 3H), 0.12 (s, 3H), 0.09 (s, 3H), 0.08 (s, 3H), 0.05 (s, 3H), 0.04 (s, 3H); $^{13}$C NMR (100 MHz, CDCl$_3$) δ 154.6, 147.9, 146.9, 134.0, 96.0, 91.2, 87.9, 85.1, 75.5, 71.7, 62.5, 41.2, 31.9, 29.73, 29.70, 29.69 (2C, accidental isochrony), 29.67, 29.65 (2C, accidental isochrony), 29.60, 29.5, 29.4, 29.3, 26.8, 26.0 (3C), 25.8 (3C), 25.7 (3C), 22.7, 18.4, 18.1, 17.9, 14.1, −4.4, −4.6, −4.7, −4.8, −5.5, −5.6; HRMS calcd. for $C_{44}H_{89}N_4O_7Si_3$ [M+H]$^+$: 869.60336, found: 869.60408.

EIDD-2356: To a stirred solution of S36 (0.120 g, 0.138 mmol) in THF (2.75 mL) under nitrogen at 0° C., was added a 1M solution of TBAF in THF (0.483 mL, 0.483 mmol). The solution was stirred at 0° C. for 5 hours, then concentrated by rotary evaporation. Automated flash chromatography (12 g column, 0 to 10% gradient of MeOH in dichloromethane) gave the title compound (0.055 g, 76%) as an off-white solid: $^1$H NMR (400 MHz, CDCl$_3$ with a drop of CD$_3$OD) δ 7.26 (d, J=8.2 Hz, 1H), 5.62 (d, J=4.4 Hz, 1H), 5.55 (d, J=8.2 Hz, 1H), 4.14-4.06 (m, 2H), 3.96-3.92 (m, 1H), 3.82-3.76 (m, 1H), 3.65 (m, 1H, obscured by MeOH-d$_4$), 3.15 (t, 7.0 Hz, 2H), 1.56 (m, 2H), 1.30-1.11 (br s, 28H), 0.79 (t, J=6.9 Hz, 3H); HRMS calcd. for $C_{26}H_{47}N_4O_7$ [M+H]$^+$: 527.34393, found: 527.34396.

96
Example 28

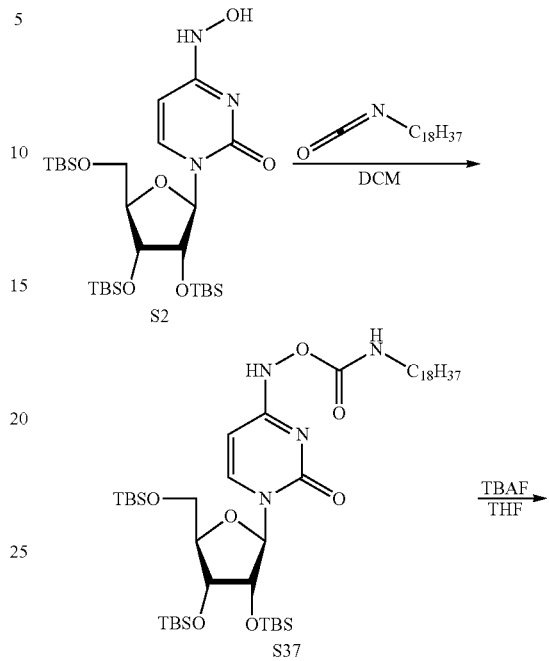

S2

S37

EIDD-2357

S37: To a stirred solution of S2 (0.090 g, 0.150 mmol) in DCM (1.5 mL) under nitrogen at rt, was added octadecyl isocyanate (0.057 mL, 0.165 mmol) dropwise via syringe over 2 minutes. The reaction was stirred at rt for 6 h, then concentrated by rotary evaporation to give crude residue. Automated flash chromatography (12 g column, 0 to 20% gradient of EtOAc in hexanes) gave S37 (0.128 g, 95%) as an off-white foam: $^1$H NMR (400 MHz, CDCl$_3$) δ 8.27 (br s, 1H), 7.51 (d, J=8.3 Hz, 1H), 6.29 (t, J=5.8 Hz, 1H), 5.90 (d, J=4.4 Hz, 1H), 5.57 (dd, J=8.2 Hz, 2.2 Hz, 1H), 4.10-4.00 (m, 3H), 3.93 (dd, J=11.6 Hz, 2.1 Hz, 1H), 3.73 (dd, J=11.7 Hz, 1.5 Hz, 1H), 3.28 (q, J=6.6 Hz, 2H), 1.55 (m, 2H), 1.26 (br s, 30H), 0.95 (s, 9H), 0.91 (s, 9H), 0.89 (s, 9H), 0.89 (m, 3H), 0.13 (s, 3H), 0.12 (s, 3H), 0.09 (s, 3H), 0.08 (s, 3H), 0.05 (s, 3H), 0.04 (s, 3H); $^{13}$C NMR (100 MHz, CDCl$_3$) δ 154.6, 147.9, 146.9, 134.0, 96.0, 91.2, 87.9, 85.1, 75.5, 71.7, 62.5, 41.2, 31.9, 29.73, 29.70 (5C, accidental isochrony), 29.67, 29.66 (2C, accidental isochrony), 29.60, 29.5, 29.4, 29.3, 26.8, 26.0 (3C), 25.8 (3C), 25.7 (3C), 22.7, 18.4, 18.1, 17.9, 14.1, −4.4, −4.6, −4.7, −4.8, −5.5, −5.6; HRMS calcd. for $C_{46}H_{93}N_4O_7Si_3$ [M+H]$^+$: 897.63466, found: 897.63589.

EIDD-2357: To a stirred solution of S37 (0.128 g, 0.143 mmol) in THF (2.85 mL) under nitrogen at 0° C., was added a 1M solution of TBAF in THF (0.499 mL, 0.499 mmol).

The solution was stirred at 0° C. for 5 hours, then concentrated by rotary evaporation. Automated flash chromatography (12 g column, 0 to 10% gradient of MeOH in dichloromethane) gave the title compound (0.059 g, 74%) as an off-white solid: $^1$H NMR (400 MHz, CDCl$_3$) δ 10.70 (br s, 1H), 7.47 (d, J=8.2 Hz, 1H), 6.56 (t, J=6.2 Hz, 1H), 5.76 (s, 1H), 5.60 (d, J=8.2 Hz, 1H), 4.32-4.20 (br m, 2H), 4.12-4.02 (br m, 2H), 3.90 (d, J=11.7 Hz, 1H), 1.56 (m, 2H), 1.26 (br s, 30H), 0.89 (t, J=7.0 Hz, 3H); HRMS calcd. for C$_{28}$H$_{51}$N$_4$O$_7$ [M+H]$^+$: 555.37523, found: 555.37531.

Example 29

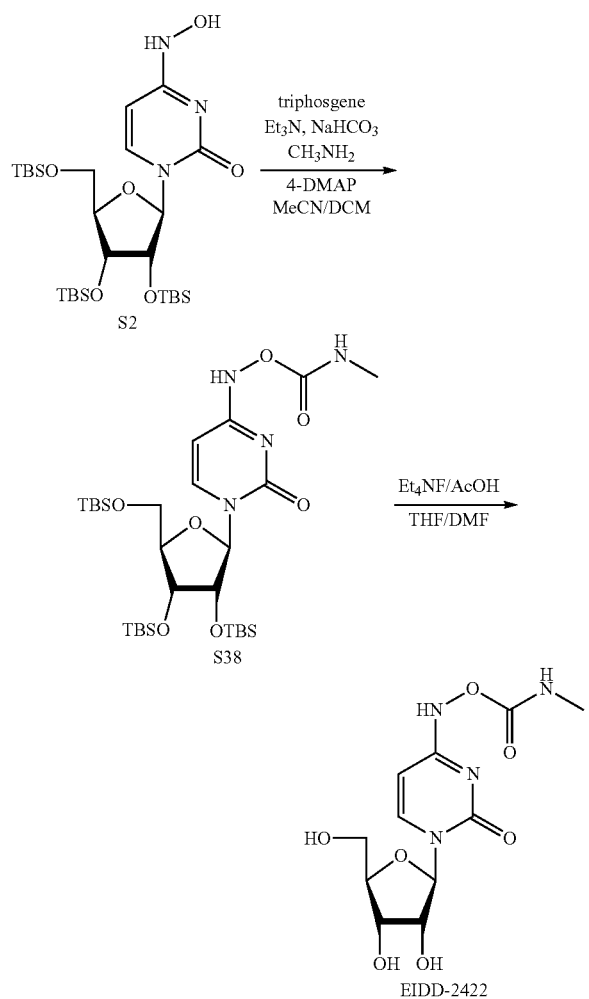

S38: To a vigorously stirred mixture of triphosgene (0.297 g, 1.00 mmol) and sodium bicarbonate (0.370 g, 4.40 mmol) in acetonitrile (5 mL) at −15° C., was added an admixed solution of methylamine (2.0 M in THF, 0.600 mL, 1.20 mmol) and triethylamine (0.488 mL, 3.50 mmol) dropwise via syringe. The mixture was warmed to ambient temperature and stirred for 6 hours. A solution of S2 (0.662 g, 1.10 mmol) and 4-DMAP (0.024 g, 0.200 mmol) in acetonitrile (5 mL) and DCM (5 mL) was prepared, and this was added dropwise to the reaction mixture via syringe. The entire mixture was stirred at ambient temperature for 16 h, diluted with dichloromethane (50 mL), washed with sat. aq. NaHCO$_3$ and brine (1×25 mL each), dried over Na$_2$SO$_4$, filtered, and concentrated by rotary evaporation. The crude was taken up in dichloromethane, and automated flash chromatography (24 g column, 5 to 35% gradient of EtOAc in hexanes) gave S38 (0.340 g, 52%) as a white waxy solid. NMR analysis showed a ~8:1 ratio of rotamers: $^1$H NMR (400 MHz, DMSO-d$_6$, major rotamer) δ 10.53 (d, J=2.2 Hz, 1H), 7.30 (d, J=8.2 Hz, 1H), 6.83 (q, J=4.9 Hz, 1H), 5.80 (d, J=6.5 Hz, 1H), 5.67 (dd, J=8.3 Hz, 2.2 Hz, 1H), 4.18 (dd, J=6.4 Hz, 4.3 Hz, 1H), 4.05 (m, 1H), 3.92 (m, 1H), 3.82 (dd, J=11.6 Hz, 4.0 Hz, 1H), 3.70 (dd, J=11.5 Hz, 2.9 Hz, 1H), 2.64 (d, J=4.7 Hz, 3H), 0.91 (s, 9H), 0.89 (s, 9H), 0.83 (s, 9H), 0.10 (s, 6H), 0.09 (s, 3H), 0.08 (s, 3H), 0.02 (s, 3H), −0.03 (s, 3H).

EIDD-2422: To a stirred solution of S38 (0.330 g, 0.500 mmol) in THF (3.75 mL) and DMF (1.25 mL) at 0° C., was added acetic acid (0.143 mL, 2.50 mmol) followed by tetraethylammonium fluoride (0.359 g, 2.40 mmol) all at once. The mixture was warmed to ambient temperature and stirred 24 hours. The mixture was concentrated by rotary evaporation, and the crude was taken up in dichloromethane. Automated flash chromatography (12 g column, 1 to 25% gradient of MeOH in dichloromethane) gave 80 mg of semipure material. This material was taken up in water, and automated reverse phase flash chromatography (30 g column, 0 to 100% gradient of acetonitrile in water) gave the desired product free from impurities. The solid was dissolved in water, frozen in a dry ice/acetone bath, and lyophilized to provide the title compound (0.057 g, 36% yield) as a white flocculent solid. NMR analysis showed a 13:1 ratio of signals in D$_2$O and a 8:1 ratio in MeOH-d$_4$, indicating solvent-dependent rotamer ratios of a single pure compound: $^1$H NMR (400 MHz, CD$_3$OD, major rotamer) δ 7.45 (d, J=8.2 Hz, 1H), 5.86 (d, J=5.1 Hz, 1H), 5.69 (d, J=8.2 Hz, 1H), 4.16-4.08 (m, 2H), 3.96 (q, J=3.2 Hz, 1H), 3.79 (dd, J=12.2 Hz, 2.8 Hz, 1H), 3.69 (dd, J=12.2 Hz, 3.3 Hz, 1H), 2.79 (s, 3H); $^1$H NMR (400 MHz, D$_2$O, major rotamer) δ 7.27 (d, J=8.2 Hz, 1H), 5.84 (d, J=5.4 Hz, 1H), 5.80 (d, J=8.2 Hz, 1H), 4.28 (t, J=5.2 Hz, 1H), 4.17 (t, J=5.2 Hz, 1H), 4.05 (q, J=4.2 Hz, 1H), 3.82 (dd, J=12.8 Hz, 3.1 Hz, 1H), 3.73 (dd, J=12.8 Hz, 4.6 Hz, 1H), 2.76 (s, 3H); $^{13}$C NMR (100 MHz, D$_2$O) δ 157.6, 150.2, 148.8, 134.0, 97.1, 88.4, 84.1, 73.1, 69.7, 61.0, 26.9; LRMS m/z 315.1 [M−H]$^−$.

Example 30

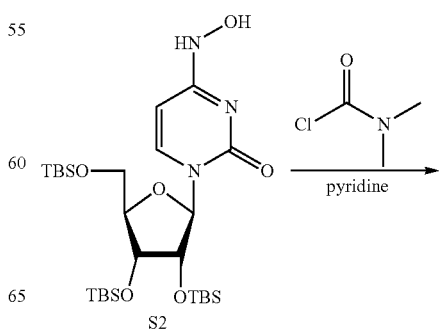

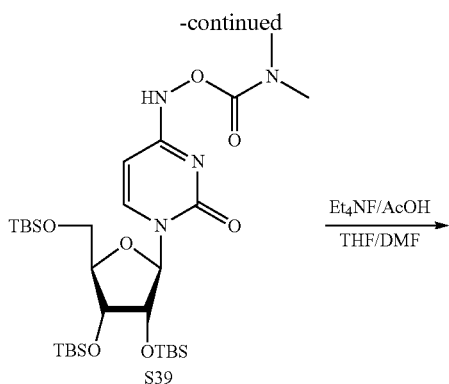

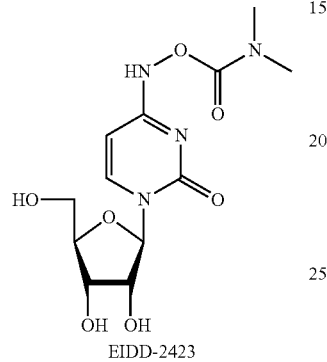

EIDD-2423

S39: To a vigorously stirred solution of S2 (1.10 g, 1.82 mmol) in pyridine (12 mL) under nitrogen at 0° C., was added dimethylcarbamyl chloride (0.184 mL, 2.00 mmol) dropwise via syringe over 5 minutes. The mixture was stirred at 0° C. for 4 hours, then warmed to ambient temperature and stirred another 16 hours. Methanol (2 mL) was added, the mixture was stirred an additional 15 minutes at room temperature, then concentrated by rotary evaporation. The crude was taken up in dichloromethane, and automated flash chromatography (40 g column, 5 to 50% gradient of EtOAc in hexanes) provided S39 (1.16 g, 95%) as a fluffy white solid. NMR analysis showed a ~10:1 ratio of rotamers: $^1$H NMR (400 MHz, DMSO-$d_6$, major rotamer) δ 10.76 (d, J=2.2 Hz, 1H), 7.28 (d, J=8.3 Hz, 1H), 5.80 (d, J=6.3 Hz, 1H), 5.70 (dd, J=8.2 Hz, 2.2 Hz, 1H), 4.20 (dd, J=6.3 Hz, 4.6 Hz, 1H), 4.05 (dd, J=4.3 Hz, 2.3 Hz, 1H), 3.92 (q, J=3.1 Hz, 1H), 3.83 (dd, J=11.5 Hz, 4.0 Hz, 1H), 3.70 (dd, J=11.5 Hz, 2.8 Hz, 1H), 2.96 (br s, 3H), 2.83 (br s, 3H), 0.91 (s, 9H), 0.89 (s, 9H), 0.83 (s, 9H), 0.10 (s, 6H), 0.09 (s, 3H), 0.08 (s, 3H), 0.02 (s, 3H), −0.01 (s, 3H).

EIDD-2423: To a stirred solution of S39 (1.16 g, 1.72 mmol) in THF (12.9 mL) and DMF (4.3 mL) at 0° C., was added acetic acid (0.493 mL, 8.62 mmol) followed by tetraethylammonium fluoride (1.24 g, 8.27 mmol) all at once. The mixture was warmed to ambient temperature and stirred 16 hours. The mixture was concentrated by rotary evaporation, and the crude was taken up in dichloromethane. Automated flash chromatography (80 g column, 1 to 15% gradient of MeOH in dichloromethane) gave 400 mg of semipure material. This material was taken up in water, and automated reverse phase flash chromatography (100 g column, 0 to 100% gradient of acetonitrile in water) gave the desired product free from impurities. The solid was dissolved in water, frozen in a dry ice/acetone bath, and lyophilized to provide the title compound (0.200 g, 35% yield) as a white flocculent solid. NMR analysis showed a 9:1 ratio of signals in $D_2O$ and a 5:1 ratio in MeOH-$d_4$, indicating solvent-dependent rotamer ratios of a single pure compound: $^1$H NMR (400 MHz, $CD_3OD$, major rotamer) δ 7.46 (d, J=8.3 Hz, 1H), 5.85 (d, J=4.8 Hz, 1H), 5.72 (d, J=8.2 Hz, 1H), 4.18-4.11 (m, 2H), 3.97 (q, J=3.5 Hz, 1H), 3.80 (dd, J=12.1 Hz, 2.8 Hz, 1H), 3.70 (dd, J=12.2 Hz, 3.2 Hz, 1H), 3.05 (br s, 3H), 2.98 (br s, 3H); $^1$H NMR (400 MHz, $D_2O$, major rotamer) □ 7.27 (d, J=8.3 Hz, 1H), 5.84 (d, J=5.4 Hz, 1H), 5.80 (d, J=8.3 Hz, 1H), 4.28 (t, J=5.4 Hz, 1H), 4.17 (d, J=5.2 Hz, 1H), 4.05 (q, J=4.3 Hz, 1H), 3.82 (dd, J=12.7 Hz, 3.2 Hz, 1H), 3.73 (dd, J=12.7 Hz, 4.5 Hz, 1H), 2.99 (br s, 3H), 2.91 (br s, 3H); $^{13}$C NMR (100 MHz, $D_2O$) δ 156.2, 150.1, 149.4, 133.9, 97.2, 88.3, 84.1, 73.0, 69.7, 61.0, 36.5, 35.7; LRMS m/z 329.0 [M−H]$^-$.

Example 31

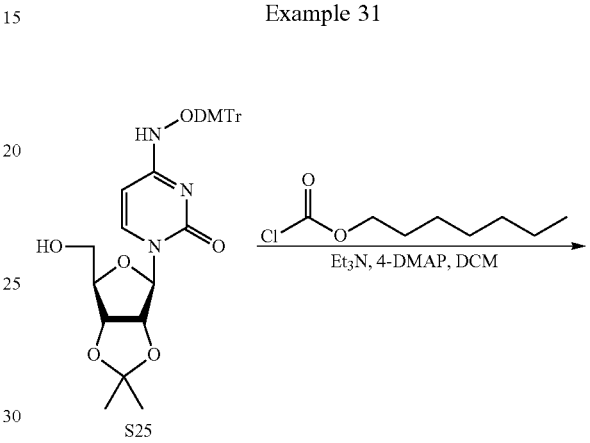

S25

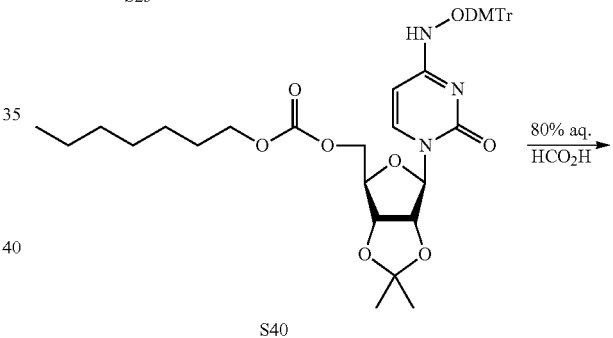

S40

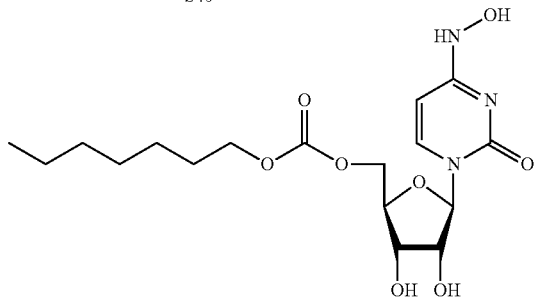

EIDD-2474

S40: A solution of S25 (0.50 g, 0.83 mmol) in anhydrous dichloromethane (5 mL) in a round bottom flask was cooled to 0° C. with an ice bath under nitrogen, and treated with pyridine (0.14 mL, 1.66 mmol) and DMAP (10 mg, 0.083 mmol), followed by dropwise addition of heptyl chloroformate (0.165 mL, 0.914 mmol). The mixture was warmed to room temperature and stirred for 2 h. After completion of the reaction, the reaction mixture was diluted with dichloromethane (25 mL) and washed with 5% aqueous hydrochloric acid (25 mL) and aqueous sodium bicarbonate (25 mL). The organic layer was dried over $Na_2SO_4$ and concentrated by rotary evaporation to give S40. The crude product was taken directly to the next step without further purification.

EIDD-2474: The entirety of crude S40 prepared as above was stirred with formic acid (10 mL) at room temperature for 12 h. The solvent was removed by rotary evaporation, and the crude product was purified by flash column chromatography using methanol and dichloromethane to yield the title compound (0.140 g, 42% over two steps) as a colorless solid: $^1$H NMR (400 MHz, DMSO-$d_6$) δ 10.05 (s, 1H), 9.61 (s, 1H), 6.85 (d, J=8.1 Hz, 1H), 5.75 (d, J=5.8 Hz, 1H), 5.57 (d, J=8.1 Hz, 1H), 5.42 (d, J=5.8 Hz, 1H), 5.30 (d, J=5.0 Hz, 1H), 4.31 (dd, J=11.7 Hz, 3.2 Hz, 1H), 4.20 (dd, J=11.8 Hz, 5.4 Hz, 1H), 4.14-4.08 (m, 1H), 4.02 (q, J=5.7 Hz, 1H), 3.97-3.90 (m, 2H), 3.10 (m, 1H), 1.61-1.18 (m, 10H), 0.90-0.86 (m, 3H); $^{13}$C NMR (100 MHz, DMSO-$d_6$) δ 154.9, 149.9, 143.6, 130.3, 99.2, 87.9, 81.0, 72.1, 70.4, 68.2, 67.8, 45.9, 31.6, 28.5, 25.6, 22.5, 14.4; LRMS m/z 402.1 $[M+H]^+$.

Example 32

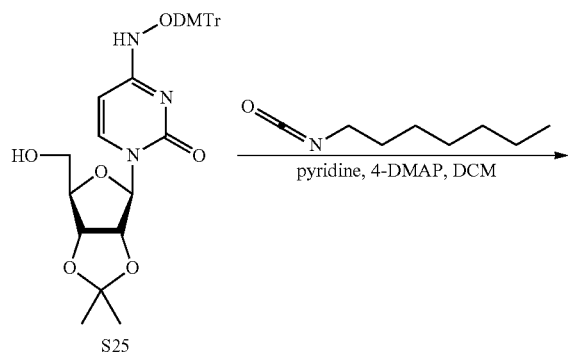

S25

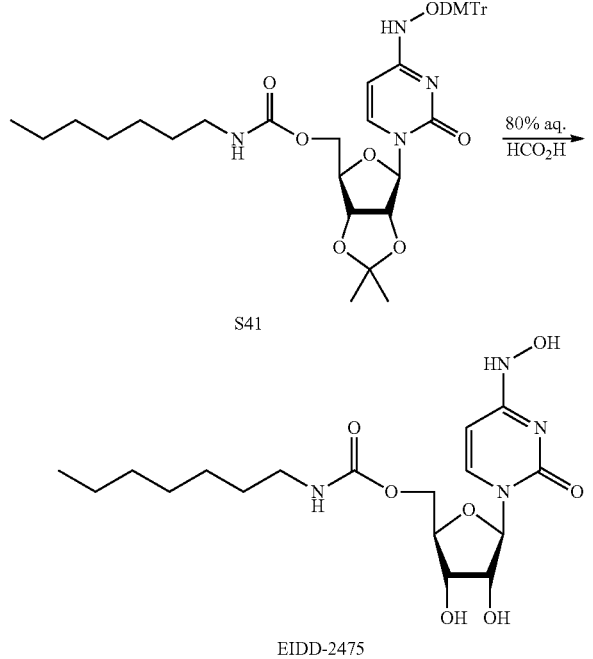

S41

EIDD-2475

S41: A solution of S25 (0.40 g, 0.66 mmol) in anhydrous dichloromethane (5 mL) in a 50 mL round bottom flask was cooled to 0° C. with an ice bath under nitrogen, and treated with pyridine (0.10 mL, 1.33 mmol) and DMAP (0.080 g, 0.66 mmol), followed by addition of heptyl isocyanate (0.16 mL, 0.99 mmol) and stirred at 40° C. for 12 h. After completion of the reaction, the reaction mixture was diluted with dichloromethane (25 mL) and washed with 5% aqueous hydrochloric acid (25 mL) and aqueous sodium bicarbonate (25 mL). The organic layer was dried over $Na_2SO_4$ and concentrated by rotary evaporation to give crude S41. The crude product was taken directly to the next step without further purification.

EIDD-2475: The entirety of crude S41 as prepared above was stirred with formic acid (10 mL) at room temperature for 12 h. The solvent was removed by rotary evaporation, and the crude product was purified by flash column chromatography using methanol and dichloromethane to yield the title compound (0.150 g, 56% over 2 steps) as a colorless solid: $^1$H NMR (400 MHz, DMSO-$d_6$) δ 9.98 (s, 1H), 9.53 (s, 1H), 7.26 (t, J=5.5 Hz, 1H), 6.83 (d, J=8.2 Hz, 1H), 5.71 (d, J=6.3 Hz, 1H), 5.52 (d, J=8.2 Hz, 1H), 4.19-3.77 (m, 5H), 2.94 (q, J=6.2 Hz, 2H), 1.48-1.10 (m, 10H), 0.83 (t, J=6.6 Hz, 3H); $^{13}$C NMR (101 MHz, DMSO-$d_6$) δ 156.3, 150.0, 143.7, 130.4, 99.1, 87.4, 81.9, 72.1, 70.6, 64.2, 31.7, 29.9, 28.9, 26.6, 22.5, 14.4; LRMS m/z 401.1 $[M+H]^+$.

Example 33

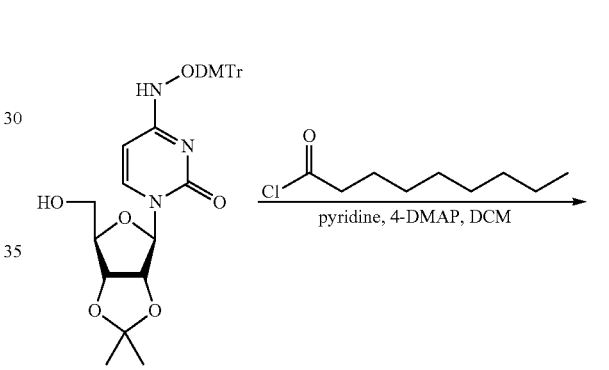

S25

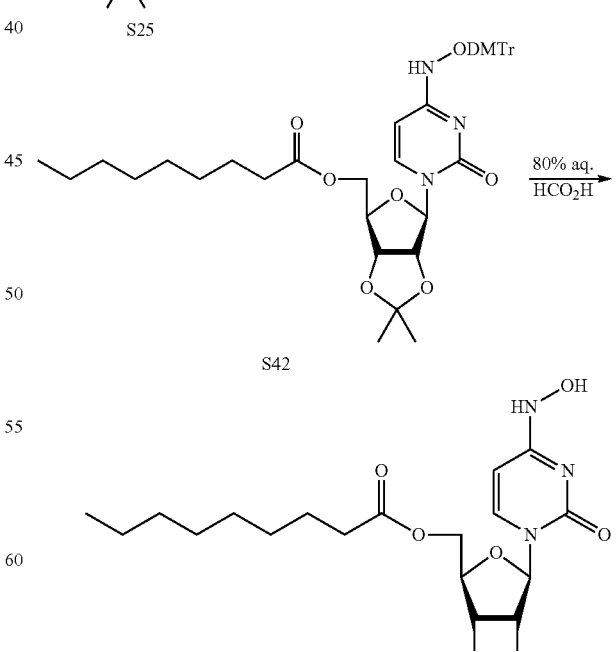

S42

EIDD-2476

S42: A solution of S25 (0.25 g, 0.41 mmol) in anhydrous dichloromethane (5 mL) in a 50 mL round bottom flask was cooled to 0° C. with an ice bath under nitrogen, and treated with pyridine (0.068 mL, 0.83 mmol) and DMAP (0.073 g, 0.41 mmol), followed by addition of nonanoyl chloride (0.082 mL, 0.45 mmol) and stirred at 40° C. for 12 h. After completion of the reaction, the reaction mixture was diluted with dichloromethane (15 mL) and washed with 5% aqueous hydrochloric acid (20 mL) and aqueous sodium bicarbonate (20 mL). The organic layer was dried over $Na_2SO_4$ and concentrated by rotary evaporation to give crude S42. The crude product was taken directly to the next step without further purification.

EIDD-2476: The entirety of crude S42 as prepared above was stirred with formic acid (5 mL) at room temperature for 12 h. The solvent was removed by rotary evaporation, and the crude product was purified by flash column chromatography using methanol and dichloromethane to yield the title compound (0.080 g, 54% over 2 steps) as a colorless solid: $^1$H NMR (400 MHz, DMSO-$d_6$) δ 9.99 (s, 1H), 9.54 (s, 1H), 6.81 (d, J=8.3 Hz, 1H), 5.69 (d, J=5.6 Hz, 1H) (dd, J=8.2 Hz, 1.8 Hz, 1H), 5.35 (d, J=5.8 Hz, 1H), 5.22 (d, J=5.1 Hz, 1H), 4.25-4.02 (m, 2H), 4.03-3.78 (m, 3H), 2.35-2.20 (m, 2H), 1.58-1.42 (m, 2H), 1.22 (m, 10H), 0.83 (t, J=3.3 Hz, 3H); $^{13}$C NMR (100 MHz, DMSO-$d_6$) δ 173.2, 149.9, 143.7, 130.3, 99.2, 88.0, 81.1, 72.3, 70.4, 64.3, 33.8, 31.7, 29.1, 29.0, 28.9, 24.9, 22.5, 14.4; LRMS m/z 400.2 [M+H]$^+$.

Example 34

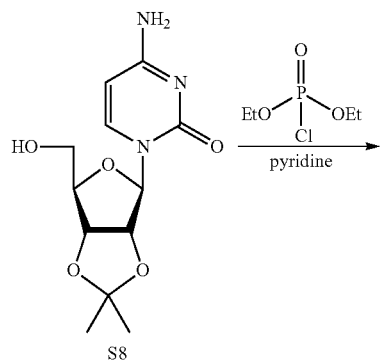

S8

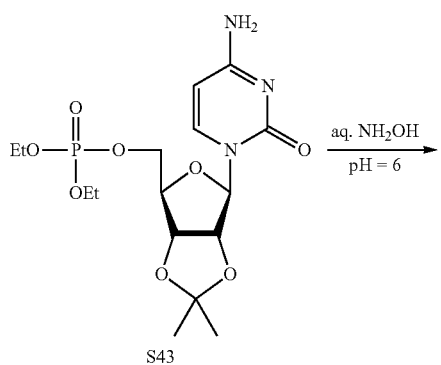

S43

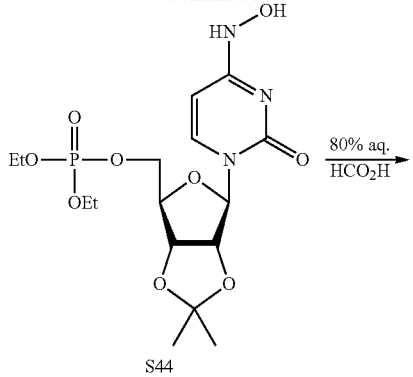

S44

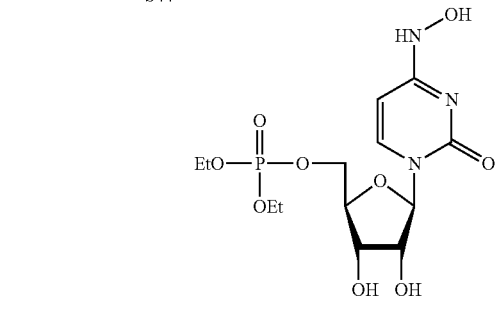

EIDD-2503

S43: To a stirred solution of S8 (5.87 g, 20.7 mmol) in pyridine (20 mL) at 0° C. under nitrogen, was added diethyl phosphorochloridate (2.99 mL, 20.7 mmol) dropwise via syringe. The mixture was stirred at 0° C. for 30 minutes, then warmed to ambient temperature and stirred an additional 30 minutes. The mixture was recooled to 0° C., MeOH (20 mL) was added, the mixture was warmed to ambient temperature and stirred 15 minutes. The mixture was concentrated by rotary evaporation and taken up in dichloromethane. Automated flash chromatography (120 g column, 1 to 10% gradient of MeOH in dichloromethane) gave S43 (4.25 g, 49%) as an off-white flaky solid: $^1$H NMR (400 MHz, DMSO-$d_6$) δ 9.28 (br s, 1H), 8.39 (br s, 1H), 7.95 (d, J=7.7 Hz, 1H), 6.04 (d, J=7.6 Hz, 1H), 5.80 (d, J=1.7 Hz, 1H), 5.07 (dd, J=6.4 Hz, 1.7 Hz, 1H), 4.79 (dd, J=6.4 Hz, 3.7 Hz, 1H), 4.30-4.24 (m, 1H), 4.21-4.07 (m, 2H), 4.01 (dq, J=8.2 Hz, 7.1 Hz, 4H), 1.49 (s, 3H), 1.29 (s, 3H), 1.22 (tq, J=7.0 Hz, 0.8 Hz, 6H); $^{31}$P NMR (162 MHz, CDCl$_3$) δ −1.21; LRMS m/z 420.1 [M+H]$^+$.

S44: A ~5 N solution of hydroxylamine hydrochloride (12.7 g, 182 mmol) in water (36.4 mL solution volume) was prepared, and adjusted to pH=6 with a small amount of aq. NaOH (10% w/w). A sealable pressure tube was charged with this solution, S43 (3.82 g, 9.11 mmol), and THF (18 mL), the flask was sealed, and the mixture was heated with stirring at 37° C. for 5 days. The mixture was cooled to room temperature, transferred to a round bottom flask, and concentrated by rotary evaporation. The crude material was taken up in methanol and immobilized on Celite. Automated flash chromatography (80 g column, 0 to 10% gradient of MeOH in dichloromethane) gave S44 (2.28 g, 58%) as a flaky white solid: $^1$H NMR (400 MHz, CDCl$_3$) δ 8.58 (br s, 1H), 7.72 (br s, 1H), 6.68 (d, J=8.2 Hz, 1H), 5.69 (d, J=2.5 Hz, 1H), 5.63 (dd, J=7.8 Hz, 1.1 Hz, 1H), 4.93 (dd, J=6.4 Hz, 2.4 Hz, 1H), 4.85 (dd, J=6.5 Hz, 3.6 Hz, 1H), 4.30-4.20 (m, 3H), 4.20-4.10 (m, 5H), 1.57 (s, 3H), 1.35 (s, 3H), 1.35 (tdd, J=7.0 Hz, 4.1 Hz, 1.0 Hz, 6H); $^{31}$P NMR (162 MHz, CDCl$_3$) δ −1.09; LRMS m/z 436.1 [M+H]$^+$.

EIDD-2503: A solution of S44 (0.25 g, 0.57 mmol) was stirred with formic acid (5 mL) at room temperature for 12 h under nitrogen. After completion of the reaction the solvent was removed by rotary evaporation, and the crude product was purified by flash column chromatography using methanol and dichloromethane to yield the title compound (0.180 g, 79%) as a colorless solid: $^1$H NMR (400 MHz, DMSO-d$_6$) δ 10.00 (s, 1H), 9.57 (s, 1H), 6.83 (d, J=8.2 Hz, 1H), 5.71 (d, J=5.9 Hz, 1H), 5.54 (dd, J=8.2 Hz, 2.0 Hz, 1H), 5.38 (d, J=5.8 Hz, 1H), 5.24 (d, J=4.7 Hz, 1H), 4.16-3.86 (m, 8H), 1.30-1.15 (m, 5H). $^{13}$C NMR (100 MHz, DMSO-d$_6$) δ 149.9, 143.7, 130.3, 110.0, 99.1, 87.8, 82.0, 72.1, 70.2, 67.2, 63.9, 16.4; $^{31}$P NMR (162 MHz, DMSO-d$_6$) δ −1.12; LRMS m/z 396.1 [M+H]$^+$.

Example 35

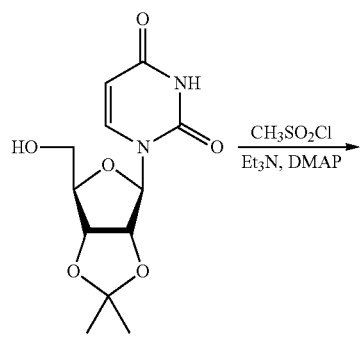

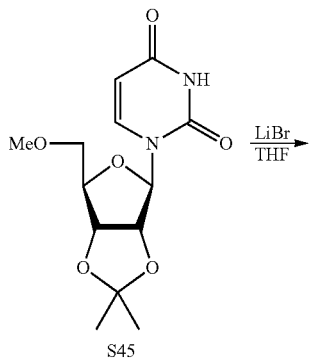

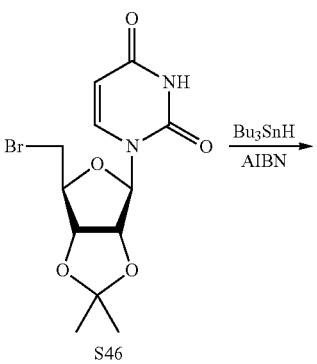

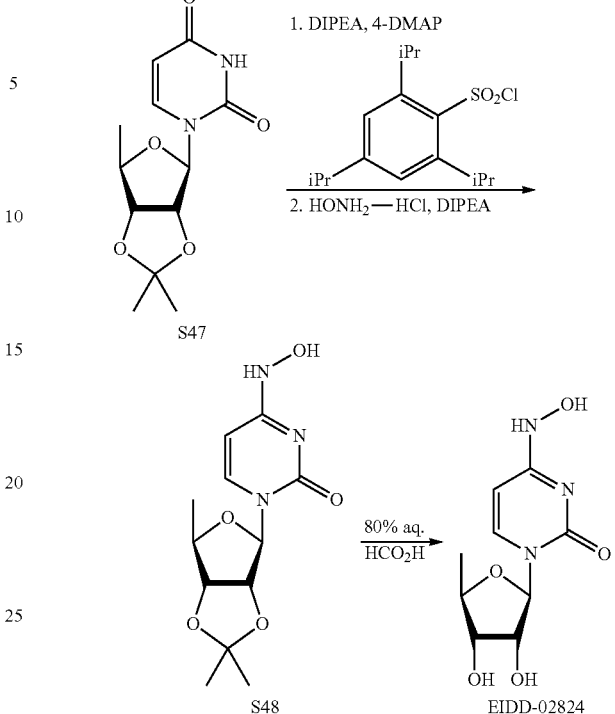

S45: A solution of 2',3'-isopropylideneuridine (4.00 g, 14.0 mmol) in anhydrous dichloromethane (50 mL) was cooled to 0° C. under nitrogen with stirring. To this solution triethylamine (3.92 mL, 28.1 mmol) and 4-DMAP (0.172 g, 1.40 mmol) were added, followed by dropwise addition of methanesulfonyl chloride (1.32 mL, 16.9 mmol). The reaction mixture was warmed to room temperature and stirred for 2 h. After completion of the reaction, the mixture was quenched with crushed ice and washed with 5% aqueous hydrochloric acid, aqueous sodium hydrogen carbonate, and brine (1×50 mL each). The organic layer was dried over Na$_2$SO$_4$ and concentrated by rotary evaporation. The crude product was purified by flash column chromatography using ethyl acetate and hexane to yield S45 (3.99 g, 78%) as a colorless foam: $^1$H NMR (400 MHz, CDCl$_3$) δ 9.97 (s, 1H), 7.27 (d, J=8.2 Hz, 1H), 5.74 (d, J=8.0 Hz, 1H), 5.60 (d, J=1.8 Hz, 1H), 5.06 (d, J=8.2 Hz, 1H), 4.88 (dd, J=6.4 Hz, 3.9 Hz, 1H), 4.45 (d, J=5.2 Hz, 2H), 4.37 (m, 1H), 3.03 (s, 3H), 1.54 (s, 3H), 1.34 (s, 3H); LRMS m/z 363.0 [M+H]$^+$.

S46: To a solution of S45 (3.00 g, 8.28 mmol) in anhydrous tetrahydrofuran (60 mL) at room temperature under nitrogen, lithium bromide (1.44 gm, 16.56 mmol) was added and the reaction mixture was refluxed for 6 h. After completion of the reaction, the concentrated by rotary evaporation and the crude product was partitioned between dichloromethane (60 mL) and water (60 mL). The aqueous layer was removed and the organic layer was washed with brine (60 mL), dried over Na$_2$SO$_4$ and concentrated by rotary evaporation. The crude product was purified by flash column chromatography using ethyl acetate and hexane to yield S45 (2.30 g, 80%) as a colorless solid: $^1$H NMR (400 MHz, CDCl$_3$) δ 9.24 (s, 1H), 7.34 (d, J=8.2 Hz, 1H), 5.76 (d, J=8.2 Hz, 1H), 5.66 (d, J=2.2 Hz, 1H), 5.01 (dd, J=6.5 Hz, 2.3 Hz, 1H), 4.88 (dd, J=6.5 Hz, 3.7 Hz, 1H), 4.38 (td, J=5.7 Hz, 3.8 Hz, 1H), 3.68 (dd, J=10.6 Hz, 6.2 Hz, 1H), 3.56 (dd, J=10.6 Hz, 5.2 Hz, 1H), 1.57 (s, 3H), 1.36 (s, 3H); LRMS m/z 348.9 [M+H]$^+$.

S47: To a suspension of S46 (2.0 g, 5.76 mmol) in anhydrous toluene (40 mL) at room temperature under nitrogen, ethanol (5 mL) was added followed by tributyltin hydride (3.11 mL, 11.52 mmol) and AIBN (0.94 gm, 5.76 mmol). The reaction mixture was refluxed for 6 h. After completion of the reaction, solvent was removed under reduced pressure, and the crude product was dissolved in dichloromethane (50 mL) and vacuum filtered through a glass frit. The filtrate was concentrated by rotary evaporation and the crude product was purified by flash column chromatography using ethyl acetate and hexane to yield S47 (1.10 g, 71%) as a colorless foam: $^1$H NMR (400 MHz, CDCl$_3$) δ 9.81 (s, 1H), 7.26 (d, J=8.0 Hz, 1H), 5.73 (d, J=8.0 Hz, 1H), 5.62 (d, J=2.2 Hz, 1H), 4.94 (dd, J=6.5 Hz, 2.2 Hz, 1H), 4.54 (dd, J=6.5 Hz, 4.6 Hz, 1H), 4.19 (qd, J=6.4 Hz, 4.7 Hz, 1H), 1.54 (s, 3H), 1.37 (d, J=6.5 Hz, 3H), 1.32 (s, 3H). LRMS m/z 269.1 [M+H]$^+$.

S48: A solution of S47 (1.00 g, 3.73 mmol) in anhydrous dichloromethane (30 mL) was cooled to 0° C. under nitrogen with stirring. To this solution N,N-diisopropylethylamine (3.25 mL, 18.64 mmol) and 4-DMAP (46 mg, 0.37 mmol) were added, followed by addition of 2,4,6-triisopropylbenzenesulfonyl chloride (1.69 g, 5.59 mmol). After the disappearance of starting material, hydroxylamine hydrochloride (0.648 g, 9.32 mmol) was added and the mixture was stirred for another 12 h at room temperature. After completion of the reaction, the reaction mixture was diluted with dichloromethane (70 mL) and washed with 5% aqueous hydrochloric acid (100 mL) followed by aqueous sodium hydrogen carbonate (100 mL) and brine (100 mL). The organic layer was dried over Na$_2$SO$_4$, filtered, and concentrated by rotary evaporation. The crude product was purified by flash column chromatography using ethyl acetate and hexane to yield S48 (0.59 g, 55.9%) as a colorless solid: $^1$H NMR (400 MHz, DMSO-d$_6$) δ 10.03 (s, 1H), 9.62 (d, J=1.8 Hz, 1H), 6.85 (d, J=8.2 Hz, 1H), 5.66 (d, J=2.8 Hz, 1H), 5.55 (dd, J=8.1 Hz, 2.1 Hz, 1H), 4.86 (dd, J=6.6 Hz, 2.8 Hz, 1H), 4.47 (dd, J=6.5 Hz, 4.9 Hz, 1H), 3.97-3.84 (m, 1H), 1.44 (s, 3H), 1.30-1.15 (m, 5H); LRMS m/z 284.1 [M+H]$^+$.

EIDD-2524: A solution of S48 (0.250 g, 0.88 mmol) was stirred in formic acid (5 mL) at room temperature for 12 h. After completion of the reaction, the mixture was concentrated by rotary evaporation, and the crude product was purified by flash column chromatography using methanol and dichloromethane to yield the title compound (0.150 g, 70%) as a colorless solid: $^1$H NMR (400 MHz, DMSO-d$_6$) δ 9.94 (s, 1H), 9.46 (s, 1H), 6.75 (d, J=8.2 Hz, 1H), 5.59 (d, J=5.1 Hz, 1H), 5.51 (d, J=8.2 Hz, 1H), 5.20 (s, 1H), 4.98 (s, 1H), 3.94 (s, 1H), 3.78-3.65 (m, 1H), 3.59 (dd, J=5.5 Hz, 3.9 Hz, 1H), 1.17 (d, J=6.4 Hz, 3H). $^{13}$C NMR (100 MHz, DMSO-d$_6$) δ 149.9, 143.8, 130.8, 99.1, 88.5, 79.0, 74.8, 72.5, 19.3; LRMS m/z 244.1 [M+H]$^+$.

Example 36

Assay Protocols
(1) Screening Assays for DENY, JEV, POWV, WNV, YFV, PTV, RVFV, CHIKV, EEEV, VEEV, WEEV, TCRV, PCV, JUNV, MPRLV Primary cytopathic effect (CPE) reduction assay. Four-concentration CPE inhibition assays are performed. Confluent or near-confluent cell culture monolayers in 96-well disposable microplates are prepared. Cells are maintained in MEM or DMEM supplemented with FBS as required for each cell line. For antiviral assays the same medium is used but with FBS reduced to 2% or less and supplemented with 50 µg/ml gentamicin. The test compound is prepared at four log$_{10}$ final concentrations, usually 0.1, 1.0, 10, and 100 µg/ml or µM. The virus control and cell control wells are on every microplate. In parallel, a known active drug is tested as a positive control drug using the same method as is applied for test compounds. The positive control is tested with each test run. The assay is set up by first removing growth media from the 96-well plates of cells. Then the test compound is applied in 0.1 ml volume to wells at 2× concentration. Virus, normally at <100 50% cell culture infectious doses (CCID$_{50}$) in 0.1 ml volume, is placed in those wells designated for virus infection. Medium devoid of virus is placed in toxicity control wells and cell control wells. Virus control wells are treated similarly with virus. Plates are incubated at 37° C. with 5% CO$_2$ until maximum CPE is observed in virus control wells. The plates are then stained with 0.011% neutral red for approximately two hours at 37° C. in a 5% CO$_2$ incubator. The neutral red medium is removed by complete aspiration, and the cells may be rinsed 1× with phosphate buffered solution (PBS) to remove residual dye. The PBS is completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well is quantified using a 96-well spectrophotometer at 540 nm wavelength. The dye content in each set of wells is converted to a percentage of dye present in untreated control wells using a Microsoft Excel computer-based spreadsheet. The 50% effective (EC$_{50}$, virus-inhibitory) concentrations and 50% cytotoxic (CC$_{50}$, cell-inhibitory) concentrations are then calculated by linear regression analysis. The quotient of CC$_{50}$ divided by EC$_{50}$ gives the selectivity index (SI) value.

Secondary CPE/Virus yield reduction (VYR) assay. This assay involves similar methodology to what is described in the previous paragraphs using 96-well microplates of cells. The differences are noted in this section. Eight half-log$_{10}$ concentrations of inhibitor are tested for antiviral activity and cytotoxicity. After sufficient virus replication occurs, a sample of supernatant is taken from each infected well (three replicate wells are pooled) and held for the VYR portion of this test, if needed. Alternately, a separate plate may be prepared and the plate may be frozen for the VYR assay. After maximum CPE is observed, the viable plates are stained with neutral red dye. The incorporated dye content is quantified as described above. The data generated from this portion of the test are neutral red EC$_{50}$, CC$_{50}$, and SI values. Compounds observed to be active above are further evaluated by VYR assay. The VYR test is a direct determination of how much the test compound inhibits virus replication. Virus that was replicated in the presence of test compound is titrated and compared to virus from untreated, infected controls. Titration of pooled viral samples (collected as described above) is performed by endpoint dilution. This is accomplished by titrating log$_{10}$ dilutions of virus using 3 or 4 microwells per dilution on fresh monolayers of cells by endpoint dilution. Wells are scored for presence or absence of virus after distinct CPE (measured by neutral red uptake) is observed. Plotting the log$_{10}$ of the inhibitor concentration versus log$_{10}$ of virus produced at each concentration allows calculation of the 90% (one log$_{10}$) effective concentration by linear regression. Dividing EC$_{90}$ by the CC$_{50}$ obtained in part 1 of the assay gives the SI value for this test.

Example 37

(2) Screening Assays for Lassa Fever Virus (LASV)

Primary Lassa fever virus assay. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $\log_{10}$ final concentrations, usually 0.1, 1.0, 10, and 100 µg/ml or µM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells, and infecting cells with 0.01 MOI of LASV strain Josiah. Cells will be incubated for 90 min: 500 µl inoculum/M12 well, at 37° C., 5% CO2 with constant gentle rocking. The inoculums will be removed and cells will be washed 2× with medium. Then the test compound is applied in 1 ml of total volume of media. Tissue culture supernatant (TCS) will be collected at appropriate time points. TCS will then be used to determine the compounds inhibitory effect on virus replication. Virus that was replicated in the presence of test compound is titrated and compared to virus from untreated, infected controls. For titration of TCS, serial ten-fold dilutions will be prepared and used to infect fresh monolayers of cells. Cells will be overlaid with 1% agarose mixed 1:1 with 2×MEM supplemented with 10% FBS and 1% penecillin, and the number of plaques determined. Plotting the $\log_{10}$ of the inhibitor concentration versus $\log_{10}$ of virus produced at each concentration allows calculation of the 90% (one $\log_{10}$) effective concentration by linear regression.

Secondary Lassa fever virus assay. The secondary assay involves similar methodology to what is described in the previous paragraphs using 12-well plates of cells. The differences are noted in this section. Cells are being infected as described above but this time overlaid with 1% agarose diluted 1:1 with 2×MEM and supplemented with 2% FBS and 1% penicillin/streptomycin and supplemented with the corresponding drug concentration. Cells will be incubated at 37° C. with 5% CO2 for 6 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective (EC50, virus-inhibitory) concentrations are then calculated by linear regression analysis.

Example 38

(3) Screening Assays for Ebola Virus (EBOV) and Nipah Virus (NIV)

Primary Ebola/Nipah virus assay. Four-concentration plaque reduction assays are performed. Confluent or near-confluent cell culture monolayers in 12-well disposable cell culture plates are prepared. Cells are maintained in DMEM supplemented with 10% FBS. For antiviral assays the same medium is used but with FBS reduced to 2% or less and supplemented with 1% penicillin/streptomycin. The test compound is prepared at four $\log_{10}$ final concentrations, usually 0.1, 1.0, 10, and 100 m/ml or µM. The virus control and cell control will be run in parallel with each tested compound. Further, a known active drug is tested as a positive control drug using the same experimental set-up as described for the virus and cell control. The positive control is tested with each test run. The assay is set up by first removing growth media from the 12-well plates of cells. Then the test compound is applied in 0.1 ml volume to wells at 2× concentration. Virus, normally at approximately 200 plaque-forming units in 0.1 ml volume, is placed in those wells designated for virus infection. Medium devoid of virus is placed in toxicity control wells and cell control wells. Virus control wells are treated similarly with virus. Plates are incubated at 37° C. with 5% $CO_2$ for one hour. Virus-compound inoculums will be removed, cells washed and overlaid with 1.6% tragacanth diluted 1:1 with 2×MEM and supplemented with 2% FBS and 1% penicillin/streptomycin and supplemented with the corresponding drug concentration. Cells will be incubated at 37° C. with 5% $CO_2$ for 10 days. The overlay is then removed and plates stained with 0.05% crystal violet in 10% buffered formalin for approximately twenty minutes at room temperature. The plates are then washed, dried and the number of plaques counted. The number of plaques is in each set of compound dilution is converted to a percentage relative to the untreated virus control. The 50% effective ($EC_{50}$, virus-inhibitory) concentrations are then calculated by linear regression analysis.

Secondary Ebola/NIpah virus assay with VYR component. The secondary assay involves similar methodology to what is described in the previous paragraphs using 12-well plates of cells. The differences are noted in this section. Eight half-$\log_{10}$ concentrations of inhibitor are tested for antiviral activity. One positive control drug is tested per batch of compounds evaluated. For this assay, cells are infected with virus. Cells are being infected as described above but this time incubated with DMEM supplemented with 2% FBS and 1% penicillin/streptomycin and supplemented with the corresponding drug concentration. Cells will be incubated for 10 days at 37° C. with 5% $CO_2$, daily observed under microscope for the number of green fluorescent cells. Aliquots of supernatant from infected cells will be taken daily and the three replicate wells are pooled. The pooled supernatants are then used to determine the compounds inhibitory effect on virus replication. Virus that was replicated in the presence of test compound is titrated and compared to virus from untreated, infected controls. For titration of pooled viral samples, serial ten-fold dilutions will be prepared and used to infect fresh monolayers of cells. Cells are overlaid with tragacanth and the number of plaques determined. Plotting the $\log_{10}$ of the inhibitor concentration versus $\log_{10}$ of virus produced at each concentration allows calculation of the 90% (one $\log_{10}$) effective concentration by linear regression.

Example 39

Anti-Dengue Virus Cytoprotection Assay:

Cell Preparation—BHK21 cells (Syrian golden hamster kidney cells, ATCC catalog #CCL-I 0), Vero cells (African green monkey kidney cells, ATCC catalog #CCL-81), or Huh-7 cells (human hepatocyte carcinoma) were passaged in DMEM supplemented with 10% FBS, 2 mM L-glutamine, 100 U/mL penicillin, and 100 µg/mL streptomycin in T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $3\times10^3$ ($5\times10^5$ for Vero cells and Huh-7 cells) cells per well in tissue culture medium and added to flat bottom microtiter plates in a volume of 100 µL. The plates were incubated at 37° C./5% $CO_2$ overnight to allow for cell adherence. Monolayers were observed to be approximately 70% confluent.

Virus Preparation—The Dengue virus type 2 New Guinea C strain was obtained from ATCC (catalog #VR-1584) and was grown in LLC-MK2 (Rhesus monkey kidney cells; catalog #CCL-7.1) cells for the production of stock virus pools. An aliquot of virus pretitered in BHK21 cells was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format-Each plate contains cell control wells (cells only), virus control wells (cells plus virus), triplicate drug toxicity wells per compound (cells plus drug only), as well as triplicate experimental wells (drug plus cells plus virus).

Efficacy and Toxicity XTT-Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI 1640. Phenazine methosulfate (PMS) solution was prepared at 0.15 mg/mL in PBS and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 40

Anti-RSV Cytoprotection Assay:

Cell Preparation-HEp2 cells (human epithelial cells, ATCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1\times10^4$ cells per well in tissue culture medium and added to flat bottom microtiter plates in a volume of 100 µL. The plates were incubated at 37° C./5% $CO_2$ overnight to allow for cell adherence. Virus Preparation—The RSV strain Long and RSV strain 9320 were obtained from ATCC (catalog #VR-26 and catalog #VR-955, respectively) and were grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, 100 µg/mL streptomycin, 1 mM sodium pyruvate, and 0.1 mM NEAA) such that the amount of virus added to each well in a volume of 100 µL was the amount determined to yield 85 to 95% cell killing at 6 days post-infection. Efficacy and Toxicity XTT-Plates were stained and analyzed as previously described for the Dengue cytoprotection assay.

Example 41

Anti-Influenza Virus Cytoprotection Assay:

Cell Preparation-MOCK cells (canine kidney cells, ATCC catalog #CCL-34) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at $1\times10^4$ cells per well in tissue culture medium and added to flat bottom microtiter plates in a volume of 100 µL. The plates were incubated at 37° C./5% $CO_2$ overnight to allow for cell adherence.

Virus Preparation—The influenza A/PR/8/34 (ATCC #VR-95), A/CA/05/09 (CDC), A/NY/18/09 (CDC) and A/NWS/33 (ATCC #VR-219) strains were obtained from ATCC or from the Center of Disease Control and were grown in MDCK cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 0.5% BSA, 2 mM L-glutamine, 100 U/mL penicillin, 100 µg/mL streptomycin, 1 mM sodium pyruvate, 0.1 mM NEAA, and 1 µg/ml TPCK-treated trypsin) such that the amount of virus added to each well in a volume of 100 µL was the amount determined to yield 85 to 95% cell killing at 4 days post-infection. Efficacy and Toxicity XTT-Plates were stained and analyzed as previously described for the Dengue cytoprotection assay.

Example 42

Anti-Hepatitis C Virus Assay:

Cell Culture—The reporter cell line Huh-luc/neo-ET was obtained from Dr. Ralf Bartenschlager (Department of Molecular Virology, Hygiene Institute, University of Heidelberg, Germany) by ImQuest BioSciences through a specific licensing agreement. This cell line harbors the persistently replicating $I_{389}$luc-ubi-neo/NS3-3'/ET replicon containing the firefly luciferase gene-ubiquitin-neomycin phosphotransferase fusion protein and EMCV IRES driven NS3-5B HCV coding sequences containing the ET tissue culture adaptive mutations (E1202G, T12081, and K1846T). A stock culture of the Huh-luc/neo-ET was expanded by culture in DMEM supplemented with 10% FCS, 2 mM glutamine, penicillin (100 µU/mL)/streptomycin (100 µg/mL) and 1X nonessential amino acids plus 1 mg/mL G418. The cells were split 1:4 and cultured for two passages in the same media plus 250 µg/mL G418. The cells were treated with trypsin and enumerated by staining with trypan blue and seeded into 96-well tissue culture plates at a cell culture density 7.5×10³ cells per well and incubated at 37° C. 5% $CO_2$ for 24 hours. Following the 24 hour incubation, media was removed and replaced with the same media minus the G418 plus the test compounds in triplicate. Six wells in each plate received media alone as a no-treatment control. The cells were incubated an additional 72 hours at 37° C. 5% $CO_2$ then anti-HCV activity was measured by luciferase endpoint. Duplicate plates were treated and incubated in parallel for assessment of cellular toxicity by XTT staining.

Cellular Viability—The cell culture monolayers from treated cells were stained with the tetrazolium dye XTT to evaluate the cellular viability of the Huh-luc/neo-ET reporter cell line in the presence of the compounds.

Measurement of Virus Replication—HCV replication from the replicon assay system was measured by luciferase activity using the britelite plus luminescence reporter gene kit according to the manufacturer's instructions (Perkin Elmer, Shelton, Conn.). Briefly, one vial of britelite plus lyophilized substrate was solubilized in 10 mL of britelite reconstitution buffer and mixed gently by inversion. After a 5 minute incubation at room temperature, the britelite plus reagent was added to the 96 well plates at 100 µL per well. The plates were sealed with adhesive film and incubated at room temperature for approximately 10 minutes to lyse the cells. The well contents were transferred to a white 96-well plate and luminescence was measured within 15 minutes using the Wallac 1450 Microbeta Trilux liquid scintillation counter. The data were imported into a customized Microsoft Excel 2007 spreadsheet for determination of the 50% virus inhibition concentration ($EC_{50}$).

Example 43

Anti-Parainfluenza-3 Cytoprotection Assay:

Cell Preparation—HEp2 cells (human epithelial cells, ATCC catalog #CCL-23) were passaged in DMEM supplemented with 10% FBS, 2 mM L-glutamine, 100 U/mL penicillin, 100 µg/mL streptomycin 1 mM sodium pyruvate, and 0.1 mM NEAA, T-75 flasks prior to use in the antiviral assay. On the day preceding the assay, the cells were split 1:2 to assure they were in an exponential growth phase at the time of infection. Total cell and viability quantification was performed using a hemocytometer and Trypan Blue dye exclusion. Cell viability was greater than 95% for the cells to be utilized in the assay. The cells were resuspended at 1×10⁴ cells per well in tissue culture medium and added to flat bottom microtiter plates in a volume of 100 µL. The plates were incubated at 37° C./5% $CO_2$ overnight to allow for cell adherence.

Virus Preparation—The Parainfluenza virus type 3 SF4 strain was obtained from ATCC (catalog #VR-281) and was grown in HEp2 cells for the production of stock virus pools. A pretitered aliquot of virus was removed from the freezer (−80° C.) and allowed to thaw slowly to room temperature in a biological safety cabinet. Virus was resuspended and diluted into assay medium (DMEM supplemented with 2% heat-inactivated FBS, 2 mM L-glutamine, 100 U/mL penicillin, and 100 µg/mL streptomycin) such that the amount of virus added to each well in a volume of 100 µL was the amount determined to yield 85 to 95% cell killing at 6 days post-infection.

Plate Format—Each plate contains cell control wells (cells only), virus control wells (cells plus virus), triplicate drug toxicity wells per compound (cells plus drug only), as well a triplicate experimental wells (drug plus cells plus virus). Efficacy and Toxicity XTT—Following incubation at 37° C. in a 5% $CO_2$ incubator, the test plates were stained with the tetrazolium dye XTT (2,3-bis(2-methoxy-4-nitro-5-sulfophenyl)-5-[(phenylamino)carbonyl]-2H-tetrazol hydroxide). XTT-tetrazolium was metabolized by the mitochondrial enzymes of metabolically active cells to a soluble formazan product, allowing rapid quantitative analysis of the inhibition of virus-induced cell killing by antiviral test substances. XTT solution was prepared daily as a stock of 1 mg/mL in RPMI1640. Phenazine methosulfate (PMS) solution was prepared at 0.15 mg/mL in PBS and stored in the dark at −20° C. XTT/PMS stock was prepared immediately before use by adding 40 µL of PMS per ml of XTT solution. Fifty microliters of XTT/PMS was added to each well of the plate and the plate was reincubated for 4 hours at 37° C. Plates were sealed with adhesive plate sealers and shaken gently or inverted several times to mix the soluble fomlazan product and the plate was read spectrophotometrically at 450/650 nm with a Molecular Devices Vmax plate reader.

Data Analysis—Raw data was collected from the Softmax Pro 4.6 software and imported into a Microsoft Excel spreadsheet for analysis. The percent reduction in viral cytopathic effect compared to the untreated virus controls was calculated for each compound. The percent cell control value was calculated for each compound comparing the drug treated uninfected cells to the uninfected cells in medium alone.

Example 44

Influenza Polymerase Inhibition Assay:

Virus Preparation—Purified influenza virus A/PR/8/34 (1 ml) was obtained from Advanced Biotechnologies, Inc. (Columbia, Md.), thawed and dispensed into five aliquots for storage at −80° C. until use. On the day of assay set up, 20 µL of 2.5% Triton N-101 was added to 180 µL of purified virus. The disrupted virus was diluted 1:2 in a solution containing 0.25% Triton and PBS. Disruption provided the source of influenza ribonucleoprotein (RNP) containing the influenza RNA-dependent RNA polymerase and template RNA. Samples were stored on ice until use in the assay.

Polymerase reaction—Each 50 µL polymerase reaction contained the following: 5 µL of the disrupted RNP, 100 mM Tris-HCl (pH 8.0), 100 mM KCl, 5 mM $MgCl_2$. 1 mM dithiothreitol, 0.25% Triton N-101, 5 µCi of [α-$^{32}$P] GTP, 100 µM ATP, 50 µM each (CTP, UTP), 1 µM GTP, and 200 µM adenyl (3'-5') guanosine. For testing the inhibitor, the reactions contained the inhibitor and the same was done for reactions containing the positive control (2'-Deoxy-2'-fluoroguanosine-5'-triphosphate). Other controls included RNP+ reaction mixture, and RNP+1% DMSO. The reaction mixture without the ApG primer and NTPs was incubated at 30° C. for 20 minutes. Once the ApG and NTPs were added to the reaction mixture, the samples were incubated at 30° C. for 1 hour then immediately followed by the transfer of the reaction onto glass-fiber filter plates and subsequent precipitation with 10% trichloroacetic acid (TCA). The plate was then washed five times with 5% TCA followed by one wash with 95% ethanol. Once the filter had dried, incorporation of [α-$^{32}$P] GTP was measured using a liquid scintillation counter (Micro beta).

Plate Format—Each test plate contained triplicate samples of the three compounds (6 concentrations) in addition to triplicate samples of RNP+reaction mixture (RNP alone), RNP+1% DMSO, and reaction mixture alone (no RNP).

Data Analysis—Raw data was collected from the Micro Beta scintillation counter. The incorporation of radioactive GTP directly correlates with the levels of polymerase activity. The "percent inhibition values" were obtained by dividing the mean value of each test compound by the RNP+1% DMSO control. The mean obtained at each concentration of 2DFGTP was compared to the RNP+reaction control. The data was then imported into Microsoft Excel spreadsheet to calculate the IC$_{50}$ values by linear regression analysis.

Example 45

HCV Polymerase Inhibition Assay:

Activity of compounds for inhibition of HCV polymerase was evaluated using methods previously described (Lam et al. 2010. Antimicrobial Agents and Chemotherapy 54(8): 3187-3196). HCV NS5B polymerase assays were performed in 20 µL volumes in 96 well reaction plates. Each reaction contained 40 ng/µL purified recombinant NS5BΔ22 genotype-1b polymerase, 20 ng/µL of HCV genotype-1b complimentary IRES template, 1 µM of each of the four natural ribonucleotides, 1 U/mL Optizyme RNAse inhibitor (Promega, Madison, Wis.), 1 mM MgCl$_2$, 0.75 mM MnCl$_2$, and 2 mM dithiothreitol (DTT) in 50 mM HEPES buffer (pH 7.5). Reaction mixtures were assembled on ice in two steps. Step 1 consisted of combining all reaction components except the natural nucleotides and labeled UTP in a polymerase reaction mixture. Ten microliters (10 µL) of the polymerase mixture was dispensed into individual wells of the 96 well reaction plate on ice. Polymerase reaction mixtures without NS5B polymerase were included as no enzyme controls. Serial half-logarithmic dilutions of test and control compounds, 2'-O-Methyl-CTP and 2'-O-Methyl-GTP (Trilink, San Diego, Calif.), were prepared in water and 5 µL of the serial diluted compounds or water alone (no compound control) were added to the wells containing the polymerase mixture. Five microliters of nucleotide mix (natural nucleotides and labeled UTP) was then added to the reaction plate wells and the plate was incubated at 27° C. for 30 minutes. The reactions were quenched with the addition of 80 µL stop solution (12.5 mM EDTA, 2.25 M NaCl, and 225 mM sodium citrate) and the RNA products were applied to a Hybond-N+membrane (GE Healthcare, Piscataway, N.J.) under vacuum pressure using a dot blot apparatus. The membrane was removed from the dot blot apparatus and washed four times with 4×SSC (0.6 M NaCl, and 60 mM sodium citrate), and then rinsed one time with water and once with 100% ethanol. The membrane was air dried and exposed to a phosphoimaging screen and the image captured using a Typhoon 8600 Phospho imager. Following capture of the image, the membrane was placed into a Micro beta cassette along with scintillation fluid and the CPM in each reaction was counted on a Micro beta 1450. CPM data were imported into a custom Excel spreadsheet for determination of compound IC$_{50}$s.

Example 46

NS5B RNA-Dependent RNA Polymerase Reaction Conditions

Compounds were assayed for inhibition of NS5B-δ21 from HCV GT-1b Con-1. Reactions included purified recombinant enzyme, 1 u/µL negative-strand HCV IRES RNA template, and 1 µM NTP substrates including either [$^{32}$P]-CTP or [$^{32}$P]-UTP. Assay plates were incubated at 27° C. for 1 hour before quench. [$^{32}$P] incorporation into macromolecular product was assessed by filter binding.

Example 47

Human DNA Polymerase Inhibition Assay:

The human DNA polymerase alpha (catalog #1075), beta (catalog #1077), and gamma (catalog #1076) were purchased from CHIMERx (Madison, Wis.). Inhibition of beta and gamma DNA polymerase activity was assayed in microtiter plates in a 50 uL reaction mixture containing 50 mM Tris-HCl (pH 8.7), KCl (10 mM for beta and 100 mM for gamma), 10 mM MgCl$_2$, 0.4 mg/mL BSA, 1 mM DTT, 15% glycerol, 0.05 mM of dCTP, dTTP, and dATP, 10 uCi [$^{32}$P]-alpha-dGTP (800 Ci/mmol), 20 ug activated calf thymus DNA and the test compound at indicated concentrations. The alpha DNA polymerase reaction mixture was as follows in a 50 uL volume per sample: 20 mM Tris-HCl (pH 8), 5 mM magnesium acetate, 0.3 mg/mL BSA, 1 mM DTT, 0.1 mM spermine, 0.05 mM of dCTP, dTTP, and dATP, 10 uCi [$^{32}$P]-alpha-dGTP (800 Ci/mmol), 20 ug activated calf thymus DNA and the test compound at the indicated concentrations. For each assay, the enzyme reactions were allowed to proceed for 30 minutes at 37° C. followed by the transfer onto glass-fiber filter plates and subsequent precipitation with 10% trichloroacetic acid (TCA). The plate was then washed with 5% TCA followed by one wash with 95% ethanol. Once the filter had dried, incorporation of radioactivity was measured using a liquid scintillation counter (Microbeta).

Example 48

HIV Infected PBMC Assay:

Fresh human peripheral blood mononuclear cells (PBMCs) were obtained from a commercial source (Biological Specialty) and were determined to be seronegative for HIV and HBV. Depending on the volume of donor blood received, the leukophoresed blood cells were washed several times with PBS. After washing, the leukophoresed blood was diluted 1:1 with Dulbecco's phosphate buffered saline (PBS) and layered over 15 mL of Ficoll-Hypaque density gradient in a 50 ml conical centrifuge tube. These tubes were centrifuged for 30 min at 600 g. Banded PBMCs were gently aspirated from the resulting interface and washed three times with PBS. After the final wash, cell number was determined by Trypan Blue dye exclusion and cells were re-suspended at 1×10^6 cells/mL in RPMI 1640 with 15% Fetal Bovine Serum (FBS), 2 mmol/L L-glutamine, 2 ug/mL PHA-P, 100 U/mL penicillin and 100 ug/mL streptomycin and allowed to incubate for 48-72 hours at 37° C. After incubation, PBMCs were centrifuged and resuspended in tissue culture medium. The cultures were maintained until use by half-volume culture changes with fresh IL-2 containing tissue culture medium every 3 days. Assays were initiated with PBMCs at 72 hours post PHA-P stimulation.

To minimize effects due to donor variability, PBMCs employed in the assay were a mixture of cells derived from 3 donors. Immediately prior to use, target cells were resuspended in fresh tissue culture medium at $1\times10^6$ cells/mL and plated in the interior wells of a 96-well round bottom microtiter plate at 50 uL/well. Then, 100 uL of 2× concentrations of compound-containing medium was transferred to the 96-well plate containing cells in 50 uL of the medium. AZT was employed as an internal assay standard.

Following addition of test compound to the wells, 50 uL of a predetermined dilution of HIV virus (prepared from 4× of final desired in-well concentration) was added, and mixed well. For infection, 50-150 $TCID_{50}$ of each virus was added per well (final MOI approximately 0.002). PBMCs were exposed in triplicate to virus and cultured in the presence or absence of the test material at varying concentrations as described above in the 96-well microtiter plates. After 7 days in culture, HIV-1 replication was quantified in the tissue culture supernatant by measurement of reverse transcriptase (RT) activity. Wells with cells and virus only served as virus controls. Separate plates were identically prepared without virus for drug cytotoxicity studies.

Reverse Transcriptase Activity Assay—Reverse transcriptase activity was measured in cell-free supernatants using a standard radioactive incorporation polymerization assay. Tritiated thymidine triphosphate (TTP; New England Nuclear) was purchased at 1 Ci/mL and 1 uL was used per enzyme reaction. A rAdT stock solution was prepared by mixing 0.5 mg/mL poly rA and 1.7 U/mL oligo dT in distilled water and was stored at −20° C. The RT reaction buffer was prepared fresh daily and consists of 125 uL of 1 mol/L EGTA, 125 uL of $dH_2O$, 125 uL of 20% Triton X-100, 50 uL of 1 mol/L Tris (pH 7.4), 50 uL of 1 mol/L DTT, and 40 uL of 1 mol/L $MgCl_2$. For each reaction, 1 uL of TTP, 4 uL of $dH_2O$, 2.5 uL of rAdT, and 2.5 uL of reaction buffer were mixed. Ten microliters of this reaction mixture was placed in a round bottom microtiter plate and 15 uL of virus-containing supernatant was added and mixed. The plate was incubated at 37° C. in a humidified incubator for 90 minutes. Following incubation, 10 uL of the reaction volume was spotted onto a DEAE filter mat in the appropriate plate format, washed 5 times (5 minutes each) in a 5% sodium phosphate buffer, 2 times (1 minute each) in distilled water, 2 times (1 minute each) in 70% ethanol, and then air dried. The dried filtermat was placed in a plastic sleeve and 4 mL of Opti-Fluor O was added to the sleeve. Incorporated radioactivity was quantified utilizing a Wallac 1450 Microbeta Trilux liquid scintillation counter.

Example 49

HBV:

HepG2.2.15 cells (100 μL) in RPMI1640 medium with 10% fetal bovine serum was added to all wells of a 96-well plate at a density of $1\times10^4$ cells per well and the plate was incubated at 37° C. in an environment of 5% $CO_2$ for 24 hours. Following incubation, six ten-fold serial dilutions of test compound prepared in RPMI1640 medium with 10% fetal bovine serum were added to individual wells of the plate in triplicate. Six wells in the plate received medium alone as a virus only control. The plate was incubated for 6 days at 37° C. in an environment of 5% $CO_2$. The culture medium was changed on day 3 with medium containing the indicated concentration of each compound. One hundred microliters of supernatant was collected from each well for analysis of viral DNA by qPCR and cytotoxicity was evaluated by XTT staining of the cell culture monolayer on the sixth day.

Ten microliters of cell culture supernatant collected on the sixth day was diluted in qPCR dilution buffer (40 μg/mL sheared salmon sperm DNA) and boiled for 15 minutes. Quantitative real time PCR was performed in 386 well plates using an Applied Biosystems 7900HT Sequence Detection System and the supporting SDS 2.4 software. Five microliters (5 μL) of boiled DNA for each sample and serial 10-fold dilutions of a quantitative DNA standard were subjected to real time Q-PCR using Platinum Quantitative PCR SuperMix-UDG (Invitrogen) and specific DNA oligonucleotide primers (IDT, Coralville, Id.) HBV-AD38-qF1 (5'-CCG TCT GTG CCT TCT CAT CTG-3'), HBV-AD38-qR1 (5'-AGT CCA AGA GTY CTC TTA TRY AAG ACC TT-3'), and HBV-AD38-qP1 (5'-FAM CCG TGT GCA/ZEN/CTT CGC TTC ACC TCT GC-3'BHQ1) at a final concentration of 0.2 μM for each primer in a total reaction volume of 15 μL. The HBV DNA copy number in each sample was interpolated from the standard curve by the SDS.24 software and the data were imported into an Excel spreadsheet for analysis.

The 50% cytotoxic concentration for the test materials are derived by measuring the reduction of the tetrazolium dye XTT in the treated tissue culture plates. XTT is metabolized by the mitochondrial enzyme NADPH oxidase to a soluble formazan product in metabolically active cells. XTT solution was prepared daily as a stock of 1 mg/mL in PBS. Phenazine methosulfate (PMS) stock solution was prepared at 0.15 mg/mL in PBS and stored in the dark at −20° C. XTT/PMS solution was prepared immediately before use by adding 40 μL of PMS per 1 mL of XTT solution. Fifty microliters of XTT/PMS was added to each well of the plate and the plate incubated for 2-4 hours at 37° C. The 2-4 hour incubation has been empirically determined to be within linear response range for XTT dye reduction with the indicated numbers of cells for each assay. Adhesive plate sealers were used in place of the lids, the sealed plate was inverted several times to mix the soluble formazan product and the plate was read at 450 nm (650 nm reference wavelength) with a Molecular Devices SpectraMax Plus 384 spectrophotometer. Data were collected by Softmax 4.6 software and imported into an Excel spreadsheet for analysis.

Example 50

Dengue RNA-Dependent RNA Polymerase Reaction Conditions

RNA polymerase assay was performed at 30° C. using 100 μl reaction mix in 1.5 ml tube. Final reaction conditions were 50 mM Hepes (pH 7.0), 2 mM DTT, 1 mM $MnCl_2$, 10 mM KCl, 100 nM UTR-Poly A (self-annealing primer), 10 μM UTP, 26 nM RdRp enzyme. The reaction mix with different compounds (inhibitors) was incubated at 30° C. for 1 hour. To assess amount of pyrophosphate generated during polymerase reaction, 30 μl of polymerase reaction mix was mixed with a luciferase coupled-enzyme reaction mix (70 μl). Final reaction conditions of luciferase reaction were 5 mM $MgCl_2$, 50 mM Tris-HCl (pH 7.5), 150 mM NaCl, 200 μU ATP sulfurylase, 5 μM APS, 10 nM Luciferase, 100 μM D-luciferin. White plates containing the reaction samples (100 μl) were immediately transferred to the luminometer Veritas (Turner Biosystems, Calif.) for detection of the light signal.

Example 51

Procedure for Cell Incubation and Analysis

Huh-7 cells were seeded at 0.5×10^6 cells/well in 1 mL of complete media in 12 well tissue culture treated plates. The cells were allowed to adhere overnight at 37°/5% $CO_2$. A 40 µM stock solution of test article was prepared in 100% DMSO. From the 40 µM stock solution, a 20 µM solution of test article in 25 ml of complete DMEM media was prepared. For compound treatment, the media was aspirated from the wells and 1 mL of the 20 µM solution was added in complete DMEM media to the appropriate wells. A separate plate of cells with "no" addition of the compound was also prepared. The plates were incubated at 37°/5% $CO_2$ for the following time points: 1, 3, 6 and 24 hours. After incubation at the desired time points, the cells were washed 2× with 1 mL of DPBS. The cells were extracted by adding 500 µl of 70% methanol/30% water spiked with the internal standard to each well treated with test article. The non-treated blank plate was extracted with 500 ul of 70% methanol/30% water per well. Samples were centrifuged at 16,000 rpm for 10 minutes at 4° C. Samples were analyzed by LC-MS/MS using an ABSCIEX 5500 QTRAP LC-MS/MS system with a Hypercarb (PGC) column.

Example 52

Procedure for Rodent Pharmacokinetic Experiment

DBA-1J mice (6-8 weeks old, female) were acclimated for ≥2 days after receipt. Mice were weighed the day before dosing to calculate dosing volumes. Mice were dosed by oral gavage with drug at 30 mg/kg, 100 mg/kg & 300 mg/kg. The mice were sampled at 8 time points: 0.5, 1, 2, 3, 4, 8 and 24 hrs (3 mice per time point for test drug). The mice were euthanized and their organs were collected (see below). In order to collected blood, mice with euthanized by $CO_2$ at the appropriate time point listed above. Blood was obtained by cardiac puncture (0.3 ml) at each time point. Following blood collection, the organs were removed from the mice (see below). The blood was processed by inverting Li-Heparin tube with blood gently 2 or 3 times to mix well. The tubes were then placed in a rack in ice water until able to centrifuge (≤1 hour). As soon as practical, the blood was centrifuged at ~2000×g for 10 min in a refrigerated centrifuge to obtain plasma. Then, using a 200 µL pipette, the plasma was transferred to a labeled 1.5 ml Eppendorf tube in ice water. The plasma was then frozen in freezer or on dry ice. The samples were stored at −80° C. prior to analysis. Organs were collected from euthanized mice. The organs (lungs, liver, kidney, spleen and heart) were removed, placed in a tube, and immediately frozen in liquid nitrogen. The tubes were then transferred to dry ice. The samples were saved in cryogenic tissue vials. Samples were analyzed by LC-MS/MS using an ABSCIEX 5500 QTRAP LC-MS/MS system with a Hypercarb (PGC) column.

Pharmacokinetic Parameters:

$T_{max}$ after oral dosing is 0.25-0.5 hr $C_{max}$'s are 3.0, 7.7 and 11.7 ng/ml after PO dosing with 30, 100 and 300 mg/kg;

Bioavailability (versus I.P. delivery) is 65% at 30 mg/kg and 39-46% at 100 and 300 mg/kg PO dosing;

EIDD-1931 plasma $T_{1/2}$ is 2.2 hr after IV dosing and 4.1-4.7 hrs after PO dosing After 300 mg/kg P.O. dose, the 24 hr plasma levels are ~0.4 µM; ~0.1 µM after 100 mg/kg dose

Example 53

Protocol for Mouse Model of Chikungunya Infection

C57BL-6J mice were injected with 100 pfus CHIK virus in the footpad. The test groups consisted of an unifected and untreated group, an infected and untreated group, an infected group receiving a high dose of 35 mg/kg i.p. of EIDD-01931, and an infected group receiving a low dose of 25 mg/kg i.p. of EIDD-01931. The two test groups receiving EIDD-01931 received compound 12 hours before challenge and then daily for 7 days. Footpads were evaluated for inflammation (paw thickness) daily for 7 days. CHIK virus induced arthritis (histology) was assessed in ankle joints using PCR after 7 days.

Example 54

N(4)-hydroxycytidine for the Prophylaxis and Treatment of Alphavirus Infections

Activity testing in Vero cell cytopathic effect (CPE) models of infection have shown that the ribonucleoside analog N(4)-hydroxycytidine (EIDD-01931) has activity against the Ross River, EEE, WEE, VEE and CHIK viruses with EC50 values of 2.45 µM, 1.08 µM, 1.36 µM, 1.00 µM and 1.28 µM, respectively. The cytotoxicity profile of the compound is acceptable, with selectivity indices ranging from a low of 8 in CEM cells to a high of 232 in Huh7 (liver) cells.

Example 55

Given that high titers of VEE virus can develop in the brain within hours of aerosol exposure, a direct-acting antiviral agent is desirable if it is able to rapidly achieve therapeutic levels of drug in the brain. A pilot pharmacokinetic study was conducted in male SD rats dosed by oral gavage with 5 and 50 mg/kg of EIDD-01931, to determine pharmacokinetic parameters and the tissue distribution profile of the compound into key organ systems, including the brain. EIDD-01931 is orally available and dose-proportional with a calculated bioavailability (% F) of 28%. Organ samples (brain, lung, spleen, kidney and liver) were collected at 2.5 and 24 hours post-dose from the 50 mg/kg dose group. EIDD-01931 was well distributed into all tissues tested; of particular note, it was readily distributed into brain tissue at therapeutic levels of drug, based on estimates from cellular data. Once in the brain, EIDD-01931 was rapidly metabolized to its active 5'-triphosphate form to give brain levels of 526 and 135 ng/g at 2.5 and 24 hours, respectively. Even after 24 hours levels of EIDD-01931 and its 5'-triphosphate in the brain are considerable, suggesting that once-daily oral dosing may be adequate for treatment.

Alternatively, drug delivery by aerosol (nasal spray) administration may immediately achieve therapeutic levels of drug in the nasal mucosa and the brain. EIDD-01931 has an acceptable toxicology profile after 6 day q.d. intraperitoneal (IP) injections in mice, with the NOEL (NO Effect Level) to be 33 mg/kg; weight loss was observed at the highest dose tested (100 mg/kg), which reversed on cessation of dosing.

Example 56

Several derivatives of EIDD-01931 have shown antiviral activity in screening against various viruses. Activity data is shown in the tables below.

|  | Norovirus GT1 HG23 | | | SARS Coronavirus Orbani Vero 76 | | |
|---|---|---|---|---|---|---|
| Structure | EC50 (ug/ml) | CC50 (ug/ml) | SI50 | EC50 (ug/ml) | CC50 (ug/ml) | SI50 |
| (structure: N-hydroxycytidine) | >100 | >100 | · | <0.1 | 36 | >360 |
| (structure: N-octanoyloxy cytidine) | | | | 0.19 | 36 | 190 |
| (structure: N-heptyloxycarbonyl cytidine) | | | | 0.28 | >100 | >360 |
| (structure: N-methoxy cytidine) | | | | >100 | >100 | |
| (structure: N-hydroxy-2'-methyl cytidine) | >100 | >100 | · | >100 | >100 | · |

| Structure | Chikungunya virus (MOI 0.5) U2OS cell line | | | |
|---|---|---|---|---|
| | Viral Inh. 10 uM | Viral Inh. 50 uM | Cell Viability 10 uM | Cell Viability 50 uM |
| [structure: N4-hydroxycytidine] | 80% ± 15% (n = 4) | 100% ± 0% (n = 4) | 97% ± 5% (n = 4) | 79% ± 10% (n = 4) |
| [structure: N4-(heptyloxycarbonyl)-N4-hydroxycytidine] | 72% ± 14% (n = 4) | 98% ± 1% (n = 4) | 93% ± 4% (n = 4) | 78% ± 8% (n = 4) |
| [structure: N4-hydroxycytidine isopropyl alaninyl phenyl phosphoramidate] | 3% ± 2% (n = 4) | 36% ± 21% (n = 4) | 99% ± 6% (n = 4) | 99% ± 8% (n = 4) |
| [structure: 5-fluoro-N4-hydroxycytidine] | 8% ± 3% (n = 4) | 51% ± 11% (n = 4) | 81% ± 4% (n = 4) | 53% ± 2% (n = 4) |

|  | Chikungunya virus (MOI 0.5) U2OS cell line | | | |
|---|---|---|---|---|
| Structure | Viral Inh. 10 uM | Viral Inh. 50 uM | Cell Viability 10 uM | Cell Viability 50 uM |
| [structure: N-heptyl carbamate oxime of cytidine] | 14% ± 11% (n = 4) | 70% ± 20% (n = 4) | 105% ± 2% (n = 4) | 96% ± 11% (n = 4) |

|  | VEEV (MOI 0.025) HeLa | | | | |
|---|---|---|---|---|---|
| Structure | EC$_{50}$ (μM) | Viral Inh. 10 uM | Viral Inh. 50 uM | Cell Viability 10 uM | Cell Viability 50 uM |
| [structure: N-hydroxycytidine] | 1.24 | 100% ± 0% (n = 4) | 100% ± 0% (n = 4) | 116% ± 24% (n = 4) | 61% ± 8% (n = 4) |
| [structure: N-heptyloxycarbonyl cytidine] | 0.57 | 100% ± 0% (n = 4) | 100% ± 0% (n = 4) | 116% ± 20% (n = 4) | 85% ± 8% (n = 4) |

-continued

| Structure | VEEV (MOI 0.025) HeLa | | | | |
|---|---|---|---|---|---|
| | EC$_{50}$ (μM) | Viral Inh. 10 uM | Viral Inh. 50 uM | Cell Viability 10 uM | Cell Viability 50 uM |
| 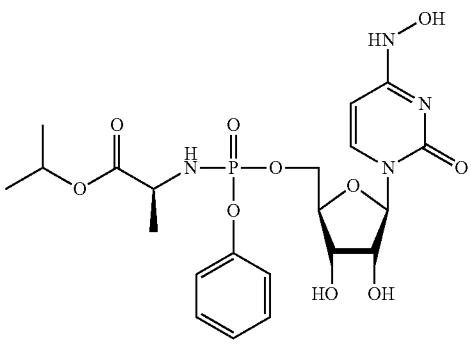  | 16.20 | 73% ± 10% (n = 4) | 100% ± 0% (n = 4) | 137% ± 16% (n = 4) | 134% ± 16% (n = 4) |
| 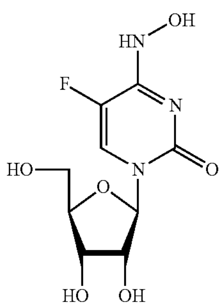  | N.A. | 61% ± 14% (n = 4) | 98% ± 1% (n = 4) | 55% ± 4% (n = 4) | 36% ± 2% (n = 4) |
| 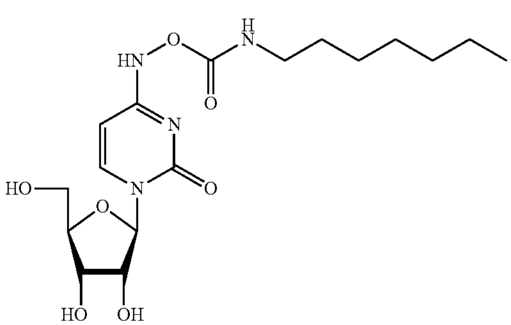  | 6.00 | 93% ± 3% (n = 4) | 100% ± 0% (n = 4) | 151% ± 16% (n = 4) | 126% ± 7% (n = 4) |

| Structure | VEEV (MOI 0.003) Astrocytes | | | |
|---|---|---|---|---|
| | Viral Inh. 10 uM | Viral Inh. 50 uM | Cell Viability 10 uM | Cell Viability 50 uM |
| [Structure: N4-hydroxycytidine] | 99% ± 0% (n = 3) | 100% ± 0% (n = 3) | 98% ± 12% (n = 3) | 86% ± 5% (n = 3) |
| [Structure: N4-heptyloxycarbonyl N-hydroxycytidine] | 94% ± 5% (n = 3) | 100% ± 0% (n = 3) | 99% ± 9% (n = 3) | 94% ± 10% (n = 3) |
| [Structure: phosphoramidate prodrug of N4-hydroxycytidine] | 49% ± 21% (n = 3) | 96% ± 2% (n = 3) | 102% ± 16% (n = 3) | 100% ± 17% (n = 3) |
| [Structure: 5-fluoro N4-hydroxycytidine] | N.A. | N.A. | N.A. | N.A. |

-continued

| Structure | VEEV (MOI 0.003) Astrocytes | | | |
|---|---|---|---|---|
| | Viral Inh. 10 uM | Viral Inh. 50 uM | Cell Viability 10 uM | Cell Viability 50 uM |
| [structure: cytidine with N-heptyl carbamate on exocyclic amine via N-O linkage] | 51% ± 32% (n = 3) | 37% ± 47% (n = 3) | 98% ± 12% (n = 3) | 85% ± 19% (n = 3) |

| Structure | MERV (MOI 0.4) VERO | | | |
|---|---|---|---|---|
| | Viral Inh. 10 uM | Viral Inh. 50 uM | Cell Viability 10 uM | Cell Viability 50 uM |
| [structure: N4-hydroxycytidine] | 99% ± 0% (n = 4) | 100% ± 0% (n = 4) | 75% ± 6% (n = 4) | 47% ± 3% (n = 4) |
| [structure: cytidine with heptyloxycarbonyl on N-O linkage to exocyclic amine] | 99% ± 0% (n = 4) | 99% ± 0% (n = 4) | 84% ± 8% (n = 4) | 58% ± 2% (n = 4) |

-continued

| Structure | MERV (MOI 0.4) VERO | | | |
|---|---|---|---|---|
| | Viral Inh. 10 uM | Viral Inh. 50 uM | Cell Viability 10 uM | Cell Viability 50 uM |
| [structure: isopropyl phosphoramidate prodrug of N-hydroxycytidine] | 29% ± 16% (n = 4) | 85% ± 11% (n = 4) | 103% ± 14% (n = 4) | 102% ± 36% (n = 4) |
| [structure: 5-fluoro-N-hydroxycytidine] | N.A. | N.A. | N.A. | N.A. |
| [structure: N-heptyl carbamate of N-hydroxycytidine] | 86% ± 6% (n = 4) | 98% ± 1% (n = 4) | 118% ± 15% (n = 4) | 91% ± 39% (n = 4) |

Example 57

Compounds Screened in a CHIKV CPE Assay

EIDD-01931    EIDD-02053

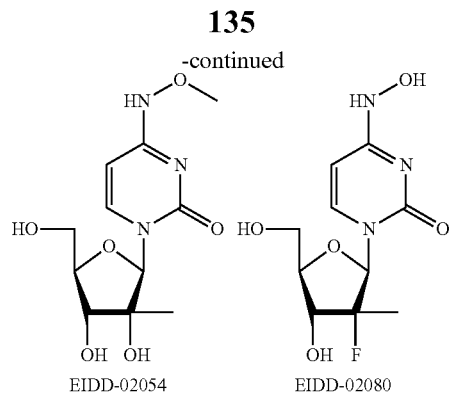
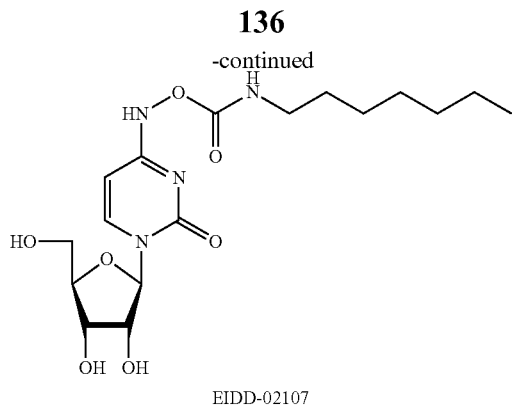
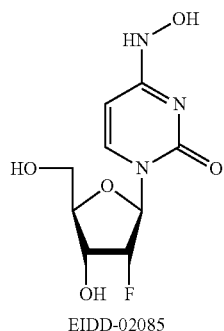
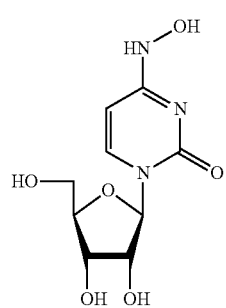
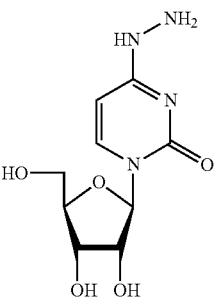
Example 58
Compounds Screened in a CHIKV CPE Assay
| EIDD- | EC$_{50}$ | CC$_{50}$ | SI |
| --- | --- | --- | --- |
| 01931-04 | 0.6 | 15.3 | 25.5 |
| 02053-01 | 72 | >500 | >6.9 |
| 02054-01 | >75 | >500 | >6.7 |
| 02080-01 | >75 | >500 | >6.7 |
| 02085-01 | >75 | >500 | >6.7 |
| 02107-01 | 29 | 165 | 5.7 |
| 02107-02 | 38 | 165 | 4.3 |
Example 59
Compounds Screened in a CHIKV CPE Assay
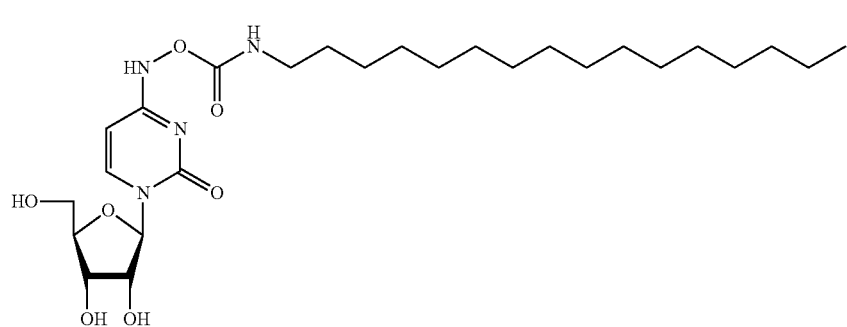

-continued
EIDD-02474
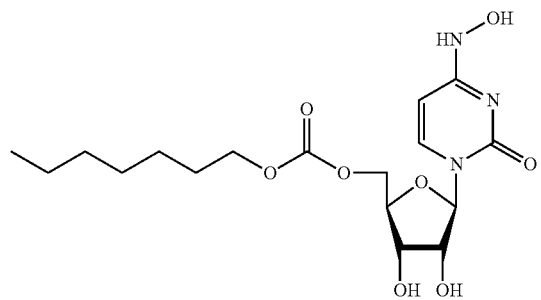
EIDD-02357
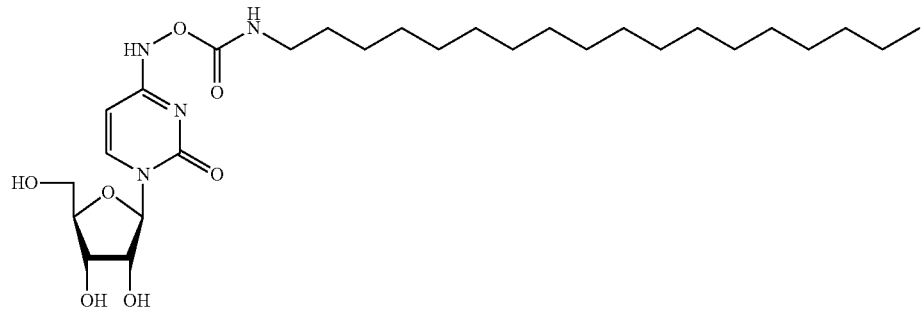
EIDD-02475
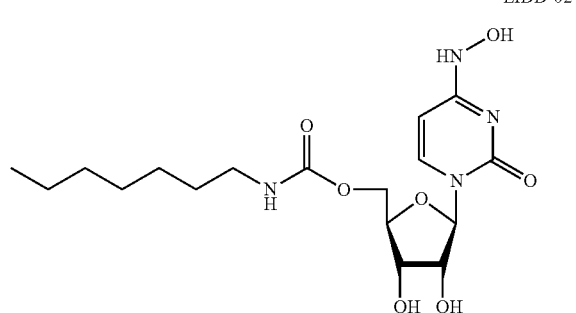
EIDD-02476
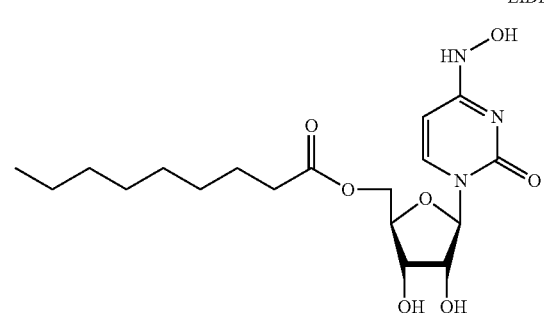
EIDD-02422
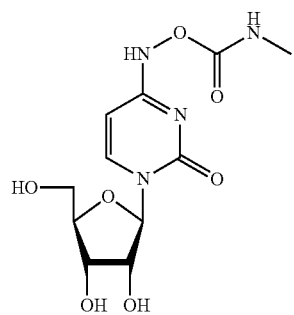
EIDD-02423
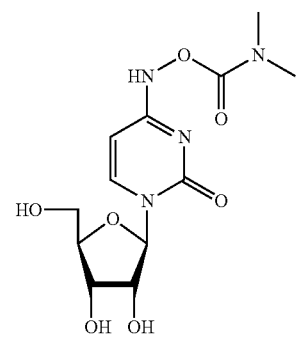
EIDD-02339
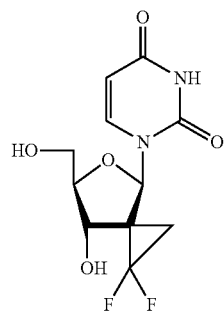
EIDD-02340
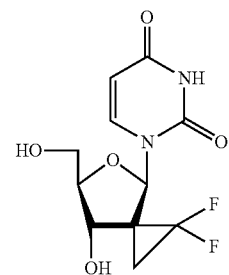

Example 60

| EIDD- | EC$_{50}$ | CC$_{50}$ | SI |
|---|---|---|---|
| 01931-04 | 0.7 | >500 | >714 |
| 01910-01 | >78 | >500 | N/D |
| 02339-01 | >78 | >500 | N/D |
| 02340-01 | >78 | >500 | N/D |
| 02356-01 | >78 | 211 | <2.7 |
| 02357-01 | >78 | 90 | <1.2 |
| 02422-01 | 32 | >500 | >15.6 |
| 02423-01 | 25 | >500 | >20 |
| 02474-01 | 0.07 | 184 | 2628.6 |
| 02475-01 | >78 | >500 | N/D |
| 02476-01 | 0.3 | 154 | 513.3 |

Example 61

Compounds Screened in a CHIKV CPE Assay

-continued
EIDD-02503
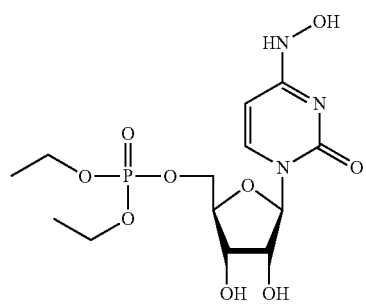
EIDD-02416
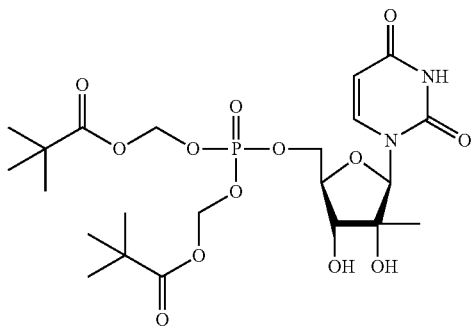
EIDD-02200
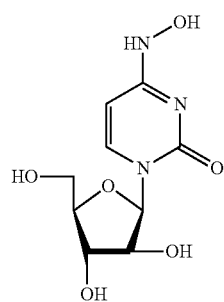
EIDD-02427
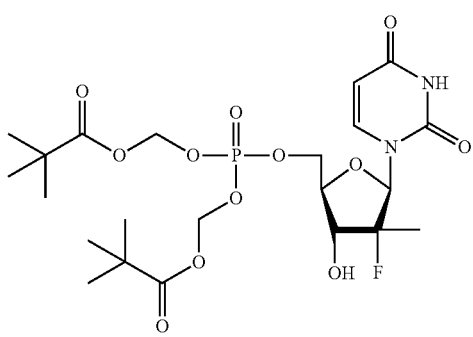
EIDD-01872
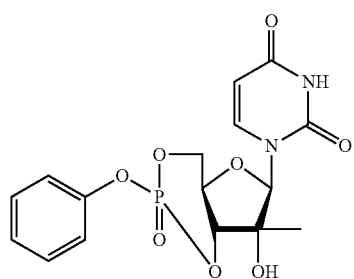
EIDD-02290
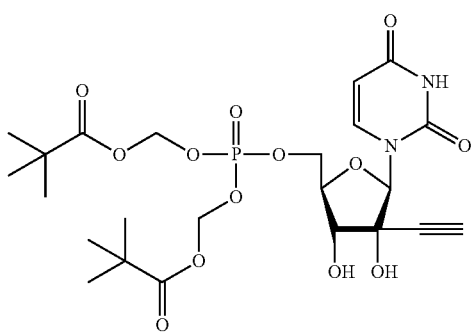
EIDD-02110
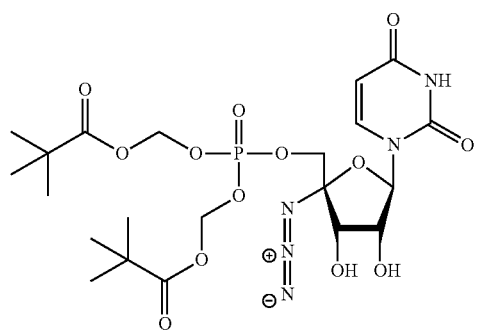

Example 62

| EIDD- | EC$_{50}$ | CC$_{50}$ | SI |
|---|---|---|---|
| 01931-04 | 1.8 | >500 | >277 |
| 02504-01 | >78 | >500 | N/A |
| 02416-01 | 27 | 53 | 2.0 |
| 02345-01 | 1.5 | >500 | >333 |
| 02261-01 | 1.5 | >500 | >333 |
| 02427-01 | 58 | 355 | 6.1 |
| 02207-01 | 10.8 | >500 | >46.3 |
| 02108-03 | 34.5 | 98 | 2.8 |
| 02503-01 | >78 | >500 | N/D |
| 02110-03 | 56 | 387 | 6.9 |
| 01872-01 | >78 | >500 | N/D |
| 02200-01 | >78 | >500 | N/D |
| 02290-01 | 64.4 | 274 | 4.3 |

Example 63

| Structure and I.D. | ZIKV (EC$_{50}$ μM) | Vero cells (CC$_{50}$ μM) |
|---|---|---|
| 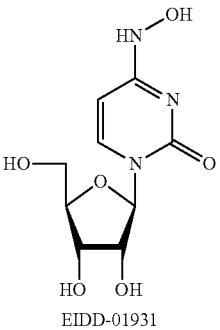 EIDD-01931 | 4.02 | 50.4 |

Example 64

Protocol for Mouse Model of Zika Infection

Figure 9:
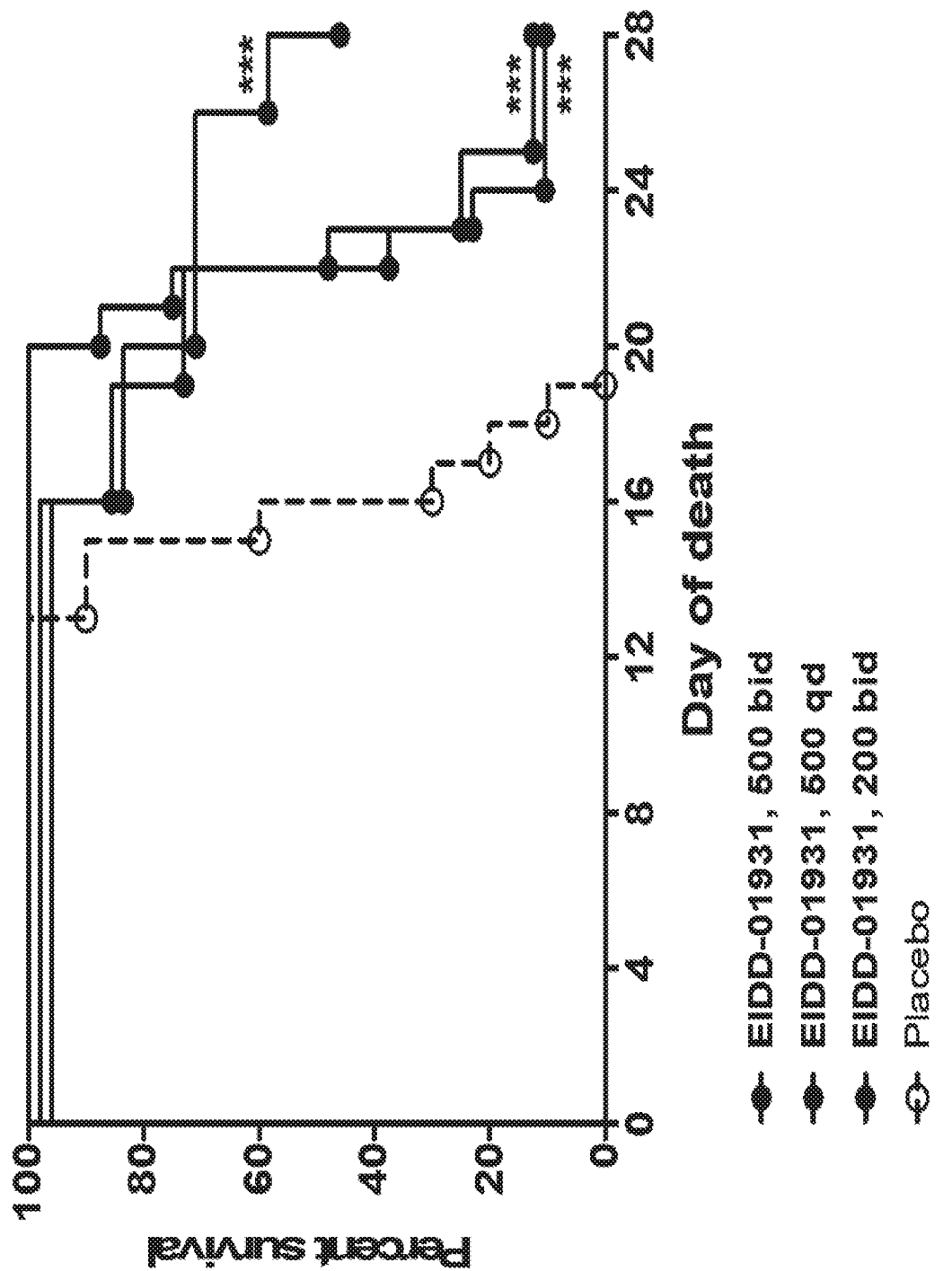
FIG. 9 shows the survival of ZIKV-challenged mice treated with an exemplary compound for 7 days.

AG129 mice were injected with 100 CCID$_{50}$ of ZIKV (Malaysian strain, P 6-740, P2) administered via s.c. injection (0.1 mL). Mice received EIDD-01931 or vehicle based on the dosing regimen shown in the table below. Mice were monitored for 28 days post-virus challenge for survival, weight change, and signs of disease including conjunctivitis, hunching, and limb weakness and paralysis. Serum was collected 5 dpi for analysis of treatment on viral RNA by QRT-PCR. Results are shown in FIG. 9.

| Group | Compound | Dose | Schedule | Virus |
|---|---|---|---|---|
| 1 | EIDD-01931 | 500 mg/kg | 0.1 ml, p.o., bid × 7, beg −2 h | ZIKV Malaysia |
| 2 | EIDD-01931 | 500 mg/kg | 0.1 ml, p.o., qd × 7, beg −2 h | ZIKV Malaysia |
| 3 | EIDD-01931 | 200 mg/kg | 0.1 ml, p.o., bid × 7, beg −2 h | ZIKV Malaysia |
| 4 | Vehicle | — | 0.1 ml, p.o., bid × 7, beg −4 h | ZIKV Malaysia |
| 5 | EIDD-01931 | 500 mg/kg | 0.1 ml, p.o., bid × 7, beg −2 h | Sham |
| 6 | Normal Controls | N/A | N/A | N/A |

Example 65

Protocol for Mouse Model of Zika Infection Varying Initiation of Treatment

Figure 10:
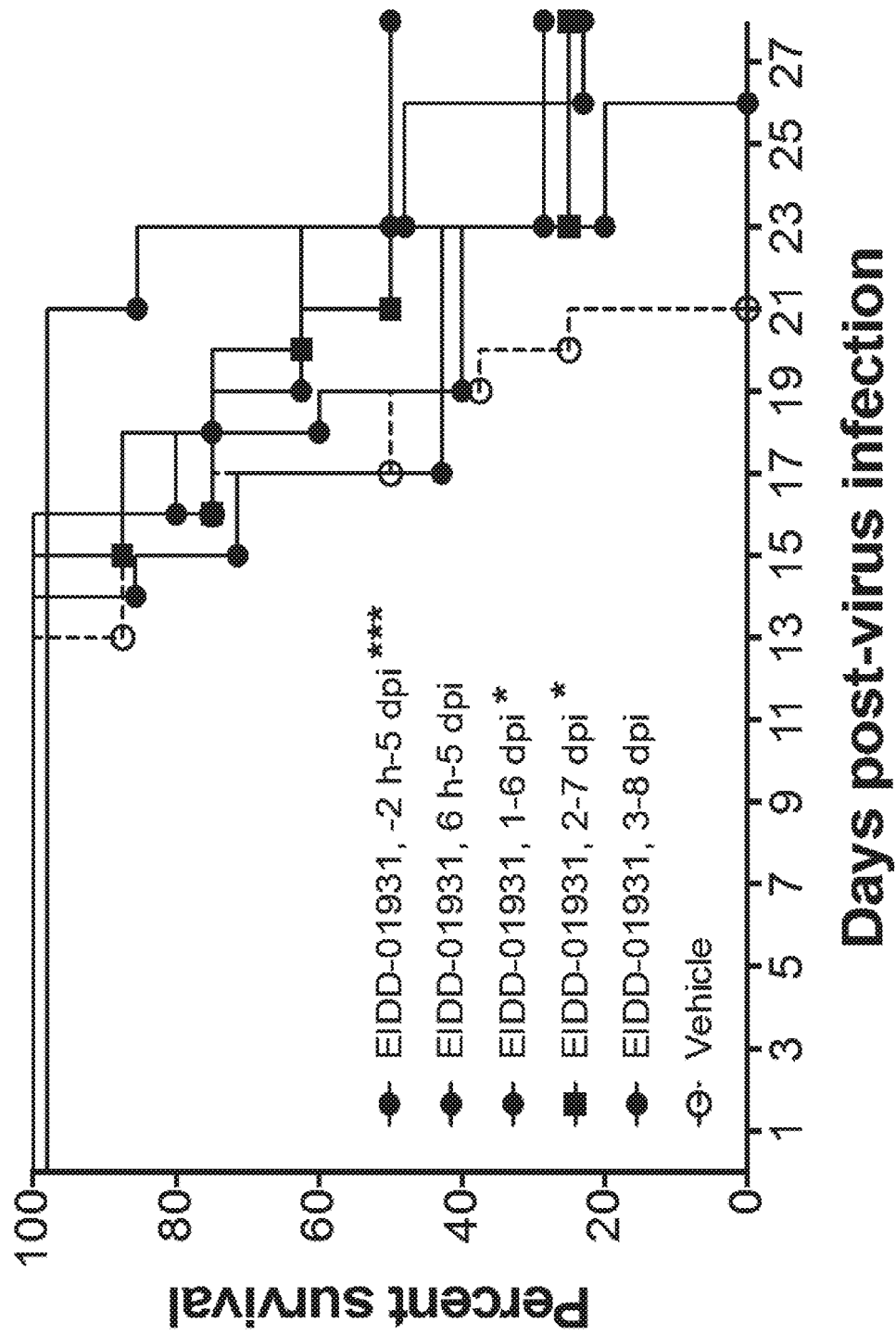
FIG. 10 shows the survival of ZIKV-challenged mice treated with an exemplary compound for 7 days, with varying treatment initiation times post-infection.

AG129 mice were injected with $10^{1.0}$ CCID$_{50}$ of ZIKV (Malaysian strain, v2826) administered via s.c. injection (0.1 mL). Mice received EIDD-01931 or vehicle based on the dosing regemin shown in the table below. Treatment was varied beginning −2, 6, 24, 48, and 72 hours post virus challenge. Mice were monitored for 28 days post-virus challenge for survival, weight change, and signs of disease including conjunctivitis, hunching, and limb weakness and paralysis. Serum was collected 5 dpi for analysis of treatment on viral RNA by QRT-PCR. Results are shown in FIG. 10.

| Grp | n | Compound | Dose | Treatment Regimen | Virus |
|---|---|---|---|---|---|
| 1 | 8 | EIDD-01931 | 500 mg/kg bid | 0.2 ml, p.o., bid × 7 beg −2 h | ZIKV |
| 2 | 8 | EIDD-01931 | 500 mg/kg bid | 0.2 ml, p.o., bid × 7 beg 6 h | ZIKV |
| 3 | 8 | EIDD-01931 | 500 mg/kg bid | 0.2 ml, p.o., bid × 7 beg 24 h | ZIKV |
| 4 | 8 | EIDD-01931 | 500 mg/kg bid | 0.2 ml, p.o., bid × 7 beg 48 h | ZIKV |
| 5 | 8 | EIDD-01931 | 500 mg/kg bid | 0.2 ml, p.o., bid × 7 beg 72 h | ZIKV |
| 6 | 8 | Vehicle | — | 0.2 ml, p.o., bid × 7 beg −2 h | ZIKV |
| 7 | 4 | Vehicle | — | 0.2 ml, p.o., bid × 6 beg −2 h | Sham |

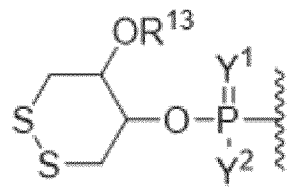

The invention claimed is:

1. A method of treating a Zika virus infection comprising administering an effective amount of a compound of Formula I, to a subject in need thereof, wherein the compound of Formula I is:

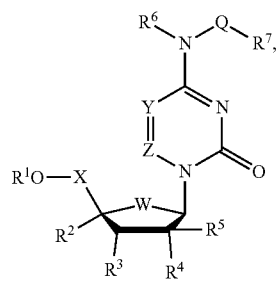

Formula I or salt thereof, wherein

Q is O, —O(C═O)—, —O(C═O)Lipid, —O(C═O)V—, NH, or NR$^7$;

V is O, NH, NR$^7$, S, CH$_2$, or CHR$^7$;

W is CH$_2$, NH, S or O;

X is CH$_2$, CHMe, CMe$_2$, CHF, CF$_2$, or CD$_2$;

Y is N or CR";

Z is N or CR";

each R" is independently selected from is H, D, F, Cl, Br, I, CH$_3$, CD$_3$, CF$_3$, alkyl, acyl, alkenyl, alkynyl, hydroxyl, formyl or SCH$_3$;

R$^1$ is hydrogen, monophosphate, diphosphate, triphosphate,

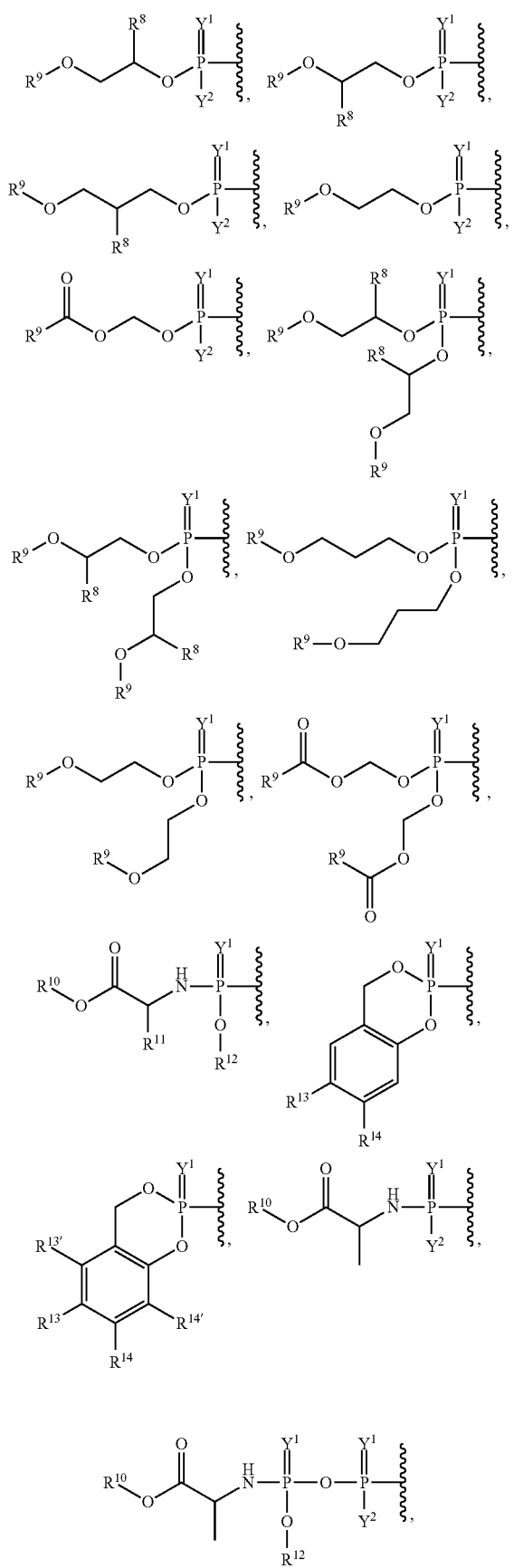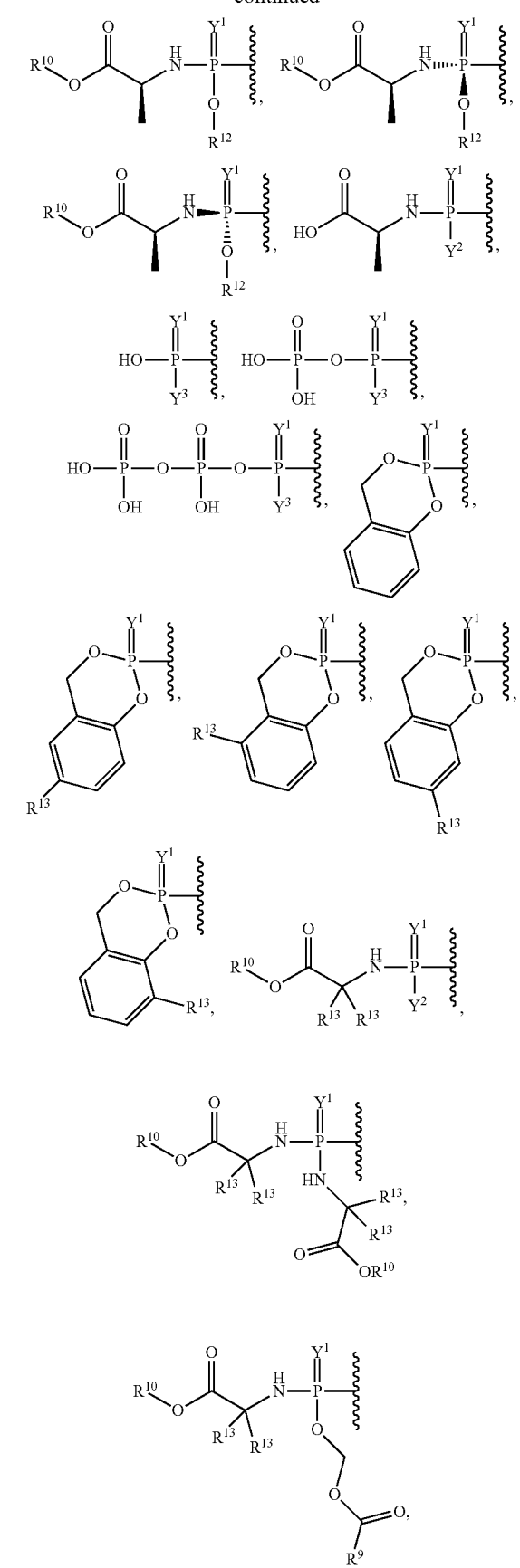

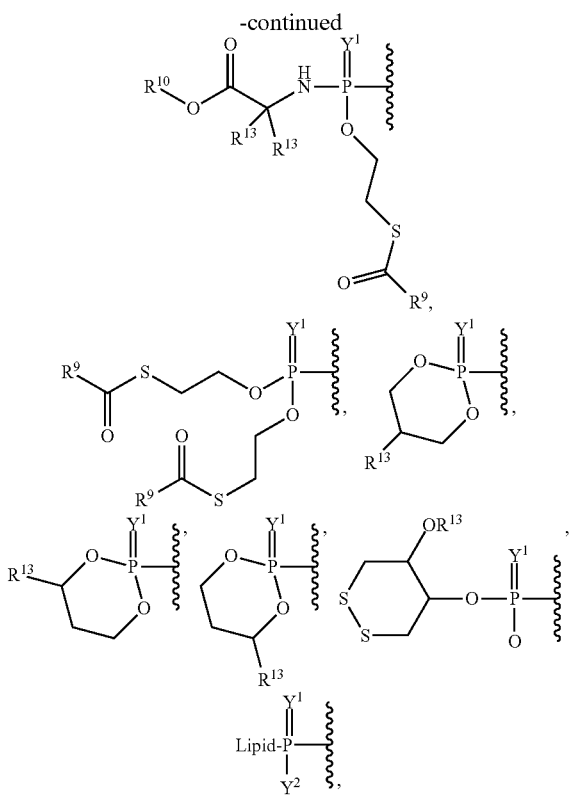

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein R$^1$ is optionally substituted with one or more, the same or different, R$^{20}$;

Y$^1$ is O or S;

Y$^2$ is OH, OR$^{12}$, OAlkyl, or BH$_3^-$M$^+$;

Y$^3$ is OH or BH$_3^-$M$^+$;

R$^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein R$^2$ is optionally substituted with one or more, the same or different, R$^{20}$;

R$^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^3$ is optionally substituted with one or more, the same or different, R$^{20}$;

R$^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^4$ is optionally substituted with one or more, the same or different, R$^{20}$;

R$^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, alkoxy, alkylthio, alkylamino, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^{20}$;

R$^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^6$ is optionally substituted with one or more, the same or different, R$^{20}$;

each R$^7$ is independently selected from absent, hydrogen, —(C═O)Oalkyl, —(C═O)alkyl, —(C═O)NHalkyl, —(C═O)N-dialkyl, —(C═O)Salkyl, hydroxy, alkoxy, alkyl, higher alkyl, (C$_6$-C$_{16}$)alkyl, (C$_6$-C$_{22}$) alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each R$^7$ is optionally substituted with one or more, the same or different, R$^{20}$;

R$^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein R$^8$ is optionally substituted with one or more, the same or different, R$^{20}$;

R$^9$ is hydrogen, methyl, ethyl, tert-butyl, alkyl, higher alkyl, (C$_6$-C$_{16}$)alkyl, (C$_6$-C$_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^9$ is optionally substituted with one or more, the same or different, R$^{20}$;

R$^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{20}$;

R$^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{20}$;

R$^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein R$^{12}$ is optionally substituted with one or more, the same or different, R$^{20}$;

R$^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein R$^{13}$ is optionally substituted with one or more, the same or different, R$^{20}$;

R$^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein R¹⁴ is optionally substituted with one or more, the same or different, R²⁰;

R¹³' is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein R¹³' is optionally substituted with one or more, the same or different, R²⁰;

R¹⁴' is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein R¹⁴' is optionally substituted with one or more, the same or different, R²⁰;

R²⁰ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)₂amino, alkylsulfinyl, alkylsulfonyl, arylsulfonyl, carbocyclyl, aryl, or heterocyclyl, wherein R²⁰ is optionally substituted with one or more, the same or different, R²¹;

R²¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a C₆₋₂₂ alkyl, alkoxy, polyethylene glycol, or aryl substituted with an alkyl group.

2. The method of claim 1, wherein the compound is administered through the lungs.

3. The method of claim 1, wherein the compound is a compound of the structure:

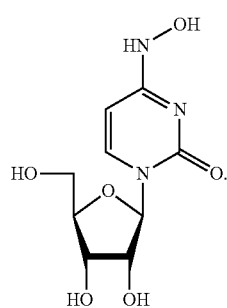

4. The method of claim 1, wherein the compound is a compound of Formula IB:

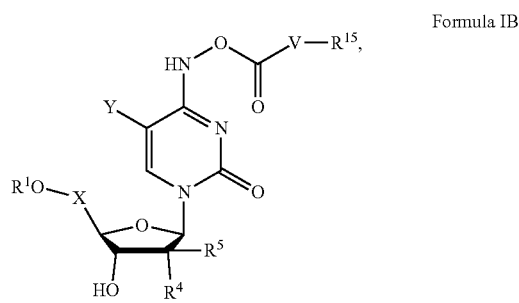

Formula IB or a salt thereof, wherein

V is absent, O, NH, NR¹⁵, S, CH₂, or CHR¹⁵;

X is CH₂, CHMe, CMe₂, CHF, CF₂, or CD₂;

Y is H, D, F, Cl, Br, I, CH₃, CD₃, CF₃, alkyl, acyl, alkenyl, alkynyl, hydroxyl, formyl or SCH₃;

R¹ is hydrogen, monophosphate, diphosphate, triphosphate,

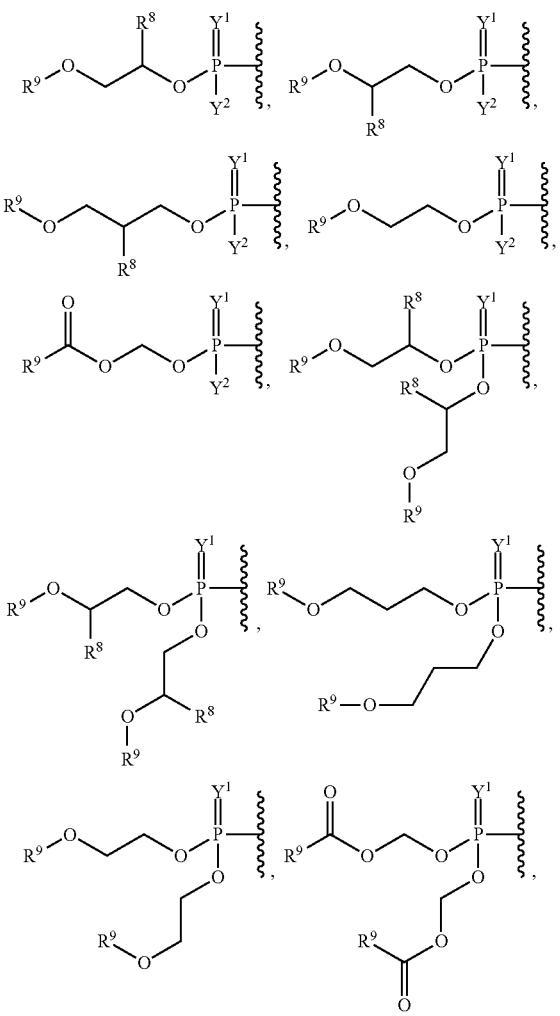

-continued

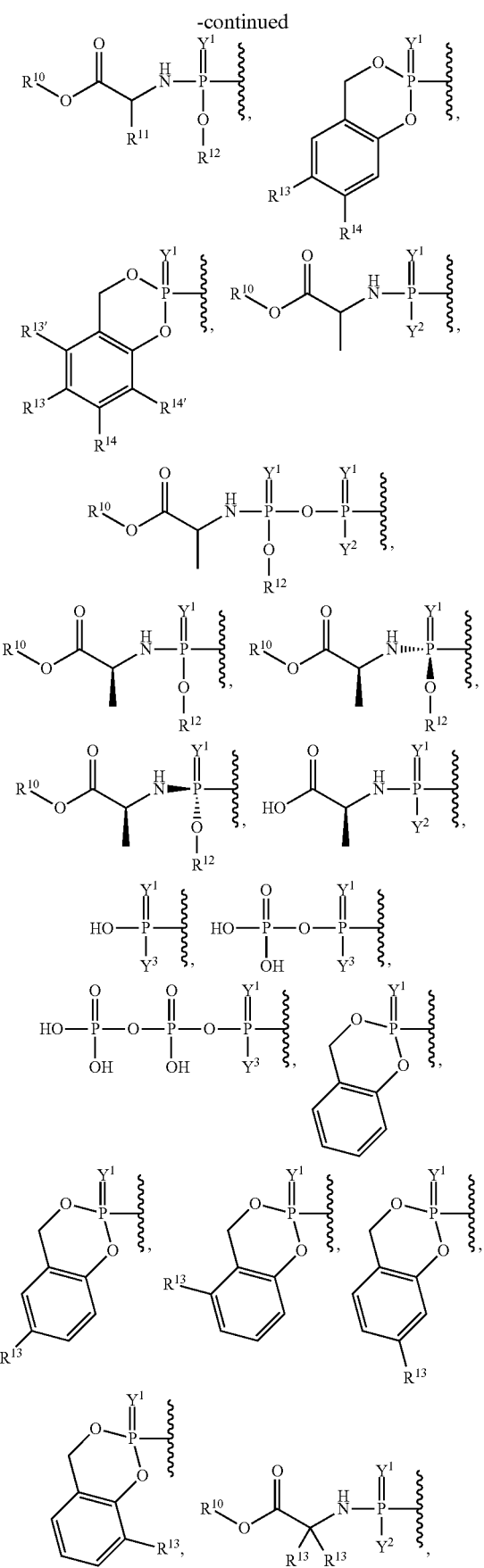

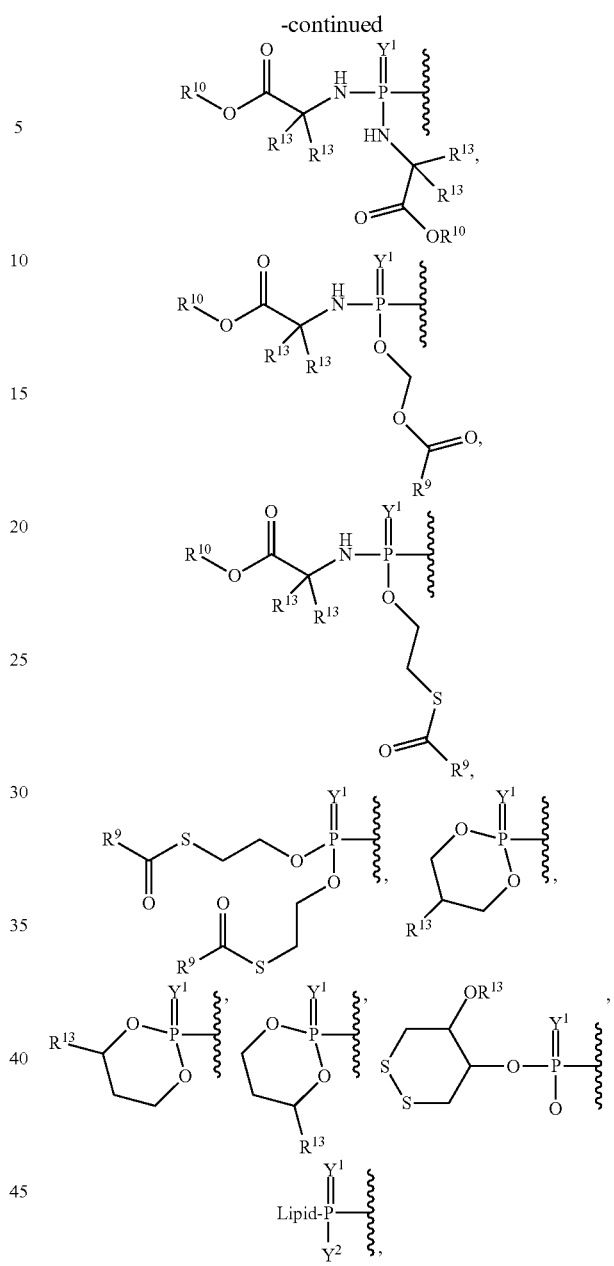

alkyl, halogen, nitro, cyano, hydroxy, amino, mercapto, formyl, carboxy, carbamoyl, carbanoyl, esteryl, alkoxy, alkylthio, alkylamino, (alkyl)$_2$amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, $(C_6-C_{16})$alkyl, $(C_6-C_{22})$alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

$R^{15}$ is hydrogen, Lipid, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6-C_{16})$alkyl, $(C_6-C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group.

5. The method of claim 1, wherein the compound is a compound of the structure:

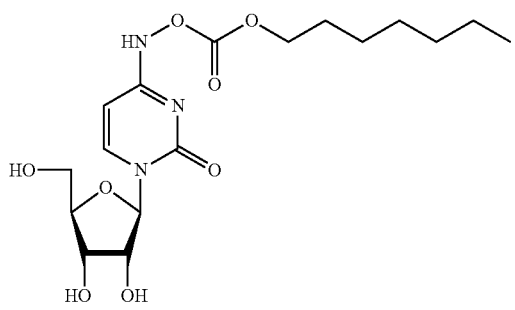

or a salt thereof.

6. The method of claim 1, wherein the compound is a compound of the structure:

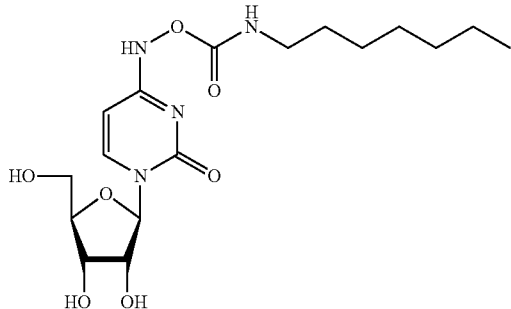

or a salt thereof.

7. The method of claim 1, wherein the compound is a compound of the structure:

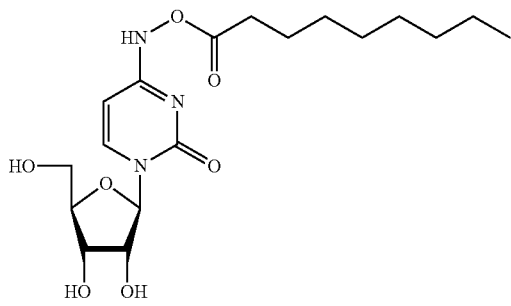

of a salt thereof.

8. The method of claim 1, further comprising administering an additional antiviral compound selected from NITD008, BCX4430, or a combination thereof.

9. The method of claim 1, wherein Q-$R^7$ is OH.

10. The method of claim 1, wherein $R^1$ is

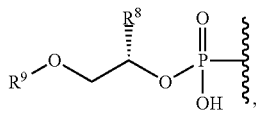

$R^8$ is hydrogen, hydroxy, or benzyloxy, and $R^9$ is ($C_6$-$C_{22}$)alkyl.

11. The method of claim 1, wherein the compound is selected from:

1-(3,4-dihydroxy-5-(hydroxymethyl)tetrahydrofuran-2-yl)-4-((nonanoyloxy)amino)pyrimidin-2-one;

1-(3,4-dihydroxy-5-(hydroxymethyl)tetrahydrofuran-2-yl)-4-((((heptyloxy)carbonyl)oxy)amino)pyrimidin-2-one; and isopropyl(((3,4-dihydroxy-5-(4-(hydroxyamino)-2-oxopyrimidin-1(2H)-yl)tetrahydrofuran-2-yl)methoxy)(phenoxy)phosphoryl)alaninate.

12. The method of claim 1, wherein the compound is a compound of Formula IC,

Formula IC

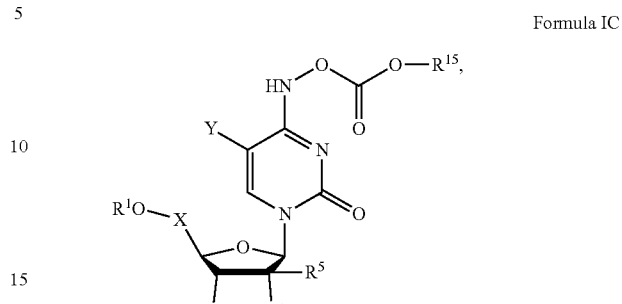

or a salt thereof, wherein

X is $CH_2$, CHMe, $CMe_2$, CHF, $CF_2$, or $CD_2$;

Y is H, D, F, Cl, Br, I, $CH_3$, $CD_3$, $CF_3$, alkyl, acyl, alkenyl, alkynyl, hydroxyl, formyl or $SCH_3$;

$R^1$ is hydrogen, monophosphate, diphosphate, triphosphate,

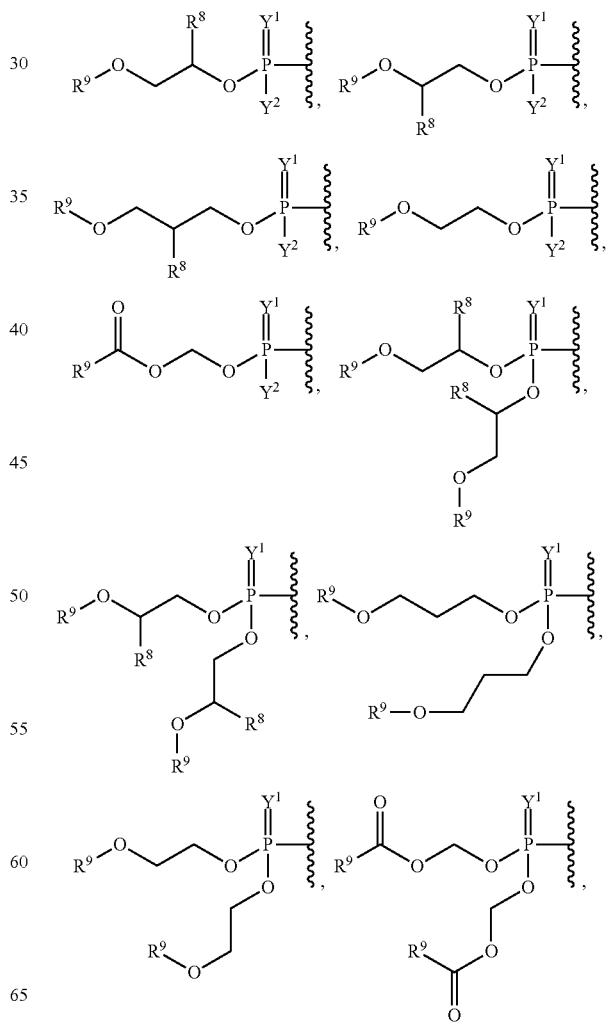

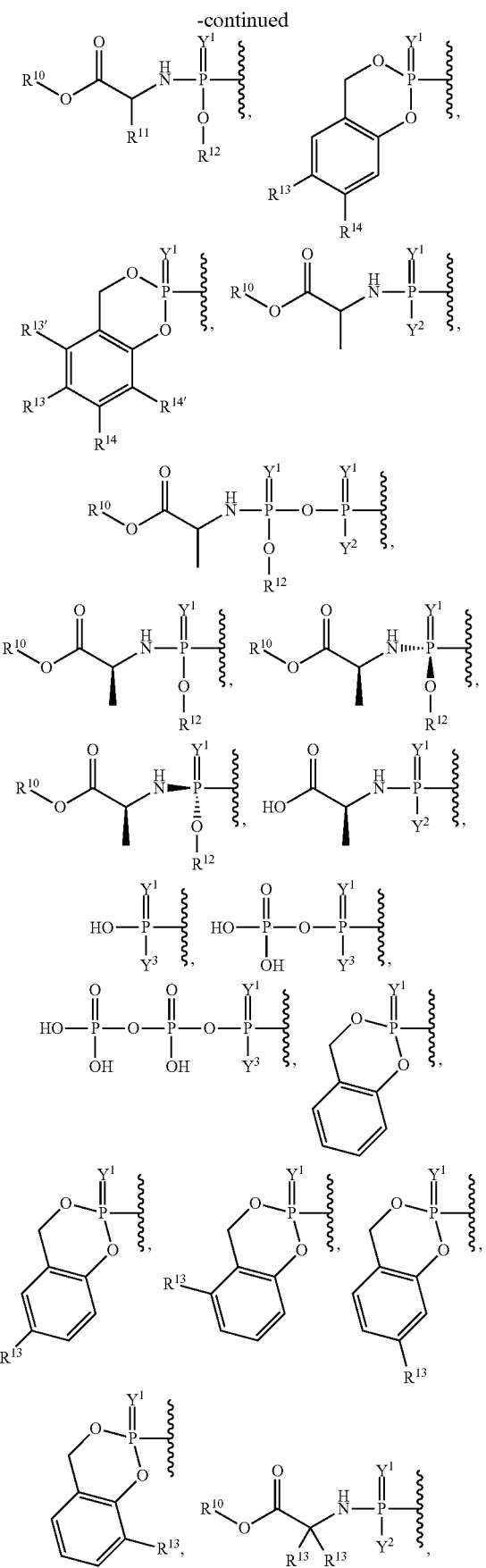

alkyl, halogen, nitro, cyano, hydroxy, amino, mercapto, formyl, carboxy, carbamoyl, carbanoyl, esteryl, alkoxy, alkylthio, alkylamino, (alkyl)₂amino, alkylsulfinyl, alkylsulfonyl, arylsulfonyl, carbocyclyl, aryl, or heterocyclyl, phosphoramidyl, or phosphate wherein R¹ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, (C$_6$-C$_{16}$)alkyl, (C$_6$-C$_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

$R^{15}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, (C$_6$-C$_{16}$)alkyl, (C$_6$-C$_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a C$_{6-22}$ alkyl, alkoxy, polyethylene glycol, or aryl substituted with an alkyl group.

13. The method of claim 1, wherein the compound is a compound of Formula ID,

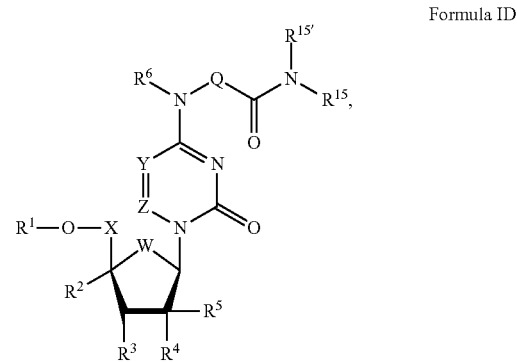

Formula ID or a salt thereof, wherein

W is CH$_2$, NH, S or O;

X is CH$_2$, CHMe, CMe$_2$, CHF, CF$_2$, or CD$_2$;

Y is N or CR'';

Z is N or CR'';

each $R^{11}$ is independently selected from is H, D, F, Cl, Br, I, CH$_3$, CD$_3$, CF$_3$, alkyl, acyl, alkenyl, alkynyl, hydroxyl, formyl or SCH$_3$;

$R^1$ is hydrogen, monophosphate, diphosphate, triphosphate,

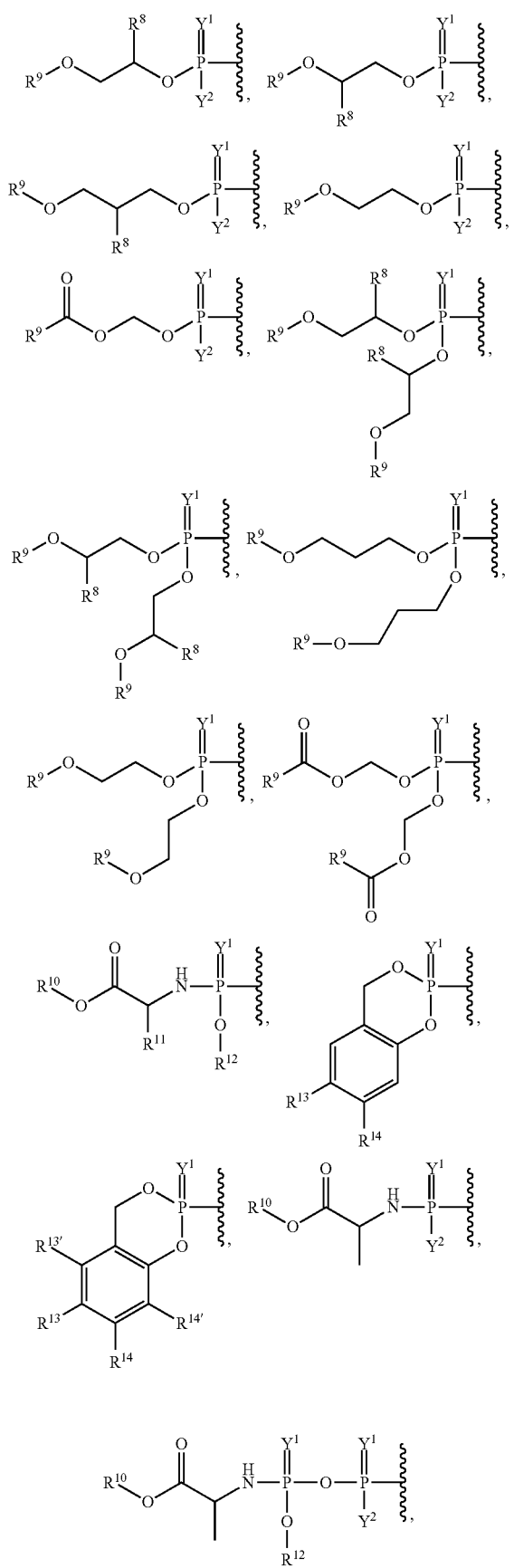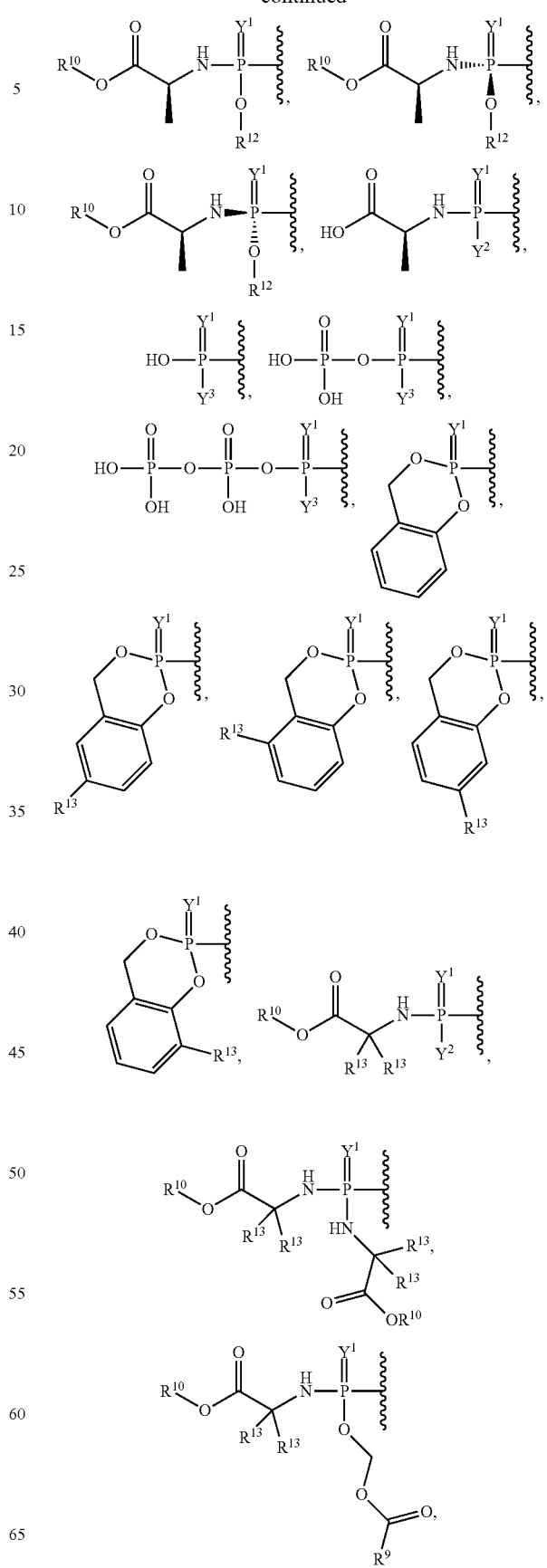
-continued

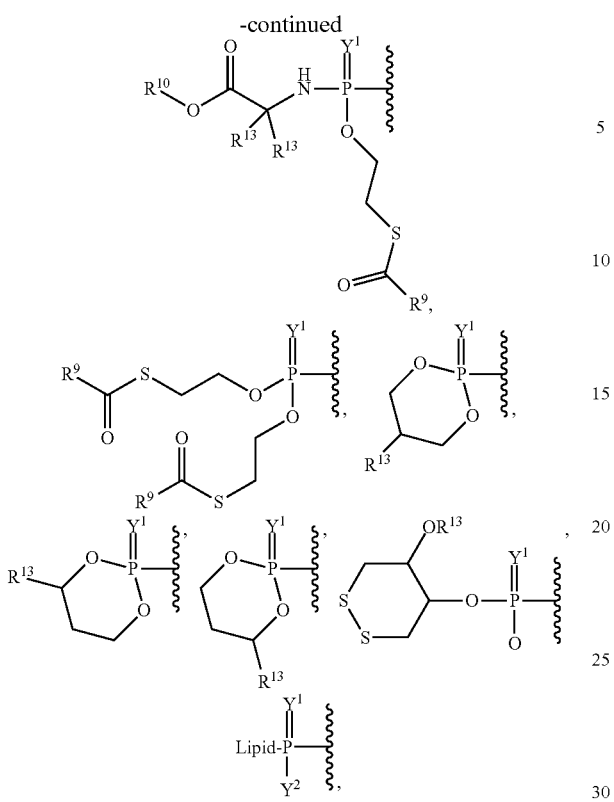

alkyl, halogen, nitro, cyano, hydroxy, amino, mercapto, formyl, carboxy, carbamoyl, carbanoyl, esteryl, alkoxy, alkylthio, alkylamino, (alkyl)₂amino, alkylsulfinyl, alkylsulfonyl, arylsulfonyl, carbocyclyl, aryl, or heterocyclyl, phosphoramidyl, or phosphate wherein $R^1$ is optionally substituted with one or more, the same or different, $R^{20}$;

$Y^1$ is O or S;

$Y^2$ is OH, $OR^{12}$, OAlkyl, or $BH_3^-M^+$;

$Y^3$ is OH or $BH_3^-M^+$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^6$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)₂amino, alkylsulfinyl, alkylsulfonyl, arylsulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, $(C_6-C_{16})$alkyl, $(C_6-C_{22})$alkyl, halogen, nitro, cyano, hydroxy, amino, mercapto, formyl, carboxy, carbamoyl, cycloalkyl, alkoxy, alkylthio, alkylamino, (alkyl)₂amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)₂amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

$R^{15}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, (C$_6$-C$_{16}$)alkyl, (C$_6$-C$_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{20}$;

$R^{15'}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, (C$_6$-C$_{16}$)alkyl, (C$_6$-C$_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^{15}$ and $R^{15'}$ can form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a C$_{6-22}$ alkyl, alkoxy, polyethylene glycol, or aryl substituted with an alkyl group.

14. The method of claim 1, wherein the compound is a compound of Formula IE,

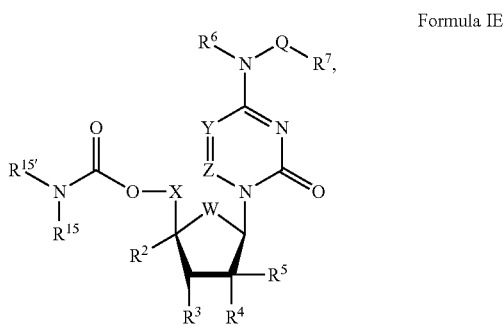

Formula IE or salt thereof, wherein
Q is O, —O(C=O)—, —O(C=O)Lipid, —O(C=O)V—, NH, or NR$^7$;
V is O, NH, NR$^7$, S, CH$_2$, or CHR$^7$;
W is CH$_2$, NH, S or O;
X is CH$_2$, CHMe, CMe$_2$, CHF, CF$_2$, or CD$_2$;
Y is N or CR";
Z is N or CR";
each $R^{11}$ is independently selected from is H, D, F, Cl, Br, I, CH$_3$, CD$_3$, CF$_3$, alkyl, acyl, alkenyl, alkynyl, hydroxyl, formyl or SCH$_3$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{20}$;

each $R^7$ is independently selected from absent, hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6$-$C_{16})$alkyl, $(C_6$-$C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^{15}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6$-$C_{16})$alkyl, $(C_6$-$C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{20}$;

$R^{15'}$ is hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, $(C_6$-$C_{16})$alkyl, $(C_6$-$C_{22})$alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^{15}$ and $R^{15'}$ can form a ring that is optionally substituted with one or more, the same or different, $R^{20}$;

If Q=—O(C=O)V— and V=NR$^7$ then the R$^7$s can together form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group.

15. The method of claim 1, wherein the compound is a compound of Formula II,

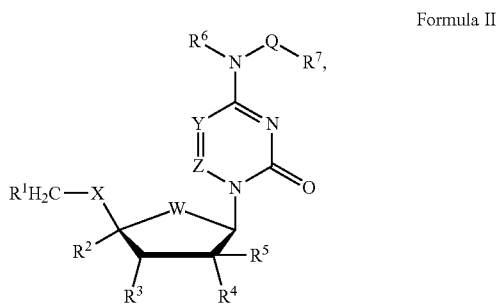

Formula II or salt thereof, wherein

Q is O, —O(C=O)—, —O(C=O)Lipid, —O(C=O)V—, NH, or NR$^7$;

V is O, NH, NR$^7$, S, CH$_2$, or CHR$^7$;

W is CH$_2$, NH, S or O;

X is CH$_2$ or O;

Y is N or CR";

Z is N or CR";

each $R^{11}$ is independently selected from is H, D, F, Cl, Br, I, CH$_3$, CD$_3$, CF$_3$, alkyl, acyl, alkenyl, alkynyl, hydroxyl, formyl or SCH$_3$;

$R^1$ is monophosphate, diphosphate, triphosphate,

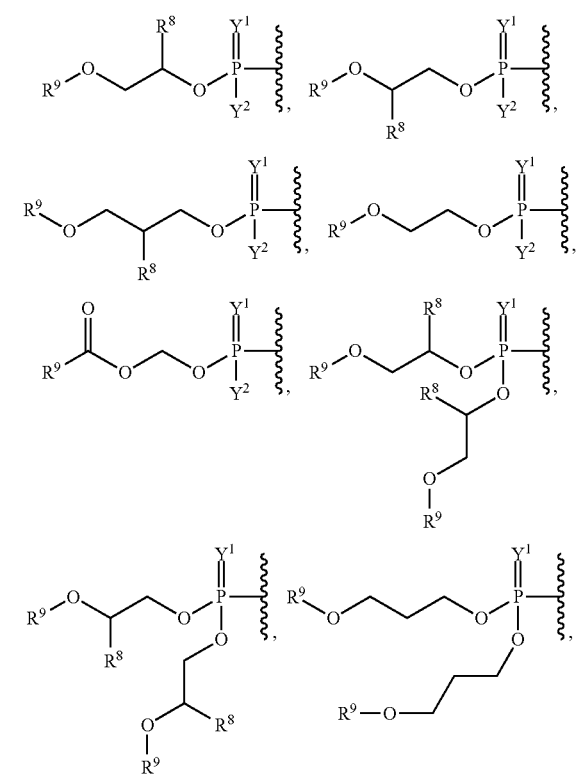

169
-continued
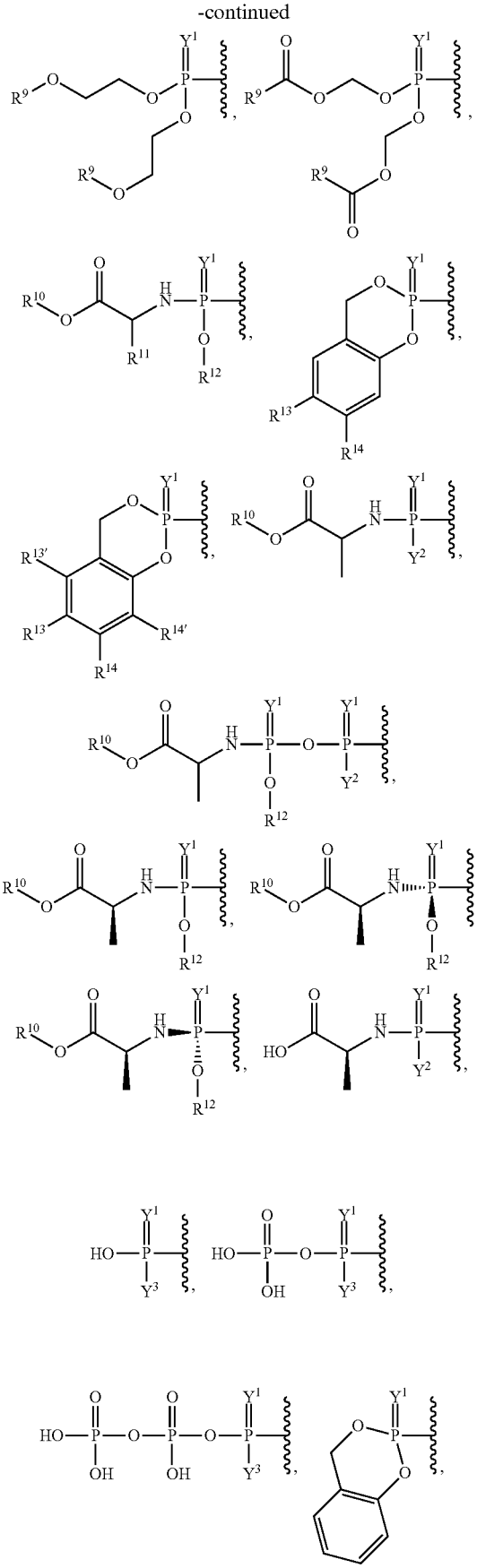
170
-continued
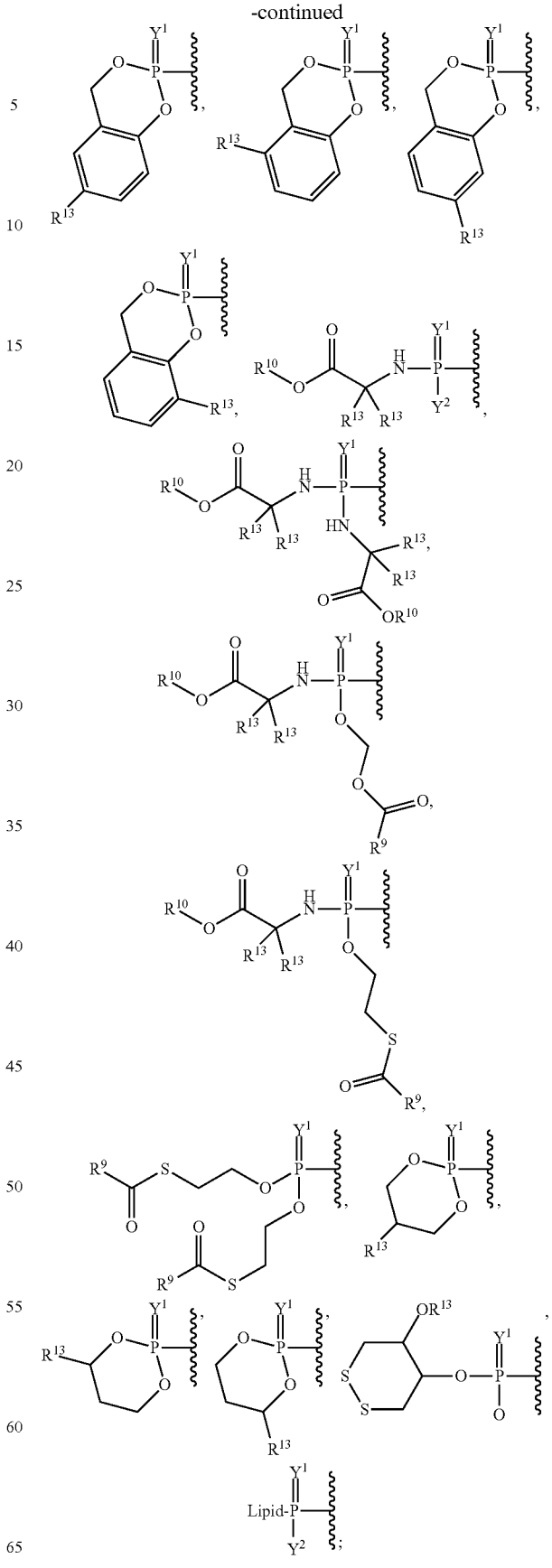

$Y^1$ is O or S;

$Y^2$ is OH, $OR^{12}$, OAlkyl, or $BH_3^-M^+$;

$Y^3$ is OH or $BH_3^-M^+$;

$R^2$ is hydrogen, alkyl, alkenyl, alkynyl, ethynyl, fluoromethyl, difluoromethyl, trifluoromethyl, chloromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, azido, or heterocyclyl, wherein $R^2$ is optionally substituted with one or more, the same or different, $R^{20}$;

$R^3$ is hydrogen, hydroxy, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^{20}$;

$R^4$ is hydrogen, hydroxy, alkyl, fluoromethyl, difluoromethyl, trifluoromethyl, hydroxymethyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^{20}$;

$R^5$ is hydrogen, hydroxy, alkoxy, alkyl, alkenyl, alkynyl, ethynyl, fluoromethyl, difluoromethyl, trifluoromethyl, hydroxymethyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{20}$;

$R^6$ is hydrogen, hydroxy, alkoxy, alkyl, ethynyl, allenyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^{20}$;

each $R^7$ is independently selected from absent, hydrogen, —(C=O)Oalkyl, —(C=O)alkyl, —(C=O)NHalkyl, —(C=O)N-dialkyl, —(C=O)Salkyl, hydroxy, alkoxy, alkyl, higher alkyl, ($C_6$-$C_{16}$)alkyl, ($C_6$-$C_{22}$)alkyl, halogen, nitro, cyano, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^7$ is optionally substituted with one or more, the same or different, $R^{20}$;

$R^8$ is hydrogen, deuterium, alkyl, alkenyl, alkynyl, halogen, nitro, cyano, hydroxy, benzyloxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^{20}$;

$R^9$ is hydrogen, methyl, ethyl, tert-butyl, alkyl, higher alkyl, ($C_6$-$C_{16}$)alkyl, ($C_6$-$C_{22}$)alkyl, halogen, nitro, cyano, hydroxy, amino, mercapto, formyl, carboxy, carbamoyl, cycloalkyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^9$ is optionally substituted with one or more, the same or different, $R^{20}$;

$R^{10}$ is hydrogen, alkyl, branched alkyl, cycloalkyl, lipid methyl, ethyl, isopropyl, cyclopentyl, cyclohexyl, butyl, pentyl, hexyl, neopentyl, benzyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{20}$;

$R^{11}$ is hydrogen, deuterium, alkyl, methyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{20}$;

$R^{12}$ is hydrogen, alkyl, aryl, phenyl, 1-naphthyl, 2-naphthyl, aromatic, heteroaromatic, 4-substituted phenyl, 4-fluorophenyl, 4-chlorophenyl, 4-bromophenyl, naphthyl, or heterocyclyl, wherein $R^{12}$ is optionally substituted with one or more, the same or different, $R^{20}$;

$R^{13}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13}$ is optionally substituted with one or more, the same or different, $R^{20}$;

$R^{14}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14}$ is optionally substituted with one or more, the same or different, $R^{20}$;

$R^{13'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{13'}$ is optionally substituted with one or more, the same or different, $R^{20}$;

$R^{14'}$ is hydrogen, deuterium, alkyl, alkenyl, alkynyl, halogen, nitro, cyano, hydroxy, amino, amido, mercapto, formyl, carboxy, carbamoyl, lipid, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{14'}$ is optionally substituted with one or more, the same or different, $R^{20}$;

If Q=—O(C=O)V— and V=$NR^7$ then the $R^7$s can together form a ring that is optionally substituted with one or more, the same or different, $R^{20}$;

$R^{20}$ is deuterium, alkyl, alkenyl, alkynyl, halogen, nitro, cyano, hydroxy, amino, amido, mercapto, formyl, carboxy, carbamoyl, azido, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$;

$R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and Lipid is a $C_{6-22}$ alkyl, alkoxy, polyethylene glycol, or aryl substituted with an alkyl group.

16. The method of claim 1, further comprising administering an additional antiviral compound.

* * * * *

UNITED STATES PATENT AND TRADEMARK OFFICE
CERTIFICATE OF CORRECTION

PATENT NO. : 10,874,683 B2
APPLICATION NO. : 16/083177
DATED : December 29, 2020
INVENTOR(S) : George R. Painter et al.

It is certified that error appears in the above-identified patent and that said Letters Patent is hereby corrected as shown below:

In the Claims

Claim 1, Column 146, Lines 1-10, the first three structures should appear as follows:

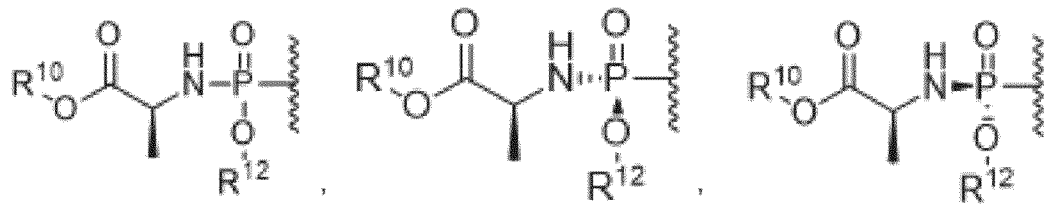

Claim 1, Column 147, Lines 20-25, the third structure should appear as follows:

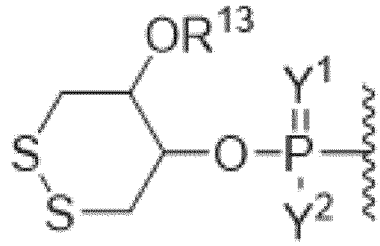

Claim 4, Column 151, Lines 25-30, the second structure should appear as follows:

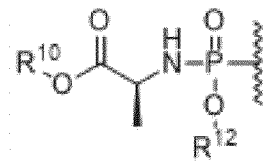

Signed and Sealed this
First Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)

Claim 4, Column 151, Lines 30-35, the two structures should appear as follows:

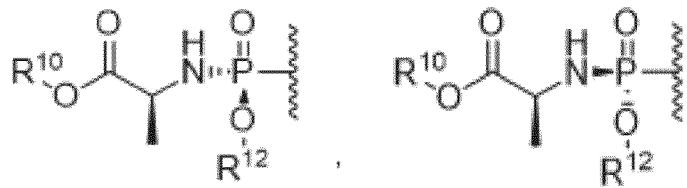

Claim 4, Column 152, Lines 40-45, the third structure should appear as follows:

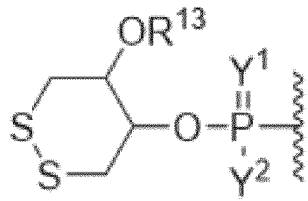

Claim 12, Column 157, Lines 25-35, the first three structures should appear as follows:

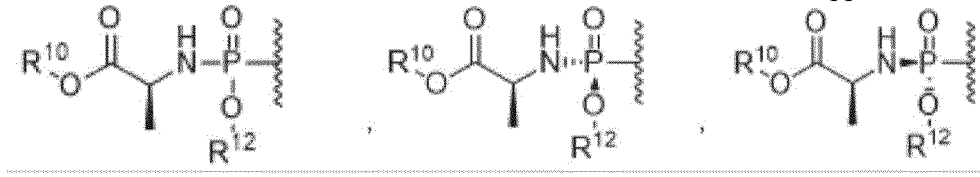

Claim 12, Column 158, Lines 40-45, the third structure should appear as follows:

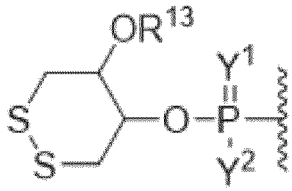

Claim 13, Column 160, Lines 40-55, the structure should appear as follows:

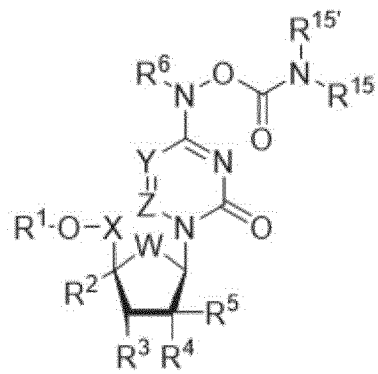

Claim 13, Column 162, Lines 1-10, the first three structures should appear as follows:

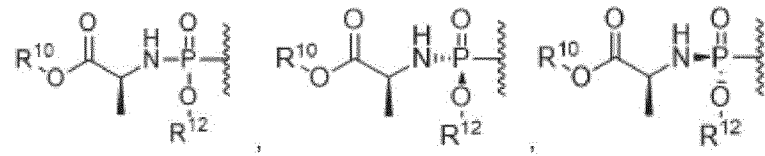

CERTIFICATE OF CORRECTION (continued)
U.S. Pat. No. 10,874,683 B2

Claim 13, Column 163, Lines 20-25, the third structure should appear as follows:

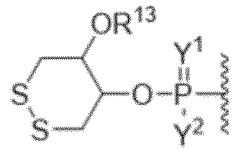

Claim 14, Column 166, Line 27, replace "$R^{11}$" with -- R" --

Claim 15, Column 168, Line 31, replace "$R^{11}$" with -- R" --

Claim 15, Column 169, Lines 35-45, the first three structures should appear as follows:

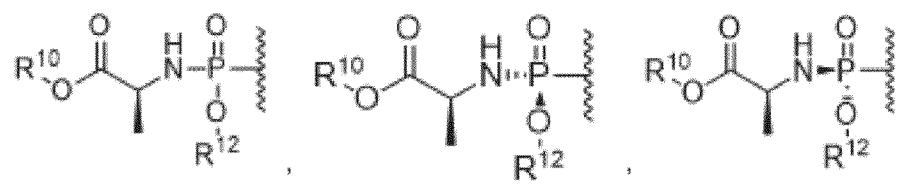

Claim 15, Column 170, Lines 55-60, the third structure should appear as follows: